(12) United States Patent
Fabro

(10) Patent No.: US 10,625,046 B2
(45) Date of Patent: Apr. 21, 2020

(54) DIAGNOSTIC CATHETERS, GUIDE CATHETERS, VISUALIZATION DEVICES AND CHORD MANIPULATION DEVICES, AND RELATED KITS AND METHODS

(71) Applicant: Ancora Heart, Inc., Santa Clara, CA (US)

(72) Inventor: Mariel Fabro, San Francisco, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 0 days.

(21) Appl. No.: 14/868,290

(22) Filed: Sep. 28, 2015

(65) Prior Publication Data

US 2016/0220785 A1 Aug. 4, 2016

Related U.S. Application Data

(63) Continuation of application No. 13/619,331, filed on Sep. 14, 2012, now Pat. No. 9,173,646, which is a
(Continued)

(51) Int. Cl.
*A61M 25/00* (2006.01)
*A61B 1/00* (2006.01)
(Continued)

(52) U.S. Cl.
CPC ..... *A61M 25/0043* (2013.01); *A61B 1/00078* (2013.01); *A61B 6/12* (2013.01);
(Continued)

(58) Field of Classification Search
CPC .. A61B 2017/00243; A61M 2210/127; A61M 25/0041; A61M 25/00
(Continued)

(56) References Cited

U.S. PATENT DOCUMENTS 3,656,185 A  4/1972 Carpentier
3,773,034 A  11/1973 Burns et al.
(Continued)

FOREIGN PATENT DOCUMENTS

EP  1 920 795 A1  5/2008
JP  2003-500121 A  1/2003
(Continued)

OTHER PUBLICATIONS

Extended European Search Report dated Sep. 6, 2011, for EP Patent Application No. 09743698.4, filed on May 7, 2009, 7 pages.
(Continued)

*Primary Examiner* — Deanna K Hall
(74) *Attorney, Agent, or Firm* — Cooley LLP

(57) ABSTRACT

Described herein are devices, methods and kits for assessing and/or enhancing the accessibility of a subvalvular space of a heart, accessing the subvalvular space of the heart (e.g., to provide access for one or more other devices), and/or positioning one or more devices in the subvalvular space of the heart. The devices described herein may, for example, comprise catheters that may be used to manipulate one or more chordae tendineae, diagnostic catheters having different sizes and/or shapes (e.g., different curvatures), guide catheters having different sizes and/or shapes (e.g., different curvatures), and visualization catheters. In some variations, the devices, methods, and/or kits may be used to visualize a target site, such as a subannular groove of a heart valve. In certain variations, the devices, methods, and/or kits may be used to manipulate chordae tendineae to provide additional space in a ventricle of a heart (e.g., enhancing the accessibility of the ventricle).

26 Claims, 133 Drawing Sheets

Related U.S. Application Data continuation of application No. 12/690,109, filed on Jan. 19, 2010, now abandoned.

(60) Provisional application No. 61/178,938, filed on May 15, 2009, provisional application No. 61/178,910, filed on May 15, 2009, provisional application No. 61/160,670, filed on Mar. 16, 2009, provisional application No. 61/160,230, filed on Mar. 13, 2009, provisional application No. 61/145,964, filed on Jan. 20, 2009.

(51) Int. Cl.
*A61B 6/12* (2006.01)
*A61B 8/12* (2006.01)
*A61B 17/00* (2006.01)
*A61B 6/00* (2006.01)
A61B 1/313 (2006.01)
A61B 17/32 (2006.01)
A61B 17/72 (2006.01)
A61M 25/04 (2006.01)

(52) U.S. Cl.
CPC ............. *A61B 6/481* (2013.01); *A61B 6/485* (2013.01); *A61B 8/12* (2013.01); *A61B 17/0057* (2013.01); *A61B 17/00234* (2013.01); *A61M 25/0041* (2013.01); A61B 1/3137 (2013.01); A61B 17/320016 (2013.01); A61B 17/7208 (2013.01); A61B 2017/00243 (2013.01); A61M 25/04 (2013.01); A61M 2210/127 (2013.01)

(58) Field of Classification Search
USPC ........................................................ 604/532
See application file for complete search history.

(56) References Cited

U.S. PATENT DOCUMENTS

| | | |
|---|---|---|
| 3,961,419 A | 6/1976 | Schwartz |
| 3,976,079 A | 8/1976 | Samuels et al. |
| 4,034,473 A | 7/1977 | May |
| 4,042,979 A | 8/1977 | Angell |
| 4,044,765 A | 8/1977 | Kline |
| 4,053,979 A | 10/1977 | Tuthill et al. |
| 4,069,825 A | 1/1978 | Akiyama |
| 4,273,127 A | 6/1981 | Auth et al. |
| 4,290,151 A | 9/1981 | Massana |
| 4,384,406 A | 5/1983 | Tischlinger |
| 4,445,509 A | 5/1984 | Auth |
| 4,489,446 A | 12/1984 | Reed |
| 4,494,542 A | 1/1985 | Lee |
| 4,576,772 A | 3/1986 | Carpenter |
| 4,726,371 A | 2/1988 | Gibbens |
| 4,758,221 A | 7/1988 | Jureidini |
| 4,817,613 A | 4/1989 | Jaraczewski et al. |
| 4,845,851 A | 7/1989 | Warthen |
| 4,848,341 A | 7/1989 | Ahmad |
| 4,850,354 A | 7/1989 | McGurk-Burleson et al. |
| 4,898,577 A | 2/1990 | Badger et al. |
| 4,898,591 A | 2/1990 | Jang et al. |
| 4,906,230 A | 3/1990 | Maloney et al. |
| 4,969,893 A | 11/1990 | Swor |
| 5,037,404 A | 8/1991 | Gold et al. |
| 5,053,047 A | 10/1991 | Yoon |
| 5,057,092 A | 10/1991 | Webster, Jr. |
| 5,064,431 A | 11/1991 | Gilbertson et al. |
| 5,084,058 A | 1/1992 | Li |
| 5,125,909 A | 6/1992 | Heimberger |
| 5,133,723 A | 7/1992 | Li et al. |
| 5,152,744 A | 10/1992 | Krause et al. |
| 5,158,540 A | 10/1992 | Wijay et al. |
| 5,163,431 A | 11/1992 | Griep |
| 5,195,990 A | 5/1993 | Weldon |
| 5,221,255 A | 6/1993 | Mahurkar et al. |
| 5,254,107 A | 10/1993 | Soltesz |
| D345,419 S | 3/1994 | Horrigan et al. |
| 5,314,407 A | 5/1994 | Auth et al. |
| 5,324,298 A | 6/1994 | Phillips et al. |
| 5,344,439 A | 9/1994 | Otten |
| 5,346,500 A | 9/1994 | Suchart |
| 5,348,536 A | 9/1994 | Young et al. |
| 5,358,479 A | 10/1994 | Wilson |
| 5,364,407 A | 11/1994 | Poll |
| 5,368,564 A | 11/1994 | Savage |
| 5,381,782 A | 1/1995 | DeLaRama et al. |
| 5,383,905 A | 1/1995 | Golds et al. |
| 5,399,164 A | 3/1995 | Snoke et al. |
| 5,403,348 A | 4/1995 | Bonutti |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,445,625 A | 8/1995 | Voda |
| 5,452,513 A | 9/1995 | Zinnbauer et al. |
| 5,474,572 A | 12/1995 | Hayhurst |
| 5,507,725 A | 4/1996 | Savage et al. |
| 5,527,323 A | 6/1996 | Jervis et al. |
| 5,542,924 A | 8/1996 | Snoke et al. |
| 5,545,168 A | 8/1996 | Burke |
| 5,565,122 A | 10/1996 | Zinnbauer et al. |
| 5,569,218 A | 10/1996 | Berg |
| 5,571,215 A | 11/1996 | Sterman et al. |
| 5,624,397 A | 4/1997 | Snoke et al. |
| 5,626,614 A | 5/1997 | Hart |
| 5,630,824 A | 5/1997 | Hart |
| 5,640,955 A | 6/1997 | Ockuly et al. |
| 5,658,263 A | 8/1997 | Dang et al. |
| 5,669,917 A | 9/1997 | Sauer et al. |
| 5,674,197 A | 10/1997 | Van Muiden et al. |
| 5,690,655 A | 11/1997 | Hart et al. |
| 5,701,905 A | 12/1997 | Esch |
| 5,718,725 A | 2/1998 | Sterman et al. |
| 5,735,290 A | 4/1998 | Sterman et al. |
| 5,741,260 A | 4/1998 | Songer et al. |
| 5,741,301 A | 4/1998 | Pagedas |
| 5,752,964 A | 5/1998 | Mericle |
| 5,755,730 A | 5/1998 | Swain et al. |
| 5,769,830 A | 6/1998 | Parker |
| 5,810,848 A | 9/1998 | Hayhurst |
| 5,810,853 A | 9/1998 | Yoon |
| 5,817,107 A | 10/1998 | Schaller |
| 5,833,632 A | 11/1998 | Jacobsen et al. |
| 5,860,993 A | 1/1999 | Thompson et al. |
| 5,868,733 A | 2/1999 | Ockuly et al. |
| 5,879,371 A | 3/1999 | Gardiner et al. |
| 5,897,537 A | 4/1999 | Berg et al. |
| 5,902,321 A | 5/1999 | Caspari et al. |
| 5,904,657 A | 5/1999 | Unsworth et al. |
| 5,906,579 A | 5/1999 | Vander Salm et al. |
| 5,911,715 A | 6/1999 | Berg et al. |
| 5,916,147 A | 6/1999 | Boury |
| 5,919,208 A | 7/1999 | Valenti |
| 5,961,440 A | 10/1999 | Schweich, Jr. et al. |
| 5,971,975 A | 10/1999 | Mills et al. |
| 5,976,120 A | 11/1999 | Chow et al. |
| 6,015,428 A | 1/2000 | Pagedas |
| 6,029,671 A | 2/2000 | Stevens et al. |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,110,184 A | 8/2000 | Weadock |
| 6,125,852 A | 10/2000 | Stevens et al. |
| 6,159,187 A | 12/2000 | Park et al. |
| 6,162,168 A | 12/2000 | Schweich, Jr. et al. |
| 6,168,588 B1 | 1/2001 | Wilson |
| 6,183,469 B1 | 2/2001 | Thapliyal et al. |
| 6,199,262 B1 | 3/2001 | Martin |
| 6,203,531 B1 | 3/2001 | Ockuly et al. |
| 6,228,096 B1 | 5/2001 | Marchand |
| 6,254,620 B1 | 7/2001 | Koh et al. |

(56) References Cited

U.S. PATENT DOCUMENTS

| | | |
|---|---|---|
| 6,258,118 B1 | 7/2001 | Baum et al. |
| 6,260,552 B1 | 7/2001 | Mortier et al. |
| 6,378,289 B1 | 4/2002 | Trudeau et al. |
| 6,406,420 B1 | 6/2002 | McCarthy et al. |
| 6,428,562 B2 | 8/2002 | Bonutti |
| 6,432,123 B2 | 8/2002 | Schwartz et al. |
| 6,491,689 B1 | 12/2002 | Ellis et al. |
| 6,540,755 B2 * | 4/2003 | Ockuly ............ A61M 25/0041 600/434 |
| 6,589,160 B2 | 7/2003 | Schweich, Jr. et al. |
| 6,591,472 B1 | 7/2003 | Noone et al. |
| 6,595,983 B2 | 7/2003 | Voda |
| 6,610,087 B1 | 8/2003 | Zarbatany et al. |
| 6,629,534 B1 | 10/2003 | St. Goar et al. |
| 6,645,160 B1 | 11/2003 | Heesch |
| 6,648,874 B2 | 11/2003 | Parisi et al. |
| 6,648,903 B1 | 11/2003 | Pierson, III |
| 6,669,687 B1 | 12/2003 | Saadat |
| 6,695,793 B2 | 2/2004 | Brennan et al. |
| 6,699,263 B2 | 3/2004 | Cope |
| 6,716,243 B1 | 4/2004 | Colvin et al. |
| 6,723,038 B1 | 4/2004 | Schroeder et al. |
| 6,733,509 B2 | 5/2004 | Nobles et al. |
| 6,746,471 B2 | 6/2004 | Mortier et al. |
| 6,749,560 B1 | 6/2004 | Konstorum et al. |
| 6,793,618 B2 | 9/2004 | Schweich, Jr. et al. |
| 6,814,744 B2 | 11/2004 | Yang et al. |
| 6,818,001 B2 | 11/2004 | Wulfman et al. |
| 6,849,077 B2 | 2/2005 | Ricci |
| 6,858,024 B1 | 2/2005 | Berg et al. |
| 6,871,085 B2 | 3/2005 | Sommer |
| 6,908,424 B2 | 6/2005 | Monier et al. |
| 6,951,557 B2 | 10/2005 | Ellis et al. |
| 6,976,995 B2 | 12/2005 | Mathis et al. |
| 6,986,775 B2 | 1/2006 | Morales et al. |
| 6,989,025 B2 | 1/2006 | Burgmeier et al. |
| 6,997,931 B2 | 2/2006 | Sauer et al. |
| 7,037,334 B1 | 5/2006 | Hlavka et al. |
| 7,048,754 B2 | 5/2006 | Martin et al. |
| 7,090,683 B2 | 8/2006 | Brock et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,214,230 B2 | 5/2007 | Brock et al. |
| 7,226,467 B2 | 6/2007 | Lucatero et al. |
| 7,232,422 B2 | 6/2007 | Gibson et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,276,062 B2 | 10/2007 | McDaniel et al. |
| 7,306,585 B2 | 12/2007 | Ross |
| 7,326,231 B2 | 2/2008 | Phillips et al. |
| 7,331,972 B1 | 2/2008 | Cox |
| 7,452,325 B2 | 11/2008 | Schaller |
| 7,618,449 B2 | 11/2009 | Tremulis et al. |
| 7,632,308 B2 | 12/2009 | Loulmet |
| 7,722,523 B2 | 5/2010 | Mortier et al. |
| 7,740,638 B2 | 6/2010 | Hyde |
| 7,776,812 B2 | 8/2010 | Lang et al. |
| 7,832,406 B2 | 11/2010 | Ellis et al. |
| 8,096,985 B2 | 1/2012 | Legaspi et al. |
| 8,388,680 B2 | 3/2013 | Starksen et al. |
| 9,173,646 B2 | 11/2015 | Fabro |
| 9,616,197 B2 | 4/2017 | Serina et al. |
| 2001/0031979 A1 | 10/2001 | Ricci |
| 2001/0041821 A1 | 11/2001 | Wilk |
| 2001/0047165 A1 | 11/2001 | Makower et al. |
| 2002/0007190 A1 | 1/2002 | Wulfman et al. |
| 2002/0035393 A1 | 3/2002 | Lashinksi et al. |
| 2002/0065536 A1 | 5/2002 | Hart et al. |
| 2002/0087169 A1 | 7/2002 | Brock et al. |
| 2002/0133092 A1 | 9/2002 | Oslund et al. |
| 2002/0183835 A1 | 12/2002 | Taylor et al. |
| 2002/0198536 A1 | 12/2002 | Trout, III et al. |
| 2003/0009196 A1 | 1/2003 | Peterson |
| 2003/0032979 A1 | 2/2003 | Mortier et al. |
| 2003/0045893 A1 | 3/2003 | Ginn |
| 2003/0060813 A1 | 3/2003 | Loeb et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0158581 A1 | 8/2003 | Levinson |
| 2003/0171736 A1 | 9/2003 | Bon |
| 2003/0208119 A1 | 11/2003 | Crowley et al. |
| 2003/0233105 A1 | 12/2003 | Gayton |
| 2004/0019378 A1 | 1/2004 | Hlavka et al. |
| 2004/0092962 A1 | 5/2004 | Thornton et al. |
| 2004/0118415 A1 | 6/2004 | Hall et al. |
| 2004/0122450 A1 | 6/2004 | Oren et al. |
| 2004/0138683 A1 | 7/2004 | Shelton et al. |
| 2004/0148020 A1 | 7/2004 | Vidlund et al. |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186486 A1 | 9/2004 | Roue et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0243102 A1 | 12/2004 | Berg et al. |
| 2004/0243227 A1 | 12/2004 | Starksen et al. |
| 2005/0054919 A1 | 3/2005 | Spear et al. |
| 2005/0055087 A1 | 3/2005 | Starksen |
| 2005/0065550 A1 | 3/2005 | Starksen et al. |
| 2005/0075723 A1 | 4/2005 | Schroeder et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0273128 A1 | 12/2005 | Reil |
| 2005/0273138 A1 | 12/2005 | To et al. |
| 2006/0025750 A1 | 2/2006 | Starksen et al. |
| 2006/0025784 A1 | 2/2006 | Starksen et al. |
| 2006/0058817 A1 * | 3/2006 | Starksen .......... A61B 17/00234 606/142 |
| 2006/0069429 A1 | 3/2006 | Spence et al. |
| 2006/0089618 A1 | 4/2006 | McFerran et al. |
| 2006/0122633 A1 | 6/2006 | To et al. |
| 2006/0129188 A1 | 6/2006 | Starksen et al. |
| 2006/0155363 A1 | 7/2006 | LaDuca et al. |
| 2006/0161177 A1 | 7/2006 | Worley et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0229697 A1 | 10/2006 | Gerdts et al. |
| 2006/0229708 A1 | 10/2006 | Powell et al. |
| 2006/0241340 A1 | 10/2006 | Schroeder et al. |
| 2006/0264975 A1 | 11/2006 | Pipenhagen et al. |
| 2006/0270976 A1 | 11/2006 | Savage et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0016287 A1 | 1/2007 | Cartledge et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0060880 A1 | 3/2007 | Gregorich et al. |
| 2007/0066994 A1 | 3/2007 | Blaeser et al. |
| 2007/0093805 A1 | 4/2007 | Auth et al. |

(56) References Cited

U.S. PATENT DOCUMENTS

| | | |
|---|---|---|
| 2007/0100356 A1 | 5/2007 | Lucatero et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2007/0135830 A1 | 6/2007 | Schaeffer |
| 2007/0250042 A1 | 10/2007 | Schneider |
| 2008/0051703 A1 | 2/2008 | Thornton et al. |
| 2008/0058765 A1 | 3/2008 | Jais et al. |
| 2008/0058868 A1 | 3/2008 | To et al. |
| 2008/0065156 A1 | 3/2008 | Hauser et al. |
| 2008/0097489 A1 | 4/2008 | Goldfarb et al. |
| 2008/0103439 A1 | 5/2008 | Torrance et al. |
| 2008/0119727 A1 | 5/2008 | Barbagli et al. |
| 2008/0119882 A1 | 5/2008 | Cox |
| 2008/0177380 A1 | 7/2008 | Starksen et al. |
| 2008/0294177 A1 | 11/2008 | To et al. |
| 2009/0012541 A1 | 1/2009 | Dahl et al. |
| 2009/0177089 A1 | 7/2009 | Govari et al. |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0023056 A1 | 1/2010 | Johansson et al. |
| 2010/0076408 A1 | 3/2010 | Krever et al. |
| 2010/0076548 A1 | 3/2010 | Konno |
| 2010/0094213 A1 | 4/2010 | Horn et al. |
| 2010/0094314 A1 | 4/2010 | Hernlund et al. |
| 2010/0121349 A1 | 5/2010 | Meier et al. |
| 2010/0145267 A1 | 6/2010 | Bishop et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2012/0101442 A1 | 4/2012 | Legaspi et al. |
| 2014/0142619 A1 | 5/2014 | Serina et al. |
| 2017/0361065 A1 | 12/2017 | Legaspi et al. |
| 2018/0043132 A1 | 2/2018 | Serina et al. |

FOREIGN PATENT DOCUMENTS

| | | |
|---|---|---|
| WO | WO-94/03227 A1 | 2/1994 |
| WO | WO-95/15715 A1 | 6/1995 |
| WO | WO-96/39942 A1 | 12/1996 |
| WO | WO-97/27799 A1 | 8/1997 |
| WO | WO-97/27807 A1 | 8/1997 |
| WO | WO-98/46142 A1 | 10/1998 |
| WO | WO-00/71195 A1 | 11/2000 |
| WO | WO-01/54618 A1 | 8/2001 |
| WO | WO-02/30310 A1 | 4/2002 |
| WO | WO-02/085251 A1 | 10/2002 |
| WO | WO-02/085252 A1 | 10/2002 |
| WO | WO-03/073913 A2 | 9/2003 |
| WO | WO-03/073913 A3 | 9/2003 |
| WO | WO-03/088875 A1 | 10/2003 |
| WO | WO-03/105667 A2 | 12/2003 |
| WO | WO-03/105667 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2004/112658 A1 | 12/2004 |
| WO | WO-2005/06293 | 7/2005 |
| WO | WO-2005/06293 A2 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/037073 A3 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/059233 A2 | 5/2007 |
| WO | WO-2007/100409 A2 | 9/2007 |
| WO | WO-2007/100409 A3 | 9/2007 |
| WO | WO-2008/028135 A2 | 3/2008 |
| WO | WO-2008/028135 A3 | 3/2008 |
| WO | WO-2008/042987 A2 | 4/2008 |
| WO | WO-2008/042987 A3 | 4/2008 |
| WO | WO-2008/048626 A2 | 4/2008 |
| WO | WO-2010/085456 A1 | 7/2010 |
| WO | WO-2010/085457 A1 | 7/2010 |

OTHER PUBLICATIONS

Final Office Action dated May 12, 2010, for U.S. Appl. No. 11/583,627, filed Oct. 18, 2006, 18 pages.
Final Office Action dated Apr. 5, 2011, for U.S. Appl. No. 12/437,495, filed May 7, 2009, 6 pages.
Final Office Action dated Jun. 20, 2013, for U.S. Appl. No. 13/315,154, filed Dec. 8, 2011, 8 pages.
Final Office Action dated Apr. 14, 2014, for U.S. Appl. No. 13/619,331, filed Sep. 14, 2012, 7 pages.
International Preliminary Report on Patentability dated Apr. 30, 2009, for PCT Application PCT/US2007/022122 filed on Oct. 16, 2007, 9 pages.
International Preliminary Report on Patentability dated Nov. 18, 2010 for PCT Patent Application No. PCT/US2009/043195, filed on May 7, 2009, 8 pages.
International Search Report dated May 6, 2008 for PCT Application PCT/US07/22122 filed on Oct. 16, 2007, 1 page.
International Search Report dated Jul. 6, 2009 for PCT Patent Application No. PCT/US2009/043195, filed on May 7, 2009, 1 page.
International Search Report dated Mar. 9, 2010, for PCT Patent Application No. PCT/US/2010/021440, filed on Jan. 19, 2010, 1 page.
International Search Report dated Mar. 19, 2010, for PCT Patent Application No. PCT/US2010/021437, filed on Jan. 19, 2010, 1 page.
Non-Final Office Action dated Aug. 19, 2009, for U.S. Appl. No. 11/583,627, filed Oct. 18, 2006, 14 pages.
Non-Final Office Action dated Sep. 2, 2010, for U.S. Appl. No. 12/437,495, filed May 7, 2009, 5 pages.
Non-Final Office Action dated Nov. 23, 2010, and Examiner Interview Summary dated Mar. 18, 2011, for U.S. Appl. No. 11/583,627, filed Oct. 18, 2006, 16 pages.
Non-Final Office Action dated Sep. 18, 2012, for U.S. Appl. No. 13/315,154, filed Dec. 8, 2011, 8 pages.
Non-Final Office Action dated Mar. 15, 2012, for U.S. Appl. No. 12/690,109, filed Jan. 19, 2010, 7 pages.
Non-Final Office Action dated Apr. 11, 2013, for U.S. Appl. No. 12/657,422, filed Jan. 19, 2010, 8 pages.
Non-Final Office Action dated Dec. 18, 2014, for U.S. Appl. No. 13/619,331, filed Sep. 14, 2012, 7 pages.
Non-Final Office Action dated Sep. 15, 2015, for U.S. Appl. No. 14/052,593, filed Oct. 11, 2013, 8 pages.
Notice of Allowance dated Oct. 14, 2011, for U.S. Appl. No. 12/437,495, filed May 7, 2009, 7 pages.
Notice of Allowance dated Nov. 6, 2012, for U.S. Appl. No. 11/583,627, filed Oct. 18, 2006, 7 pages.
Supplementary European Search Report dated Jun. 2, 2010, for EP Patent Application No. 07852809.8, filed on Oct. 16, 2007, 7 pages.
Supplementary European Search Report dated Apr. 27, 2012, for EP Patent Application No. 10 733 791.7, filed on Aug. 19, 2011, 8 pages.
Towne, W.D. (1973). "Letter to the Editor: Classification of Chordae Tendineae," *Circulation* 47:209.
U.S. Appl. No. 61/160,670, filed Mar. 16, 2009, by Fabro et al.
U.S. Appl. No. 61/083,109, filed Jul. 23, 2008, by Johansson, Peter.
U.S. Appl. No. 61/104,681, filed Oct. 10, 2008, by Serina et al.
U.S. Appl. No. 61/104,686, filed Oct. 10, 2008, by To et al.
U.S. Appl. No. 61/145,964, filed Jan. 20, 2009, by Fabro, Mariel.
U.S. Appl. No. 61/160,018, filed Mar. 13, 2009, by Johansson, Peter.

(56) References Cited

OTHER PUBLICATIONS

U.S. Appl. No. 61/160,230, filed Mar. 13, 2009, by Meier et al.
U.S. Appl. No. 61/178,910, filed May 15, 2009, by Serina et al.
U.S. Appl. No. 61/178,938, filed May 15, 2009, by Fabro, Mariel.
U.S. Appl. No. 14/052,593, filed Oct. 11, 2013, by Serina et al.
Written Opinion of the International Searching Authority dated May 6, 2008 for PCT Application PCT/US07/22122 filed on Oct. 16, 2007, 7 pages.
Written Opinion of the International Searching Authority dated Jul. 6, 2009 for PCT Patent Application No. PCT/US2009/043195, filed on May 7, 2009, 5 pages.
Written Opinion of the International Searching Authority dated Mar. 9, 2010, for PCT Patent Application No. PCT/US/2010/021440, filed on Jan. 19, 2010, 5 pages.
Written Opinion of the International Searching Authority dated Mar. 19, 2010, for PCT Patent Application No. PCT/US/2010/021437, filed on Jan. 19, 2010, 8 pages.
Notice of Allowance dated Feb. 23, 2017, for U.S. Appl. No. 14/052,593, filed Oct. 11, 2013, 9 pages.
European Search Report dated Dec. 6, 2011, for EP Patent Application No. 11187159.6, filed on Oct. 16, 2007, 5 pages.
Extended European Search Report dated Jun. 2, 2010, for EP Patent Application No. 07852809.8, filed on Oct. 16, 2007, 8 pages.
Extended European Search Report dated May 10, 2012, for EP Application No. 10733791.7, filed on Aug. 19, 2011, 9 pages.
Final Office Action dated Nov. 20, 2014, for U.S. Appl. No. 13/315,154, filed Dec. 8, 2011, 8 pages.
Final Office Action dated Feb. 11, 2016, for U.S. Appl. No. 13/315,154, filed Dec. 8, 2011, 11 pages.
Final Office Action dated Aug. 11, 2016, for U.S. Appl. No. 14/052,593, filed Oct. 11, 2013, 10 pages.
Notice of Allowance dated Jun. 19, 2015, for U.S. Appl. No. 13/619,331, filed Sep. 14, 2012, 7 pages.
Non-Final Office Action dated Jun. 22, 2012, for U.S. Appl. No. 12/657,390, filed Jan. 19, 2010, 10 pages.
Non-Final Office Action dated Mar. 26, 2014, for U.S. Appl. No. 13/315,154, filed Dec. 8, 2011, 7 pages.
Non-Final Office Action dated May 7, 2015, for U.S. Appl. No. 13/315,154, filed Dec. 8, 2011, 8 pages.
Non-Final Office Action dated Oct. 6, 2016, for U.S. Appl. No. 13/315,154, filed Dec. 8, 2011, 9 pages.
Extended European Search Report dated Dec. 3, 2018, for EP Patent Application No. 18167829.3, filed on Oct. 16, 2007, 8 pages.
Non-Final Office Action dated Nov. 5, 2018, for U.S. Appl. No. 15/474,877, filed Mar. 30, 2017, 10 pages.
Notice of Allowance dated Apr. 9, 2019, for U.S. Appl. No. 15/479,718, filed Apr. 5, 2017, 7 pages.

\* cited by examiner

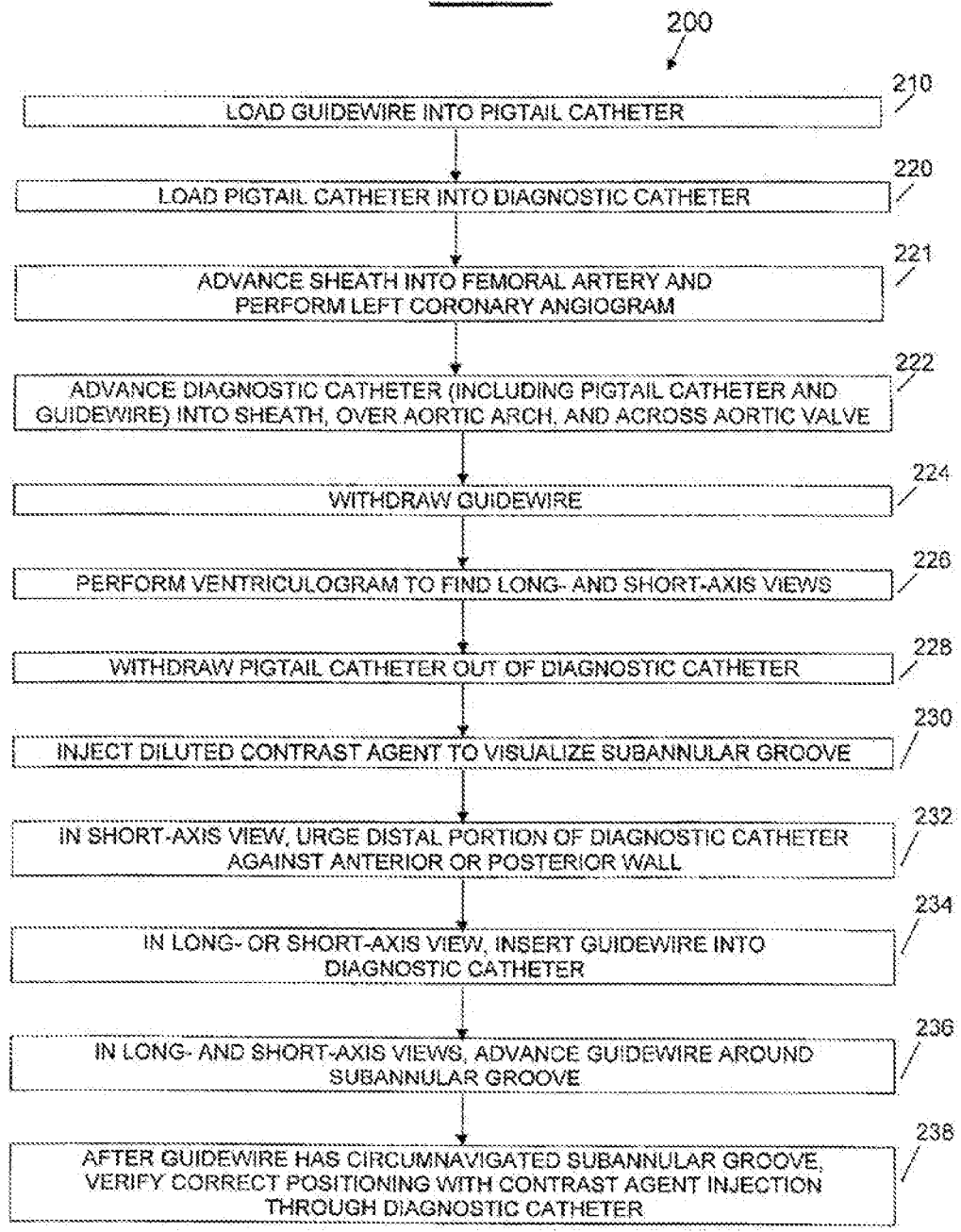

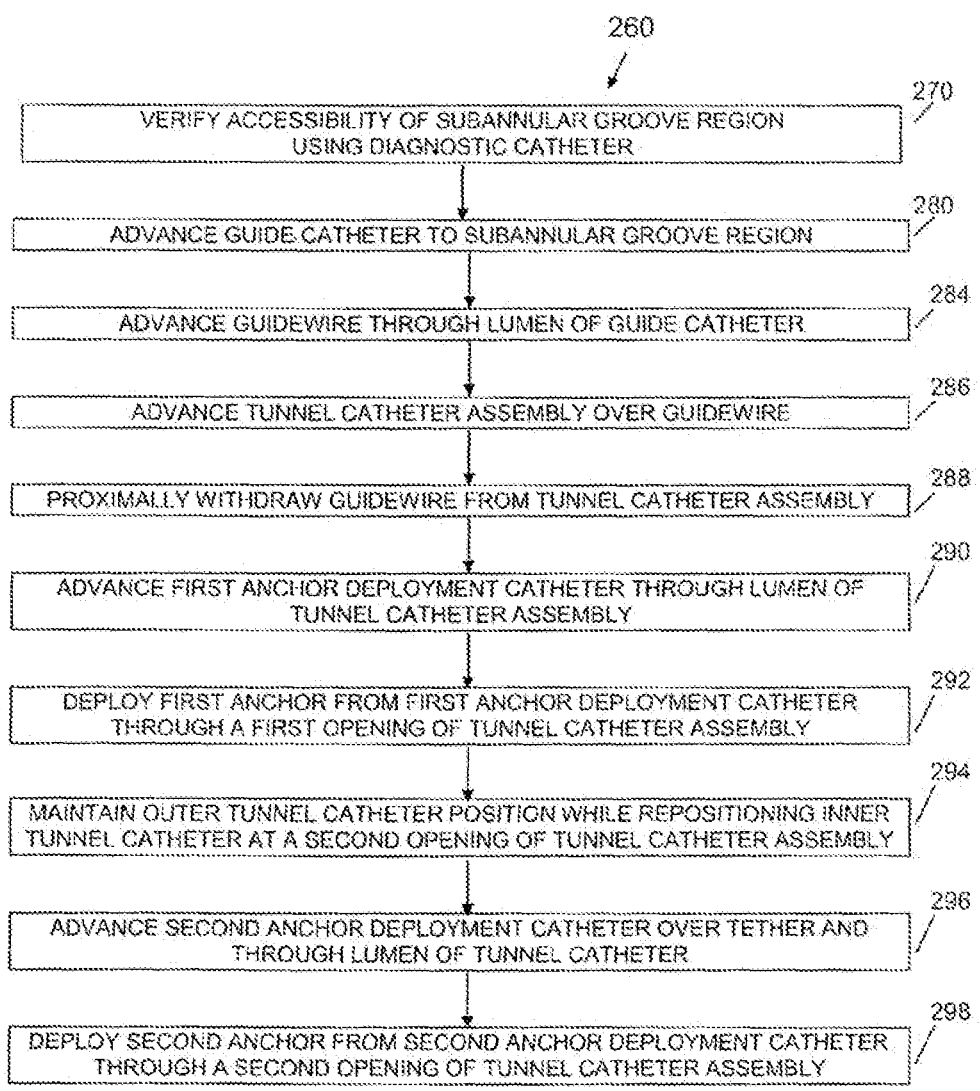

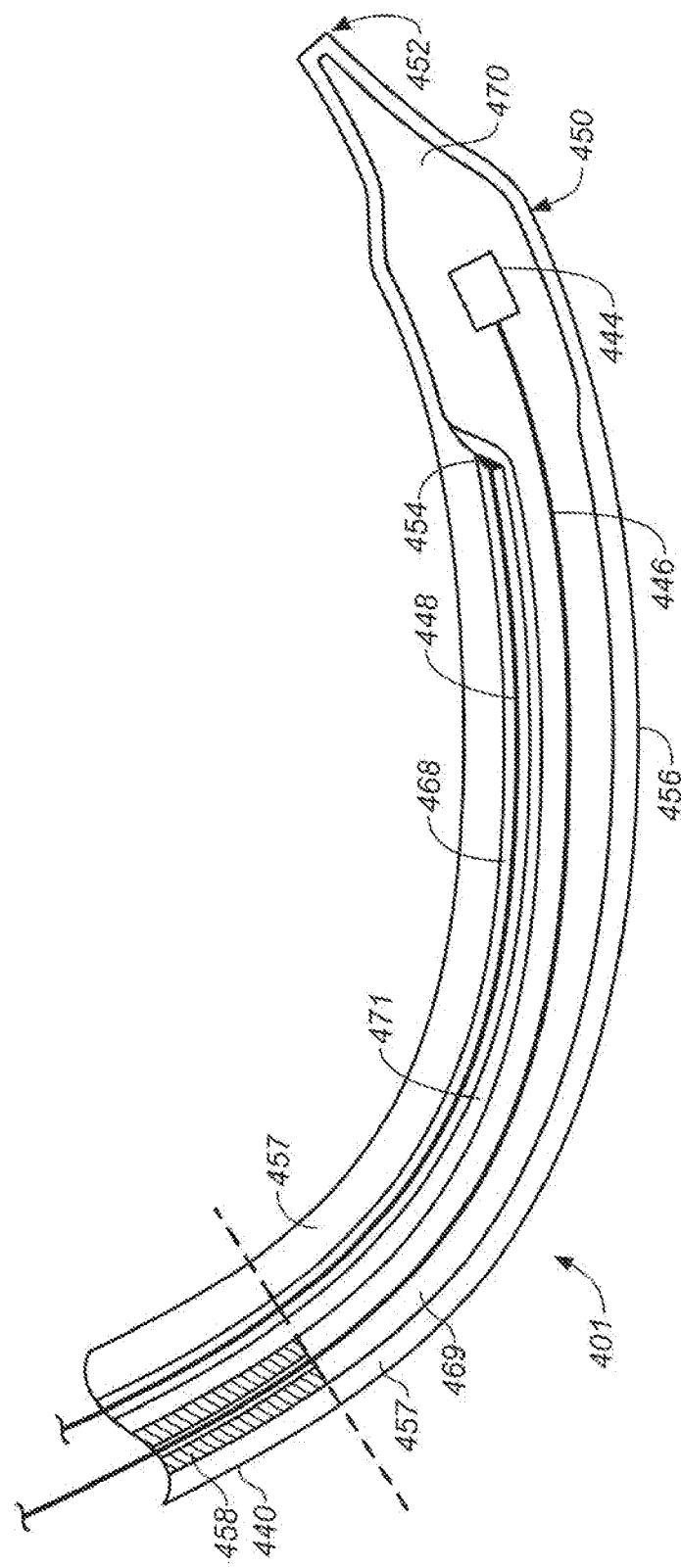

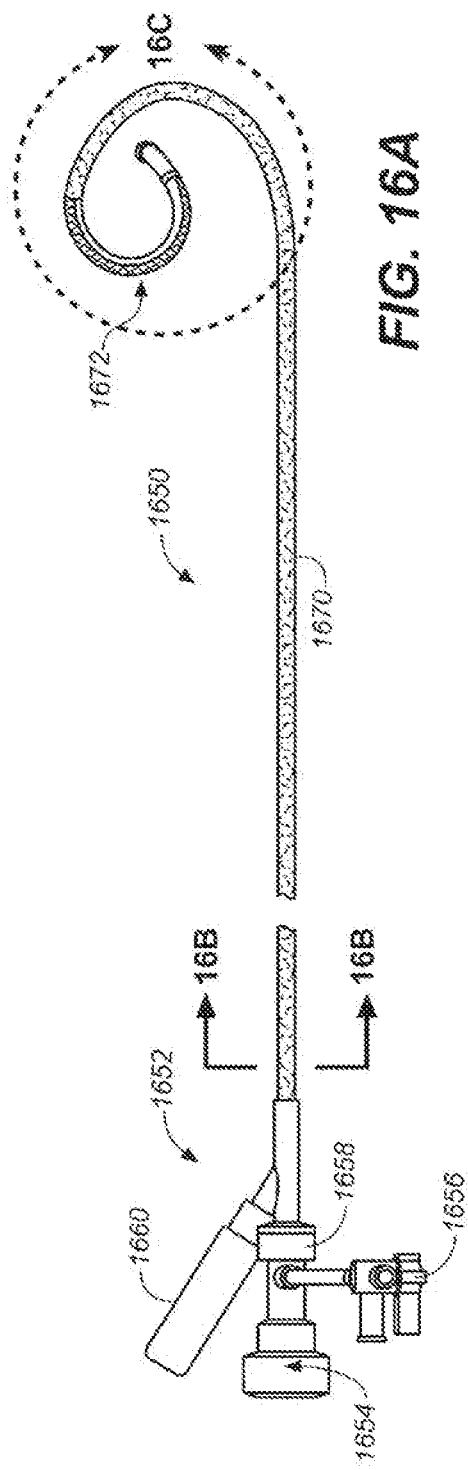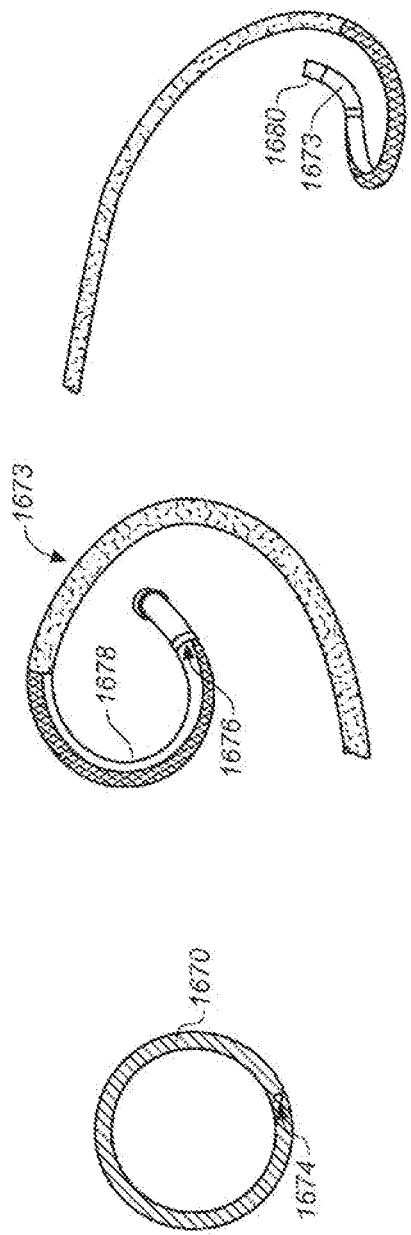

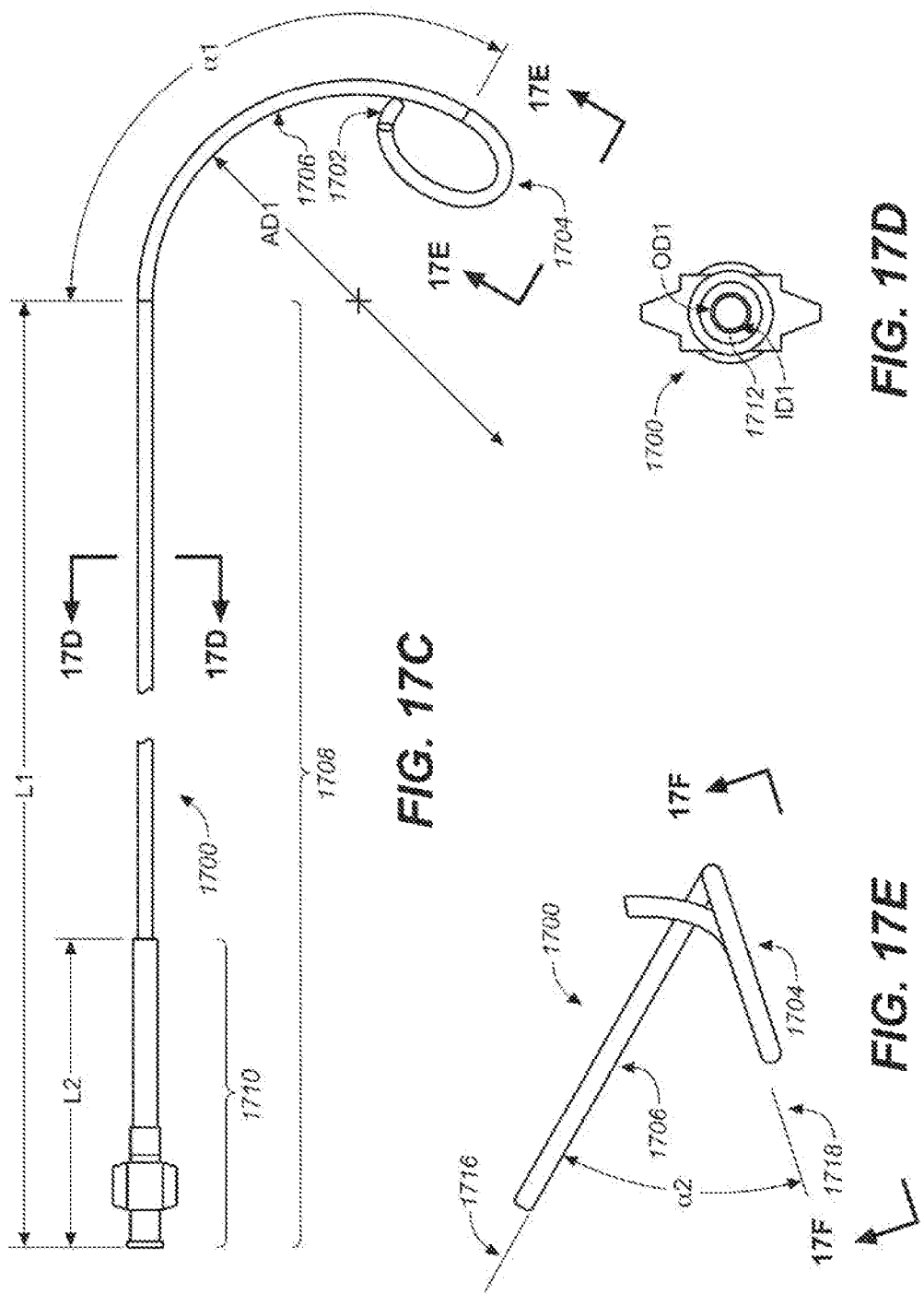

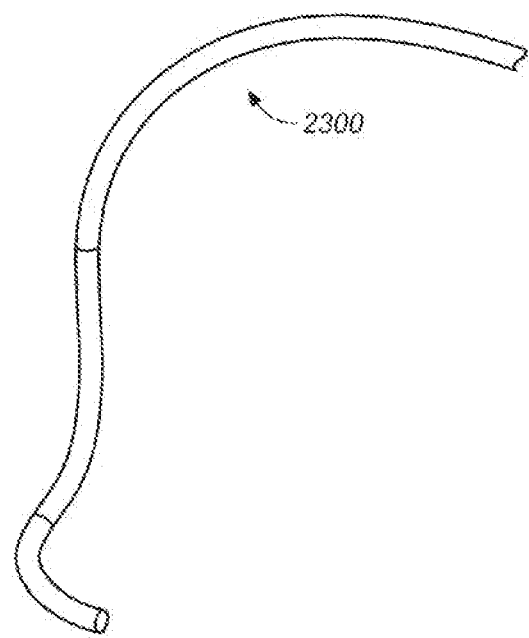
FIG. 23A
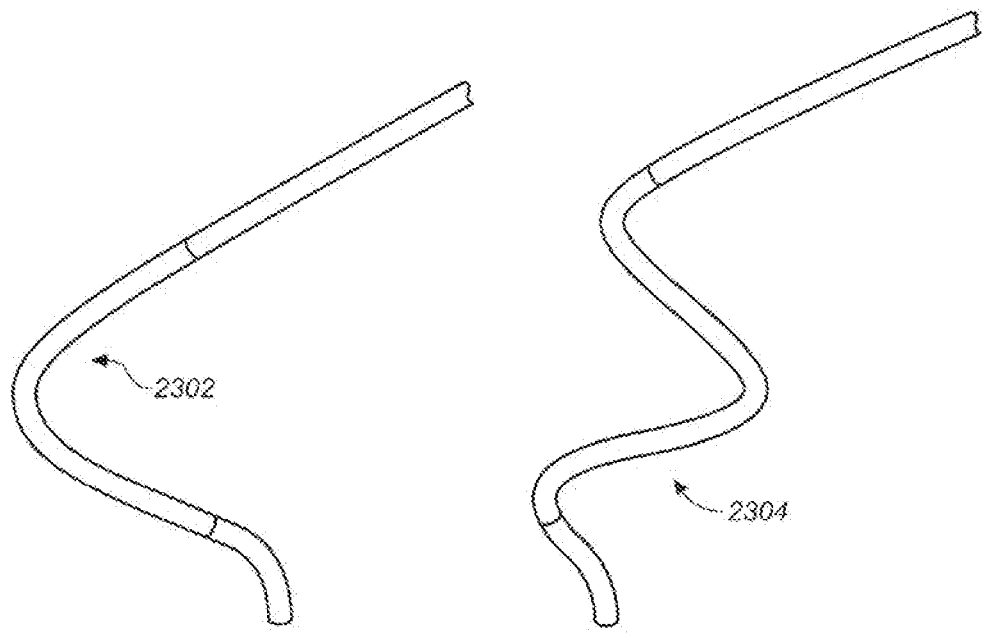
FIG. 23B  FIG. 23C

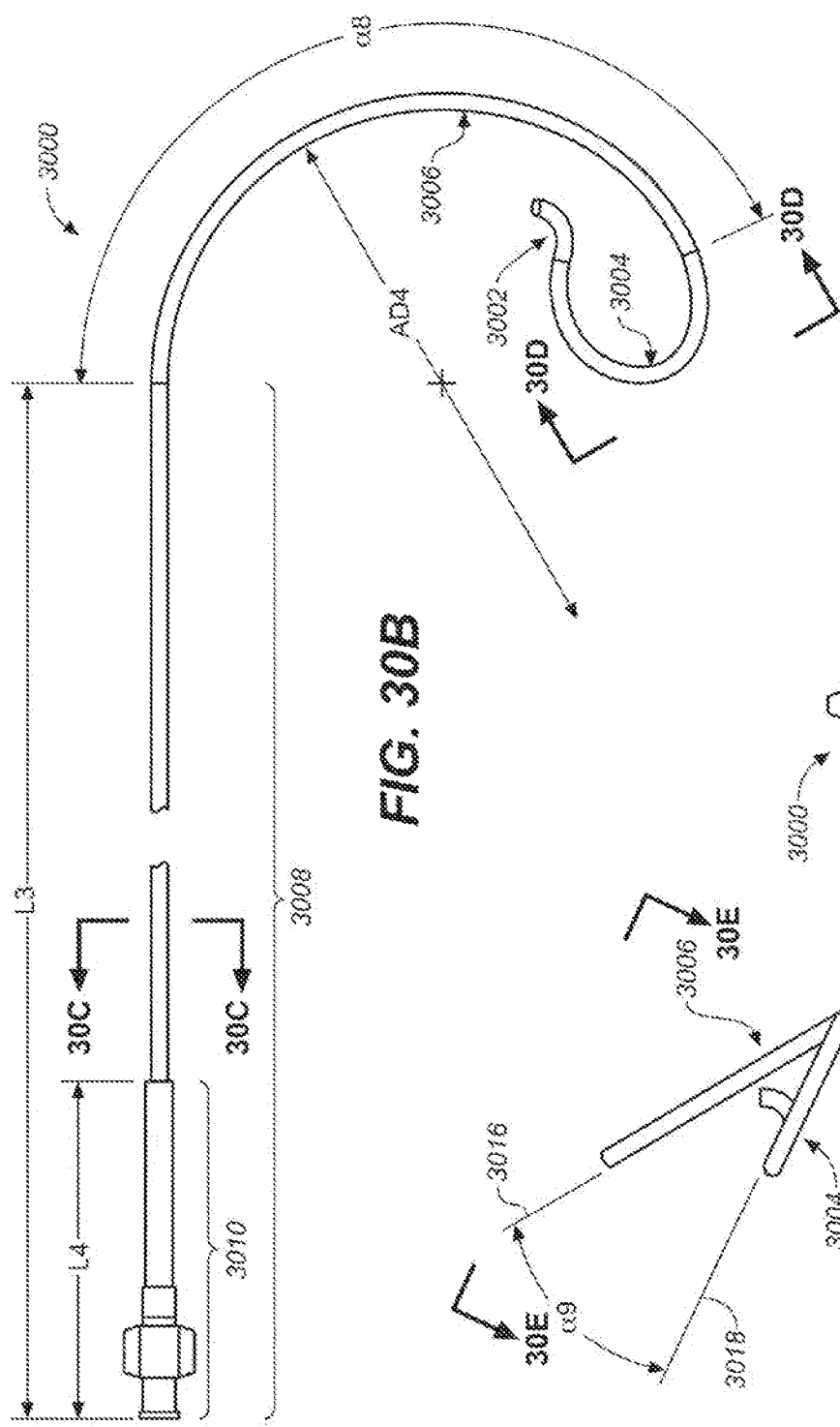

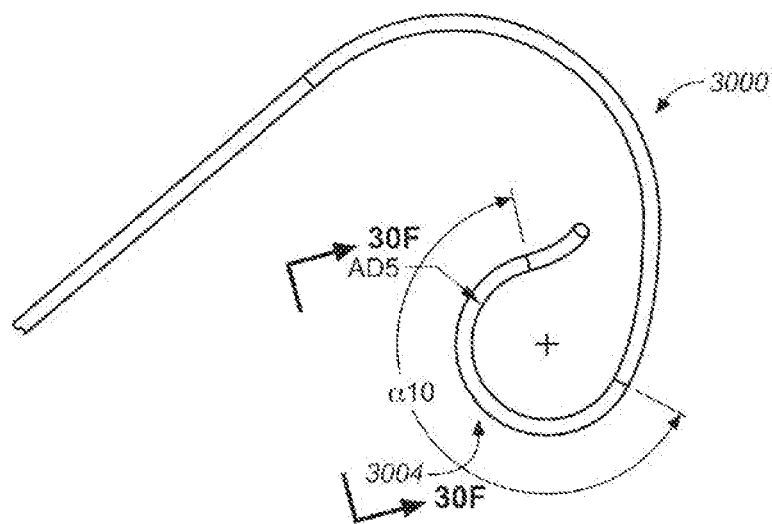
FIG. 30E
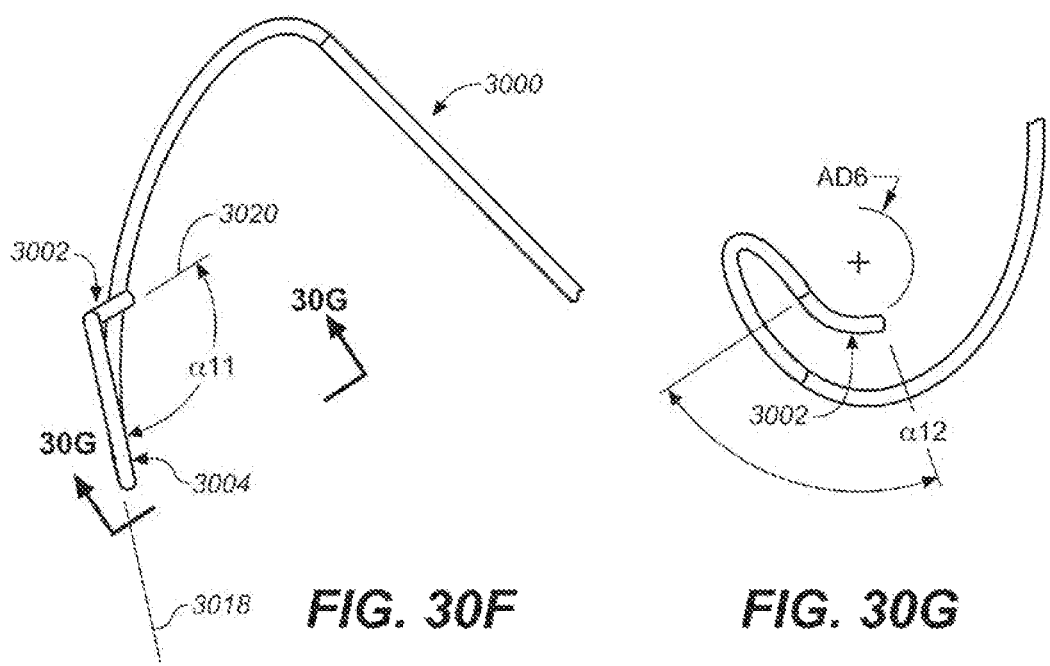
FIG. 30F  FIG. 30G

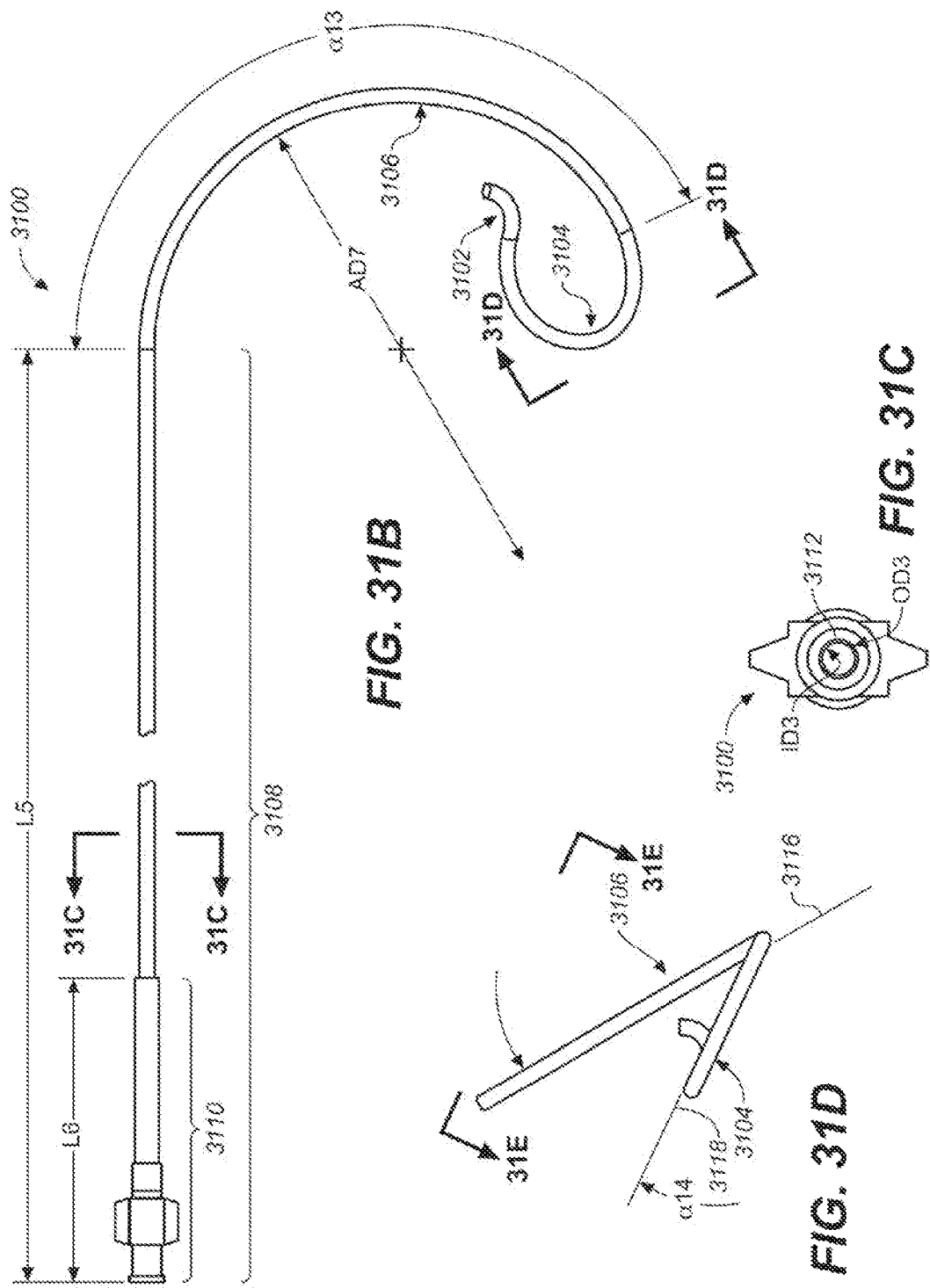

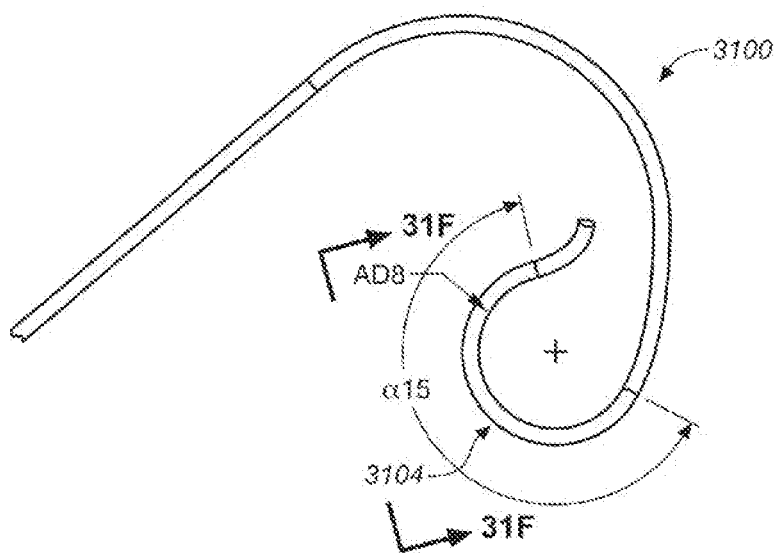
FIG. 31E
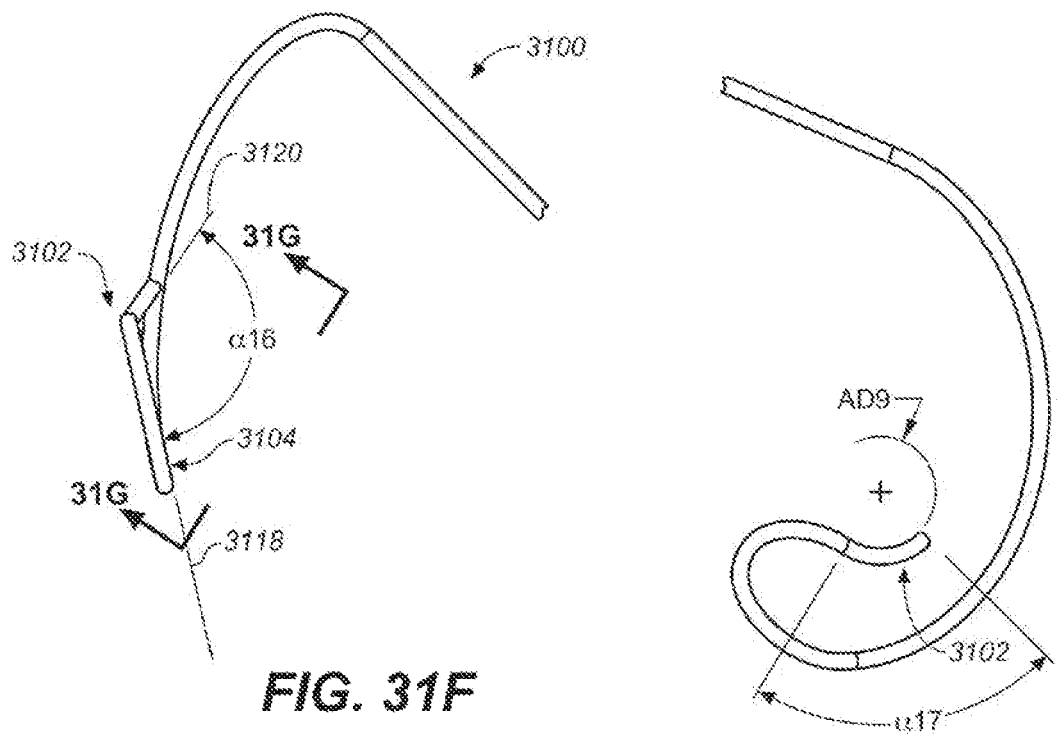
FIG. 31F
FIG. 31G

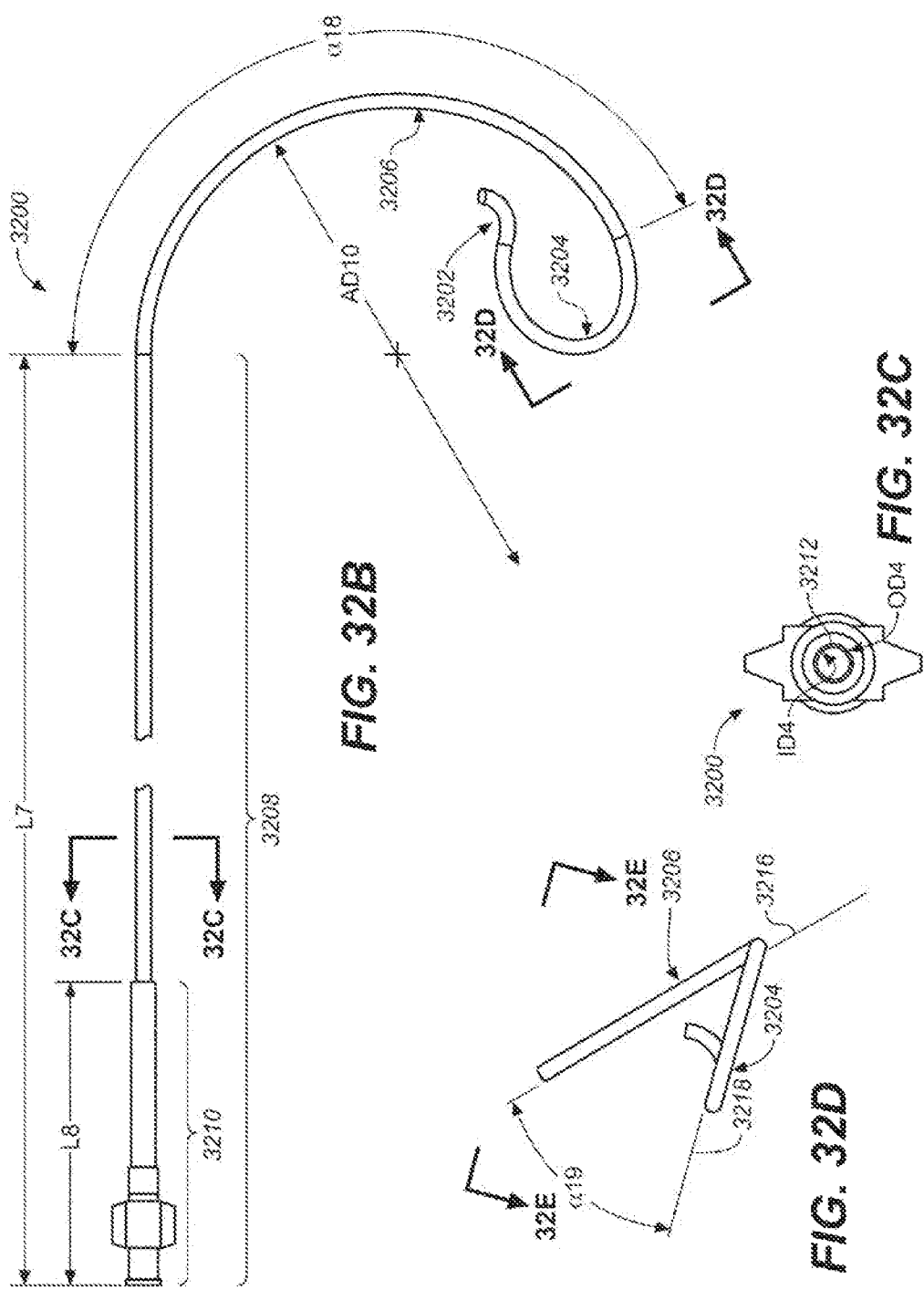

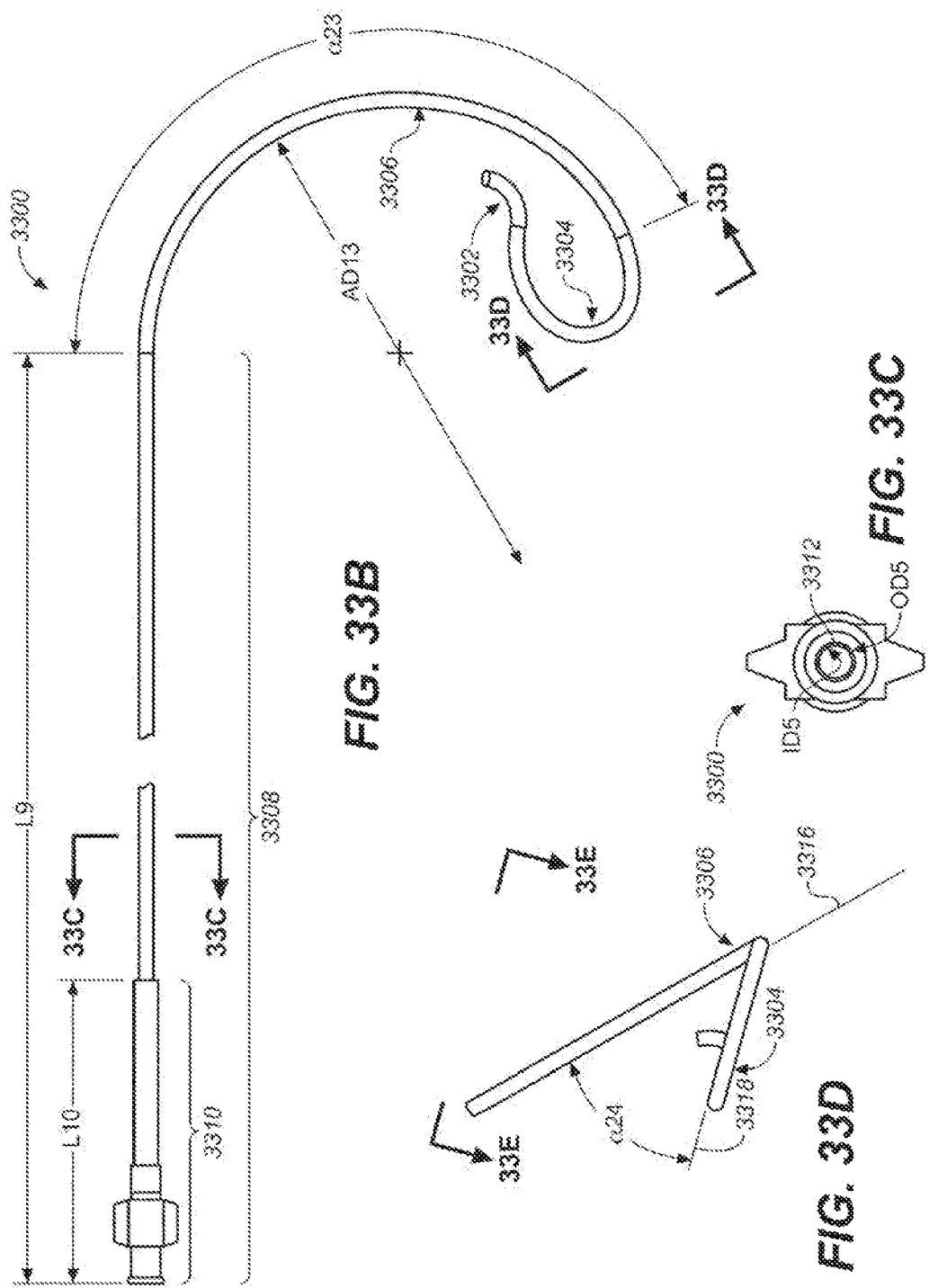

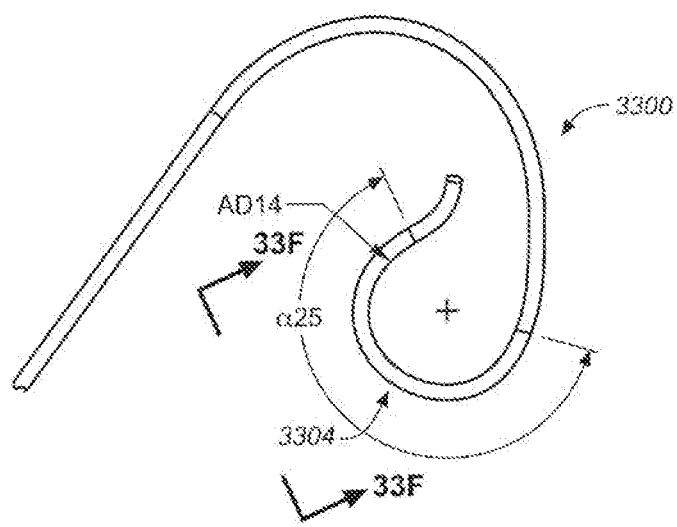
FIG. 33E
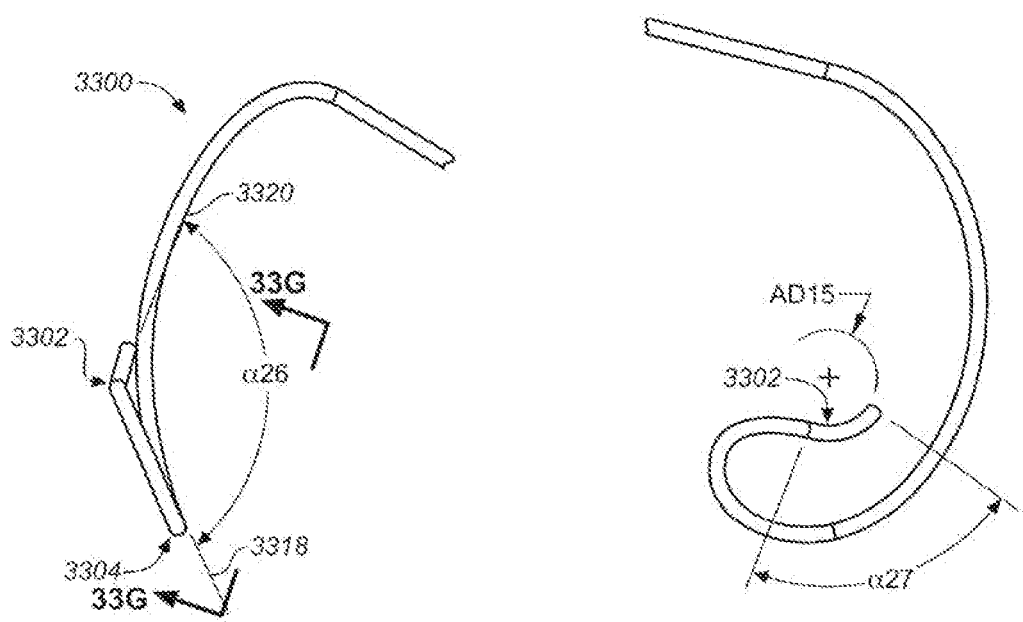
FIG. 33F
FIG. 33G

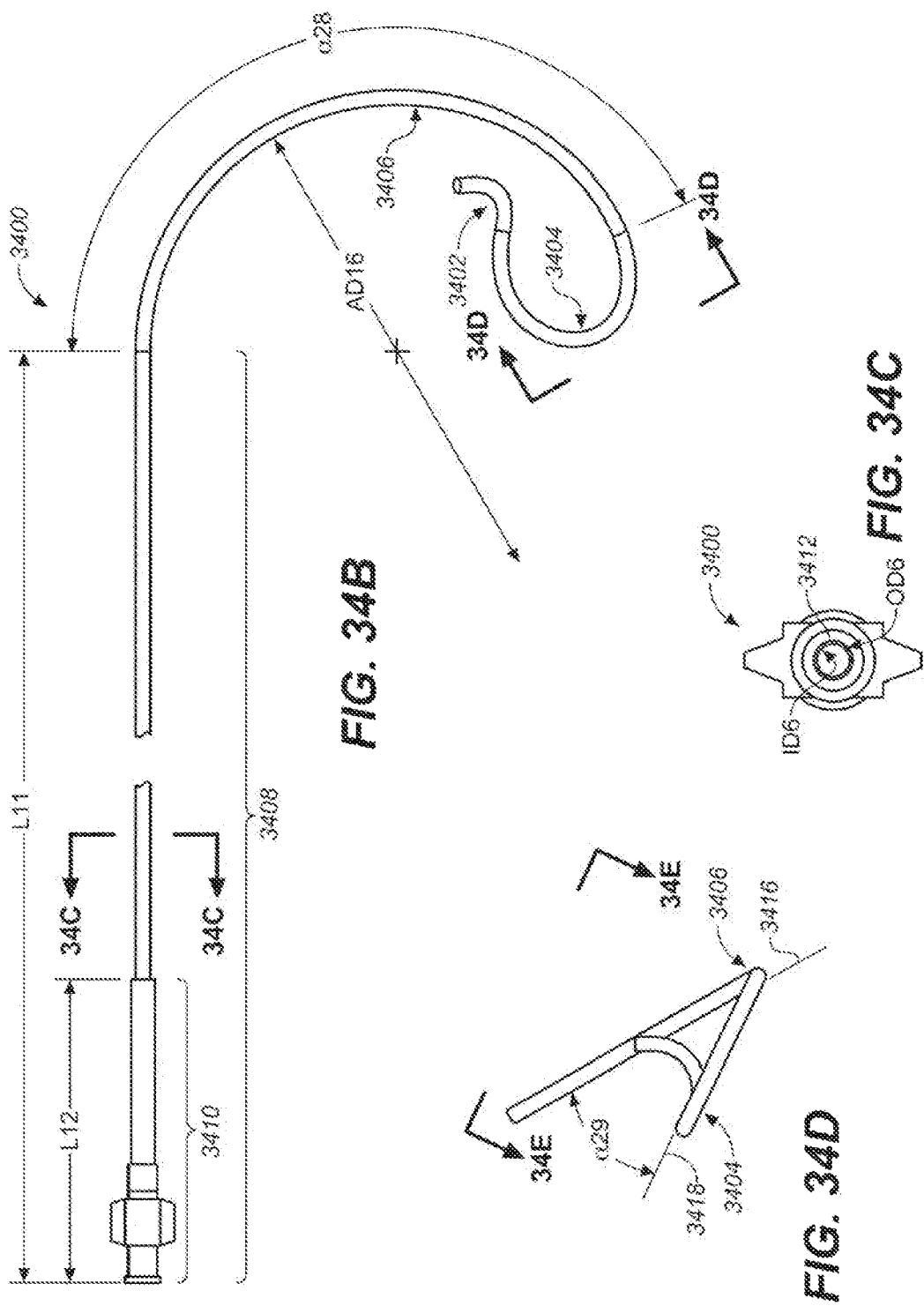

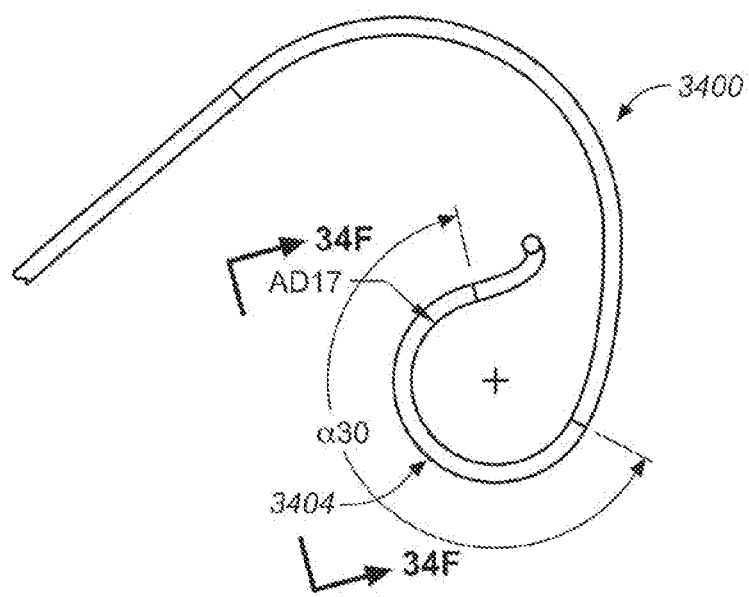
FIG. 34E
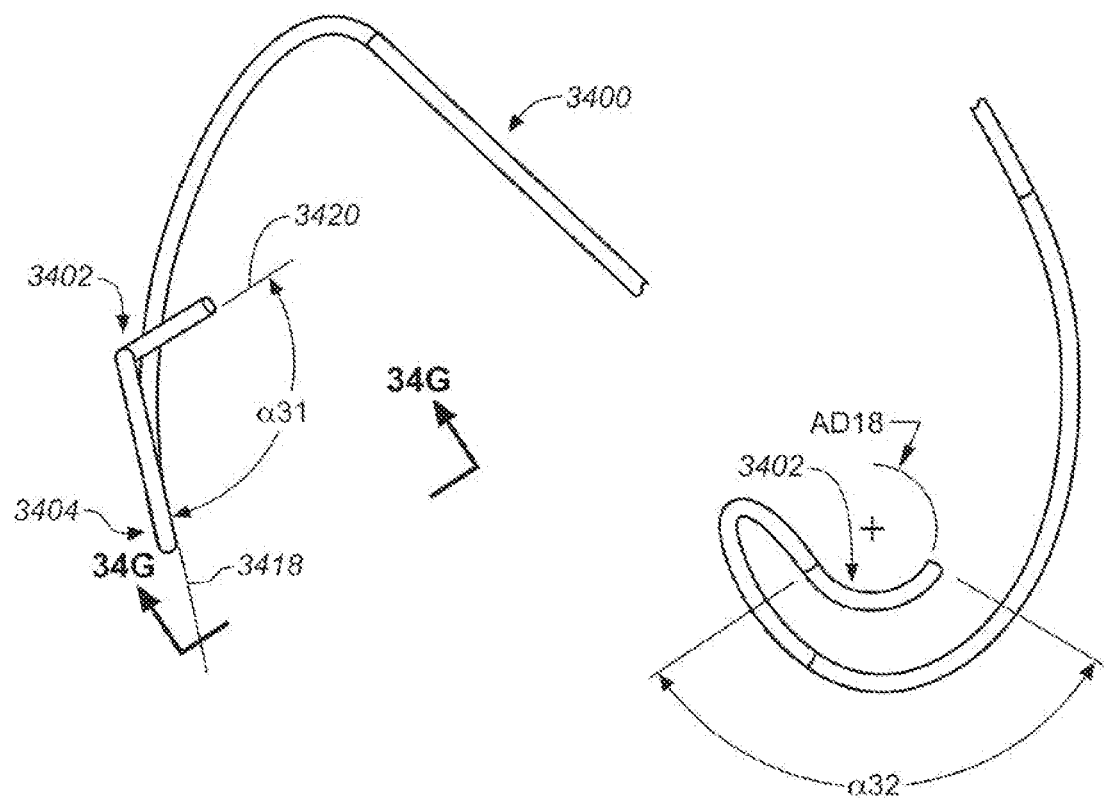
FIG. 34F
FIG. 34G

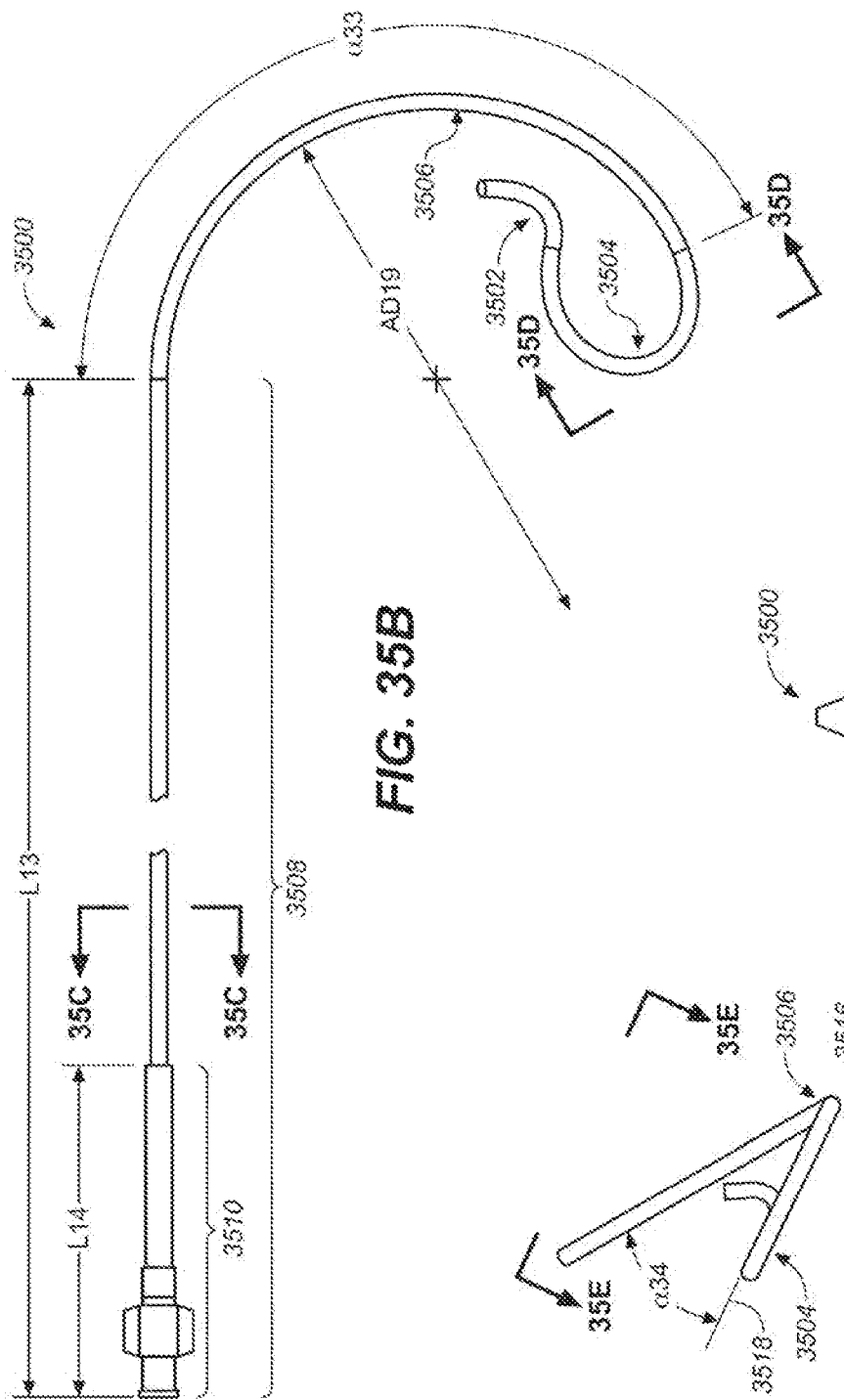
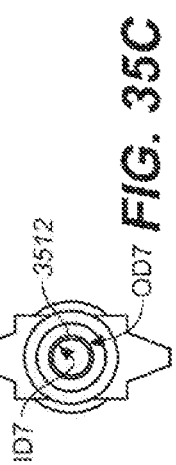
FIG. 35B
FIG. 35C
FIG. 35D

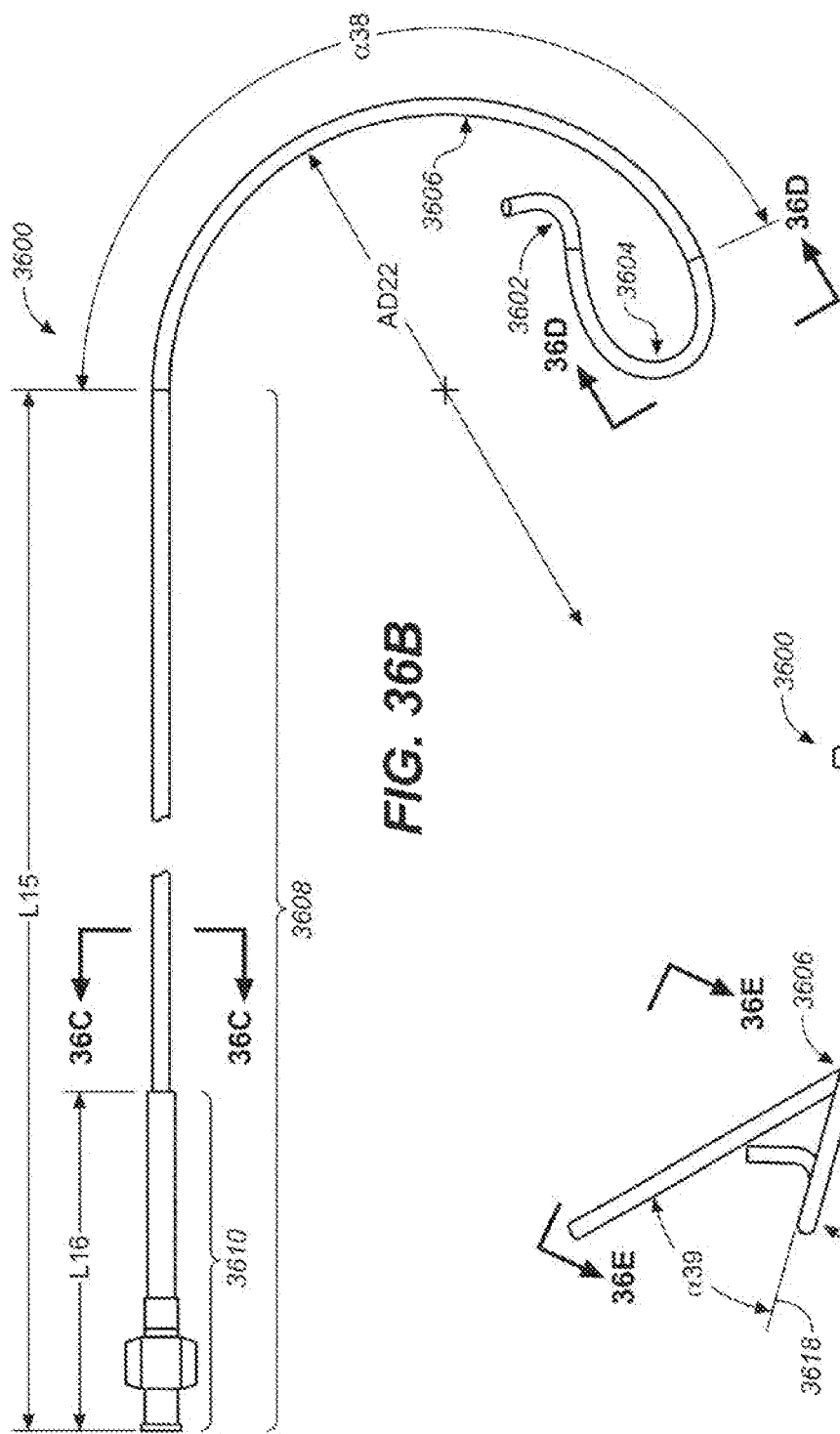

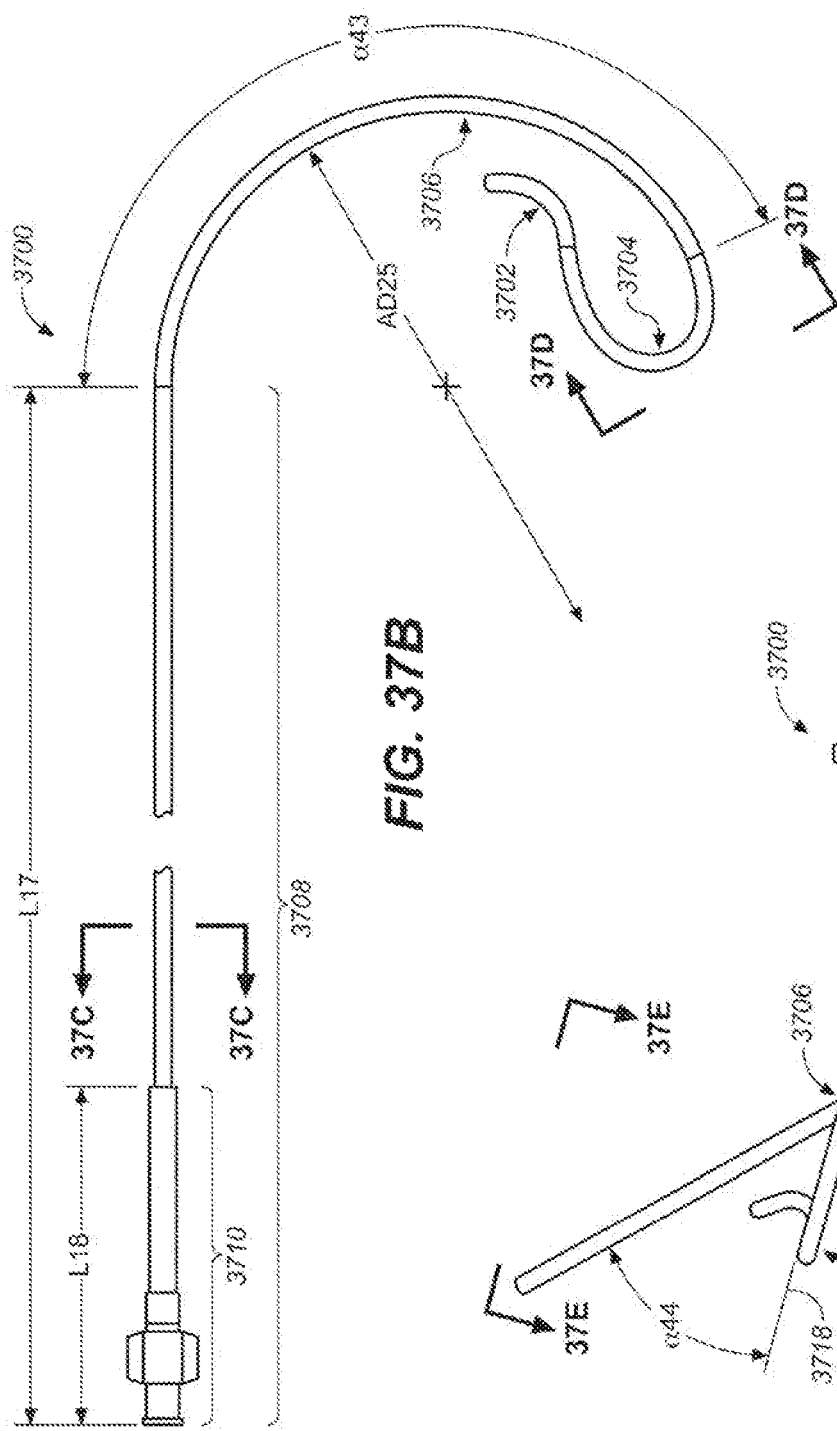
*FIG. 37B*
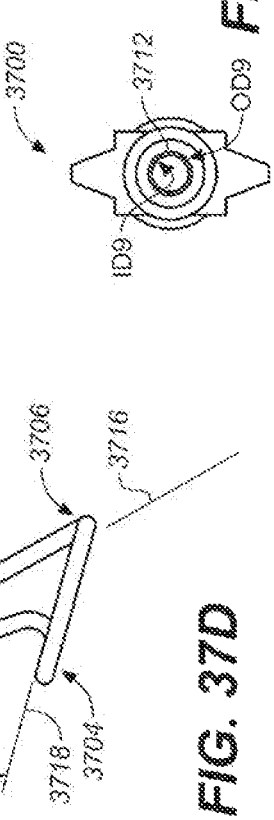
*FIG. 37C*
*FIG. 37D*

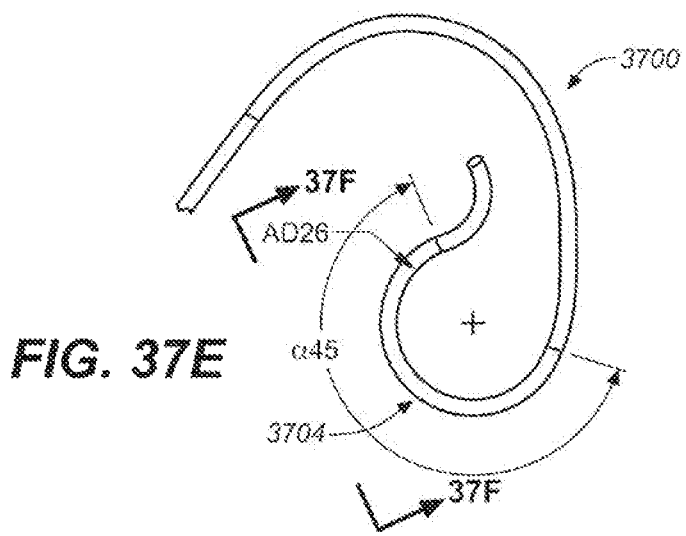
FIG. 37E
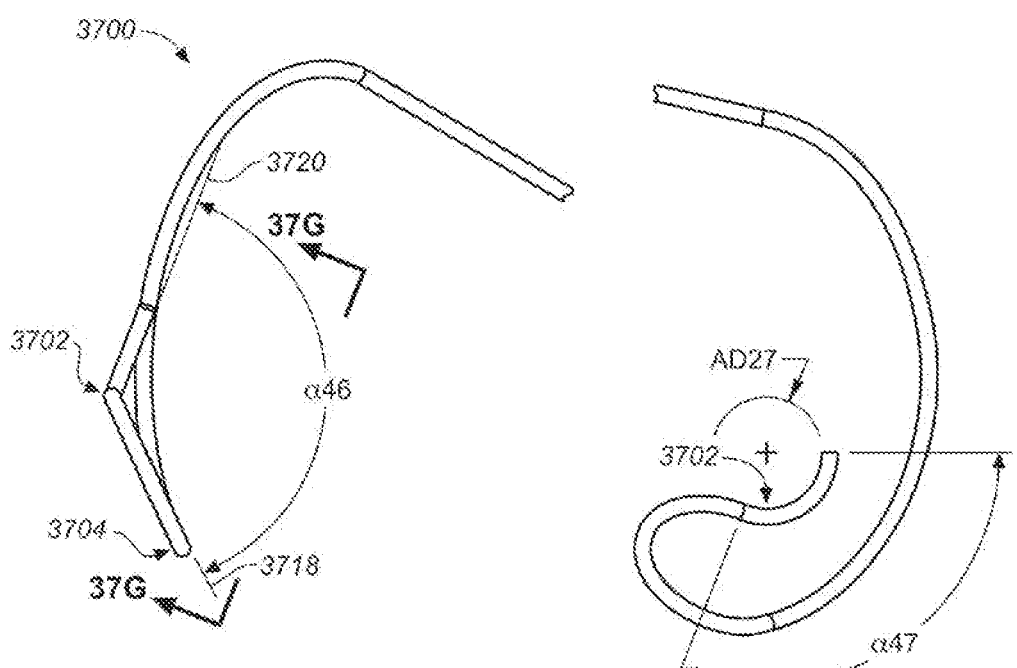
FIG. 37F  FIG. 37G

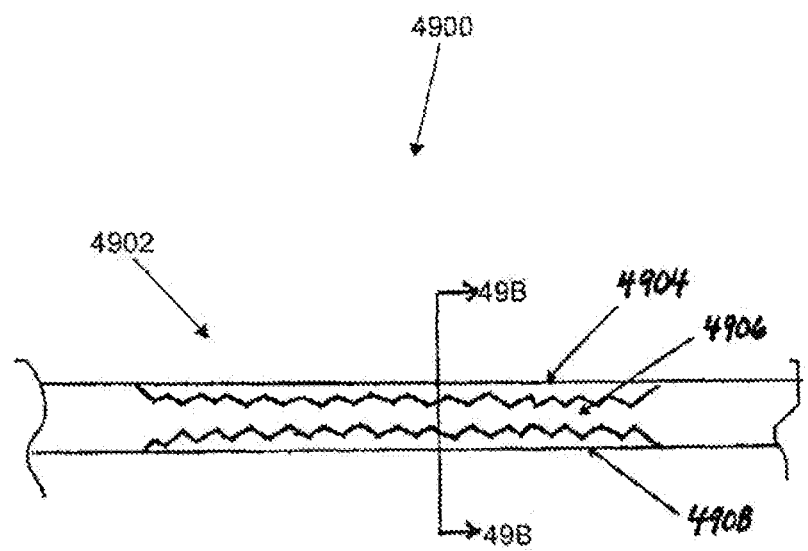
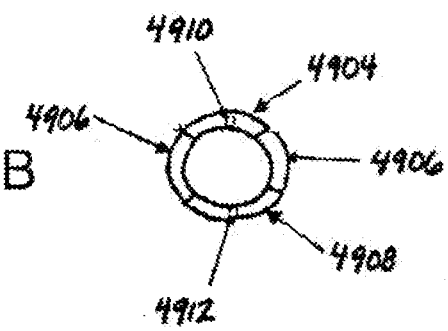

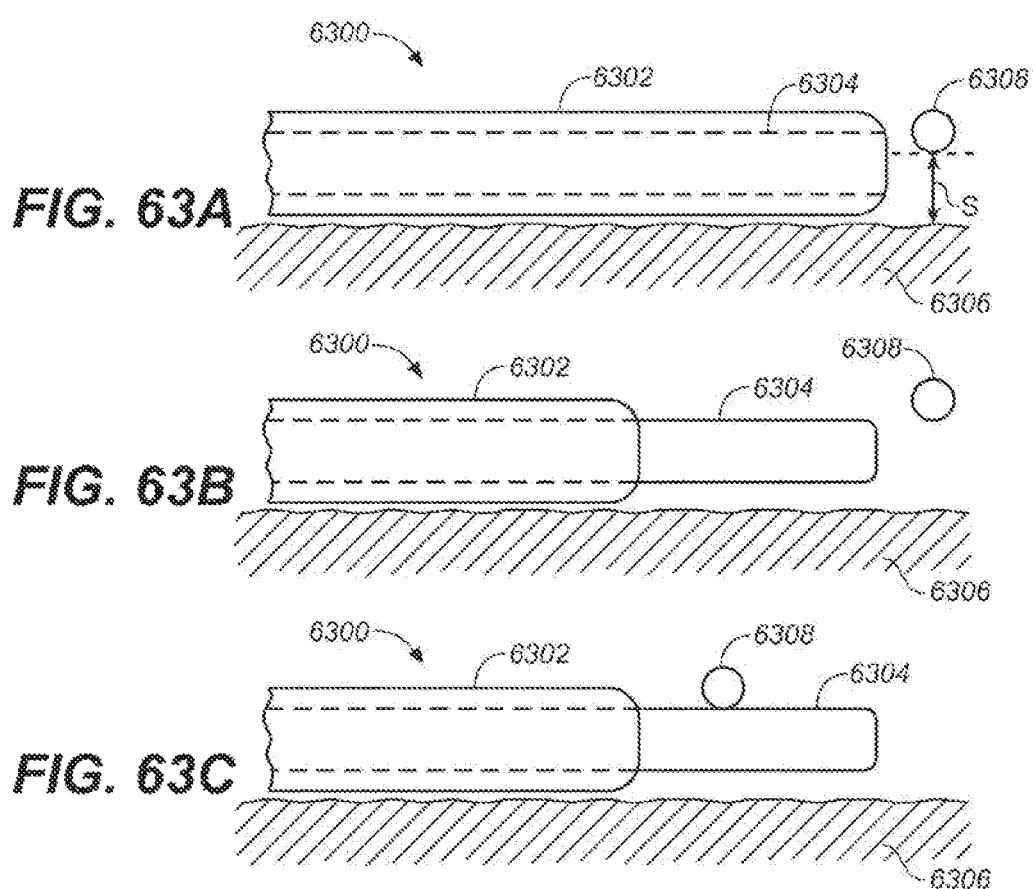

DIAGNOSTIC CATHETERS, GUIDE CATHETERS, VISUALIZATION DEVICES AND CHORD MANIPULATION DEVICES, AND RELATED KITS AND METHODS

CROSS-REFERENCE TO RELATED APPLICATIONS

This application is a continuation of U.S. patent application Ser. No. 13/619,331, filed on Sep. 14, 2012, now issued as U.S. Pat. No. 9,173,646, which is a continuation of U.S. patent application Ser. No. 12/690,109, filed on Jan. 19, 2010, now abandoned, which claims the benefit of U.S. Provisional Application No. 61/145,964, filed on Jan. 20, 2009, U.S. Provisional Application No. 61/160,230, filed on Mar. 13, 2009, U.S. Provisional Application No. 61/160,670, filed on Mar. 16, 2009, U.S. Provisional Application No. 61/178,910, filed on May 15, 2009, and U.S. Provisional Application No. 61/178,938, filed on May 15, 2009, the disclosures of all of which are incorporated herein by reference in their entirety.

TECHNICAL FIELD

The devices, methods, and kits described herein related generally to heart valve repair and/or replacement procedures, such as mitral valve repair procedures. More specifically, the devices, methods, and kits described herein relate to assessing the accessibility of a subvalvular space of a heart (e.g., using one or more diagnostic methods and/or devices), enhancing the accessibility of a subvalvular space of a heart (e.g., using a chordae tendineae manipulation device), assessing the placement and positioning of one or more devices in a subvalvular space of a heart (e.g., using one or more visualization methods and/or devices), and/or providing one or more instruments with access to a subvalvular space of a heart.

BACKGROUND

Blood returning to the heart from the peripheral circulation and the lungs generally flows into the atrial chambers of the heart and then to the ventricular chambers, which pump the blood back out of the heart. During ventricular contraction, the atrio-ventricular valves between the atria and ventricles (i.e., the tricuspid and mitral valves) close to prevent backflow or regurgitation of blood from the ventricles back to the atria. The closure of these valves, along with the aortic and pulmonary valves, maintains the unidirectional flow of blood through the cardiovascular system. Disease of the valvular apparatus can result in valve dysfunction, in which some fraction of the ventricular blood regurgitates back into the atrial chambers.

Traditional treatment of heart valve stenosis or regurgitation, such as mitral or tricuspid regurgitation, involves an open-heart surgical procedure to replace or repair the valve. Current accepted treatments of the mitral and tricuspid valves include: valvuloplasty, in which the affected leaflets are remodeled to perform normally; repair of the chordae tendineae (also referred to herein as "chords") and/or papillary muscle attachments; and surgical insertion of an "annuloplasty" ring, which involves suturing a flexible support ring over the annulus to constrict the radial dimension. Other surgical techniques to treat heart valve dysfunction include fastening (or stapling) the valve leaflets to each other or to other regions of the valve annulus to improve valve function.

Additionally, advances have been made in the techniques and tools used in minimally invasive heart surgery. For example, to avoid open heart procedures (which may require that the patient's heart be stopped and that the patient be put on a bypass machine), devices and methods have been developed for performing heart surgery via intravascular or percutaneous access. Some challenges in performing these procedures include positioning the treatment catheters or other devices at a desired location for performing the procedure, and deploying an implant or other treatment device at a desired location.

When the minimally invasive heart surgery to be performed is valve repair (e.g., mitral valve repair), part of the valve anatomy itself may be used to overcome certain positioning challenges that may arise during the valve repair procedure. Specifically, the subannular space, such as the subannular groove, which is described in further detail below, may be used for catheter and device placement. See, e.g., U.S. patent application Ser. No. 10/461,043 (issued as U.S. Pat. No. 6,986,775); Ser. No. 10/656,797 (published as US 2005/0055087 A1); Ser. No. 10/741,130 (published as US 2004/0193191 A1); Ser. No. 10/776,682 (published as US 2005/0107810 A1); Ser. No. 10/792,681 (published as US 2004/0243227 A1); Ser. No. 10/901,019 (published as US 2005/0065550 A1); Ser. No. 10/901,555 (published as US 2006/0058817 A1); Ser. No. 10/901,554 (published as US 2005/0107812 A1); Ser. No. 10/901,455 (published as US 2006/0025750 A1); and Ser. No. 10/901,444 (published as US 2006/0025784 A1), all of which are incorporated herein by reference in their entirety. As described in some of these applications, a catheter may be advanced to, and seated in, the subannular groove and may be used to accurately position one or more devices, tools, etc. (e.g., implants and/or other catheters) for valve treatment. In this way, difficulty in accessing the valve annulus (e.g., as a result of error in implant placement and/or entanglement with chordae tendineae, as discussed below) may be reduced.

As mentioned briefly above, the heart includes chordae tendineae, which are tendons in the left and right ventricles, some of which connect the heart's papillary muscles to its mitral and tricuspid valves. These chords help to hold the mitral and tricuspid valve leaflets in position, preventing the valves from moving into the atria when the ventricles contract. Primary or first-order chords attach papillary muscles to the free edges of the valve leaflets, secondary or second-order chords attach papillary muscles to the ventricular surfaces of the valve leaflets, and tertiary or third-order chords connect the ventricular walls to the undersurfaces of the posterolateral leaflets. In some cases, the chords (especially the tertiary or third-order chords) may present obstacles to a heart valve repair procedure. As an example, they may obstruct the advancement of a catheter within a subvalvular space during a heart valve repair procedure (e.g., the catheter may become entangled in the chords).

In view of the above, it would be desirable, whether in a minimally invasive procedure or another type of procedure, to enhance the deliverability of devices, implants, and/or tools to valvular tissue during a heart valve repair procedure. For example, it would be desirable to reduce the extent of interference presented by chords during a heart valve repair procedure. It would also be desirable to provide additional devices, methods, and kits for visualizing one or more regions of a heart (and/or implants within one or more regions of a heart). Furthermore, it would be desirable to provide devices, methods, and kits for assessing the accessibility of a heart region, and/or for accessing a heart region.

BRIEF SUMMARY

Described here are devices, methods, and kits that involve assessing the accessibility and/or geometry of a subvalvular space of a heart, such as a subannular groove region of the heart (e.g., beneath a mitral valve). For example, one or more diagnostic catheters and/or visualization methods and devices (e.g., visualization catheters) may be used in such assessment. Additionally, devices, methods, and kits for accessing a subvalvular space of a heart are described here. An example of a device that may be used to access a subvalvular space of a heart is a guide catheter. In some variations, a visualization method may be employed to ensure accuracy in placing and positioning a guide catheter in the subvalvular space. Moreover, devices, methods, and kits that may be used to provide or enhance access to a subvalvular space of a heart (e.g., a subannular groove region of the heart) are described here. The access may be provided or enhanced by, for example, manipulating one or more chords to remove obstructions or obstacles presented by the chords. As an example, certain devices, methods, and/or kits described here may be used to provide a catheter with access to a subvalvular space of a heart by cutting and/or otherwise manipulating one or more chords that might interfere with the placement and positioning of the catheter in the subvalvular space. Cutting or otherwise manipulating one or more chords may make it easier to access a subvalvular space of a heart during a procedure, such as a heart valve repair procedure, and to deliver one or more tools (e.g., heart valve repair tools) to a target site. Such enhanced delivery may result in decreased procedure time and/or reduced likelihood of damage to cardiac tissue during the repair procedure, thereby benefiting the patient.

Some variations of methods described here may comprise visualizing a subvalvular space of a heart to assess its geometry and/or accessibility. In certain variations, the methods may comprise advancing a catheter to a position proximate to the subannular groove and delivering one or more radiopaque contrast agents into the subvalvular space (e.g., through a port in a catheter). One example of a radiopaque contrast agent is a solution of a compound containing iodine (e.g., a diatrizoate meglumine solution), although other appropriate radiopaque contrast agents may alternatively or additionally be used. In certain variations, the solution may be diluted, such as with saline (e.g., in a 1:1 ratio). During and/or after delivery of the radiopaque contrast agent or agents, one or more distribution patterns of the radiopaque contrast agent(s) may be viewed using X-ray fluoroscopy. These distribution patterns may, for example, be used to determine and/or adjust the position of the catheter, as well as to view and identify the location and/or orientation of one or more implants in the subvalvular space. In certain variations, a method may comprise circumnavigating the subannular groove with the distal portion of a catheter to visualize the subannular groove, the anatomy surrounding the subannular groove, and/or implants positioned proximate to or at least partially in the subannular groove.

Examples of implants that may be viewed under X-ray fluoroscopy include anchors, which may or may not be coupled together (e.g., with a tether), and plication elements, such as local plication elements or staples. In some variations, an implant may comprise one or more non-plicating elements, such as one or more non-plicating anchors. Any portion of an implant may be radiopaque. For example, if an implant comprises two or more anchors coupled together with a tether, at least a portion of the tether may be radiopaque. Moreover, more than one portion of an implant may be radiopaque. For example, at least a portion of an anchor and/or a tether of an implant may be radiopaque. Catheters or other devices may also include one or more radiopaque portions.

Also described here are methods for visualizing a region of a heart using ultrasonic energy. In some variations of these methods, a distal portion of a catheter, such as a diagnostic catheter or guide catheter, may be advanced to a position proximate to, or at least partially within, the subannular groove of a heart valve. The catheter may comprise one or more ultrasonic transducers that may, for example, be coupled to the catheter body (e.g., disposed within a lumen in a distal portion of the catheter). The transducer or transducers may transmit and receive ultrasonic energy, thereby allowing visualization of the anatomy proximate the transducer(s) and/or the catheter, and a determination of the relative positions of the anatomy and the catheter. Certain variations of the methods may include rotating and/or translating the transducer(s) substantially independently of the catheter.

In some variations, the methods may comprise determining and/or adjusting the position of a catheter based upon a location and/or orientation visualized using ultrasound. The location and/or orientation of one or more implants may also be determined using the methods described here. In certain variations, the methods may include circumnavigating the subannular groove with a catheter comprising a transducer so that the subannular groove, the surrounding anatomy, and/or implants coupled to or near the subannular groove may be visualized. In some variations, a method may comprise using both ultrasound to view the area in and around a heart valve region, and X-ray fluoroscopy to determine the location and/or orientation of a radiopaque implant or device, such as a catheter.

Other methods for verifying the position of a catheter in a heart valve region are also provided. These methods may include, for example, advancing a first catheter comprising an ultrasonic transducer through a second catheter (e.g., a guide catheter). The first catheter may be advanced through the second catheter such that the transducer extends beyond a distal end of the second catheter. This may allow a region around the distal end of the second catheter to be visualized, so that the position of the second catheter relative to known anatomic structures (e.g., the ventricular wall, papillary muscles, valve leaflets and/or chordae tendineae) may be ascertained or verified.

Some variations of the methods described here may also be used to position a catheter proximate to or within the subannular groove. Some such variations may include using ultrasound to visualize the advancement of a distal portion of a first catheter to a position proximate to or at least partially within the subannular groove. A second catheter (e.g., a guide catheter) may then be advanced to a position proximate to or at least partially within the subannular groove by sliding the second catheter along the first catheter. In some variations, these methods may include advancing a distal portion of the first catheter circumferentially along the subannular groove, advancing a distal portion of the second catheter through the first catheter to a position within the subannular groove, and withdrawing the first catheter from the second catheter while leaving the second catheter positioned in the subannular groove.

Devices for visualizing the subannular groove, the anatomy near the subannular groove, and/or implants and/or devices in or near the subannular groove are also described herein. In some variations, a visualization device may comprise a catheter comprising at least a distal portion and a proximal portion (e.g., coupled to the distal portion). The catheter may also comprise one or more (e.g., two, three, four, or five) ultrasonic transducers and/or scopes (e.g., rigid scopes or flexible scopes, such as fiber scopes).

In some variations in which a catheter comprises one or more ultrasonic transducers, the ultrasonic transducer(s) may, for example, be disposed in one or more window regions of the distal portion that are at least partially transparent to ultrasonic energy. In certain variations, a window region may comprise a thin polymer film (e.g., having a thickness of about 0.007 inch or less), and/or may extend over a substantial portion of a distal portion of a catheter. In some variations, a catheter may comprise a distal portion having an inner diameter of at least about 0.035 inch (e.g., to accommodate rotation of a transducer). In certain variations, the catheter may further include a second lumen, in which at least one ultrasonic transducer may be disposed.

In some variations, a tensioning element may pass through a first lumen of the catheter and may be coupled to a distal portion of the catheter, thereby allowing the distal portion to be steered by applying tension to the tensioning element. When the distal portion is flexed (e.g., to form a configuration of approximately maximum flexion), the catheter may have a cross-sectional diameter of, for example, about 1.0 inch to about 1.5 inches (e.g., about 1.2 inches to about 1.4 inches, such as about 1.25 inches). In some variations, the distal portion may be more flexible than the proximal portion. For example, a tensioning element may be used to steer the distal portion without inducing substantial movement of the proximal portion. As an example, tension may be applied to the tensioning element to manipulate the distal portion without substantial movement of the proximal portion. Enhanced flexibility of the distal portion may, for example, provide for good catheter maneuverability without compromising pushability.

In certain variations in which a catheter comprises one or more scopes, the scope(s) may, for example, be disposed in one or more lumens of the catheter. In some variations, a catheter may comprise one or more scope housings, such as a bubble-shaped housing. In some such variations, a scope may be partially disposed within a lumen of the catheter, and a distal portion of the scope may be positioned within the scope housing. The scope housing may be formed of one or more clear or transparent materials, so that the scope may be used to visualize the surroundings of the scope housing. A device, such as a catheter, may comprise one or more rotatable scopes, scope housings, and/or other components, and/or may comprise one or more non-rotatable or fixed components.

In some variations, a catheter (e.g., a diagnostic catheter, visualization catheter, chord manipulation catheter, guide catheter, anchor deployment catheter, etc.) may be curved. This curvature may, for example, enhance the catheter's stability and/or functionality, and/or its ability to access a target site. For example, a curved guide catheter that provides access to a subannular groove of a mitral valve may be used to help position a guidewire so that the guidewire at least partially (e.g., completely) encircles the subannular groove. In certain variations, the guide catheter may position the guidewire such that the guidewire experiences little or no apparent interference with chordae tendineae and/or is level with the mitral valve in its distal portion. In some variations, a catheter (e.g., a diagnostic catheter, visualization catheter, chord manipulation catheter, guide catheter, anchor deployment catheter, etc.) may comprise a compound curve (i.e., including at least two different curve regions, such as three, four, or five curve regions). At least some of the curves of the compound curve may define different planes. The different planes may, for example, correspond to different anatomical landmarks. In certain variations, a catheter may have one or more curves that correspond to anatomical features of a specific patient. In some variations, a catheter may be pre-shaped to engage or fit within a subannular groove of a heart.

Also described here are methods for accurately positioning one or more catheters (e.g., diagnostic catheters, guide catheters, etc.) in a subvalvular space of a heart. For example, a method may comprise positioning a guide catheter in a subvalvular space of a heart such that the guide catheter will be highly effective in orienting one or more interventional devices in the subvalvular space. This may, for example, result in relatively accurate deployment and positioning of implants and/or other treatment devices in the subvalvular space. Additionally, the guide catheter may be positioned so that the likelihood of medical complications arising from use of the guide catheter may be relatively small. Catheters (e.g., diagnostic catheters, guide catheters, etc.) may be advanced to a target site and positioned at the target site using one or more visualization methods described here. These methods may be used to achieve highly accurate advancement and positioning of the catheters. The visualization methods may be used with the catheters described here, or may be used with other catheters, and vice-versa. Moreover, the visualization methods described here may be used to advance and position other types of devices, as appropriate.

In certain variations, a relatively small diagnostic catheter may be used to assess the accessibility and/or geometry of a subvalvular space of a heart. The diagnostic catheter may alternatively or additionally be used to gather information that, in turn, may be used to help predict therapeutic device shapes or configurations suitable for specific patient anatomies. The diagnostic catheter may, for example, be a 6 Fr catheter (i.e., having an outer diameter of 2 millimeters) or a 9 Fr catheter (i.e., having an outer diameter of 3 millimeters). Other suitable sizes may also be used. In some cases, the diagnostic catheter may indicate that a region would be inaccessible by a larger catheter, such as a larger guide catheter, unless modifications are made to the region prior to advancement of the guide catheter therethrough. For example, the region may include chordae tendineae that prevent a catheter from being able to be advanced through the region.

In the event that the diagnostic catheter indicates that a region is accessible for a larger catheter, or in the event that a previously inaccessible region is rendered accessible, then a larger guide catheter (e.g., a 14 Fr guide catheter—i.e., having an outer diameter of 4.67 millimeters) may be advanced to the region. Of course, it should be understood that some methods may comprise advancing a guide catheter to a region without advancing a diagnostic catheter to the region first. A larger guide catheter that has been advanced to a subvalvular space of a heart may be used, for example, to orient, direct, and/or provide support for one or more interventional devices that are to be used in the subvalvular space. For example, a curved guide catheter may be routed into a subvalvular space of a heart and used to provide an anchor deployment catheter with access to the subvalvular space. Once properly positioned in the subvalvular space, the anchor deployment catheter may then be used to deploy one or more anchors (e.g., multiple tethered anchors) into tissue in the subvalvular space. The anchors may be used, for example, to repair the heart tissue (e.g., in the case of tethered anchors, by having their tether tensioned to cinch the anchors together and compress or gather the tissue). In cases in which the smaller diagnostic catheter indicates that the subvalvular space is accessible by the larger guide catheter, the larger guide catheter may be advanced into the subvalvular space immediately after such indication, or at a later time (e.g., at least about 1 day later, at least about 2 days later, at least about 3 days later, at least about 4 days later, at least about 5 days later, at least about 1 week later, at least about 10 days later, at least about 2 weeks later, at least about 1 month later, or at least about 2 months later). In some variations, one or more visualization methods and/or devices (e.g., a visualization catheter) may be used to help advance the guide catheter into the subvalvular space, and to properly position the guide catheter there.

Of course, it is contemplated that the various different devices (e.g., diagnostic catheters, visualization catheters, chord manipulation devices, guide catheters, etc.) described herein may be used separately from each other—i.e., use of one of the diagnostic catheters in a procedure does not require use of one of the visualization catheters, chord manipulation devices, or guide catheters in the procedure. Similarly, use of one of the visualization catheters does not require use of one of the diagnostic catheters, chord manipulation devices, or guide catheters, and use of one of the guide catheters does not require use of one of the diagnostic catheters, chord manipulation devices, or visualization catheters. Additionally, use of one of the chord manipulation devices does not require use of one of the diagnostic catheters, guide catheters, or visualization catheters. Moreover, use of one of the visualization methods described here does not require use of one of the catheters and/or other devices described here, and vice-versa.

Although catheters and other devices and methods are described here in the context of heart repair, they may be used in any procedure for which they are appropriate. As an example, a diagnostic catheter may be used to assess the accessibility of a target site prior to stenting the target site and/or prior to performing a percutaneous transluminal coronary angioplasty (PTCA) at the target site. Moreover, a visualization method described here may be used anywhere in which its use is appropriate, and in some cases may be used to position a device that is not a catheter or an implant.

As discussed above, some variations of devices and methods may be used to manipulate one or more chords in a heart ventricle. As an example, in certain variations, a method of accessing a subvalvular space of a heart may comprise advancing a first device into the subvalvular space of the heart, assessing whether the first device will pass between at least one chorda tendinea (e.g., a plurality of chordae tendineae) and a ventricular wall of the heart, and manipulating the chorda tendinea or chordae tendineae in response to an assessment that the first device will not pass between the chorda tendinea or chordae tendineae and the ventricular wall of the heart. A chorda tendinea may be manipulated by, for example, cutting it, grasping it, and/or heating it. In some variations, a plurality of chordae tendineae may be manipulated by gathering them.

The first device may comprise a catheter, and in certain variations, may comprise at least one sensor. In some variations, the method may further comprise passing a second device, such as a catheter, into the subvalvular space of the heart after manipulating the chorda tendinea or chordae tendineae. The subvalvular space may be located beneath a mitral valve of the heart.

In certain variations, a method of accessing a subvalvular space of a heart may comprise advancing a first device into a ventricle of a heart, using the first device to gather at least two chordae tendineae together to provide additional space between the chordae tendineae and a ventricular wall of the heart, and advancing a second device, such as a catheter, into the additional space. Gathering the chordae tendineae together may comprise advancing a catheter comprising a hook into the ventricle and hooking the chordae tendineae with the hook. In certain variations, the method may comprise hooking the chordae tendineae with the hook in a first region of the ventricle, and advancing the hook in the direction of a valve in the ventricle to gather the chordae tendineae together. In some variations, the ventricle may comprise a left ventricle and the valve may comprise a mitral valve.

While devices and methods having specific configurations and features are described here, it should be understood that any features, components or characteristics that are described here with respect to specific devices or methods may be applied to other devices or methods, as appropriate.

In some variations, one or more of the devices (e.g., catheters) described here may comprise at least one radiopaque structure or marking. The radiopaque structure or marking may be used, for example, to help properly align the device, and/or one or more other devices, during use. As an example, in certain variations, a catheter may comprise one or more radiopaque markings that may be used to help identify the catheter's position in the body of a subject using X-ray fluoroscopy. Contrast agent may be used to further identify the catheter's position in the subject's body, as described in additional detail below. As another example, in some variations, a chord manipulation device may comprise one or more radiopaque markings that may be used to identify the device's position in the heart (e.g., prior to deploying a cutter from the device). Such markings may, for example, help to limit the likelihood of damage to heart tissue (e.g., by non-target deployment of a cutter).

Certain variations of methods described here may comprise securing anchors to heart valve tissue after assessing and/or enhancing the accessibility of the heart valve tissue, and/or after accessing the heart valve tissue. As an example, in some variations, a method may comprise securing anchors to heart valve tissue before, during, and/or after cutting or otherwise manipulating one or more chords.

Devices described here may have any appropriate configuration and in some variations, may comprise a catheter configured for advancement into a subvalvular space of a heart. The catheter may, for example, include an elongated member comprising a proximal end, a distal end, and a lumen therethrough. The elongated member may comprise a first curve region defining a first plane and a second curve region defining a second plane. In certain variations, the first and second planes may be at a first angle of about 30° to about 90° (e.g., about 30° to about 65°, such as about 40°; about 50° to about 80°, such as about 60°) relative to each other. For example, the first and second planes may be approximately orthogonal to each other. In some variations, the elongated member of the catheter may further comprise a third curve region defining a third plane. In some such variations, the second and third planes may, for example, be at a second angle of about 0° to about 50° (e.g., about 1° to about 50°; about 5° to about 45°, such as about 20°; about 15° to about 35°, such as about 25°; about 20° to about 45°, such as about 30°) relative to each other. The elongated member may further comprise additional curve regions defining additional planes. The angle between two planes defined by any of the curve regions of an elongated member of a catheter may be, for example, from about 0° to about 90°. For example, the angle may be from about 0° to about 50°, such as about 5° to about 45° (e.g., 20°), about 15° to about 35° (e.g., 25°), or about 20° to about 45° (e.g., 30°). In certain variations, the angle may be from about 15° to about 90°, such as about 15° to about 45°, about 20° to about 65°, about 30° to about 90°, about 50° to about 80° (e.g., 60°), or about 30° to about 65° (e.g., 40°).

As used herein, values and ranges provided for an angle between two planes may refer to the smaller angle between the two planes. For example, if two planes intersect to define two 30° angles and two 150° angles, then the smaller angle would be one of the 30° angles. Alternatively or additionally, when a catheter comprises a first curve region defining a first plane, a second curve region defining a second plane, and a third curve region defining a third plane, values and ranges provided herein for an angle between two of the planes may refer to an angle located within a space defined by the three planes. In certain variations, values and ranges provided herein for an angle between two of the planes may refer to an angle located outside of a space defined by the three planes.

In a catheter comprising one or more curve regions, at least one of the curve regions (e.g., a valve curve region) may form an arc having an arc diameter that may be from about 0.75 inch to about 1.5 inches (e.g., about 0.8 inch to about 1.3 inches, or about 0.8 inch to about 1.1 inches, such as about 1 inch). Alternatively or additionally, the arc may define a central angle that may be, for example, from about 60° to about 270° (e.g., about 90° to about 270°, about 110° to about 270°, about 150° to about 250°, or about 200° to about 250°, such as about 229.5°); about 60° to about 180° (e.g., about 60° to about 160°, about 100° to about 160°, or about 130° to about 160°, such as about 153°); about 60° to about 120° (e.g., about 75° to about 120°, or about 100° to about 120°, such as about 114.75°); about 60° to about 80° (e.g., about 70° to about 80°, such as about) 76.5°; or about 90° to about 120° (e.g., about 90° to about 100°, such as about 90°).

Some variations of catheters may comprise an elongated member comprising at least one deflectable portion. The deflectable portion may, for example, comprise at least two different polymers, such as two polymers having different durometers from each other. In certain methods, the deflectable portion may be deflected to, for example, help the catheter to be more easily navigated to a target site.

A catheter described here may have a size of, for example, 4 Fr to 16 Fr (e.g., 4 Fr to 14 Fr, 4 Fr to 10 Fr, 4 Fr to 9 Fr, or 5 Fr to 10 Fr). In other words, the catheter may have an outer diameter of, for example, 1.33 millimeters to 5.33 millimeters (e.g., 1.33 millimeters to 4.67 millimeters, 1.33 millimeters to 3.33 millimeters, 1.33 millimeters to 3 millimeters, or 1.67 millimeters to 3.33 millimeters). In some variations, the size of a catheter may be at least partially determined by the function of the catheter. For example, a diagnostic catheter may generally be of a smaller size than its corresponding guide catheter. In certain variations, a catheter may be sized and/or shaped for coupling with one or more other catheters.

Some variations of methods described here for accessing a subvalvular space of a heart may comprise advancing a first catheter (e.g., a diagnostic catheter) to the subvalvular space of the heart, advancing a first guidewire through a first lumen of the first catheter and into the subvalvular space of the heart, and advancing the first guidewire around at least a portion of a subannular groove region in the subvalvular space of the heart. In this way, the accessibility of the subannular groove region by a second guidewire advanced through a second lumen of a second catheter (e.g., a guide catheter) may be assessed. In some variations, the method may comprise withdrawing the first catheter and first guidewire from the subvalvular space of the heart. In certain variations, the method may comprise advancing the second catheter to the subvalvular space of the heart after the first catheter and first guidewire have been withdrawn from the subvalvular space of the heart. In some variations, the second guidewire may be advanced through the second lumen of the second catheter and around at least a portion of the subannular groove region. In certain variations, an anchor deployment catheter may be advanced over the second guidewire, and/or one or more anchors may be deployed from one or more anchor deployment catheters into the subannular groove region. In some variations, the method may comprise advancing the second catheter to the subvalvular space of the heart at least about 1 day (e.g., at least about 2 days, at least about 3 days, at least about 4 days, at least about 5 days, at least about 1 week, at least about 10 days, at least about 2 weeks, at least about 1 month, at least about 2 months) after the first catheter and first guidewire have been withdrawn from the subvalvular space of the heart. Alternatively, the second catheter may be advanced to the subvalvular space immediately after the first catheter and first guidewire have been withdrawn, or may even be advanced over the first catheter and/or first guidewire.

In certain variations, the placement and/or positioning of the second catheter may be achieved using one or more of the visualization methods described here. For example, after the first catheter and first guidewire have been withdrawn, a visualization catheter may be advanced into the subvalvular space of the heart, and specifically into the subannular groove region. Using the visualization catheter, the operator may inject one or more radiopaque contrast agents into the heart. The contrast agent(s) may be viewed under X-ray fluoroscopy to properly position the second catheter in the subvalvular space of the heart. In certain variations, the visualization catheter may be advanced through the second catheter to access the subvalvular space of the heart and to help with the positioning of the second catheter with respect to the subvalvular space.

Catheters described here may be made from any suitable material or combination of materials. A catheter may comprise the same material or materials along its length, or may comprise at least two portions (e.g., a proximal portion and a distal portion) comprising different materials. In some variations, a catheter may comprise one or more polymers (e.g., throughout the length of the catheter, in a distal and/or proximal portion of the catheter, etc.). Examples of polymers that may be suitable for use in a catheter include high-density polyethylene (HDPE), low density polyethylene (LDPE), polypropylene, polytetrafluoroethylene (e.g., TEFLON™ polymer), polyamides (e.g., nylon), polyurethanes, ethylene vinyl acetate copolymers, polyethers, polyether block amide polymers (e.g., polyether-block co-polyamide polymers, such as PEBAX® polyether block amide copolymer, including but not limited to PEBAX® 35D polymer, PEBAX® 40D polymer, PEBAX® 55D polymer, PEBAX® 63D polymer, and PEBAX® 72D polymer), silicone rubber, and copolymers, blends, and composites thereof.

In some variations, a catheter may comprise a combination of two or more different polymers. As an example, a portion of a catheter (e.g., a distal portion) may comprise PEBAX® 72D polymer and PEBAX® 35D polymer. In certain variations in which a catheter comprises two or more different polymers, the catheter may comprise discrete polymeric sections (at least two of which comprise different polymers). The discrete polymeric sections may, for example, be formed by coextruding the polymers so that they are adjacent each other, or by individually forming each polymeric section and then coupling them to each other (e.g., using heat fusing methods). In certain variations, a catheter may comprise multiple polymers that are combined with each other (e.g., in a mixture). In some variations, a catheter may comprise at least two portions comprising polymers having different durometers. For example, a catheter may comprise one portion comprising a first PEBAX® polymer, and another portion comprising a second PEBAX® polymer having a different durometer from the first PEBAX® polymer.

As described above, some catheters may comprise proximal and distal portions having different flexibilities. For example, a catheter may comprise a distal portion that is more flexible than a proximal portion of the catheter. This may, for example, cause the catheter to exhibit good pushability, while also exhibiting good maneuverability. In some variations, the proximal portion of a catheter may be reinforced (e.g., with a braided or woven mesh, or with a metal) to provide it with relative stiffness or hardness (e.g., which may enhance the pushability of the catheter). Also, as discussed above, some catheters may be at least partially radiopaque. For example, a catheter may comprise one or more radiopaque materials (e.g., in a wall portion of the catheter). As an example, certain variations of catheters may comprise a polymer composite comprising one or more radiopaque materials, such as barium sulfate ($BaSO_4$) or bismuth trioxide ($Bi_2O_3$), and/or may comprise one or more radiopaque markers (e.g., formed by one or more metals).

BRIEF DESCRIPTION OF THE DRAWINGS

FIG. 2A is a flowchart representation of a variation of a method for assessing the accessibility of a subvalvular space of a heart, and FIG. 2B is a flowchart representation of a variation of a method for deploying anchors into a subvalvular space of a heart.

FIG. 4 is a cross-sectional depiction a variation of a catheter that may be used to visualize a region of a heart.

FIG. 16A is a side perspective view of a variation of a guide catheter; FIG. 16B is a cross-sectional view of the guide catheter of FIG. 16A, taken along line 16B-16B; FIG. 16C is an enlarged view of region 16C of FIG. 16A; and FIG. 16D is a perspective view of a portion of the guide catheter of FIG. 16A.

FIG. 17C is a side view of the diagnostic catheter of FIGS. 17A and 17B after the diagnostic catheter has been rotated; FIG. 17D is a cross-sectional view of the diagnostic catheter as shown in FIG. 17C, taken along line 17D-17D; FIG. 17E is a view of the diagnostic catheter as shown in FIG. 17C, taken along line 17E-17E.

FIGS. 23A-23K are perspective views of different variations of diagnostic catheters having different shapes.

FIG. 30B is a side view of the diagnostic catheter of FIG. 30A after the diagnostic catheter has been rotated; FIG. 30C is a cross-sectional view of the diagnostic catheter as shown in FIG. 30B, taken along line 30C-30C; FIG. 30D is a view of the diagnostic catheter as shown in FIG. 30B, taken along line 30D-30D; FIG. 30E is a view of the diagnostic catheter as shown in FIG. 30D, taken along line 30E-30E; FIG. 30F is a view of the diagnostic catheter as shown in FIG. 30E, taken along line 30E-30F; and FIG. 30G is a view of the diagnostic catheter as shown in FIG. 30F, taken along line 30G-30G.

FIG. 31B is a side view of the diagnostic catheter of FIG. 31A after the diagnostic catheter has been rotated; FIG. 31C is a cross-sectional view of the diagnostic catheter as shown in FIG. 31B, taken along line 31C-31C; FIG. 31D is a view of the diagnostic catheter as shown in FIG. 31B, taken along line 31D-31D; FIG. 31E is a view of the diagnostic catheter as shown in FIG. 31D, taken along line 31E-31E; FIG. 31F is a view of the diagnostic catheter as shown in FIG. 31E, taken along line 31F-31F; and FIG. 31G is a view of the diagnostic catheter as shown in FIG. 31F, taken along line 31G-31G.

FIG. 32B is a side view of the diagnostic catheter of FIG. 32A after the diagnostic catheter has been rotated; FIG. 32C is a cross-sectional view of the diagnostic catheter as shown in FIG. 32B, taken along line 32C-32C; FIG. 32D is a view of the diagnostic catheter as shown in FIG. 32B, taken along line 32D-32D.

FIG. 33B is a side view of the diagnostic catheter of FIG. 33A after the diagnostic catheter has been rotated; FIG. 33C is a cross-sectional view of the diagnostic catheter as shown in FIG. 33B, taken along line 33C-33C; FIG. 33D is a view of the diagnostic catheter as shown in FIG. 33B, taken along line 33D-33D; FIG. 33E is a view of the diagnostic catheter as shown in FIG. 33D, taken along line 33E-33E; FIG. 33F is a view of the diagnostic catheter as shown in FIG. 33E, taken along line 33F-33F; and FIG. 33G is a view of the diagnostic catheter as shown in FIG. 33F, taken along line 33G-33G.

FIG. 34B is a side view of the diagnostic catheter of FIG. 34A after the diagnostic catheter has been rotated; FIG. 34C is a cross-sectional view of the diagnostic catheter as shown in FIG. 34B, taken along line 34C-34C; FIG. 34D is a view of the diagnostic catheter as shown in FIG. 34B, taken along line 34D-34D; FIG. 34E is a view of the diagnostic catheter as shown in FIG. 34D, taken along line 34E-34E; FIG. 34F is a view of the diagnostic catheter as shown in FIG. 34E, taken along line 34F-34F; and FIG. 34G is a view of the diagnostic catheter as shown in FIG. 34F, taken along line 34G-34G.

FIG. 35B is a side view of the diagnostic catheter of FIG. 35A after the diagnostic catheter has been rotated; FIG. 35C is a cross-sectional view of the diagnostic catheter as shown in FIG. 35B, taken along line 35C-35C; FIG. 35D is a view of the diagnostic catheter as shown in FIG. 35B, taken along line 35D-35D.

FIG. 36B is a side view of the diagnostic catheter of FIG. 36A after the diagnostic catheter has been rotated; FIG. 36C is a cross-sectional view of the diagnostic catheter as shown in FIG. 36B, taken along line 36C-36C; FIG. 36D is a view of the diagnostic catheter as shown in FIG. 36B, taken along line 36D-36D.

FIG. 37B is a side view of the diagnostic catheter of FIG. 37A after the diagnostic catheter has been rotated; FIG. 37C is a cross-sectional view of the diagnostic catheter as shown in FIG. 37B, taken along line 37C-37C; FIG. 37D is a view of the diagnostic catheter as shown in FIG. 37B, taken along line 37D-37D; FIG. 37E is a view of the diagnostic catheter as shown in FIG. 37D, taken along line 37E-37E; FIG. 37F is a view of the diagnostic catheter as shown in FIG. 37E, taken along line 37F-37F; and FIG. 37G is a view of the diagnostic catheter as shown in FIG. 37F, taken along line 37G-37G.

FIG. 49A is a schematic elevational view of still another variation of a deformable zone of a catheter, and FIG. 49B is a cross-sectional view of the deformable zone depicted in FIG. 49A.

FIGS. 63A-63E show another variation of a device, and another variation of a method, for cutting one or more chords.

DETAILED DESCRIPTION

Figure 1A:
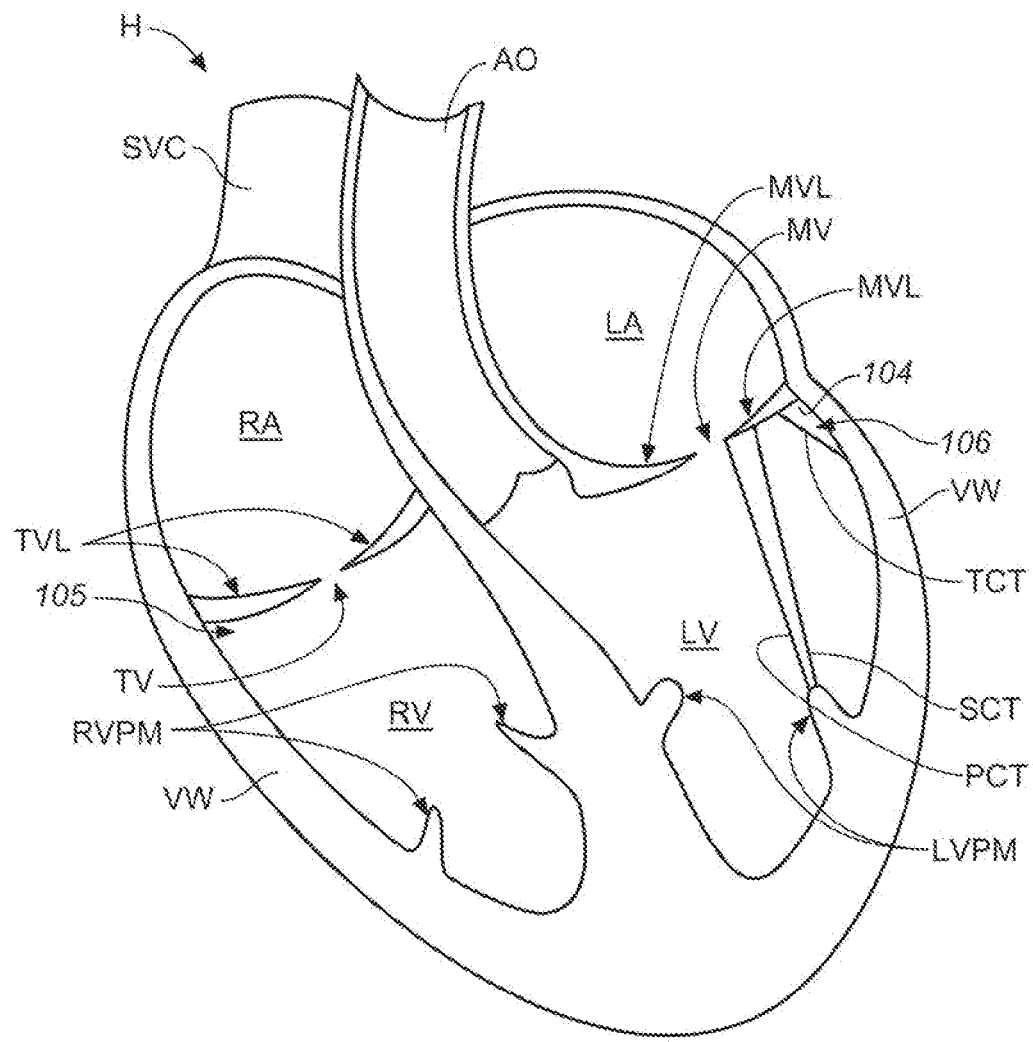
FIG. 1A is an illustrative depiction of a cross-sectional view of a heart.

Although a number of surgically implanted ventricular devices and procedures, such as the implantation of an annuloplasty ring or edge-to-edge leaflet repair, are available for treating valvular dysfunction, each procedure presents its own set of risks to the patient or technical challenges to the physician. For example, the ability to accurately and reliably position a cardiac implant during a beating heart procedure, whether by open chest or minimally invasive access, remains elusive to the average practitioner. In particular, the percutaneous or transvascular implantation of a ventricular device described herein poses a significant challenge due to the instability from the wall motion of a beating heart. Moreover, chords in a subvalvular space of a heart, such as tertiary or third-order chords, may present obstacles to the advancement and/or accurate positioning of one or more heart valve repair tools in the subvalvular space.

The devices, methods and kits described here may generally be used to reshape atrio-ventricular valves or myocardium to improve hemodynamic performance. In some variations, in order to allow such a reshaping process to take place, one or more chords in a subvalvular space of a heart may be cut and/or otherwise manipulated. This may, for example, provide additional space for the advancement of one or more tools that may be used to repair and/or assess the subvalvular space, such as one or more of the diagnostic catheters, visualization catheters, and/or guide catheters described herein.

The implantation procedures described here are preferably transvascular, minimally invasive or other "less invasive" surgical procedures, but can also be performed with open or limited access surgical procedures. When used for treatment of a cardiac valve dysfunction, the methods may generally involve assessing the accessibility of a target site in a subvalvular space of a heart using one or more diagnostic catheters. If the target site is deemed accessible, or if the accessibility of the target site is improved (e.g., by removing one or more interfering chords), then the methods may also involve accessing the target site using a guide catheter, positioning one or more anchor deployment devices at the target site using a guide tunnel (also sometimes referred to as a tunnel catheter) advanced through a lumen of the guide catheter, deploying a plurality of slidably coupled anchors from the anchor deployment device(s), and drawing the anchors together to reduce the annular dimensions. More specifically, drawing the anchors together typically causes the tissue between the anchors to contract. This, in turn, may compress the annular tissue and cause separated valve leaflets to coapt, thereby reducing or ending valve regurgitation. In some variations, self-securing anchors may be used—such self-securing anchors may have any of a number of different configurations, and may be used with other self-securing anchors, and/or with anchors that do not self-secure.

As discussed above, in some variations, a curved diagnostic catheter having essentially the same shape or a similar shape as a curved guide catheter (but having a smaller cross-sectional profile than the curved guide catheter) may be used to evaluate whether the guide catheter will be able to access a subvalvular space of a heart. If the subvalvular space is determined to be sufficiently accessible, then the procedure may proceed as described above. In some cases in which the subvalvular space is deemed inaccessible because of the presence of one or more chords, it may be rendered accessible by, for example, cutting the chord(s) that cause the inaccessibility.

Using a smaller diagnostic catheter to assess the accessibility and/or geometry of the target site prior to advancement of a larger guide catheter may make it less likely that the heart tissue will be inadvertently damaged by the guide catheter, or that the patient will be subjected to an unsuccessful procedure. For example, if a diagnostic catheter indicates that a subvalvular space of a heart would not be accessible by a guide catheter, then the patient would not be subjected to having guide catheter advancement begin, only to experience the guide catheter failing to reach the target site. A patient may also recover more quickly after advancement of a smaller diagnostic catheter, relative to recovery after a failed attempt at advancing a larger guide catheter.

It should be noted that certain variations of the methods described here may not include assessing the accessibility of a target site with one or more diagnostic catheters. For example, a method may include accessing a target site with a guide catheter, without assessing the accessibility of the target site with a diagnostic catheter first.

As discussed above, catheters, including one or more of the catheters described here, may include one or more curves. For example, a diagnostic catheter, visualization catheter, chord manipulation catheter, guide catheter, and/or anchor deployment catheter may be curved. Generally, the curvature of a diagnostic catheter may be selected, for example, to optimize placement and positioning of the diagnostic catheter within a subvalvular space of a heart. Similarly, the curvature of a visualization catheter or guide catheter may also be selected to optimize placement and positioning of the visualization catheter or guide catheter within a subvalvular space of a heart. Likewise, the curvature of a chord manipulation catheter may be selected to closely align with the geometry of a subvalvular space of a heart, so that the chord manipulation catheter may provide relatively accurate analysis of the subvalvular space. Additionally, the curvature of a guide catheter may be selected to facilitate the ability of a guidewire advanced therethrough to navigate the subannular groove.

Also described herein are methods for visualizing a catheter and/or the area surrounding a catheter during advancement of the catheter to a target site and/or positioning of the catheter at the target site. Such methods may involve the use of, for example, X-ray fluoroscopy and/or ultrasound (e.g., intravascular ultrasound, or IVUS). Some variations of visualization methods may employ echocardiography (e.g., intracardiac echocardiography). In some cases, rigid or flexible scopes, such as fiber scopes, may be used. The visualization methods may enable visualization of, for example, one or more catheters or other devices advanced to the subannular groove, the anatomy of or around the subannular groove, and/or implants delivered therein or thereto (e.g., during a minimally invasive heart valve repair procedure). In certain variations, one or more visualization methods and/or devices, such as a visualization catheter, may be used to help position a diagnostic catheter, a chord manipulation catheter, a guide catheter, and/or one or more other devices. This may result in enhanced positioning of the catheters or other devices (e.g., thereby reducing error in implant placement). It should be understood that while the methods and devices described herein focus on visualization of the subannular groove region, the methods and devices may be used to visualize any body region of interest, as appropriate.

As discussed above, also described here are devices, methods, and kits for manipulating one or more chords in a subvalvular space of a heart. For example, the chords may be severed and/or otherwise manipulated (e.g., pushed aside, gathered, etc.). Cutting or otherwise manipulating chords in a heart may, for example, help to provide room for a catheter (e.g., a guide catheter) to be delivered to a subvalvular space of the heart. The chord manipulation devices may generally be configured to cut or otherwise manipulate one or more chords that may prevent catheters and/or other tools from being used in the subvalvular space. As an example, a device may comprise a cutting catheter configured to cut chords that obstruct advancement of a guide catheter to a target site, while leaving chords that provide sufficient space for passage of a guide catheter. In some variations, a cutting catheter may be used to provide sufficient room for one or more anchor deployment devices so that one or more anchors may be deployed into the cardiac tissue.

Catheters and Heart Valve Repair Procedures

Turning now to the figures, FIG. 1A shows a cross-sectional view of a heart (H) including an aorta (AO), a superior vena cava (SVC), a right atrium (RA), a right ventricle (RV), a left atrium (LA), and a left ventricle (LV). As shown in FIG. 1A, a mitral valve (MV) comprising mitral valve leaflets (MVL) separates left atrium (LA) from left ventricle (LV), while a tricuspid valve (TV) comprising tricuspid valve leaflets (TVL) separates right atrium (RA)

from right ventricle (RV). There are two mitral valve leaflets (MVL), the anteromedial leaflet and the posterolateral leaflet. In some cases, mitral valve leaflets (MVL) and/or tricuspid valve leaflets (TVL) may be referred to more generally herein as leaflets (L). Heart (H) also includes papillary muscles in its right ventricle (RVPM), as well as papillary muscles in its left ventricle (LVPM). Additionally, the mitral valve and the tricuspid valve each comprise a valve annulus (not shown), discussed in further detail below.

FIG. 1A also shows a primary chorda tendinea (PCT), secondary chorda tendinea (SCT), and tertiary chorda tendinea (TCT) in left ventricle (LV)—of course, these are only illustrative chords, and it should be understood that a heart typically has many of each of these different types of chords.

As shown in FIG. 1A, right ventricle (RV) includes a subvalvular space (105), and left ventricle (LV) includes a subvalvular space (106). The subvalvular space, as used herein, generally includes the portion of the ventricular chamber that is bound peripherally by the ventricular wall (VW), superiorly by the atrio-ventricular valve leaflets, and centrally by the primary chordae tendineae (PCT), and is located along the circumference of the valve annulus. The subannular groove region (104), as used herein, includes the space bordered by the inner surface of the ventricular wall (VW), the inferior surface of valve leaflets (MVL) or (TVL), and the tertiary chordae tendineae (TCT) connected directly to the ventricular wall (VW) and a leaflet (L). While FIG. 1A shows a subannular groove region (104) in left ventricle (LV), right ventricle (RV) also has a corresponding subannular groove region. Devices and methods described here with respect to the subannular groove region in the left ventricle may, of course, be used on the subannular groove region in the right ventricle, as appropriate.

Figure 1B:
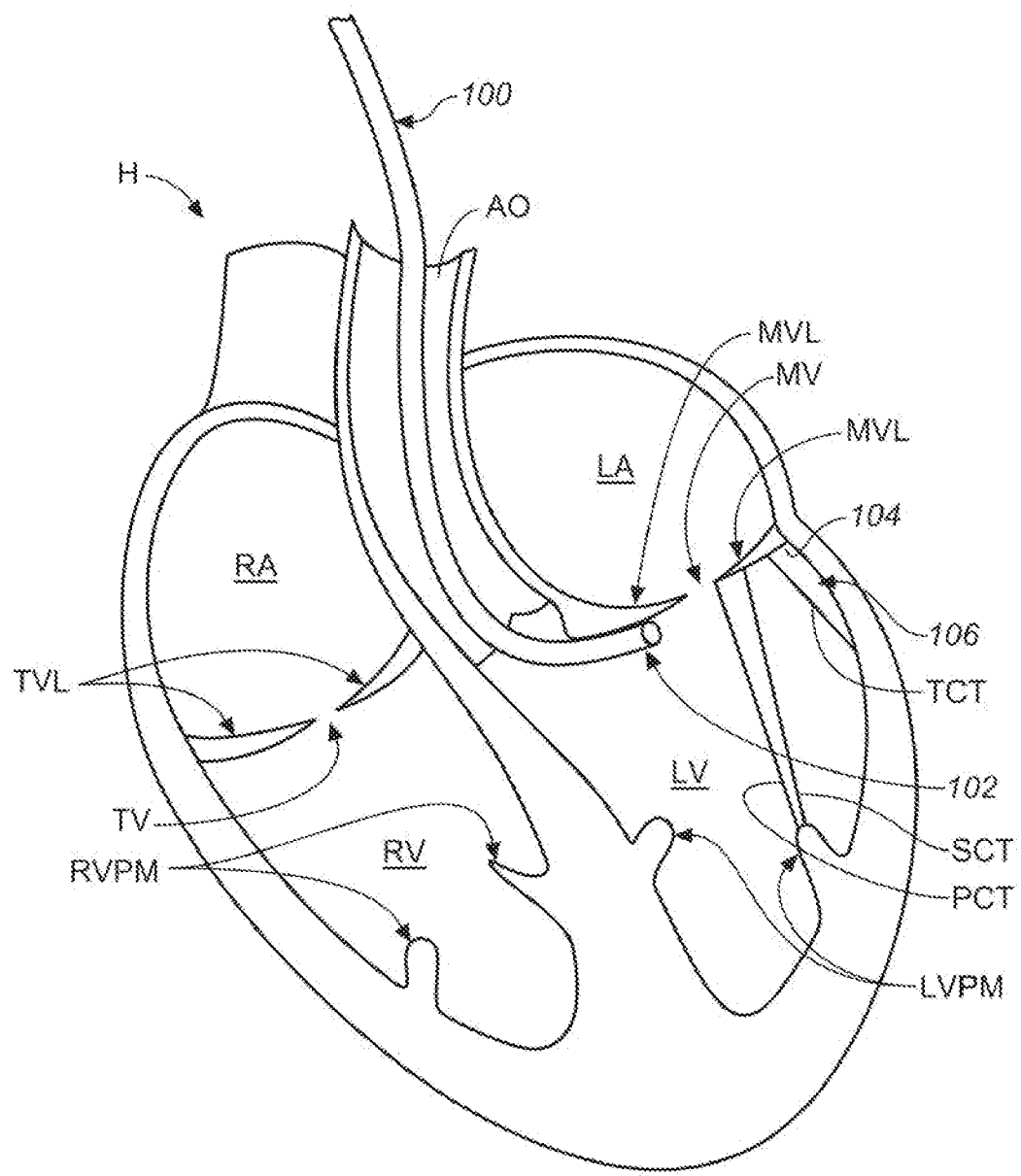
FIG. 1B is another illustrative depiction of a cross-sectional view of the heart of FIG. 1A, with a variation of a guide catheter advanced through the aorta into the left ventricle.

FIG. 1B shows a cross-sectional depiction of heart (H) with one variation of a guide catheter (100) advanced in a retrograde direction through aorta (AO) and into left ventricle (LV) (e.g., after being inserted into the femoral artery). "Retrograde," as used herein, generally refers to a direction opposite the expected flow of blood. This access route may be used to reach subvalvular space (106). The distal portion of the catheter may then be advanced, for example, under the posterolateral mitral valve leaflet and into subannular groove region (104). Guide catheter (100) is generally a flexible elongate catheter which may, for example, have one or more curves or bends toward its distal end to facilitate placement of the distal end (102) of the guide catheter at the desired location. Distal end (102) of guide catheter (100) may be configured to be positioned at an opening into subvalvular space (106) or within subvalvular space (106), such that subsequent delivery devices may be passed through guide catheter (100) into subvalvular space (106). Although the retrograde aortic access route preferably starts from a percutaneous or peripheral access site, in some variations, aortic access may be achieved by an incision in the ascending aorta, descending aorta, aortic arch or iliac arteries, following surgical, thoracoscopic or laparoscopic access to a body cavity.

In certain variations, other spaces bound by or relating to one or more cardiac structures may be used as a target region of the heart. These structures include but are not limited to the base of the ventricle, the mitral valve, the tricuspid valve, the primary chordae tendineae, the secondary chordae tendineae, the tertiary chordae tendineae, the anterior mitral valve leaflet chordae tendineae, the posterior mitral valve leaflet chordae tendineae, the interleaflet chordae tendineae, the papillary muscle, the anterior-lateral papillary muscle, the posterior-medial papillary muscle, the ventricular apical region, and the ventricular apex. As an example, in some variations, a supra-apical space from about the base of the mitral valve leaflets to just above the ventricular apex or apical region may be the target region. As another example, in certain variations, the target region may be the peripapillary muscle region, which includes the space about 1 centimeter above and about 1 centimeter below the level of the papillary muscle region, as well as the spaces between the papillary muscles. In some variations, the target region may be the endocardial surface abutting or accessible from the given space or cardiac structures. In still other variations, the target region may be a region located between the base and apex of a ventricle and between longitudinal borders drawn through the papillary muscles (e.g., either a posterior-lateral or an anterior-medial ventricular endocardial surface). In other variations, the target region may exclude the space along the longitudinal axis from the base of a ventricle to the apex of the ventricle (e.g., the target region may be tubular or toroidal in configuration, with an internal border relating to a chorda tendinea).

FIG. 2A provides a flowchart depiction of a variation of a method (200) for assessing the accessibility of a target site within a region of a heart valve annulus. As shown there, this illustrative method comprises loading a guidewire into a pigtail catheter (210). The guidewire may, for example, have a diameter of 0.035 inch (0.089 centimeter) and/or a length of 102.36 inch (260 centimeters), and/or the pigtail catheter may, for example, be a 6 Fr pigtail catheter (i.e., having an outer diameter of 2 millimeters). These examples are only intended to be illustrative, however, and other suitable guidewires and/or pigtail catheters may be used. Moreover, in some variations, such as some variations in which a relatively small diagnostic catheter (e.g., 6 Fr, or having an outer diameter of two millimeters) is used, a pigtail catheter may not be used. For instance, a J-tip guidewire or a floppy angled tip may be sufficient to track within the vasculature and cross the aortic valve.

Referring again to FIG. 2A, method (200) further includes loading the pigtail catheter into a diagnostic catheter (220). This may be achieved using, for example, a peel-away introducer sheath (e.g., to temporarily straighten the pigtail catheter during loading). Next, a sheath (e.g., a 9 Fr sheath, or a sheath having an outer diameter of 3 millimeters) may be advanced into a femoral artery, and a left coronary angiogram may be performed in a lateral view (221). The fluoroscopic view may be adjusted to approximate the long axis of the left ventricle (i.e., to achieve a long-axis view, described in further detail below). Thereafter, the diagnostic catheter (including the loaded pigtail catheter and guidewire) may be advanced into the sheath, over the aortic arch, and across the aortic valve (222). The diagnostic catheter may be advanced into and positioned within the body under fluoroscopic guidance, for example, as discussed in further detail below.

After the diagnostic catheter has been advanced, the guidewire may be withdrawn (224), and a ventriculogram may be performed through the pigtail catheter to find the short- and long-axis views (226). A short-axis view may be obtained, for example, by adjusting the fluoroscope to a projection of the face of the mitral valve (from the ventricular side). In some variations, the short-axis view may be verified by such cues as a circular pattern of injected contrast agent, minimal exposure of the apical region in the projection, and possible appearance of the papillary muscles. A long-axis view may be obtained, for example, by adjusting the fluoroscope to an edge-on or profile projection of the mitral valve. This view may be verified by such cues as a linear pattern of injected contrast agent, highlighting the valve which lies between the ventricle and the atrium. Short- and long-axis views are discussed in additional detail below.

Next, the pigtail catheter may be withdrawn from the diagnostic catheter (228), and radiopaque contrast agent may be injected through the diagnostic catheter to visualize the subannular groove (230). In some variations, the radiopaque contrast agent may be diluted (e.g., in a 1:1 dilution). The method may then comprise urging the distal portion of the diagnostic catheter against the anterior or posterior wall in the short-axis view (232). This may be achieved, for example, by carefully torquing the diagnostic catheter. In some variations in which an anterior approach is used in a procedure on a mitral valve, it may be desirable to place the distal tip of the diagnostic catheter directly below the anterior commissure of the mitral valve. Similarly, in certain variations in which a posterior approach is used in a procedure on a mitral valve, it may be desirable to place the distal tip of the diagnostic catheter directly below the posterior commissure of the mitral valve.

In some variations, the position of the diagnostic catheter may be confirmed by injecting small amounts of contrast agent through the diagnostic catheter. For example, alignment of the catheter with the edge of the pattern created by the injected contrast agent may indicate that the catheter is accurately positioned at the target site. In certain variations, the diagnostic catheter may be further manipulated to achieve the desired positioning and stability of its distal portion against the anterior or posterior wall of the heart and behind the chordae tendineae in the subannular groove. The correct positioning of the diagnostic catheter may then be re-confirmed by injecting contrast agent through the diagnostic catheter. Typically, it is desired that the tip of the diagnostic catheter lie parallel to the mitral valve annulus (in the long-axis view) and apposed against the anterior or posterior wall of the mitral valve annulus (in the short-axis view). Next, the guidewire (either the same guidewire or a new one) may be inserted into the diagnostic catheter in the long- or short-axis view (234), and may be advanced around the subannular groove (and behind the chordae tendineae) in both the long- and short-axis views (236). Finally, after the guidewire has circumnavigated the subannular groove, the correct positioning of the guidewire may be verified by injecting contrast agent through the diagnostic catheter (238). If there is a significant amount of contrast agent between the endocardium and the guidewire (in the short-axis view), then the guidewire may be repositioned and the verification step repeated, until the guidewire has been correctly positioned.

In certain variations, method (200) may be repeated multiple (e.g., two or three) times with the same subject. As an example, the method may be repeated using different diagnostic catheters having different sizes and/or different shapes.

It should be understood that method (200) may be modified according, for example, to the preferences of the operator. As an example, the method may be modified so that it does not include loading a guidewire into a pigtail catheter. As an alternative, the method may comprise providing a pigtail catheter that has been preloaded with a guidewire. As another example, in some variations (e.g., some variations in which a 6 Fr diagnostic catheter (having an outer diameter of 2 millimeters) is used), a pigtail catheter may not be used. As an additional example, the method may not take place in the order shown in FIG. 2A. For example, the sheath may be advanced into the femoral artery and a left coronary angiogram may be performed (221) prior to loading the guidewire into the pigtail catheter (210). As a further example, in some variations, either before or after urging the distal portion of the diagnostic catheter against the anterior wall (232), the diagnostic catheter may be positioned as closely as possible to being level with the mitral valve. This positioning may be confirmed, for example, by injection of contrast agent viewed under X-ray fluoroscopy. As an additional example, in some variations, instead of or in addition to inserting the guidewire into the diagnostic catheter in the long-axis view (234), the guidewire may be inserted into the diagnostic catheter using a different view (e.g., a short-axis view). As another example, while a particular access route for the diagnostic catheter has been described, any suitable access route may be used. Other alternative variations of method (200) may also be used, as appropriate.

FIG. 2B provides a flowchart depiction of one variation of a method (260) for deploying at least two anchors of an implant into a region of a heart valve annulus. As shown there, this illustrative method comprises verifying the accessibility of a subannular groove region of a heart using a diagnostic catheter (270) (e.g., using method (200) described above with reference to FIG. 2A). Method (260) also comprises advancing a guide catheter to the subannular groove region (280), advancing a guidewire through a lumen of the guide catheter (284), advancing a guide tunnel over the guidewire (286), and proximally withdrawing the guidewire from the guide tunnel (288). The guide catheter may be advanced into and positioned within the body under fluoroscopic guidance, for example. In some variations, the guide catheter may be placed and/or positioned at the target site using one or more of the visualization methods and/or devices described below. Advancement of the guide catheter to the subannular groove region (280) may take place immediately after verifying the accessibility of the subannular groove region using a diagnostic catheter (270). Alternatively, advancement of the guide catheter to the subannular groove region may take place after a certain amount of time has elapsed (e.g., at least about 1 day, at least about 2 days, at least about 3 days, at least about 4 days, at least about 5 days, at least about 1 week, at least about 10 days, at least about 2 weeks, at least about 1 month, at least about 2 months, etc.) from verifying the accessibility of the subannular groove region using a diagnostic catheter.

In this particular variation, the guide tunnel comprises an outer catheter with a passageway in which an inner catheter slidably resides. However, other appropriate variations of guide tunnels may be used. Referring still to FIG. 2B, after the guidewire has been proximally withdrawn, a first anchor deployment catheter may be advanced through the lumen of the guide tunnel (290) and a first anchor may be deployed from the first anchor deployment catheter, through an opening in the guide tunnel, and into a first region of the heart valve annular tissue (292). The first anchor is typically coupled or secured to a guide element (or coupling member), such as a tether. In this way, after the first anchor is secured to heart tissue, the guide element will remain coupled to the first anchor. The guide element may then be used as a track or monorail for the advancement of one or more additional anchor deployment catheters thereover, and/or for the deployment of one or more additional anchors thereover. However, the guide element is also a component of the implant that interconnects the multiple anchors. A portion of the guide element facilitates the cinching of the implant and remains in the body with the anchors after any anchor deployment catheters have been removed from the body.

While method (260) has been described above, other variations of methods may be employed, depending on the needs of the patient and operator preference. For example, in some variations, a guide catheter may be advanced into the subannular groove region of a heart without first verifying the accessibility of the subannular groove region using a diagnostic catheter. In certain variations, a method may comprise deploying multiple anchors through a single opening in a guide tunnel (e.g., using the same anchor deployment catheter or different anchor deployment catheters). In some variations, a method may comprise simultaneously deploying multiple anchors through multiple openings in a guide tunnel.

Guide elements may be made from any suitable or desirable biocompatible material, and may be made of a single material or a combination of materials (e.g., a guide element may be in the form of one long piece of material, or may comprise two or more pieces). Moreover, guide elements may be braided or not braided, woven or not woven, and/or reinforced and/or impregnated with one or more additional materials. As non-limiting examples, a guide element may be made from (1) a suture material (e.g., absorbable suture materials such as polyglycolic acid and polydioxanone, natural fibers such as silk, and artificial fibers such as polypropylene, polyester, polyester impregnated with polytetrafluoroethylene, nylon, etc.), (2) a suture-like material, (3) a metal (absorbable or non-absorbable), (4) a metal alloy (e.g., stainless steel), (5) a shape memory material, such as a shape memory alloy (e.g., a nickel titanium alloy), (6) other biocompatible material, or (7) any combination thereof. In some variations, a guide element may be in the form of a DACRON® polyester strip. In certain variations, a guide element may comprise high-density polyethylene (HDPE), ultra-high molecular weight polyethylene (UHMWPE), and/or polyetheretherketone (PEEK). Some variations of guide elements may have a braided textile construction. Certain variations of guide elements may be in the form of a wire. Additionally, a guide element may include multiple layers, and/or may include one or more coatings. For example, a guide element may be in the form of a polymer-coated wire. In some variations, a guide element may comprise a combination of one or more sutures and one or more wires. As an example, a guide element may be formed of a suture that is braided with a wire. Certain variations of guide elements may be in the form of monofilament or multifilament textile yarns or fibers. In some variations, a guide element may be formed of one or more electrode materials. In certain variations, a guide element may be formed of one or more materials that provide for the telemetry of information (e.g., regarding the condition of the target site).

Some variations of guide elements may include one or more therapeutic agents (e.g., drugs, such as time-release drugs). As an example, a guide element may be partially or entirely coated with one or more therapeutic agents. In certain variations, a guide element may be used to deliver one or more growth factors and/or genetic regenerative factors. In some variations, a guide element may be coated with one or more materials (e.g., a polymer) that encapsulate or control the release rate of one or more therapeutic agents, and/or in which one or more therapeutic agents are embedded. The therapeutic agents may be used, for example, to treat a target site in which the guide element is disposed (and, in some cases, to which the guide element is fixedly attached or otherwise secured). In certain variations, a guide element may include one or more lumens through which one or more therapeutic agents may be delivered.

After the first anchor has been deployed in the region of the heart valve annular tissue, the first anchor deployment catheter may be withdrawn proximally from the guide tunnel. While maintaining the existing position of the outer catheter of the guide tunnel about the subannular groove region, the inner catheter of the guide tunnel may be repositioned at a second opening of the outer catheter (294). A second anchor deployment catheter may then be advanced over the guide element through the lumen of the guide tunnel (296). While use of a second anchor deployment catheter has been described, in some variations, subsequent deployment of anchors may be achieved by removing and reloading the first anchor deployment catheter. In other variations, the first anchor deployment catheter may be loaded with a plurality of anchors and may not need to be withdrawn from the guide tunnel to deliver subsequent anchors.

During advancement of the second anchor deployment catheter over the guide element, the guide element may enter the second anchor deployment catheter through an opening at its distal end, and exit the second anchor deployment catheter through an opening in its side wall that is proximal to its distal end. As an alternative, the guide element may enter the second anchor deployment catheter through an opening at its distal end, and exit the second anchor deployment catheter through an opening at its proximal end, or at any other location proximal to the distal end. As another alternative, the guide element may enter the second anchor deployment catheter through an opening at its distal end, exit the second anchor deployment catheter through an opening at its distal end, enter a side lumen of the second anchor deployment catheter, and exit the side lumen at a location proximal to its point of entry into the side lumen. Other appropriate guide element routing configurations may also be used.

After the second anchor deployment catheter has been advanced over the guide element through the lumen of the guide tunnel, a second anchor may be deployed into a second region of the heart valve annular tissue using a second opening of the guide tunnel (298). While this variation of a method includes deploying one anchor through one opening in a guide tunnel and then deploying another anchor through another opening in the guide tunnel, some variations of methods may alternatively or additionally include deploying anchors in a different manner. As an example, a method may include deploying multiple (i.e., at least two) anchors through a single opening in a guide tunnel. Two or more of the anchors may be deployed using the same anchor deployment catheter, and/or two or more of the anchors may be deployed using different anchor deployment catheters. As another example, a method may include simultaneously deploying multiple anchors through multiple openings in a guide tunnel. Other suitable variations of methods may also be employed.

The procedure described above represents one variation of a method that may be used to treat the annular tissue of the mitral valve. In other variations, other tissues or structures of the heart and vasculature may also be treated, including but not limited to the subvalvular apparatus, septal structures and the myocardium. In still other variations, one or more cinchable implants may be deployed in non-cardiac tissues or structures, for example, to treat gastrointestinal disorders such as obesity or genitourinary conditions such as incontinence, or to perform cosmetic and reconstructive procedures.

FIGS. 3A-3K provide a more detailed depiction of the method shown in flowchart form in FIG. 2B, as well as a portion of the method shown in flowchart form in FIG. 2A.

Figure 3A:
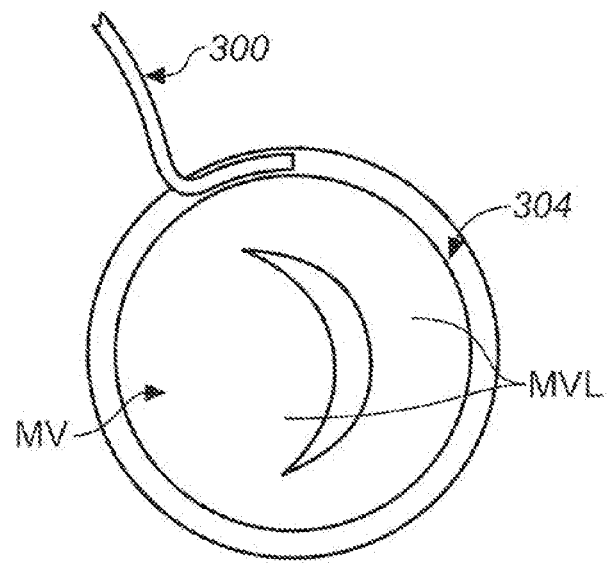
FIGS. 3A-3K schematically depict a variation of a method for delivering multiple tissue anchors into a subvalvular space of a heart.
Figure 3B:
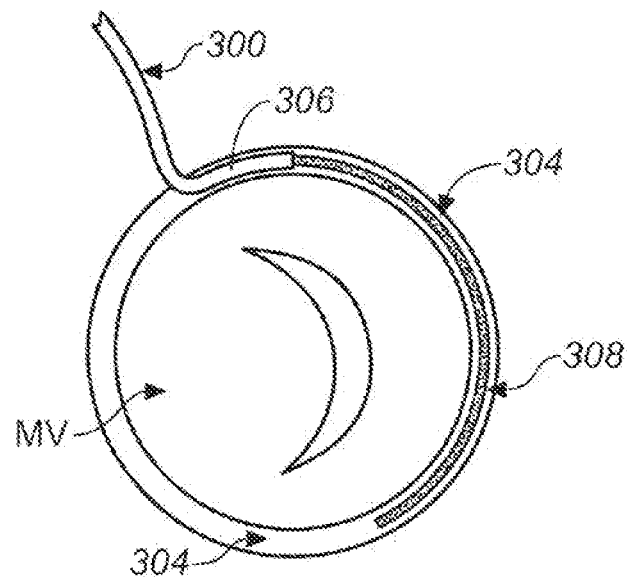

In FIGS. 3A-3K, the mitral valve (MV) is depicted schematically from an inferior perspective looking in a superior direction, but in other variations the tricuspid valve, pulmonary valve or aortic valve may be accessed. Referring to FIG. 3A, a diagnostic catheter (300) may be advanced into the subvalvular space (306) (FIG. 3B) of a heart, and more specifically into the subannular groove region (304) of the heart. As shown in FIG. 3B, after diagnostic catheter (300) has been positioned at the desired location in subannular groove region (304), a guidewire (308) may be advanced through a lumen of diagnostic catheter (300) and at least partially routed around subannular groove region (304). The diagnostic catheter may be used to help determine whether the anatomy of the subject (here, the subvalvular space) is appropriate for passage of a guide catheter and routing of a guidewire therethrough. For example, here the diagnostic catheter may be used to help determine whether a guide catheter can be advanced to the subvalvular space and a guidewire can be advanced through the guide catheter and around all or a portion of the subannular groove region. Diagnostic catheter (300) may be, for example, from 5 Fr to 9 Fr in size (i.e., such that the diagnostic catheter has an outer diameter of 1.67 millimeters to 3 millimeters). Specific, non-limiting examples of diagnostic catheter sizes that may be appropriate include 6 Fr (2 millimeters outer diameter), 7 Fr (2.33 millimeters outer diameter), and 9 Fr (3 millimeters outer diameter), although other appropriate sizes may also be used.

Figure 3C:
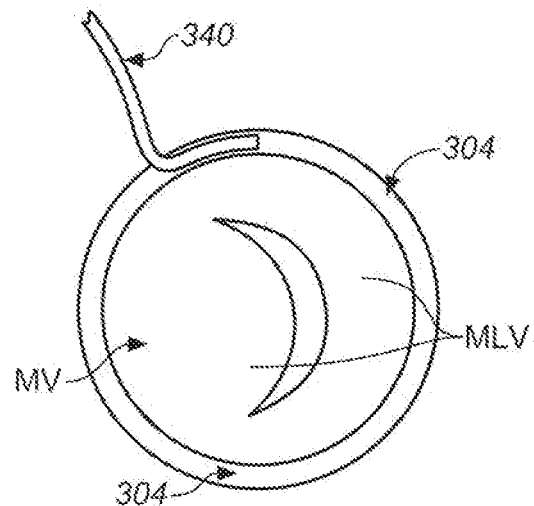
Figure 3D:
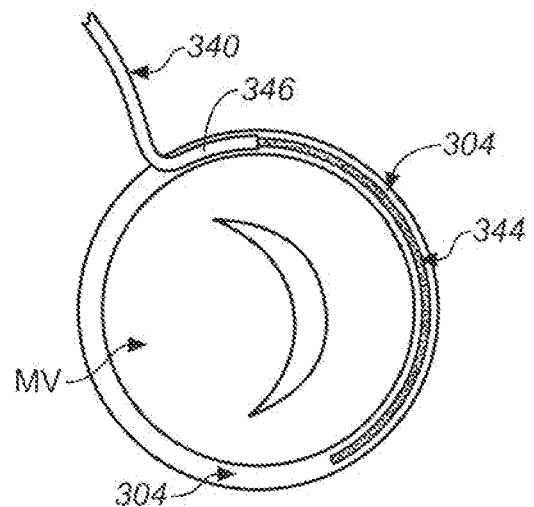

If it is determined that the subject's anatomy will accept a guide catheter and guidewire, then the guidewire and diagnostic catheter may be withdrawn from the heart. Next, and as shown in FIG. 3C, a guide catheter (340) may be advanced to subannular groove region (304) using any of the access routes (or any other suitable access routes) described herein. Guide catheter (340) may have a size of, for example, from 6 Fr to 16 Fr (e.g., 14 Fr), or 2 millimeters outer diameter to 5.33 millimeters outer diameter (e.g., 4.67 millimeters outer diameter). Other suitable sizes may also be used. Guide catheter (340) may also have an atraumatic tip. As shown in FIG. 3D, after guide catheter (340) has been positioned at the desired location in subannular groove region (304), a guidewire (344) may be advanced through the lumen of guide catheter (340). Guidewire (344) may be advanced beyond the distal end (346) of guide catheter (340), so that guidewire (344) extends farther along subannular groove region (304) than guide catheter (340), as shown in FIG. 3D.

Figure 3E:
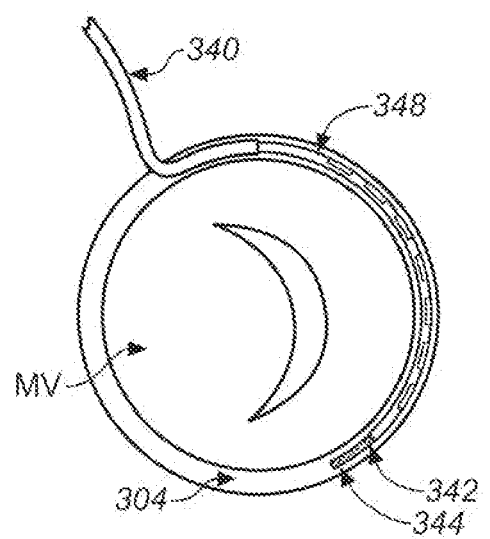

After guidewire (344) has been positioned in subannular groove region (304), a guide tunnel (348) may be advanced through guide catheter (340), over guidewire (344), as shown in FIG. 3E. As shown in FIG. 3E, a distal portion (342) of guidewire (344) extends from the distal end of guide tunnel (348). Guide tunnel (348) may be any suitable catheter, and in some instances, it may be desirable that the guide tunnel be pre-shaped or pre-formed at its distal end, such as the guide tunnel illustrated in FIG. 3E. In certain variations, guide tunnel (348) may have a pre-shaped distal portion that is curved. In this way, the guide tunnel may more easily conform to the geometry of the atrio-ventricular valve. Guide tunnels are described, for example, in U.S. patent application Ser. No. 12/366,553 (published as US 2009/0222083 A1), which is incorporated herein by reference in its entirety.

It should also be understood that any of the catheters or guidewires described here may be pre-shaped or pre-formed to include any number of suitable curves, angles or configurations, and/or may be steerable. In some variations, the radius of curvature of a curved distal section of a catheter may be generally larger than that of the subannular groove. When such a catheter is urged or situated against the subannular groove, the distal end of the catheter may naturally point outward against the annulus and ventricular wall. In other variations, the catheter may have a curved distal section having a radius of curvature that is approximately the same as that of the subannular groove.

Figure 3F:
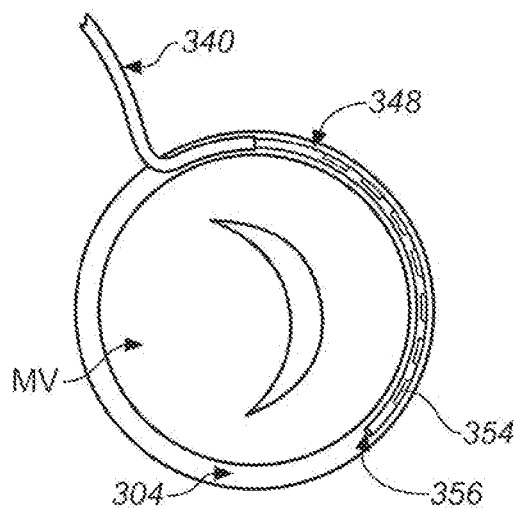

After guide tunnel (348) has been positioned in subannular groove region (304), guidewire (344) may be withdrawn proximally, as shown in FIG. 3F. An anchor deployment catheter (not shown) may then be advanced through the lumen of guide tunnel (348) and toward opening (354) at or adjacent to the distal tip (356) of guide tunnel (348). In the variation depicted in FIG. 3G, the anchor deployment catheter remains within guide tunnel (348), and an anchor (358) is deployed through opening (354) to attach to the body tissue. In other variations, however, the anchor deployment catheter may be extended through opening (354) of guide tunnel (348).

In some variations, opening (354) may be the distal-most anchor deployment opening of guide tunnel (348). In certain variations, one or more openings may have a separate lumen in guide tunnel (348), so that anchors deployed from such openings would not interfere with or restrict the deployment of subsequent tissue anchors distal to those openings. Furthermore, although FIG. 3G depicts opening (354) as a side opening of guide tunnel (348), in some variations, opening (354) may be located at distal tip (356) and may be the same opening shown with a distally protruding guidewire (344) in FIG. 3E.

Figure 3G:
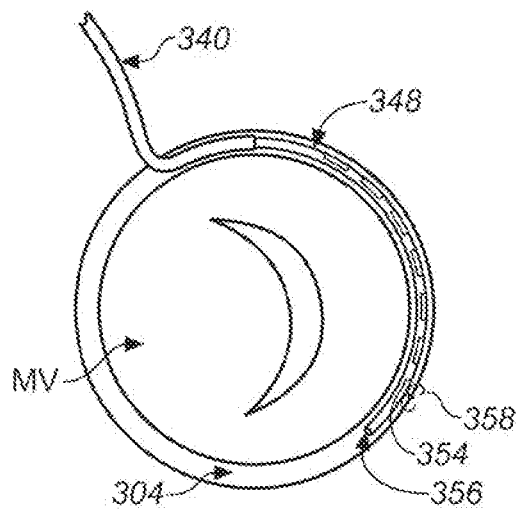

Anchor (358), shown in FIG. 3G, may be configured to self-expand as it exits the anchor deployment catheter and guide tunnel (348) to self-secure into the annular tissue accessible from subannular groove region (304). It should be understood that one or more anchors of an implant may be deployed into the annulus directly, while other anchors may be secured to other tissue in the vicinity of subannular groove region (304). For example, one or more anchors may be secured to the tissue below the annulus. Anchor deployment may be monitored, for example, under fluoroscopy. After anchor (358) has been deployed, the anchor deployment catheter may be proximally withdrawn. A tether (360), attached to anchor (358) and seen best in FIGS. 31 and 3J, may then be used to facilitate the insertion of additional anchor deployment catheters toward the implantation site.

Figure 3H:
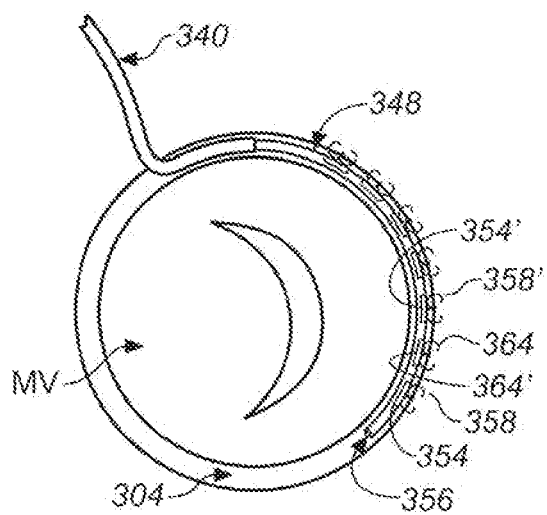
Figure 3I:
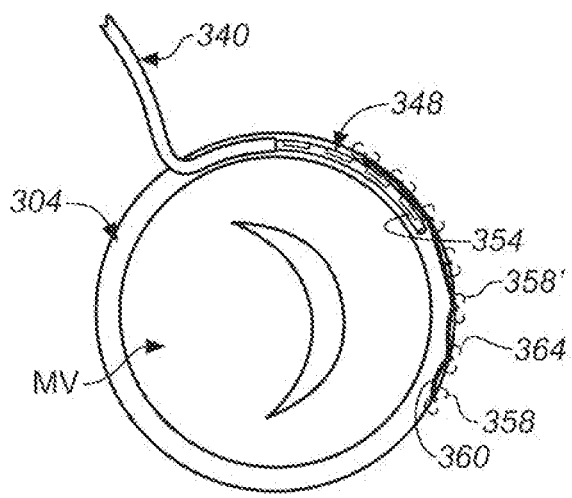

In this particular variation, as demonstrated in FIG. 3H, guide tunnel (348) is maintained in the same position while additional anchors (364) and (358') are deployed from additional openings (364') and (354') along guide tunnel (348). In some variations, one or more anchor deployment catheters may be serially inserted into guide tunnel (348) using tether (360) to serially guide anchors (364) and (358') through openings (364') and (354'). In certain variations, the anchor deployment catheters may be loaded with one or more anchors at the point-of-use, while in other variations the anchor deployment catheters may be pre-loaded at the point-of-manufacture. In some variations, the anchor deployment catheters may be reloaded at the point-of-use, while in other variations, the anchor deployment catheters may be single-use devices that are discarded after anchor deployment. In certain variations, the anchor deployment catheters may be configured to hold two or more anchors (358), (358') and (364) and may be capable of deploying multiple anchors without requiring withdrawal of the anchor deployment catheter between anchor deployments. Still other multi-anchor deployment catheters may be configured to deploy multiple anchors simultaneously through multiple openings of guide tunnel (348).

Anchors (358), (358') and (364) may be deployed from the anchor deployment catheter and guide tunnel (348) in any suitable fashion, including but not limited to using a push-pull wire or a plunger, or any other suitable actuation technique. Similarly, anchors (358), (358') and (364) may be coupled to tether (360) by any suitable attachment method. For example, one or more knots, welded regions, and/or adhesives may be used. Alternate variations for anchor deployment and anchor attachments are described, for example, in U.S. patent application Ser. No. 11/583,627 (published as US 2008/0172035 A1) and Ser. No. 12/505,332, filed on Jul. 17, 2009, both of which are incorporated herein by reference in their entirety. Additionally, anchor deployment methods, devices, and kits are described, for example, in U.S. patent application Ser. No. 11/201,949 (published as US 2007/0055206 A1); U.S. patent application Ser. No. 12/366,553 (published as US 2009/0222083 A1); U.S. Provisional Application Ser. No. 61/160,230, filed on Mar. 13, 2009; and U.S. Provisional Application Ser. No. 61/178,910, filed on May 15, 2009, all of which are incorporated herein by reference in their entirety.

"Anchors," for the purposes of this application, are defined to mean any fasteners. Thus, the anchors may comprise C-shaped or semicircular hooks, curved hooks of other shapes, straight hooks, barbed hooks, single or multiple loop anchors, clips of any kind, T-tags, rivets, plication elements (e.g., local plication elements such as staples), or any other suitable fastener(s). In one variation, anchors may comprise two tips that curve in opposite directions upon deployment, forming two intersecting semi-circles, circles, ovals, helices or the like. In some variations, the tips may be sharpened or beveled. In certain variations, the anchors may be self-forming. By "self-forming" it is meant that the anchors are biased to change from a first undeployed shape to a second deployed shape upon release of the anchors from a restraint. Such self-forming anchors may change shape as they are released from a housing or deployed from a lumen or opening to enter annular tissue, and secure themselves to the tissue. Self-forming anchors may be made of any suitable material or materials, such as spring stainless steel, or super-elastic or shape-memory materials such as nickel-titanium alloy (e.g., Nitinol).

In certain variations, anchors may be made of a non-shape-memory material and may be loaded into an anchor deployment catheter in such a way that they change shape upon release. For example, anchors that are not self-forming may be secured to tissue via crimping, firing or other application of mechanical force to facilitate tissue penetration and/or securement. Even self-securing anchors may be crimped in some variations, to provide enhanced attachment to tissue. Other types of mechanical force may alternatively or additionally be applied to self-forming anchors. In certain variations, anchors may comprise one or more bioactive agents, including biodegradable metals and polymers. In some variations, anchors may comprise electrode components. Such electrodes, may, for example, sense various parameters including but not limited to impedance, temperature and electrical signals. In other variations, such electrodes may be used to supply energy to tissue at ablation or sub-ablation amounts.

In some variations, an implant may comprise multiple self-expanding, non-plicating anchors. In certain variations, an implant may comprise multiple T-tag anchors. Some variations of anchors may comprise fibrous or porous materials in the shape of bars, rods, pledgets, or the like. In some cases, the fibrous or porous materials may expand in volume. Additionally, while the deployment of multiple anchors of the same shape over a single guide element has been described, in certain variations, a single guide element may be used to deploy multiple anchors having different shapes or non-uniform implantation sites. Similarly, in some variations, a single guide element may be used in the deployment of multiple anchors having different sizes. Illustrative examples of suitable anchors are described in more detail, for example, in U.S. patent application Ser. No. 11/202,474 (published as US 2005/0273138 A1), which is incorporated herein by reference in its entirety.

In the variations depicted in FIGS. 3A-3K, before a second anchor deployment catheter is advanced through guide tunnel (348), tether (360) is threaded into the second anchor deployment catheter and is slidably engaged with a second anchor (364). In some variations, second anchor (364) may be preloaded into the second anchor deployment catheter before threading tether (360), while in other variations, the second anchor may be pre-threaded before being loaded into the second anchor deployment catheter. Any of a number of different methods may be used to thread a guide element, such as tether (360), into an anchor deployment catheter, and to engage the guide element with an anchor. Other methods are described, for example, in U.S. patent application Ser. No. 11/202,474 (published as US 2005/0273138 A1), which is incorporated herein by reference in its entirety. Threading devices are described, for example, in U.S. patent application Ser. No. 11/232,190 (published as US 2006/0190030 A1), which is also incorporated herein by reference in its entirety.

Figure 3J:
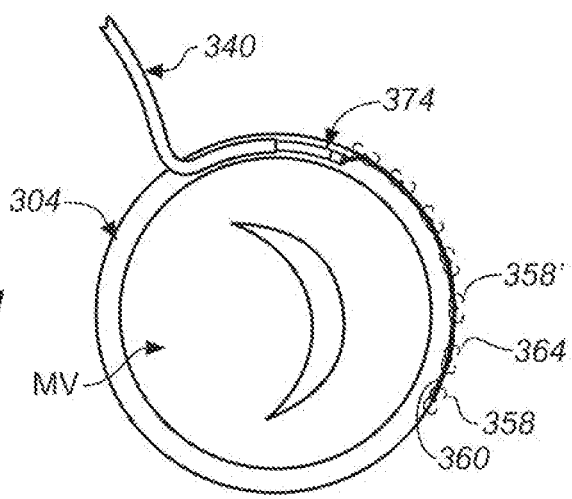
Figure 3K:
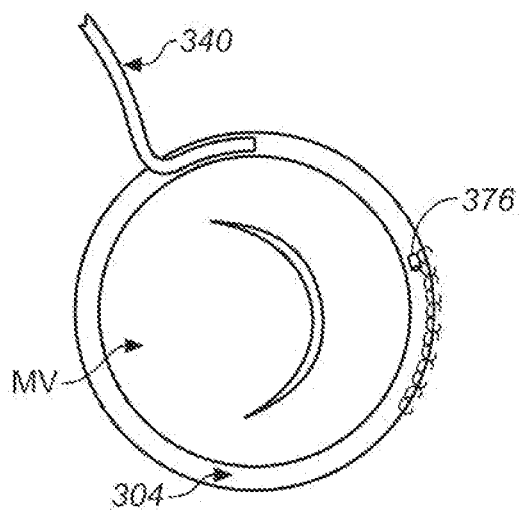

With reference to FIG. 3J, after all of anchors (358), (358') and (364) have been deployed into body tissue, guide tunnel (348) may be withdrawn from guide catheter (340). A termination catheter (374) may then be inserted through guide catheter (340) over tether (360). Termination catheter (374) may be used to facilitate tensioning of tether (360), thereby cinching anchors (358), (358') and (364) together to remodel the annular tissue. The effect of this cinching on the valve geometry and blood flow may be viewed, for example, using ultrasound. Termination catheter (374) may also be used to secure the cinched anchors (358), (358') and (364) with a termination member (376) that resists tether loosening or slippage, as illustrated in FIG. 3K. In other variations, termination catheter (374) may secure tether (360) to an anchor or to body tissue without the use of termination member (376). Devices and methods for performing termination of cinchable implants are described, for example, in U.S. patent application Ser. No. 11/232,190 (published as US 2006/0190030 A1); Ser. No. 11/270,034 (published as US 2006/0122633 A1); Ser. No. 12/576,955, filed on Oct. 9, 2009; and Ser. No. 12/577,044, filed on Oct. 9, 2009, all of which are incorporated herein by reference in their entirety.

The catheters and other elongated members described herein, including the diagnostic catheters, guide catheters, guide tunnels, and anchor deployment catheters, may be formed of any of a number of different materials. Moreover, at least two of the catheters that are used in a procedure may be formed of the same material or materials, and/or at least two of the catheters may comprise one or more different materials. In some variations, a method of treating heart valve tissue may comprise using a diagnostic catheter and a guide catheter, where the diagnostic catheter is essentially a scaled-down version of the guide catheter. For example, both of the catheters may be formed of the same material or materials, and may have the same shape. Alternatively, a method may comprise using a diagnostic catheter and a guide catheter that differ from each other in at least one aspect (in addition to having different sizes). For example, the diagnostic catheter and guide catheter may have the same shape, but may be formed of different materials. As an example, the diagnostic catheter may be formed of one or more materials that are stiffer than the material or materials used to form the guide catheter.

Non-limiting examples of suitable materials for the catheters described here include polymers, such as polyether-block co-polyamide polymers (e.g., PEBAX® polyether block amide copolymers, including but not limited to PEBAX® 35D polymer, PEBAX® 40D polymer, PEBAX® 55D polymer, PEBAX® 63D polymer, and PEBAX® 72D polymer), copolyester elastomers, thermoset polymers, polyolefins (e.g., polypropylene or polyethylene, including high-density polyethylene (HDPE) and low-density polyethylene (LDPE)), polytetrafluoroethylene (e.g., TEFLON™ polymer) or other fluorinated polymers, ethylene vinyl acetate copolymers, polyamides, polyimides, polyurethanes (e.g., POLYBLEND™ polymer), polyvinyl chloride (PVC), fluoropolymers (e.g., fluorinated ethylene propylene (FEP), perfluoroalkoxy (PFA) polymer, polyvinylidenefluoride (PVDF), etc.), polyetheretherketones (PEEKs), silicones, and copolymers and combinations (e.g., blends) thereof. Examples of polyamides include nylon 6 (e.g., ZYTEL® HTN high performance polyamides from DuPont™), nylon 11 (e.g., RILS AN® B polyamides from Arkema Inc.), and nylon 12 (e.g., GRILAMID® polyamides from EMS-Grivory, RILSAN® A polyamides from Arkema Inc., and VESTAMID® polyamides from Degussa Corp.). Other polymers and/or non-polymeric materials may also be used in a catheter. Moreover, any of the materials (e.g., polymers) that are used in a catheter may be combined (e.g., blended), if it is suitable to do so.

In certain variations, a catheter may comprise one or more reinforced polymers. For example, a catheter may comprise one or more polymers reinforced with one or more metals and/or metal alloys (e.g., stainless steel or a shape memory metal such as Nitinol). Polymers may also be reinforced with textile and/or metal meshes, braids, and/or fibers. In some variations, a catheter may comprise one or more polymer composites comprising one or more particulate or fibrous fillers. When composites are used, the fillers may be selected to impart a variety of physical properties, such as toughness, stiffness, density, and/or radiopacity. For example, a catheter may comprise a polymer composite comprising barium sulfate ($BaSO_4$), which may impart the catheter with radiopacity.

As described above, in some variations, a catheter (e.g., a diagnostic catheter, a visualization catheter, a chord manipulation catheter, a guide catheter, etc.) may be formed of multiple polymers. As an example, a catheter may be formed of a blend of different polymers, such as a blend of high-density polyethylene (HDPE) and low-density polyethylene (LDPE). As another example, a catheter may be formed of different polymers having different durometers. For example, a catheter may include different durometer polymers along its length. As an example, in certain variations, a catheter may have a proximal shaft comprising a 72 Shore D Durometer Nylon, a distal transition segment comprising a 50 Shore D Durometer Nylon, a distal segment comprising a 35 Shore D Durometer Nylon, and an atraumatic tip comprising a 25 Shore D Durometer PEBAX® polymer. As another example, in some variations, a catheter may comprise multiple different segments or portions comprising PEBAX® polymers having different durometers, such as PEBAX® 35D polymer, PEBAX® 40D polymer, PEBAX® 55D polymer, PEBAX® 63D polymer, PEBAX® 72D polymer, or a combination of PEBAX® 72D polymer and PEBAX® 35D polymer. In a catheter comprising different segments or portions with different durometer polymers, the segments or portions may all have the same length, or at least two of the segments or portions may have different lengths.

While the wall of a catheter may be formed of a single layer, some variations of catheters may include walls having multiple layers (e.g., two layers, three layers, etc.). For example, FIG. 4 shows a catheter (401) (discussed in further detail below) comprising an outer catheter wall (457) common to both its proximal section (440) and its distal section (456), as well as an inner reinforcing wall (458) that is provided only for proximal section (440). Outer catheter wall (457) may, for example, comprise one or more flexible polymers. Inner reinforcing wall (458) may be formed, for example, from a braided or woven mesh (e.g., a polymer or metal braided or woven mesh). This may help to stiffen the proximal section (e.g., providing catheter (401) with enhanced pushability). Additional detail regarding catheter (401) is provided below.

In some variations, a catheter may include at least two sections that are formed of different materials and/or that include different numbers of layers. Additionally, certain variations of catheters may include multiple (e.g., two, three) lumens. Catheter lumens and/or walls may, for example, be lined and/or reinforced (e.g., with braiding or winding). The reinforcing structures, if any, may comprise any appropriate material or materials. For example, they may comprise one or more metals and/or non-metals. In certain variations, they may comprise one or more polymers having a relatively high durometer.

Figure 5:
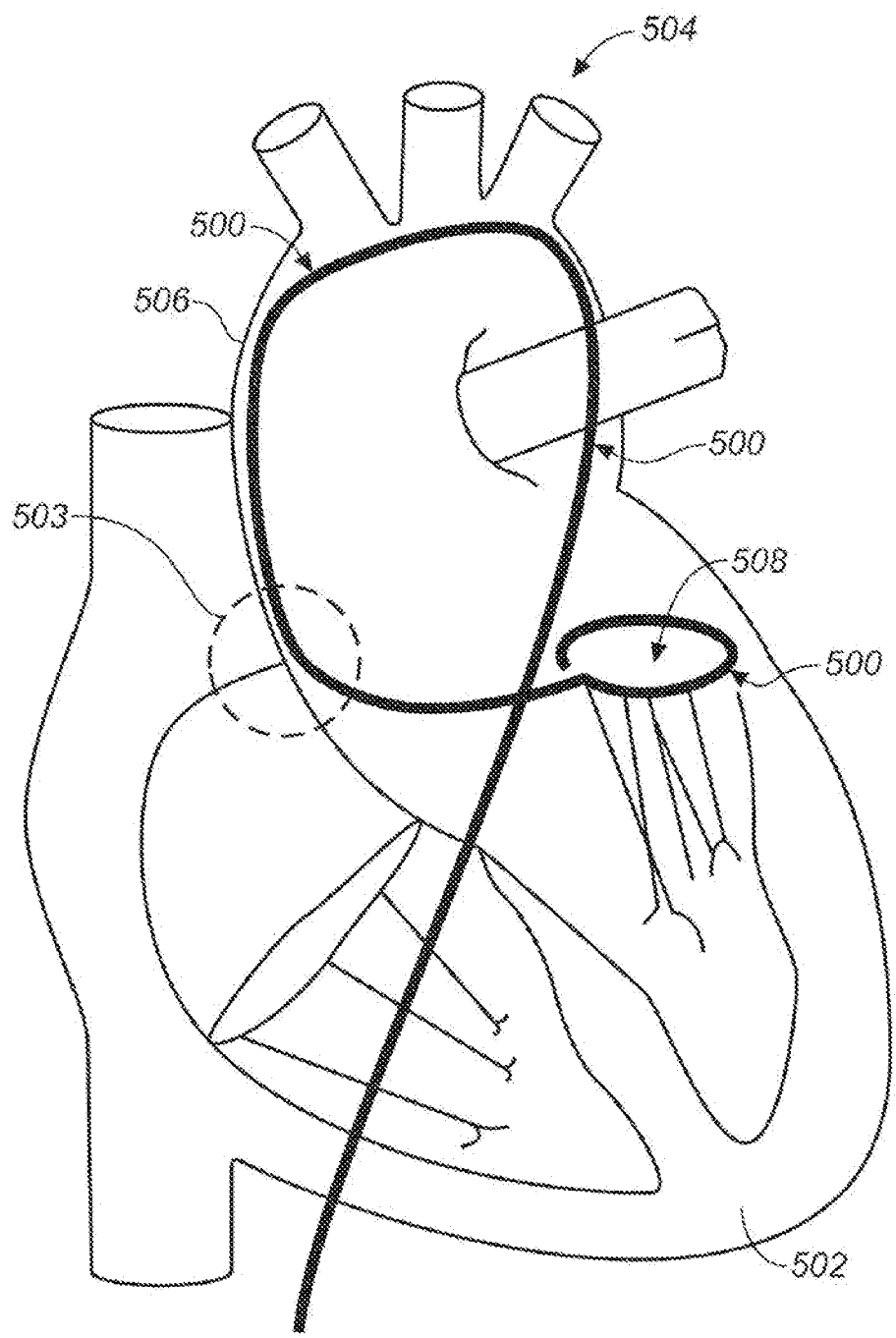
FIG. 5 is an illustrative depiction of a pathway within a heart for a catheter to access a mitral valve region of the heart.

As discussed above, during a mitral valve repair procedure, a diagnostic catheter may be advanced into the subannular valve region along a particular path. The path may, for example, be designed to limit the likelihood of the diagnostic catheter becoming trapped or blocked along the way (e.g., by chordae tendineae). A guidewire may be advanced from the diagnostic catheter and along the subannular groove. FIG. 5 illustrates one variation of a path that may be used by a diagnostic catheter and guidewire. Of course, any path that may be successfully used by a diagnostic catheter may also be appropriate for use by, for example, a guide catheter or a visualization catheter, or any other appropriate catheter.

As shown in FIG. 5, a path (500) follows an anterior approach to the subannular groove region of a heart (502). While an anterior approach is shown, in some variations, a posterior approach may alternatively be used. Path (500) includes bracing points (e.g., bracing point (503)) against the greater curvature of the aortic arch (504) and within the ascending aorta (506). These bracing points may, for example, provide enhanced stability and support to the diagnostic catheter and/or guidewire (e.g., by contacting the tissue wall) when they are advanced and positioned within the heart. The bracing points may also allow the diagnostic catheter to be positioned relatively easily (e.g., with minimal or no adjustment after being routed to the target site). It should be understood that while certain exemplary bracing points are shown, a catheter path may alternatively or additionally include other bracing points. Moreover, any appropriate number of bracing points may be employed, and in some cases a catheter path may not have any bracing points.

FIG. 5 also shows the mitral valve region (508) of heart (502). As shown, path (500) curves along a portion of mitral valve region (508). Although not shown, in some cases a guidewire may be routed around a subannular groove and may cross back across the aortic valve in the antegrade direction. This may, for example, enhance the stability of the guidewire's positioning, and/or may provide an extra indication of whether the guidewire is positioned behind the chordae tendineae (since it may be easier to cross back across the aortic valve if the guidewire is positioned behind the chordae tendineae).

Visualization Devices and Methods

In some instances, one or more variations of methods may be used to visualize the advancement and positioning of a catheter, such as a diagnostic catheter or guide catheter, within the heart. These methods may be used, for example, to help properly position and orient the catheter. In certain variations, one or more of the methods described herein may be used to visualize a subannular groove region of a heart valve, such as a subannular groove region of a mitral valve or a subannular groove region of a tricuspid valve. As discussed below, some of the methods may employ X-ray fluoroscopy to visualize the subannular groove region, while other methods may employ ultrasound techniques. In certain variations, a combination of visualization methods may be used to visualize a subannular groove region. As an example, a method of visualizing a subannular groove region (or another region of a heart, or a non-cardiac region) may use both X-ray fluoroscopy and ultrasound. In X-ray fluoroscopy, X-ray images are obtained using an X-ray source and a detector placed on opposite sides of the patient. The X-ray source irradiates a first side of the patient, and the detector detects X-ray signals transmitted through the patient. In ultrasonography, reflections of high-frequency sound waves are used to form an image of a target site in the body.

In some variations, a visualization method may comprise using fluoroscopic projections to help guide a catheter into a region of a heart, such as a subannular groove region. The method may comprise visualizing the subannular groove region and catheter placement therein using a pattern created by injected contrast agent as a fluoroscopic cue. The method may alternatively or additionally be used to assess guidewire placement in the subannular groove region. For example, a catheter may be advanced to a position proximate to the subannular groove region of a heart valve (e.g., a mitral valve) and a radiopaque contrast agent may be delivered from the catheter (e.g., through a port in the catheter). The presence of the contrast agent in the heart may allow the subannular groove region to be visualized under X-ray fluoroscopy. This, in turn, may allow one or more catheters, other devices, and/or implants to be accurately positioned and/or deployed in the subannular groove region. More specifically, once the contrast agent has been delivered to the subannular groove region, one or more spatial distribution patterns of the contrast agent, such as a series of time-dependent distribution patterns, may be viewed under X-ray fluoroscopy. As an example, a series of spatial distribution patterns may be acquired at spaced-apart time intervals using X-ray fluoroscopy. The position and/or orientation of a catheter may then be determined and/or adjusted based upon the observed spatial distribution patterns of the radiopaque contrast agent.

In some variations of visualization methods, a first catheter may be used to inject one or more radiopaque materials into a subannular groove region of a heart, thereby allowing X-ray fluoroscopy to be used to identify the location of the subannular groove. The first catheter may then be used to guide or position a second catheter within at least a portion of the subannular groove. For example, the first catheter may be inserted at least partially into the subannular groove after the location of the subannular groove has been identified. Then, the second catheter may be advanced over or within the first catheter and into the subannular groove. After the advancement of the second catheter, the first catheter may be withdrawn while the second catheter remains in place, allowing for the insertion of other tools or catheters into the subannular groove via the second catheter.

In some variations, a C-arm X-ray fluoroscope may be used to obtain fluoroscopic images. Examples of commercially available C-arm X-ray fluoroscopes include those provided by GE (e.g., the INNOVA™ X-ray system), Philips (e.g., the Eleva system), and Siemens (e.g., the AXIOM system or the Artis zee multi-purpose system). During use, a C-arm X-ray fluoroscope may be manipulated in certain ways and according to certain parameters, in order to obtain a desired fluoroscopic image.

Figure 6A:
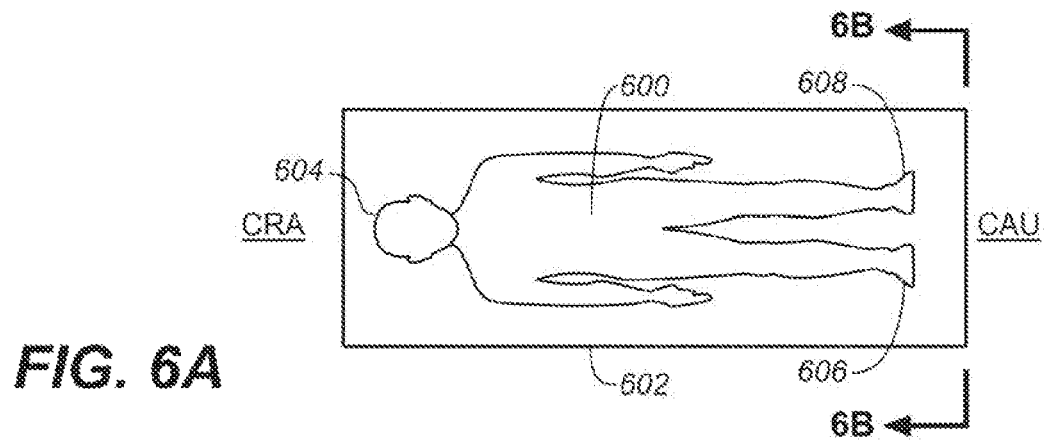
FIG. 6A is an illustrative top view of a subject on an operating table.
Figure 6B:
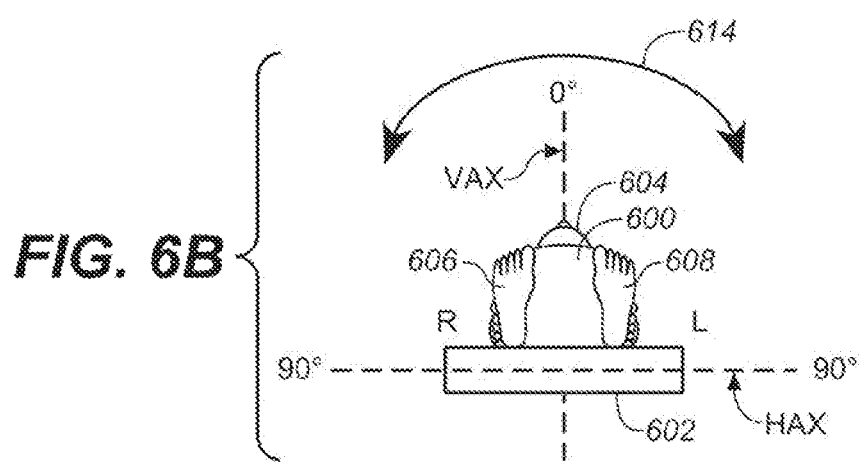
FIG. 6B is an illustrative view of the subject of FIG. 6A, taken along line 6B-6B.
Figure 6C:
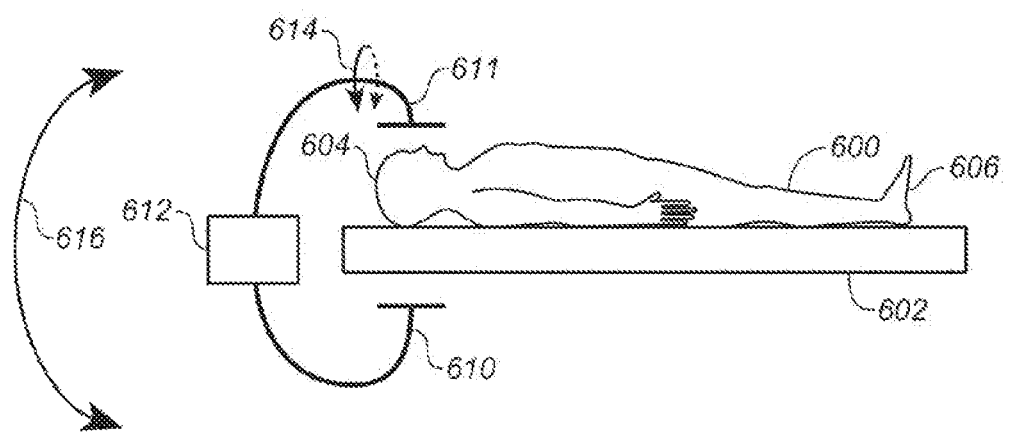
FIG. 6C is an illustrative side view of the subject of FIG. 6A under a variation of a C-arm X-ray fluoroscope.

For example, FIG. 6A is an illustration of a top view of a human subject (600) on an operating table (602), the subject having a head (604) and feet (606) and (608). When the subject is positioned on the operating table, the region in which head (604) is located may be referred to as the cranial region, while the region in which feet (606) and (608) are located may be referred to as the caudal region. Referring also now to FIGS. 6B and 6C, the top portion (611) of the C-arm (610) of a C-arm X-ray fluoroscope (612) may be positioned toward or away from the cranial region during imaging. In other words, top portion (611) may be upright, or may be rotated along arrow (616) (FIG. 6C) by as much as 45°, either toward the cranial region or away from the cranial region. When tilted toward the cranial region, top portion (611) is said to be in a cranial (CRA) orientation. When tilted away from the cranial region, top portion (611) is said to be in a caudal (CAU) orientation.

Additionally, operating table (602) defines a horizontal axis (HAX), as well as a vertical axis (VAX) at a 90° angle with respect to the horizontal axis. As shown in FIG. 6B, the subject has a right side (R) and a left side (L). Top portion (611) of C-arm (610) may be tilted toward right side (R) or left side (L), as indicated by arrow (614) (in which dashed lines indicate that the arrow is going into the plane of the paper), by an angle of at most 90°. In other words, the C-arm may be tilted by as much as 90° to left side (L), or as much as 90° to right side (R). Of course, top portion (611) of C-arm (610) may also tilt by any amount between and including 0° and 90°, to either side. When the top portion of the C-arm is tilted toward left side (L), the angle is considered to be a left anterior oblique (LAO) angle, and when the top portion of the C-arm is tilted toward right side (R), the angle is considered to be a right anterior oblique (RAO) angle.

Figure 6D:
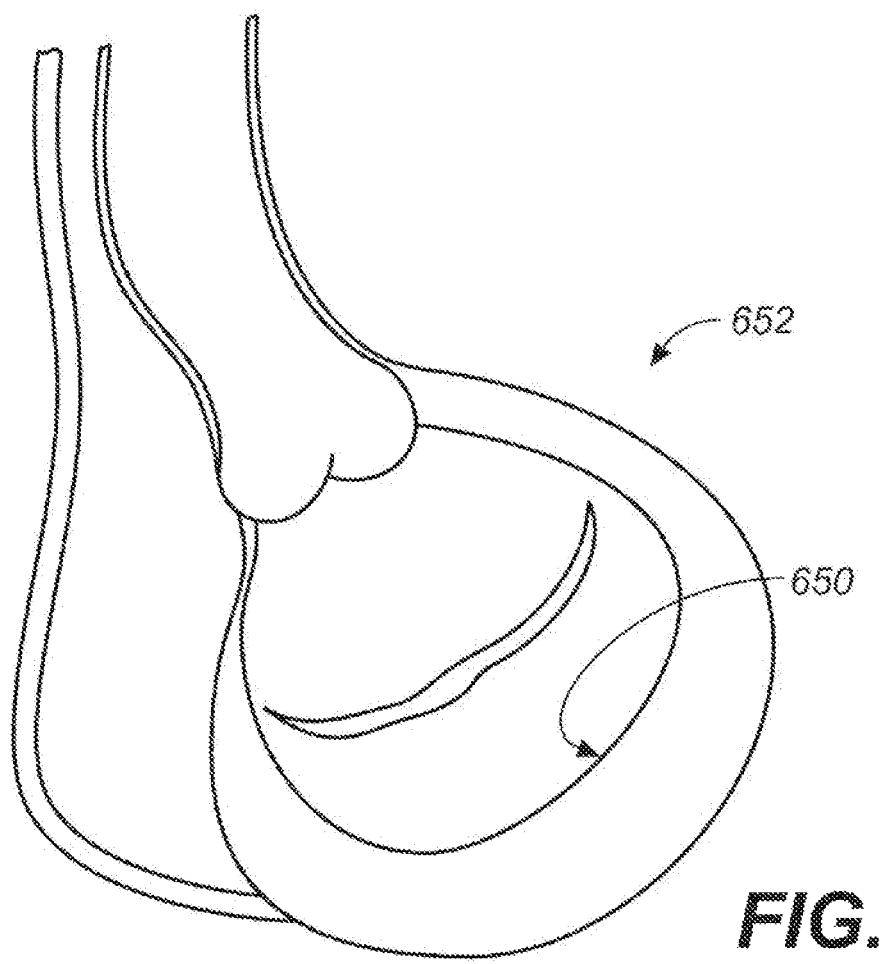
FIG. 6D is an illustrative depiction of a short-axis view of a subvalvular space of a heart, looking up at the mitral valve.

FIG. 6D shows an illustration of a short-axis view of a mitral valve subvalvular space (650) of a heart (652). As used herein, a "short-axis view" refers to an en face perspective view of the ventricular space below either the mitral valve or the tricuspid valve. It should be noted that the imaging methods described here with respect to the mitral valve may also be applied to the tricuspid valve—however, the angles or projections for the tricuspid valve may be different from those for the mitral valve.

When it is desired to provide a short-axis view using a C-arm X-ray fluoroscope, the subject may be positioned in the supine position, and the fluoroscope may be oriented in a left anterior oblique (LAO)/caudal (CAU) orientation. In some variations in which an LAO/CAU orientation is used, the minimum LAO value may be 30° and/or the maximum LAO value may be 50°. Alternatively or additionally, in certain variations in which an LAO/CAU orientation is used, the minimum CAU value may be 1° and/or the maximum CAU value may be 30°. Another orientation that may be used to provide a short-axis view is the left anterior oblique (LAO)/cranial (CRA) orientation. In some variations in which an LAO/CRA orientation is used, the LAO value may be 48° and/or the CRA value may be 0°. Other appropriate values may also be used.

Figure 6E:
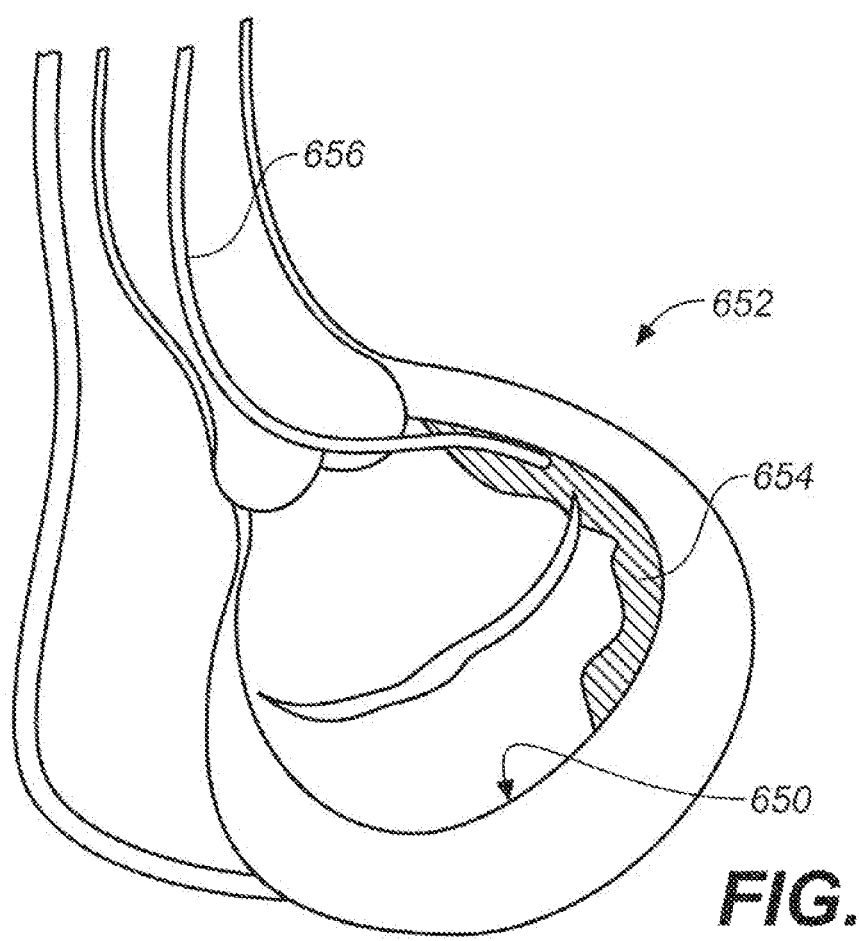
FIG. 6E is the short-axis view of FIG. 6D, with a variation of a catheter advanced into the subvalvular space of the heart, and used to inject contrast agent into the subvalvular space.

FIG. 6E shows a short-axis view of mitral valve subvalvular space (650) upon injection of a radiopaque contrast agent (654) from a catheter (656). The resulting image may be used to position, and/or to verify the positioning of, another catheter (not shown) within the subannular groove. For example, a guide catheter or an anchor deployment catheter may be positioned using the image.

Figure 6F:
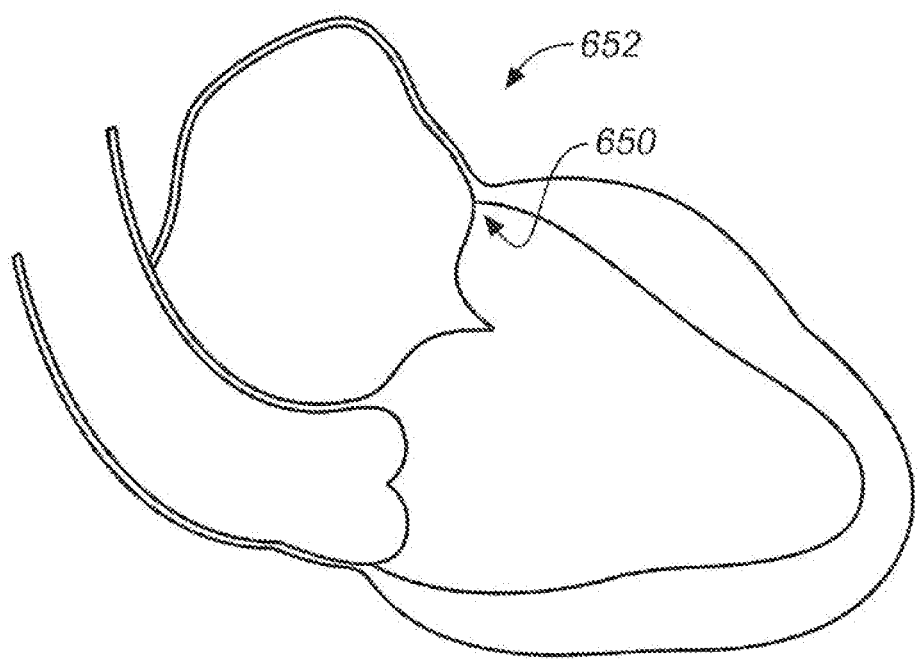
FIG. 6F is an illustrative depiction of a long-axis view of a subvalvular space of a heart.

FIG. 6F shows a long-axis view of mitral valve subvalvular space (650). As used herein, a "long-axis view" refers to a profile perspective of the ventricular space below either the mitral valve or the tricuspid valve. When it is desired to provide a long-axis view using a C-arm X-ray fluoroscope, in certain variations, the fluoroscope may be positioned in a right anterior oblique (RAO) orientation. In some variations in which an RAO/CAU orientation is used, the minimum RAO value may be 35° and/or the maximum RAO value may be 44°. Alternatively or additionally, in certain variations in which an RAO/CAU orientation is used, the minimum CAU value may be 0° and/or the maximum CAU value may be 3°. In some variations in which an RAO/CRA orientation is used, the minimum RAO value may be 0° or 30°, and/or the maximum RAO value may be 61° or 50°. In certain variations in which an RAO/CRA orientation is used, the minimum CRA value may be 0° and/or the maximum CRA value may be 50° or 4°. The appropriate angle range for any of the orientations described herein may depend, for example, on the characteristics of the particular subject's anatomy that is being imaged.

Figure 6G:
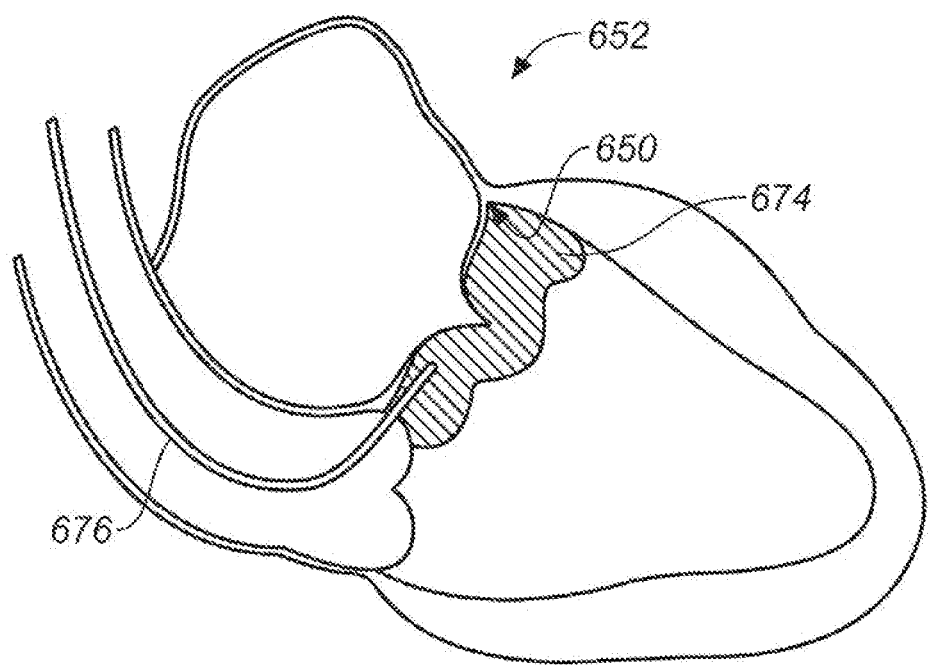
FIG. 6G is the long-axis view of FIG. 6F, with a variation of a catheter advanced into the subvalvular space of the heart, and used to inject contrast agent into the subvalvular space.

FIG. 6G shows a long-axis view of mitral valve subvalvular space (650) when radiopaque contrast agent (674) is injected into mitral valve subvalvular space (650) using a catheter (676). The resulting fluoroscopic image may be used to position, and/or to verify the positioning of, catheter (676) and/or one or more other devices (e.g., catheters) within the subannular groove. For example, the image may be used to position a guide catheter or an anchor deployment catheter.

In some variations, a physician or other operator may alternate between short- and long-axis views of a subvalvular space in order to obtain accurate positioning of a catheter within the subvalvular space. For example, a physician may start with a short-axis view (e.g., using an LAO/CAU orientation), and then may switch to a long-axis view (e.g., using an RAO/CRA orientation). Alternatively, the physician may start with a long-axis view and then switch to a short-axis view. A physician or other operator may switch back and forth between different views until the desired positioning has been achieved.

FIGS. 7A-7C and 8A-8F further illustrate the use of a radiopaque contrast agent to visualize the subannular groove of a heart. As previously described, during such a visualization procedure, a catheter may inject radiopaque contrast agent into the subannular groove of a heart. The contrast agent may, for example, be delivered from the catheter through a delivery port. In some variations, the delivery port of the catheter may be in the form of an opening in a wall portion of the catheter proximal to the distal end or tip of the catheter, or may be in the form of an opening in the distal end or tip itself. If the delivery port is not inserted against or into the subannular groove, contrast agent delivered through the delivery port may diffuse out into the left ventricular chamber. This diffusion of the contrast agent may function as a visual indication (under X-ray fluoroscopy) that the catheter is not properly seated in or against the subannular groove. If, on the other hand, the contrast agent is channeled into the subannular groove when the contrast agent is delivered into the heart, then this may indicate that the catheter is properly seated in or against the subannular groove.

Figure 7A:
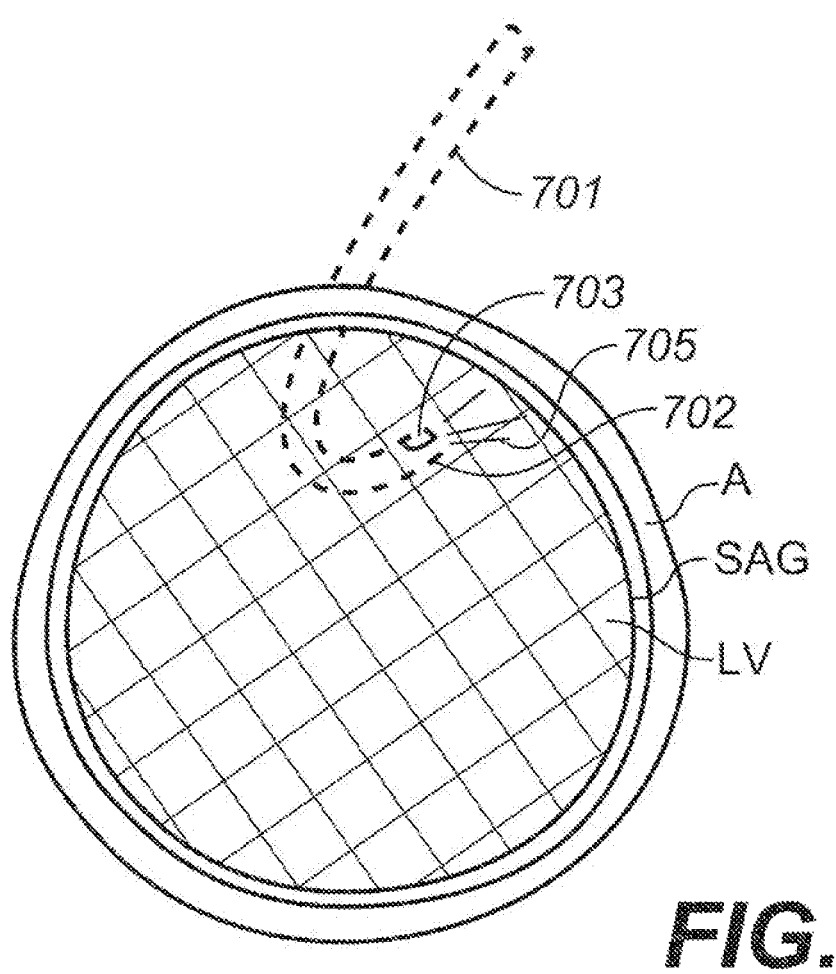
FIGS. 7A-7C depict a variation of a method for visualizing a subannular groove region of a heart using contrast agent.
Figure 7B:
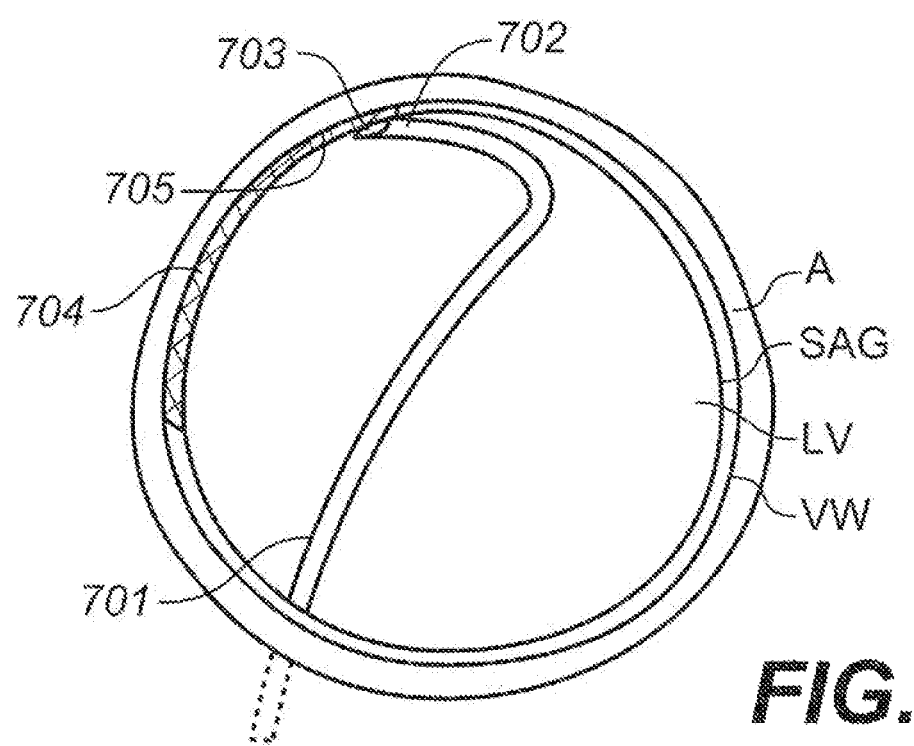
Figure 7C:
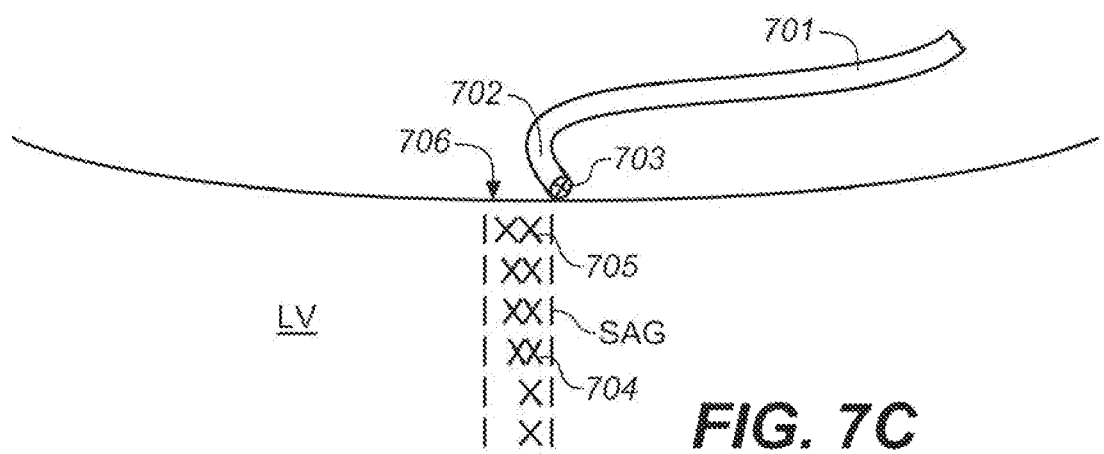

FIGS. 7A-7C provide an illustrative depiction of an exemplary visualization method. First, FIG. 7A provides a short-axis view of an annulus (A) and the corresponding subannular groove (SAG). In FIG. 7A, a catheter (701) has accessed the left ventricle (LV), but the delivery port (703) at the distal end (702) of catheter (701) is not seated in or against the subannular groove (SAG). As a result, when contrast agent (705) is delivered through delivery port (703), the contrast agent diffuses throughout the left ventricular chamber, as indicated by the hatched region. Conversely, and as illustrated in the short-axis view provided in FIG. 7B and the long-axis view provided in FIG. 7C, if delivery port (703) is seated in or against the subannular groove, as contrast agent (705) is ejected out of delivery port (703), the contrast agent will trace out a defined streak or arc (704) in the subannular groove, indicated by cross-hatching. Under X-ray fluoroscopy, this streak or arc (704) provides a visual indication of proper positioning of catheter (701) in or against the subannular groove (SAG).

When a distal portion (e.g., the distal end) of a catheter is radiopaque, the position of the distal portion relative to the ventricular wall and subannular groove may be determined by its position within the contrast pattern (e.g., streak or arc) created by injecting radiopaque contrast agent into the subannular groove. For example, referring to the short-axis view shown in FIG. 7B, the outer periphery of streak or arc (704) defines the interior surface of the left ventricular wall (VW) (endocardium), which is proximate to the annulus. Thus, in the short-axis view, as radiopaque distal end (702) of catheter (701) gets closer to the ventricular wall or annulus, the amount of contrast between distal end (702) and the outer periphery of contrast streak or arc (704) will decrease. Similarly, and referring to the long-axis view shown in FIG. 7C, the closer radiopaque distal end (702) of catheter (701) is to the ventricular wall and therefore to the annulus, the less contrast there will be between the superior border (706) of streak or arc (704) and radiopaque distal end (702) of catheter (701).

Any suitable radiopaque contrast agents may be used in the methods described here. Generally, radiopaque contrast agents may be used in any way that improves the ability to distinguish certain tissue (e.g., the subannular groove region) from other tissue, or any portion of an implant, catheter, anchor deployment device, tool or the like from the subannular groove region or other tissue. Radiopaque contrast agents increase the absorption of X-rays and result in a positive contrast in X-ray fluoroscopy (i.e., an opaque image or shadow where the radiopaque contrast agent is present). Radiopaque contrast agents typically may include any soluble or insoluble compound that increases absorption of X-rays. Some variations of radiopaque contrast agents may comprise iodine. For example, a contrast agent may comprise an aqueous solution of one or more iodine-containing salts, such as: a salt of a diatrizoate (e.g., sodium diatrizoate such as HYPAQUE™ contrast medium, or sodium meglumine diatrizoate such as RENOGRAFIN-76™ contrast medium); a salt of 5-acetamido-2,4,6-triiodo-N-methyl-isophthalamic acid (e.g., the N-methylglucamine salt, meglumine iothalamate (e.g., CONRAY™ contrast agent)); a salt of acetrizoate (e.g., sodium acetrizoate such as URO-KON™ contrast medium); a salt of 3-5-diiodo-4-pyridone-N-acetic acid (e.g., the diethanolamine salt, iodopyracet such as DIODRAST™ contrast medium); or a salt of ioxaglate (e.g., sodium meglumine ioxaglate such as HEXABRIX™ contrast medium). In certain variations, combinations of radiopaque contrast agents may be used. As an example, an aqueous solution of diatrizoate meglumine and diatrizoate sodium may be used in some instances. In some variations, nonionic radiopaque contrast agents may be used. For example, iohexol (e.g., OMNIPAQUE™ contrast agent) and iodixanol (e.g., VISIPAQUE™ contrast medium) may be used in aqueous solution.

The type of contrast agent that is used, as well as its concentration, may be selected based on any of a variety of different factors, such as the X-ray absorption properties of the radiopaque compound (e.g., determined in part by the number of iodine atoms), the irradiation scheme and image capture scheme to be used (e.g., the intensity of the X-ray irradiation used to form the image, the time duration of the X-ray acquisition, the type of detector used, and the degree of contrast desired), and/or other issues specific to the patient (e.g., kidney disease, or the presence of other systemic drugs). In some cases in which a significant amount of radiopaque contrast agent is desirable, a contrast agent filter may be used (e.g., to minimize kidney damage).

Figure 8A:
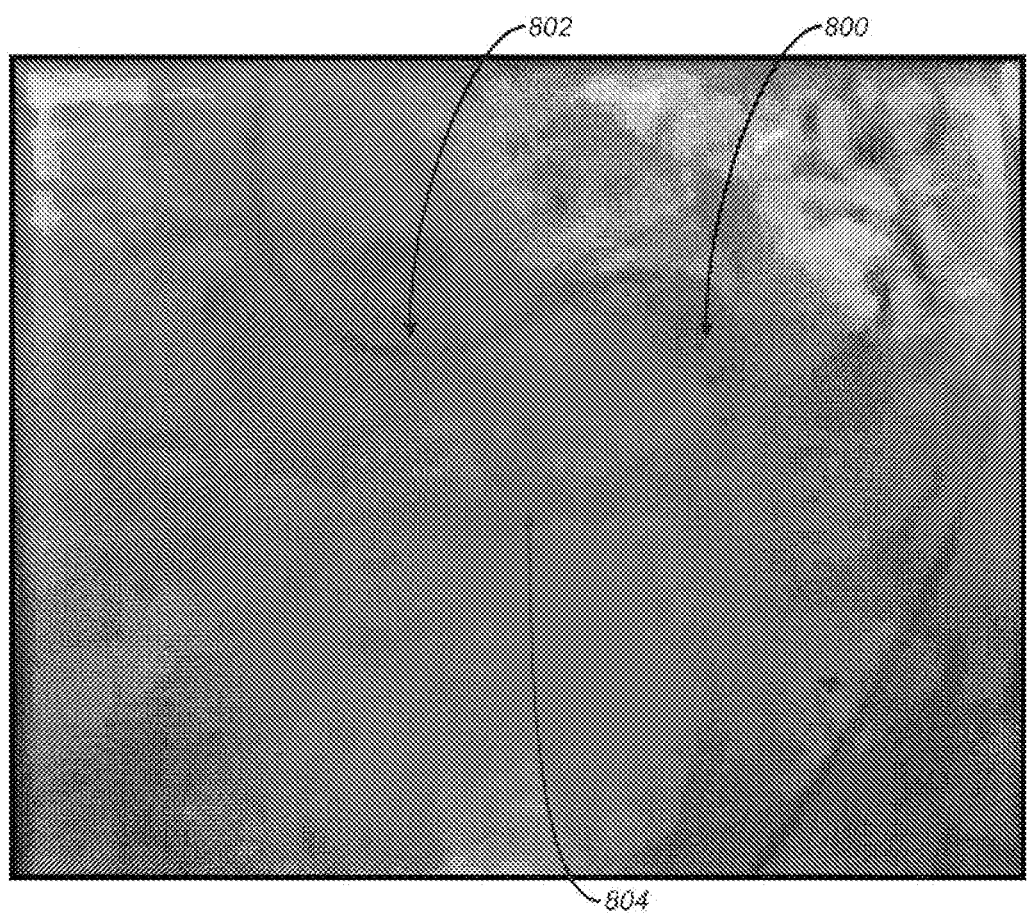
FIG. 8A is a fluoroscopic image (short-axis view) of a subvalvular space of a heart after contrast agent has been injected into it.
Figure 8B:
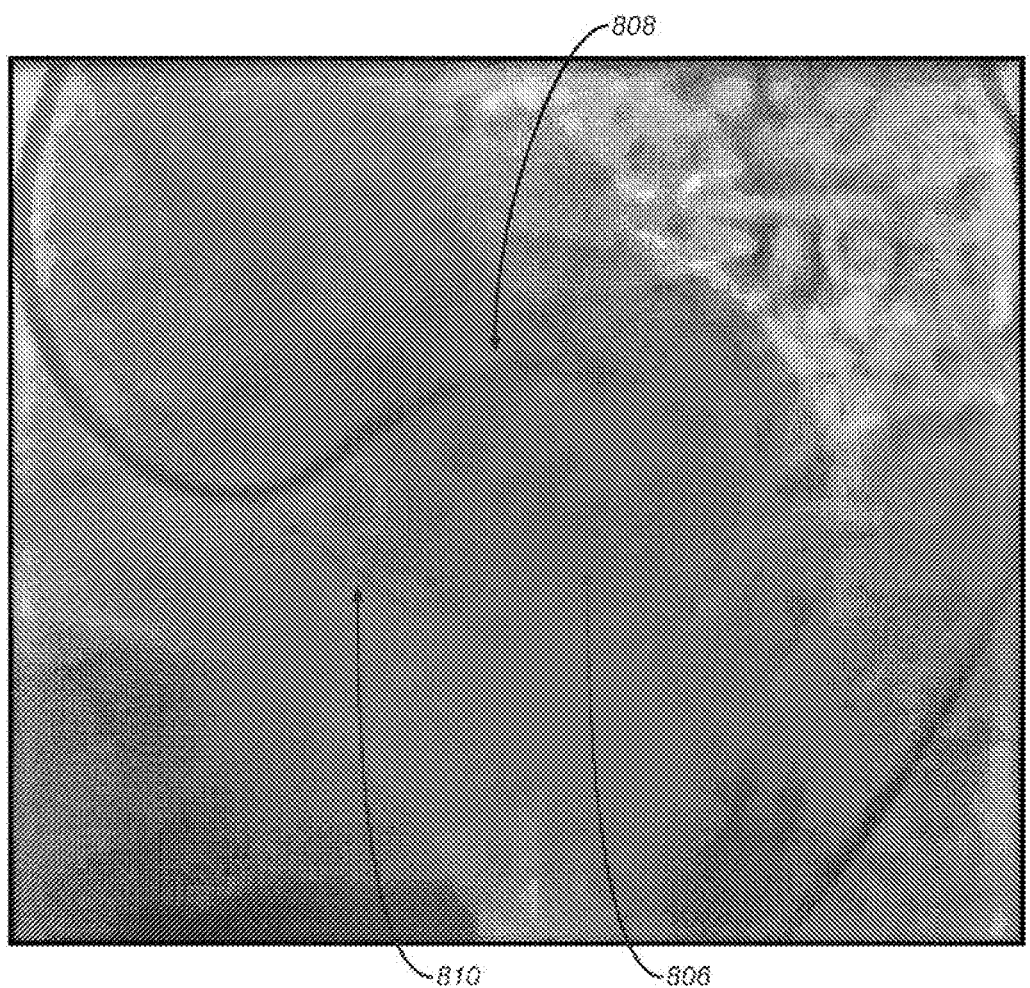
FIG. 8B is another fluoroscopic image (short-axis view) of a subvalvular space of a heart after contrast agent has been injected into it.
Figure 8C:
FIG. 8C is a fluoroscopic image (short-axis view) of a guide catheter positioned in a subannular groove of a heart, with an accompanying injection of contrast agent.

FIG. 8A is a fluoroscopic image of a short-axis view of a subannular groove obtained using a radiopaque contrast agent. As shown there, contrast agent (800) has been injected into the subannular groove, and a guide catheter (802) and guidewire (804) have been positioned in the subannular groove. Guidewire (804) circumnavigates the subannular groove. The alignment of the guide catheter and the guidewire with the edge of the contrast agent is indicative of proper positioning of the guide catheter and guidewire in the subannular groove. Similarly, FIG. 8B is another fluoroscopic image of a short-axis view of a subannular groove obtained using a radiopaque contrast agent (806). As shown there, a catheter (808) and a guidewire (810) have been positioned in a subannular groove, as indicated by the alignment of catheter (808) and guidewire (810) with the edge of contrast agent (806). As shown in FIG. 8B, guidewire (810) circumnavigates the subannular groove. FIG. 8C is an additional fluoroscopic image of a short-axis view of a subannular groove showing the positioning of a guide catheter (812) such that the guide catheter is aligned relative to an accompanying injection of contrast agent. FIG. 8E is a fluoroscopic image of a long-axis view of a subvalvular space of an ovine heart (beneath the mitral valve), in which a catheter (850) is positioned. FIG. 8F is a fluoroscopic image of a short-axis view of a subannular groove region of an ovine heart, showing the position of a catheter (862) and a guidewire (864) in the subannular groove region.

In some variations of methods, one or more radiopaque contrast agents may be injected into a subannular groove region of a heart to help identify the location of an implant (all or a portion of which may be radiopaque) in the subannular groove region. First, X-ray fluoroscopy may be used to obtain one or more spatial distribution patterns of the radiopaque contrast agent or agents. Then, the distribution pattern or patterns may be used to visualize a location and/or orientation of an implant (e.g., an anchor) relative to the subannular groove region. Where a radiopaque image of the implant does not overlap with the radiopaque streak or arc from the contrast agent(s), that portion of the implant has not been reached by the streak. For example, that portion of the implant may be located in a region that is inaccessible by the streak (e.g., embedded into a ventricular wall or located outside of the subannular groove). Any suitable implant or combination of implants having sufficient radiopacity may be viewed in this way. Some viewable implants may comprise at least one anchor, such as two or more anchors (e.g., that are coupled together by a tether). One or more of the anchors, or one or more portions thereof, and/or one or more tethers, may be radiopaque. Moreover, in certain variations, all or a portion of a catheter may be radiopaque.

Figure 8D:
FIG. 8D is a fluoroscopic image (short-axis view) of a catheter and implant in a subvalvular space of a heart.
Figure 8E:
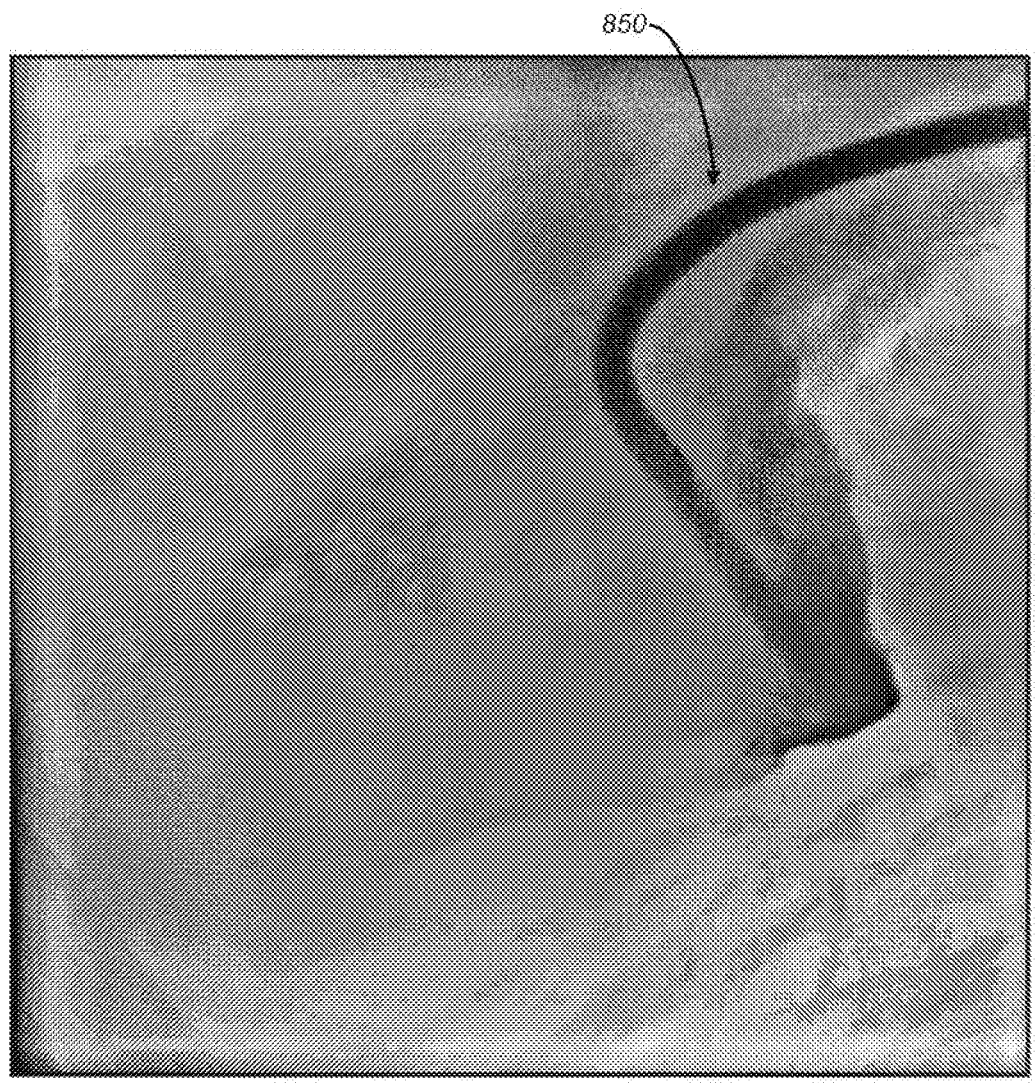
FIG. 8E is a fluoroscopic image (long-axis view) of a subvalvular space in an ovine heart showing placement of a catheter in the subvalvular space.
Figure 8F:
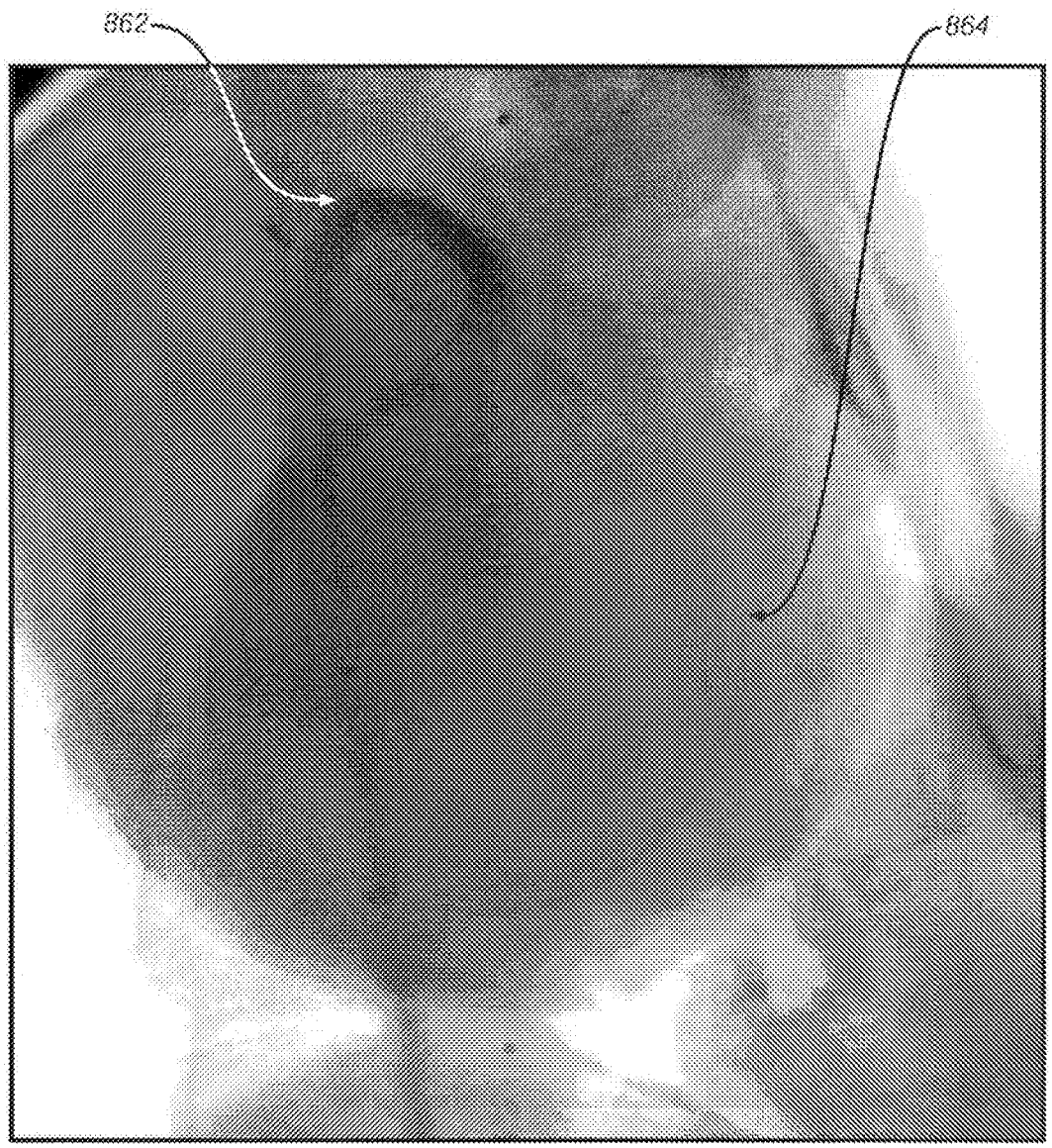
FIG. 8F is a fluoroscopic image (short-axis view) of a subvalvular space in an ovine heart showing placement of a guidewire and a catheter in the subvalvular space.

In some variations, one or more tissue anchors that are at least partially positioned in the subannular groove may be visualized, as illustrated in the short-axis view shown in the fluoroscopic image of FIG. 8D. As shown there, a catheter (890) has been positioned in a subannular groove of a heart, and anchors, such as an anchor (892), have been deployed into the subannular groove region. The positioning of the anchors beyond the edge of the contrast pattern in FIG. 8D indicate that the anchors are embedded in the myocardium, and that they are not exposed to the ventricular chamber.

Implants, portions of implants, catheters, or portions of catheters used in the methods described here may be rendered radiopaque by any suitable method. For example, implants may be formed of one or more biocompatible radiopaque metals or metal alloys, such as Nitinol. Some implants may be coated or partially coated (e.g., by plating or sputtering) with one or more biocompatible metals, such as gold, silver, titanium, tantalum, or alloys thereof. Certain variations of implants may be filled with one or more radiopaque materials, such as barium sulfate ($BaSO_4$), bismuth trioxide ($Bi_2O_3$), or a radiopaque metal. Implants or catheters may be made with a polymer or coated with a polymer or ink that contains a radiopaque material, such as a polymer composite containing metal markers (e.g., tungsten markers) and/or another radiopaque material such as barium sulfate or bismuth trioxide. Polymers used to make implants or catheters radiopaque may also have chemically bound radiopaque moieties (e.g., iodine-containing moieties), to reduce the possibility of the radiopaque material leaching into surrounding areas.

Figure 9:
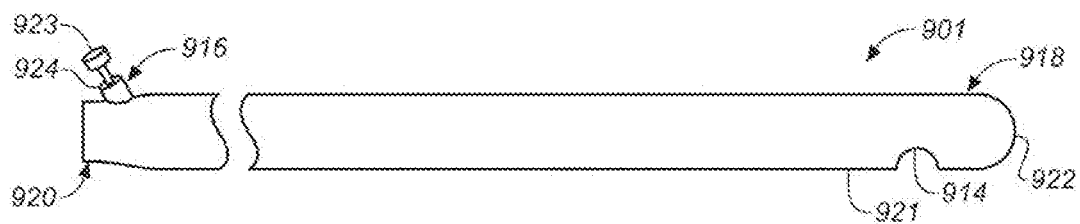
FIG. 9 is a side view of a variation of a catheter that may be used to deliver contrast agent to a target site in a heart.

Any appropriate catheter or other device may be used to deliver radiopaque material, such as radiopaque contrast agent, to a target region (e.g., a subannular groove) in a heart. For example, FIG. 9 shows a variation of a catheter (901) that may be used to deliver radiopaque contrast agent to a subannular groove region of a heart. Catheter (901) may be flexible and/or steerable. As shown in FIG. 9, catheter (901) has a delivery port (914) in its distal portion (918), near its distal end (922). Delivery port (914) is configured to deliver one or more contrast agents therethrough. Although FIG. 9 depicts delivery port (914) as positioned along a side wall (921) of catheter (901) near distal end (922), other variations of catheters may include one or more contrast agent delivery ports positioned in their distal end. Catheter (901) also comprises an input port (916) near its proximal end (920). While not shown here, some variations of catheters may alternatively or additionally comprise one or more input ports located at their proximal end, and/or in one or more other locations of the catheter. Input port (916) includes a plunger (923) adapted to force one or more liquids into and through a tube or syringe body (924), so that the liquid eventually exits the catheter through delivery port (914). While one variation of an input port has been shown, other variations of input ports, including input ports suitable for injecting a solution, may be used as appropriate.

Methods for visualizing a heart valve region, such as the subannular groove region, as well as implants and/or devices within the heart valve region, may employ any suitable image capture techniques. As described above, in some variations, X-ray images may be obtained using X-ray fluoroscopy. In certain variations, more than one irradiation angle may be used to obtain X-ray images. For example, as shown in FIGS. 7A-7C and 8A-8F, images may be collected along the short axis and/or long axis of a patient's heart.

In certain variations, images taken from multiple angles may be used to construct a three-dimensional image of a heart valve region, such as the subannular groove, surrounding anatomy, and/or implants. In addition, X-ray fluoroscopy may be used to create a real-time image (i.e., as the radiopaque substance is injected into the patient). X-ray fluoroscopy may also be used to create a series of time-dependent images (e.g., at time intervals of 60 Hz, 30 Hz, 10 Hz, 1 Hz, 0.5 Hz, or 0.1 Hz), to visualize the time-dependent dispersion of the radiopaque material throughout the patient. Images may be sampled at regularly spaced time intervals in an automated manner, or in any sequence of predetermined intervals. For example, the intervals may be programmed into a controller of an X-ray fluoroscopy system and/or may be provided in a sequence manually determined by an operator (e.g., a physician). The X-ray fluoroscopy signals and/or images produced from X-ray fluoroscopy signals may be analyzed or processed digitally and/or using analog techniques. Any suitable method or combination of methods (e.g., amplification, filtering to enhance contrast or reduce noise, extraneous signals, scattered signals, or the like, or image correction to account for geometrical effects, or the like) may be employed. In certain variations, the acquisition of X-ray images may be synchronized (e.g., triggered) with the delivery of the radiopaque material to allow for more precise determination of time-dependent measurements.

In some variations, a fluoroscopic visualization method may employ both short- and long-axis views in assessing placement of a catheter in a subannular groove region (e.g., in the subannular groove itself) of a heart. As discussed above, the short-axis view generally provides an en face perspective of the ventricular space below the mitral valve, while the long-axis view generally provides a profile perspective of the ventricular space below the mitral valve. When these two views are imaged, injection of contrast agent into the imaged site will generally highlight the border between the ventricular wall and the ventricular chamber. The catheter may then be referenced against the contrast pattern to determine whether the catheter is, for example, well-apposed against the endocardium, lodged or deployed in the myocardium, level with the mitral valve, or diverging from the mitral valve. Devices that are advanced through the catheter and around the subannular groove should generally be aligned with the edges of the contrast patterns provided by the short- and long-axis views. Thus, the contrast patterns may be used to determine whether alignment is proper.

Guidewire placement may also be evaluated using the above method. Typically, a guidewire that has successfully circumnavigated the subannular groove (and, in some cases, that crosses the aortic valve in the antegrade direction) will be aligned with the edge of the short-axis view in the contrast pattern and will be very stable. This alignment may also provide a strong indication that the guidewire is apposed against the endocardium, and that it does not interfere with the chordae tendineae. Lack of alignment of the guidewire with the contrast pattern in the short-axis view may be indicative of interference with chordae tendineae or migration toward the center of the ventricular chamber. Additionally, dynamic behavior showing a lack of stability of the guidewire may also suggest that the guidewire is not entirely situated behind the chordae tendineae and against the endocardium.

While visualization methods using X-ray fluoroscopy have been described, other variations of methods may alternatively or additionally be used to visualize a region of a heart. As an example, ultrasonography may be employed to visualize a region of a heart. For example, in some variations, a visualization method may include advancing a catheter (e.g., a steerable catheter) to a position proximate to or at least partially within the subannular groove of a heart valve. The catheter may comprise at least one ultrasonic transducer or probe (e.g., positioned within at least one lumen of the catheter and/or in a distal portion of the catheter). The transducer may be temporarily or permanently coupled (e.g., secured, joined, or linked) to the catheter. During use, the transducer may transmit and receive ultrasonic energy, thereby allowing for visualization of structures proximate the transducer (e.g., anatomy such as the subannular groove or structures surrounding the subannular groove, implants, the catheter, and the relative positions thereof, such as the relative positions of the anatomy and the catheter). In some variations, a method may include visualizing the location and/or orientation of a catheter, and determining and/or adjusting the position of the catheter accordingly. The catheter may continue to be adjusted until the desired orientation and position have been achieved.

The ultrasonic transducer or transducers may be used to visualize and/or position the catheter at a target site, such as in the subannular groove of the mitral valve or tricuspid valve. In some variations, the visualization catheter may be a pre-formed or pre-shaped catheter, or a steerable catheter that may provide enhanced control and placement of the ultrasonic transducer (and, therefore, enhanced viewing). In some variations of methods, the subannular groove of a heart valve region may be circumnavigated with the distal end of a visualization catheter to visualize the surrounding region (e.g., the subannular groove itself, the anatomy surrounding the subannular groove such as the annulus or the mitral valve, and/or implants near or in the subannular groove, such as implants used to repair a heart valve annulus).

Figure 10:
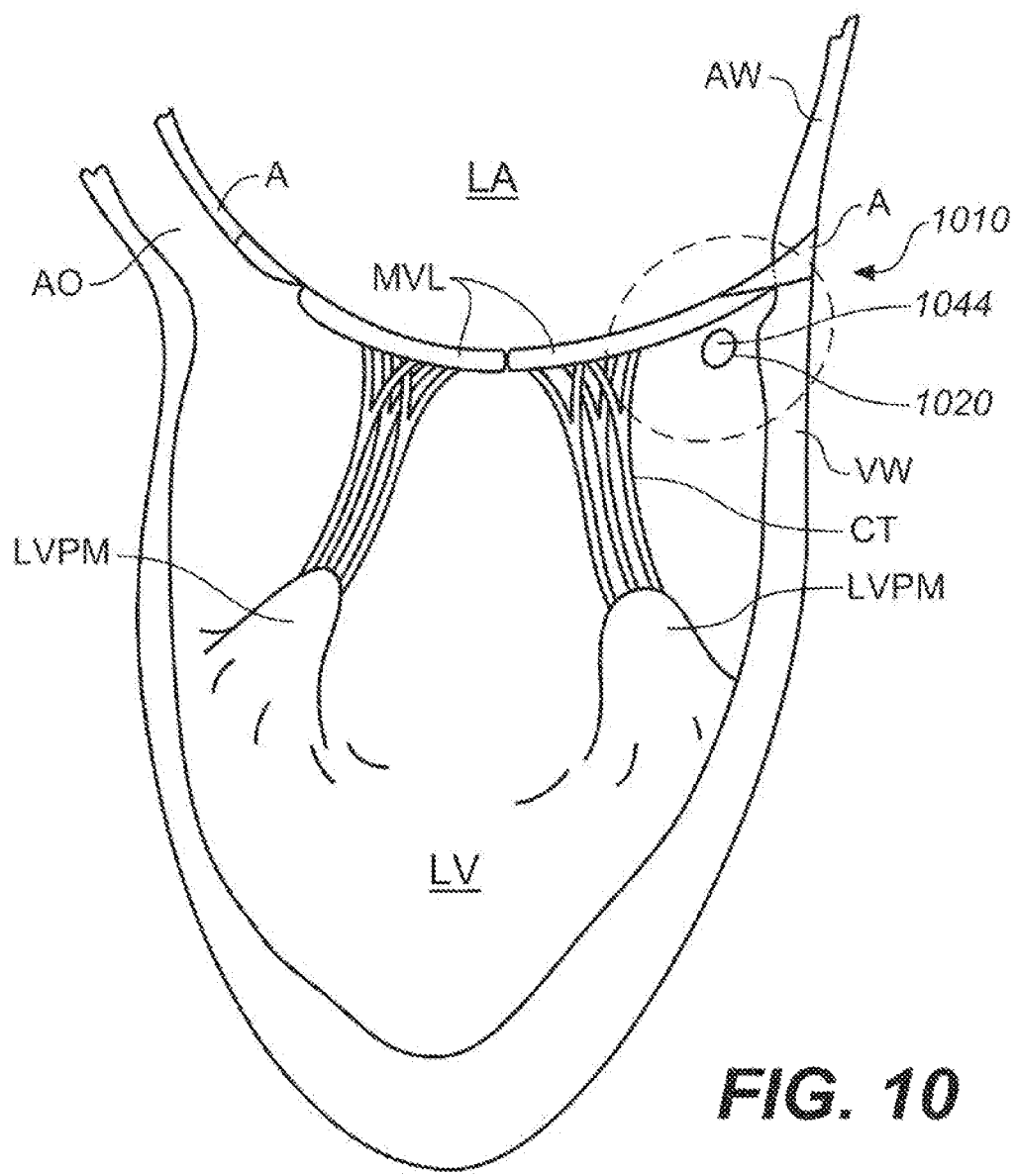
FIG. 10 depicts a variation of a method for visualizing a subannular groove of a heart (and the surrounding area) using ultrasound.

FIG. 10 is an illustrative depiction of a portion of a heart, showing a catheter (1020) comprising an ultrasonic transducer (1044). As shown there, catheter (1020) (and, therefore, ultrasonic transducer (1044)) has been positioned in the subannular groove in the left ventricle (LV) of the heart, generally below the annulus (A) and between the ventricular wall (VW) and chordae tendineae (CT). The area enclosed by the dashed contour (1010) in FIG. 10 is a cross-section of the localized field of view provided by ultrasonic transducer (1044). This localized field of view may be used, for example, to establish the catheter's position with respect to the endocardium and/or the mitral valve. The catheter may be guided into the subannular groove using signal output (e.g., real-time output) from the transducer. The location and/or orientation visualized with the transducer may be used to determine the position of the catheter and/or to adjust the position of the catheter relative to the valve leaflets, chordae tendineae, and/or other anatomy. For example, the visualized location or orientation may be used to position and/or steer the catheter beneath the mitral valve leaflets and behind chordae tendineae.

Any suitable ultrasonic transducer or combination of ultrasonic transducers may be used in the methods described here. For example, piezoelectric transducers or capacitive micro-electromechanical ultrasonic transducers may be used. In some variations, the transducers may operate (i.e., emit and detect ultrasound frequencies) at about 5 MHz, about 10 MHz, about 15 MHz, about 20 MHz, about 25 MHz, about 30 MHz, about 35 MHz, about 40 MHz, about 45 MHz, or about 50 MHz. A higher frequency transducer may be used where greater contrast is required. Moreover, transducers having any of a variety of appropriate physical dimensions may be used. For example, in some variations, a transducer may be sized so that it can be disposed within a catheter (e.g., within a lumen of the catheter). As an example, in certain variations, a transducer may have a cross-sectional dimension that allows it to be disposed within a catheter having an inner diameter of about 0.5 millimeter to about 8 millimeters (e.g., about 0.5 millimeter, about 0.6 millimeter, about 0.7 millimeter, about 0.8 millimeter, about 0.9 millimeter, about 1.0 millimeter, about 1.1 millimeters, about 1.2 millimeters, about 1.3 millimeters, about 1.4 millimeters, about 1.5 millimeters, about 2 millimeters, about 3 millimeters, about 4 millimeters, about 5 millimeters, about 6 millimeters, about 7 millimeters, or about 8 millimeters). In some variations, the size of a transducer may be selected according to the desired spatial resolution. For example, a relatively small transducer may be used to visualize relatively small features of the anatomy in or surrounding the subannular groove of a heart, and/or relatively small features of implants. In certain variations, a transducer may be positioned within a catheter, facing radially outward from the center of the catheter. In some variations, a transducer may be rotated and or translated substantially independently of a catheter. For example, the transducer may be secured to a connector threaded through a lumen of the catheter. The transducer may be translated by translating the connector along the length of the catheter. Alternatively or additionally, the connector may be rotated to rotate the transducer around an axis defined by the connector, without causing corresponding movement by the catheter body.

Some variations of catheters may comprise more than one ultrasonic transducer (e.g., to expand the viewable area). For example, a catheter may comprise an array of transducers. Transducers may be arranged in a longitudinal array (e.g., along an axis generally parallel to the length of the catheter) and/or in a ring-like array (e.g., circumferentially around the distal tip of the catheter, where each transducer's output is generally emitted in a distal direction or radially outward from the catheter). Other appropriate transducer arrangements may also be used. In variations in which more than one transducer is used, each transducer may be individually addressable. Moreover, in certain variations incorporating more than one transducer, some transducers may be used to transmit ultrasonic energy, while other transducers may be used to receive reflected ultrasonic energy from surrounding structures.

Additional variations of methods are described here. These methods may be used to ascertain or verify the position of a guide catheter in a subannular groove of a heart, and/or to position a guide catheter in the subannular groove. In some variations, a method may comprise advancing a first catheter comprising an ultrasonic transducer distally through a guide catheter positioned in the vicinity of the subannular groove of a heart valve. The first catheter may be advanced sufficiently through the guide catheter such that the ultrasonic transducer extends beyond a distal end of the guide catheter. The ultrasonic transducer may then be used to view or verify the location of the guide catheter relative to a region surrounding the distal end of the first catheter by transmitting and receiving ultrasonic energy. The viewable region may include, for example, the subannular groove, anatomical structures near the subannular groove (e.g., the annulus or the mitral valve), implants positioned near or in the subannular groove, and/or portions of the first catheter and the guide catheter.

In some variations, the first catheter may alternatively or additionally be used to position or adjust the position of the guide catheter in the subannular groove. In some such variations, after the first catheter has been advanced distally through the guide catheter such that the transducer extends distally from the distal end of the guide catheter, the first catheter may be advanced to a position proximate to, or at least partially within, the subannular groove. The transducer may be used to visualize a region in and/or around the subannular groove. The guide catheter may then be advanced to a position proximate to or at least partially within the subannular groove by sliding the guide catheter along the first catheter. In certain variations, once the guide catheter is positioned as desired within the subannular groove, the first catheter may be withdrawn. The guide catheter may then be used to access the subannular groove with other catheters, devices, and/or tools.

Figure 11A:
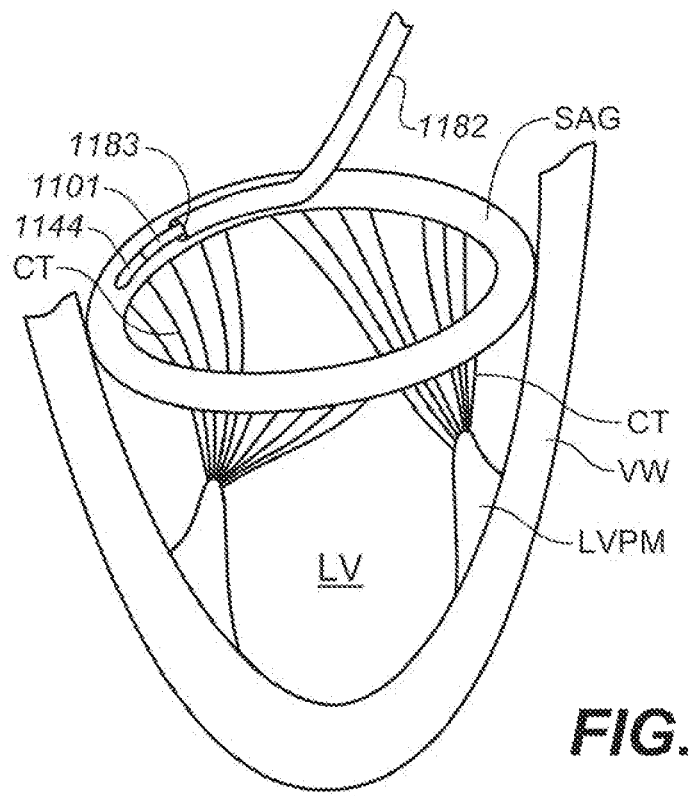
FIGS. 11A and 11B illustrate a variation of a method for accessing a subannular groove of a heart using ultrasound.
Figure 11B:
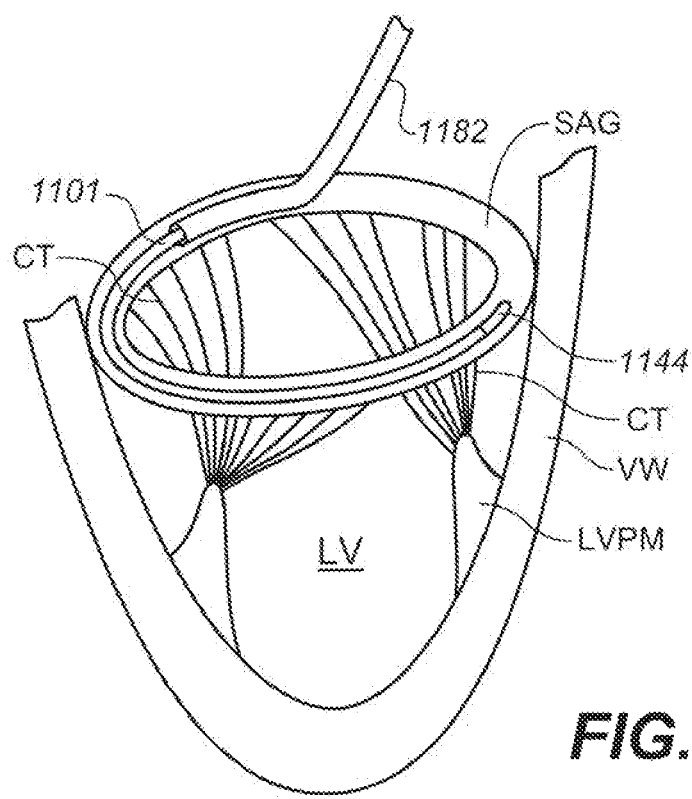

As an example, FIG. 11A depicts the advancement of a visualization catheter (1101) through a guide catheter (1182). As shown there, visualization catheter (1101), which comprises an ultrasonic transducer (1144), is distally advanced until ultrasonic transducer (1144) extends just beyond the distal end (1183) of guide catheter (1182). Once so positioned, ultrasonic transducer (1144) may be used to view the surrounding anatomy. In some variations, images from ultrasonic transducer (1144) may be used to position the combined visualization catheter (1101) and guide catheter (1182) within the subannular groove. Referring now to FIG. 11B, visualization catheter (1101) may be circumnavigated around the subannular groove. As visualization catheter (1101) is threaded through the subannular groove, nearby anatomical structures and implants may also be imaged. Further, guide catheter (1182) may be extended through the subannular groove (e.g., along with visualization catheter (1101) or over visualization catheter (1101), with visualization catheter (1101) acting as a guidewire or rail). Thereafter, visualization catheter (1101) may be withdrawn while guide catheter (1182) remains in place (e.g., to receive other catheters, devices, and/or tools). Alternatively or additionally, in certain variations, visualization catheter (1101) may be used to guide a guidewire around the subannular groove, behind the chordae tendineae.

Catheters comprising one or more ultrasonic transducers may comprise, for example, a proximal section that is joined to a distal section, and may also comprise a transition section between the proximal and distal sections. In some variations, the distal section may include a window region that is at least partially transparent to ultrasonic energy. The ultrasonic transducer or transducers may be disposed in the window region. In certain variations, the catheter may include one or more tensioning elements that pass through a first lumen of the catheter and that are secured to the distal section. Tension may be applied to the tensioning element or elements to steer the distal section of the catheter. In some variations, the distal section may be more flexible than the proximal section. In certain variations, the tensioning element or elements may be tensioned to enable movement (i.e., steering) of the distal section without substantially moving or disturbing the proximal section. In some variations, a catheter may include at least two lumens, with a tensioning element disposed in one lumen, and an ultrasonic transducer disposed in another lumen.

Figure 12:
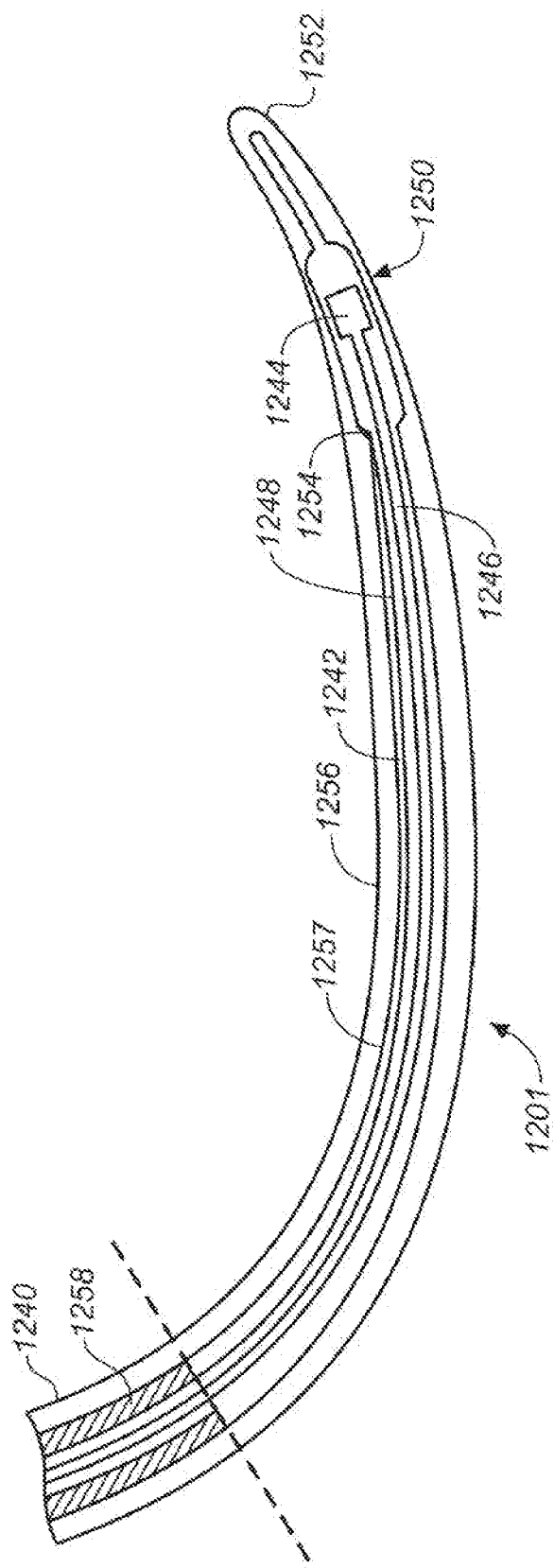
FIG. 12 is a cross-sectional depiction of a variation of a catheter that may be used to visualize a region of a heart.

FIG. 12 illustrates an example of a suitable catheter that may be used with one or more of the methods provided herein. As shown there, a catheter (1201) has a distal section (1256) joined to a proximal section (1240), with a dashed line denoting the boundary between the two sections. The distal section may be joined with the proximal section in any suitable manner. For example, the distal and proximal sections may form a continuous or integral unit. Alternatively, the distal and proximal sections may be in the form of two distinct units that have been attached to each other (e.g., by bonding through fusion or with an adhesive, or by mechanical coupling). In some variations, the catheter may comprise a transition section interposed between the proximal and distal sections, where the transition section joins the proximal and distal sections to each other. Again, the distal section, transition section, and proximal section may form a single continuous or integral unit, or may comprise discrete units that have been attached together. In the variation shown in FIG. 12, the proximal and distal sections have a common wall (1257), but the proximal section has an extra reinforcing wall (1258). Distal section (1256) includes a window region (1250). Optionally, and as illustrated, distal section (1256) may include a tip region (1252) distal to the window region (1250), where the tip region can be softer or more flexible than the bulk of the distal section, and/or can have a reduced outer diameter relative to the window region.

Catheter (1201) comprises at least one ultrasonic transducer (1244). In some variations, and as shown, ultrasonic transducer (1244) may be secured to a connector (1246) that passes through a lumen (1242) of both the distal and proximal sections of the catheter. In some catheters, connector (1246) may be used to position ultrasonic transducer (1244). For example, the connector may be adapted to translate the ultrasonic transducer longitudinally along the length of the catheter (e.g., to position the transducer longitudinally within the window region), to remove the transducer from the window region, and/or to remove the transducer from the catheter altogether. Some connectors may position the transducer by rotation (e.g., the transducer may be positioned by rotation around an axis defined by the connector). Thus, in certain variations in which lumen (1242) houses the transducer, the inner diameter of lumen (1242) may be large enough to accommodate rotation of the transducer. For example, in some variations, lumen (1242) may have an inner diameter of at least about 0.5 millimeter (e.g., about 0.5 millimeter, about 0.6 millimeter, about 0.7 millimeter, about 0.8 millimeter, about 0.9 millimeter, about 1.0 millimeter, about 1.1 millimeters, about 1.2 millimeters, about 1.3 millimeters, or even larger). In certain variations, connector (1246) may function as a rotation shaft, rapidly and continuously rotating the transducer about an axis defined by the connector. The connector may automatically rotate the transducer (e.g., at a fixed or programmed velocity or interval, or in response to a trigger), or the connector may be manually controlled to rotate the transducer. In some variations, the connector may rotate the transducer under a combination of manual and automatic control. Lumen (1242) may be coated or lined with one or more lubricious substances, such as high-density polyethylene (HDPE) or polytetrafluoroethylene (PTFE). This may, for example, cause the lumen to provide a relatively low-friction environment in which connector (1246) and/or ultrasonic transducer (1244) may translate and/or rotate.

Referring still to FIG. 12, transducer (1244) is disposed in window region (1250) of distal section (1256). Window region (1250) is at least partially transparent to the ultrasonic energy emitted and detected by the transducer. For example, window region (1250) may comprise one or more windows that can transmit ultrasonic energy having the frequency emitted and detected by the transducer. In some variations, the windows may be in the form of openings in the catheter wall that allow passage of ultrasonic energy. Alternatively or additionally, the window region may comprise one or more windows comprising a thin polymer layer (e.g., a polymer thin film having a thickness of about 0.002 inch, about 0.003 inch, about 0.004 inch, about 0.005 inch, about 0.006 inch, or about 0.007 inch). Examples of polymers which may be suitable for one or more windows in a window region include polyethylene (e.g., high-density polyethylene (HDPE)), nylon (e.g., nylon 6, nylon 11, nylon 12), PEBAX® polymers, polyurethanes, and polyimides. Other suitable materials may alternatively or additionally be used. In certain variations, the windows may be continuous with the catheter wall in the window region (e.g., a window may be in the form of a thinned-out region of the wall). In some variations, the windows may be separate elements applied to the window region of the catheter, such as thin polymer films secured (e.g., by fusion, adhesives, or mechanical attachment) over openings in the catheter. In certain variations, a catheter may include one or more combinations of different types of windows.

In variations in which a window region comprises multiple windows, the windows may be configured in any suitable fashion. For example, windows may be arranged circumferentially around a catheter, and/or longitudinally along the length of a catheter. Moreover, window sizes or shapes may vary according to the application. For example, window sizes or shapes may be determined by structural considerations, catheter size and/or shape, catheter wall thickness, size and/or number of transducers, size and/or position of anatomy or implant being viewed, or any combination of factors.

Any suitable ultrasonic transducer or combination of ultrasonic transducers may be used in the catheters, including piezoelectric or capacitive micro-electromechanical ultrasonic transducers. The transducers can operate at, for example, about 5 MHz, about 10 MHz, about 15 MHz, about 20 MHz, about 25 MHz, about 30 MHz, about 35 MHz, about 40 MHz, about 45 MHz, or about 50 MHz. Moreover, transducers having varying physical dimensions may be used. For example, a transducer may have a cross-sectional dimension that allows it to be disposed, and in some cases rotated, in a lumen of a catheter.

Referring again to FIG. 12, signals to and from the transducer may also be carried by connector (1246). In some variations, connector (1246) may comprise a single connector that can transmit signals to and from the transducer and that can position the transducer. In other variations, connector (1246) may comprise multiple connectors, such as one or more connectors for positioning the transducer, as well as one or more other connectors for transmitting signals to and from the transducer.

Referring still to FIG. 12, as described above, more than one transducer may be used in the catheters described herein. As an example, although schematically illustrated as a single block for simplicity, ultrasonic transducer (1244) may comprise one or more arrays of transducers. If an array of transducers is used, the transducers may be arranged in any suitable manner. For example, and as described briefly above, transducer (1244) may represent a longitudinal array (e.g., multiple transducers positioned along an axis generally parallel to the length of the catheter), or a ring-like array (e.g., transducers positioned circumferentially around connector (1246), where each transducer's output is generally emitted in a distal direction, or each transducer's output is generally emitted in a direction radially outward from the interior of the catheter).

As discussed above, when more than one transducer is used, each transducer may be individually addressable. That is, connector (1246) may be adapted to transmit signals to and/or from each transducer independently. In variations of catheters incorporating more than one transducer, some of the transducers may be used to transmit ultrasonic energy, while other transducers may be used to receive reflected ultrasonic energy from surrounding structures. Connector (1246) may be adapted to position more than one transducer independently. For example, connector (1246) may comprise two or more independently translatable and/or rotatable wires, where each wire is connected to a separate transducer and is adapted to position its connected transducer separately from the other transducer(s). Further, catheters with more than one transducer may also comprise more than one connector, where each connector is adapted to control (e.g., position and/or transmit signals to or from) a separate transducer or group of transducers.

Still referring to FIG. 12, a tensioning element (1248) (e.g., a flexor tendon such as a polymeric cable) passes through lumen (1242), through both the distal and proximal sections of the catheter. Additionally, tensioning element (1248) is secured to the distal section of the catheter at a securing position (1254). In some variations, the tensioning element may be permanently secured to the distal section (e.g., mechanically locked or bonded), while in other variations, the tensioning element may be removably secured to the distal section (e.g., using a clip, clamp, hook, or the like). Moreover, some variations of catheters may comprise a tensioning element that is secured to the catheter at more than one location. Alternatively or additionally, a catheter may comprise more than one tensioning element. Tension applied to the tensioning element, either manually by a medical professional or automatically, may cause the flexible distal section of the catheter to move. The tensioning element may be secured to the distal section at any suitable position that enables the steering of the distal section and/or fine-tuning of the position of the distal section. In general, if the tensioning element is secured near the distal end of the distal section, tension applied to the tensioning element may provide preferential movement and more direct control of the distal tip. If the tensioning element is secured near the window region (as shown in the example illustrated in FIG. 12), tension applied to the tensioning element may provide more direct control over positioning of the window region. The securing position (1254) for tensioning element (1248) may be located at any suitable position relative to window region (1250) (e.g., proximal to, distal to, or within the window region).

In some variations, proximal section (1240) of catheter (1201) may be stiffer or harder (i.e., may have a higher durometer) than distal section (1256). The proximal section may be rendered stiffer than distal section using any suitable method. As an example, in certain variations, the wall of the proximal section may be thicker than the wall of the distal section. As another example, in some variations, the wall of the proximal section may have structural features that impart increased stiffness or hardness to the wall. For example, the wall of the proximal section may be formed from a braided or woven material, or ribs, spines or the like may extend longitudinally along the wall, transversely through the thickness of the wall, or circumferentially around the wall (e.g., in a helical manner). Such structural features may be integral to the wall (e.g., formed on or in the wall during a molding process), or may be in the form of one or more separate elements that are added to the wall (e.g., one or more reinforcing bands, coatings, fibers, meshes, or the like that are applied to the wall).

In some variations, a proximal section of a catheter may comprise a wall including multiple layers (e.g., for added stiffness). For example, FIG. 12 shows an inner wall (1258) located only in proximal section (1240), which may increase the stiffness of proximal section (1240). The walls of the proximal section may be made in part or in whole from one or more materials that are different from the material(s) of the walls of the distal section (e.g., to increase the relative stiffness of the proximal section). In some variations, the stiffness of the proximal section may be at least about 20% greater (e.g., about 20% greater, about 30% greater, about 40% greater, about 50% greater, about 60% greater, about 70% greater, about 80% greater, about 90% greater, about 100% greater, about 150% greater, or about 200% greater, or even more), than the stiffness of the distal section. Factors that may affect the relative stiffness of the proximal and distal sections include, for example, the geometries of the sections, the material compositions of the sections, and the material hardnesses (durometers) of the sections.

As described above, the distal and proximal sections may be joined in any suitable manner. For example, as illustrated in FIG. 12, they may be integral or may have a common wall (1257). Alternatively, the proximal and distal sections may be formed separately, and may later be joined by any suitable method (e.g., by fusing the two sections together, securing the two sections to each other with an adhesive, or mechanically coupling the two sections to each other). In some variations, a transition section may be interposed between the proximal and distal sections.

The relative stiffness of the proximal section may be selected such that inducing movement in the distal section by application of force on the tensioning element may not result in substantial corresponding movement in the proximal section. That is, the stiffness of the proximal section may at least partially shield or decouple the proximal section from movement in the distal section. As an example, in some variations, a point on the flexible distal section may be translated and/or rotated by a distance of at least about 0.5 millimeter (e.g., about 0.5 millimeter, about 1 millimeter, about 2 millimeters, about 3 millimeters, about 4 millimeters, about 5 millimeters, about 6 millimeters, about 7 millimeters, about 8 millimeters, about 9 millimeters, or about 1 centimeter, or even farther), without any detectable motion in the proximal section.

Figure 13A:
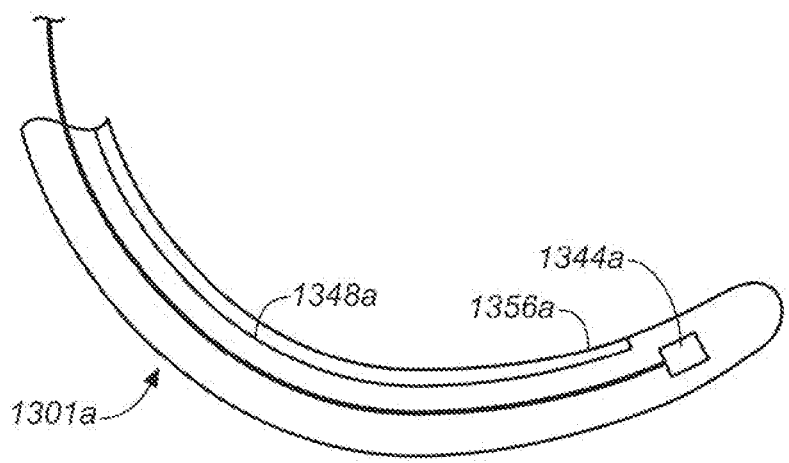
FIGS. 13A-13C depict different variations of catheters comprising tensioning elements for steering.
Figure 13B:
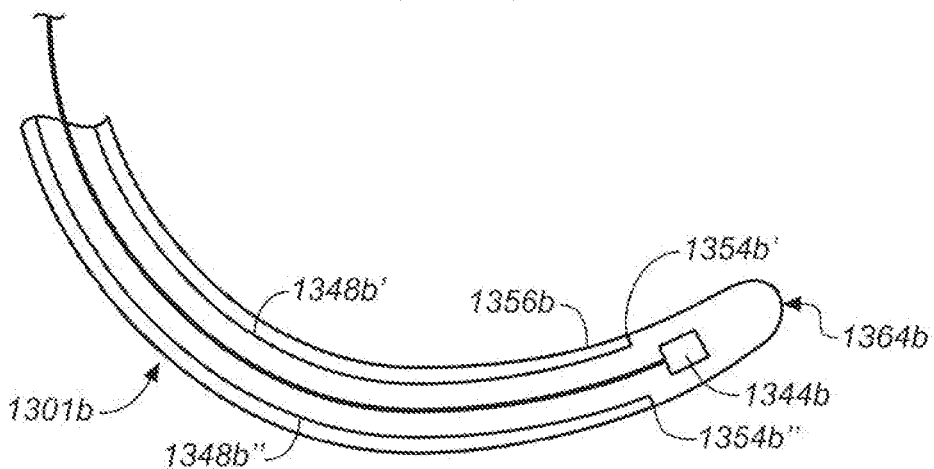
Figure 13C:
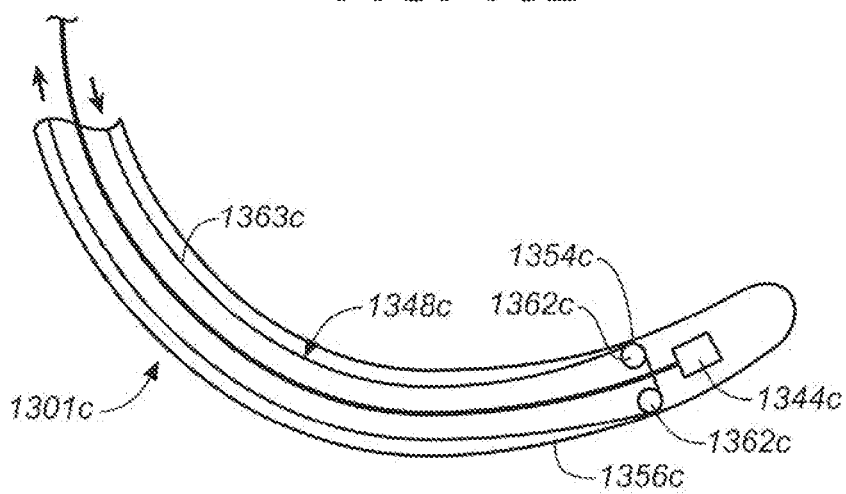

Referring now to FIGS. 13A-13C, any of a variety of different tensioning elements (e.g., having different lengths and/or made of different materials) may be used in the devices described herein. For example, FIG. 13A shows a catheter (1301a) comprising an ultrasonic transducer (1344a) and a tensioning element (1348a) in the form of a wire or tendon (e.g., a flexor tendon, such as a polymeric cable). In some variations, tensioning element (1348a) may comprise a stiff wire or tendon that can support force applied in both distal and proximal directions, to thereby steer the distal section (1356a) of catheter (1301a). This, in turn, may provide control over the positioning of ultrasonic transducer (1344a), which is located in distal section (1356a). In other variations, tensioning element (1348a) may primarily support only force applied in a proximal direction, and the resiliency of the flexible distal section (1356a) may function to pull the distal section in a distal direction when proximal force on tensioning element (1348*a*) is released or reduced.

As shown in FIG. 13B and as discussed briefly above, in some variations, a catheter may comprise more than one tensioning element. For example, FIG. 13B shows a catheter (1301*b*) that, in addition to comprising an ultrasonic transducer (1344*b*), comprises multiple tensioning elements (1348*b*') and (1348*b*") arranged around the circumference of catheter (1301*b*). The tensioning elements may be arranged in any suitable configuration (e.g., at positions that are about 180° apart from each other, or that are about 90° apart from each other). The tensioning elements may or may not be uniformly distributed around the catheter. The multiple tensioning elements may be secured to the distal section (1356*b*) of catheter (1301*b*) at positions (1354*b*') and (1354*b*") that are approximately equidistant from the catheter's distal end (1364*b*). Alternatively, the multiple tensioning elements may be secured at positions that are not equidistant from the distal end. In some of these variations, the tensioning elements may comprise one or more materials that are capable of supporting force primarily in a proximal direction only (e.g., a flexible wire, cable or suture made of polymer or metal, etc.). In such variations, the resiliency of the distal section may apply an opposing force, thereby causing the distal section to move distally when a proximal force on one or more tensioning elements is reduced or released. In still other variations, the tensioning elements may be in the form of relatively stiff wires or tendons capable of supporting force in both distal and proximal directions. Force may be applied to the tensioning element(s) separately or simultaneously, to enable steering of distal section (1356*b*).

In still other variations, and as illustrated in FIG. 13C, a catheter (1301*c*) may include a tensioning element (1348*c*) and pulleys (1362*c*). While two pulleys are shown, one pulley or more than two pulleys may be used in some variations, as appropriate. As shown, the tensioning element may be wound around the pulleys, which may be attached to the distal section (1356*c*) of catheter (1301*c*) (e.g., at a position (1354*c*)). Opposite forces (indicated by arrows) may be applied to opposite ends of a cord (1363*c*) (e.g., a polymeric or metal suture, or a flexible metal wire) that is wound around pulleys (1362*c*), to allow steering of the distal section of the catheter. As shown, the distal section of the catheter incorporates at least one ultrasonic transducer (1344*c*), such that the catheter may be used, for example, to visualize its own positioning, and/or the positioning of one or more other devices, at a target site. While pulleys are shown, in some variations, one or more pulley-like structures or arrangements may alternatively or additionally be used. Moreover, in certain variations, only one pulley may be used, or more than two pulleys may be used.

FIG. 4, previously discussed above, illustrates another variation of a suitable catheter that may be used with one or more of the methods described herein. As shown there, catheter (401) comprises a proximal section (440) joined to a distal section (456), as well as two lumens (468) and (469). Both lumens may pass through at least a portion of each of the proximal and distal sections of the catheter. Additionally, in variations in which the catheter includes a transition section between the proximal and distal sections, both lumens will pass through the transition section. As shown in FIG. 4, the lumens may have a common wall (471). Catheter (401) also comprises a tensioning element (448) threaded through the first lumen (468) and secured to distal section (456) at a position (454) proximate a window region (450). The securing position (454) for tensioning element (448) may be located at any suitable position relative to window region (450) (e.g., proximal to, distal to, or within the window region). Any appropriate tensioning elements may be used, such as a flexor tendon or one or more of the tensioning elements illustrated in FIGS. 13A-13C.

Still referring to FIG. 4, catheter (401) further comprises an ultrasonic transducer (444) and a corresponding connector (446). Second lumen (469), which houses connector (446), may be open to the interior (470) of window region (450), which houses ultrasonic transducer (444). In some variations, the inner diameter of second lumen (469) may be large enough to accommodate rotation of ultrasonic transducer (444). Moreover, the interior wall surface of second lumen (469) may be lined or coated with one or more lubricious substances (e.g., high-density polyethylene (HDPE) or polytetrafluoroethylene (PTFE)), which may allow connector (446) and/or ultrasonic transducer (444) to rotate and/or translate in a low-friction environment within the lumen.

Figure 14:
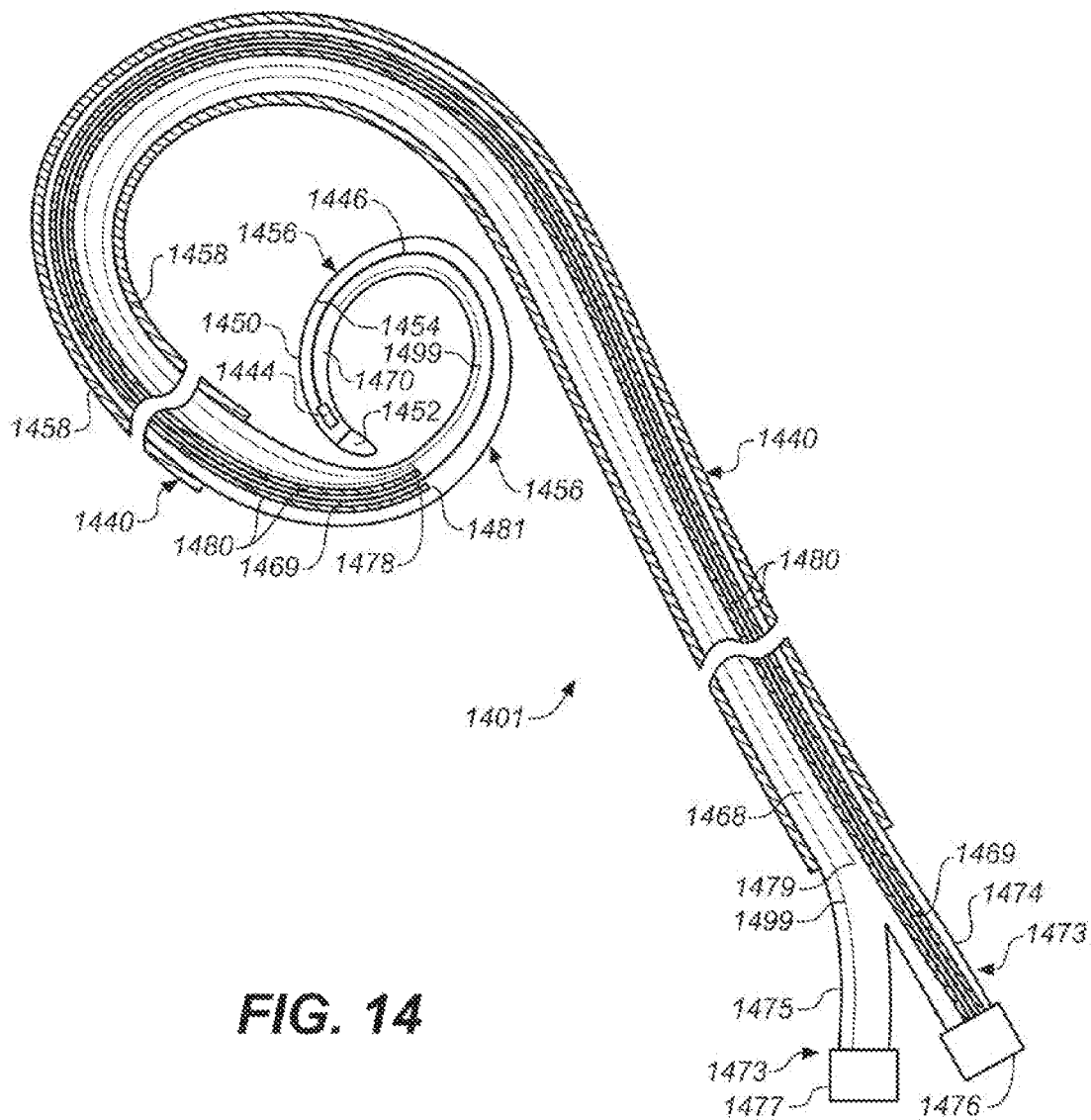
FIG. 14 depicts another variation of a catheter that may be used to visualize a region of a heart.

FIG. 14 shows another example of a steerable catheter (1401) that may be used, for example, to view the subannular groove of a heart, anatomy near the subannular groove, and/or implants in and/or near the subannular groove. As shown in FIG. 14, catheter (1401) comprises a proximal section (1440) joined to a distal section (1456) comprising a window region (1450) and a distal tip (1452). At least one ultrasonic transducer (1444) is housed within window region (1450). Ultrasonic transducer (1444) is connected to a connector (1446) extending proximally through the catheter to a first branch (1474) of the proximal end (1473) of the catheter. Catheter (1401) also comprises a tensioning element (1499) extending from a securing point (1454) in distal section (1456) to a second branch (1475) of proximal end (1473).

First branch (1474) of proximal end (1473) may be interfaced with a controller (1476) that controls ultrasonic transducer (1444). Controller (1476) may rotate and/or translate ultrasonic transducer (1444) via connector (1446), for example. In some variations, controller (1476) may also transmit signals to, or receive signals from, ultrasonic transducer (1444) via connector (1446). Controller (1476) may in turn be interfaced with a signal processor, microprocessor and display unit to analyze and prepare images from the signals received from the transducer and to display those images to a user (e.g., a medical professional or operator). Second branch (1475) of proximal end (1473) is interfaced with a user control (1477) that allows the user to steer distal section (1456) of catheter (1401) by applying force to, or releasing force from, tensioning element (1499). The user control (1477) may comprise a lever, a knob, a handle, or the like.

Still referring to FIG. 14, catheter (1401) in this variation comprises two lumens (1468) and (1469). The first lumen (1469) is open to the interior (1470) of the window region housing transducer (1444), and extends continuously from the interior (1470) of the window region to proximal end (1473) of catheter (1401). The second lumen (1468) houses tensioning element (1499). Second lumen (1468) may extend distally to just proximal of the window region (1450) or, as illustrated here, may terminate at a position (1478) more proximal to the window region. Additionally, second lumen (1468) may extend proximally to the proximal end (1473) or, as illustrated here, may terminate at a point (1479) that is distal to the proximal end. The proximal section (1440) of catheter (1401) may be reinforced (e.g., with a reinforcing layer (1458)) so that it is stiffer and/or harder than the distal section (1456). A reinforcing layer may be disposed on the exterior surface of the catheter wall, as illustrated here in FIG. 14, or on the interior surface of the catheter wall. In some variations, the catheter wall itself may be reinforced, for example by using embedded mesh, fibers, fillers, combinations thereof, or the like.

In certain variations, first lumen (1469) may be at least partially lined with a lubricious sheath or coating (1480). The lubricious sheath or coating may be made of any suitable material, such as high-density polyethylene (HDPE) or polytetrafluoroethylene (PTFE), and may provide a low-friction environment in which connector (1446) may rotate and/or translate relatively easily. In some variations, the lubricious sheath or coating may extend along the entire length of the catheter, while in other variations, the lubricious sheath or coating may extend along only a portion of the catheter. For example, in the variation shown, lubricious sheath or coating (1480) extends distally from the first branch (1474) of the proximal end (1473) a point (1481) that is proximal to the window region (1450).

As described previously, the proximal section of the catheter may be stiffer or harder than the distal section. This may, for example, help to shield the proximal section from movement in the more flexible distal section. In some variations, the relative stiffness or hardness of the proximal section may be provided by, for example, increasing the catheter wall thickness in the proximal section, forming the proximal section of one or more stiffer or harder materials than the distal section, and/or applying one or more reinforcing structures (e.g., woven or braided meshes, ribs and/or spines) to an exterior surface of the catheter wall, an interior surface of the catheter wall, and/or the bulk of the catheter wall. In certain variations, a combination of features may be used to achieve relative stiffness in a proximal section. In some variations of catheters including two lumens, it may be desirable to reinforce only the walls of one of the lumens in the proximal section of the catheter. For example, with respect to catheter (401) depicted in FIG. 4, only the walls of the lumen (469) housing the transducer (444) have been reinforced with an inner braided wall (458).

Some variations of the catheters described here may have an extended window region. For example, a substantial portion of the flexible distal section of a catheter may be at least partially transparent to ultrasonic energy. By a "substantial portion of the distal section," it is meant that the surface area of the window region (i.e., a region that is at least partially transparent to ultrasonic energy) comprises at least about 10% (e.g., at least about 15%, at least about 25%, at least about 35%, at least about 45%, at least about 55%, at least about 65%, at least about 75%, at least about 85%, or at least about 95%) of the surface area of the flexible distal section.

Figure 15:
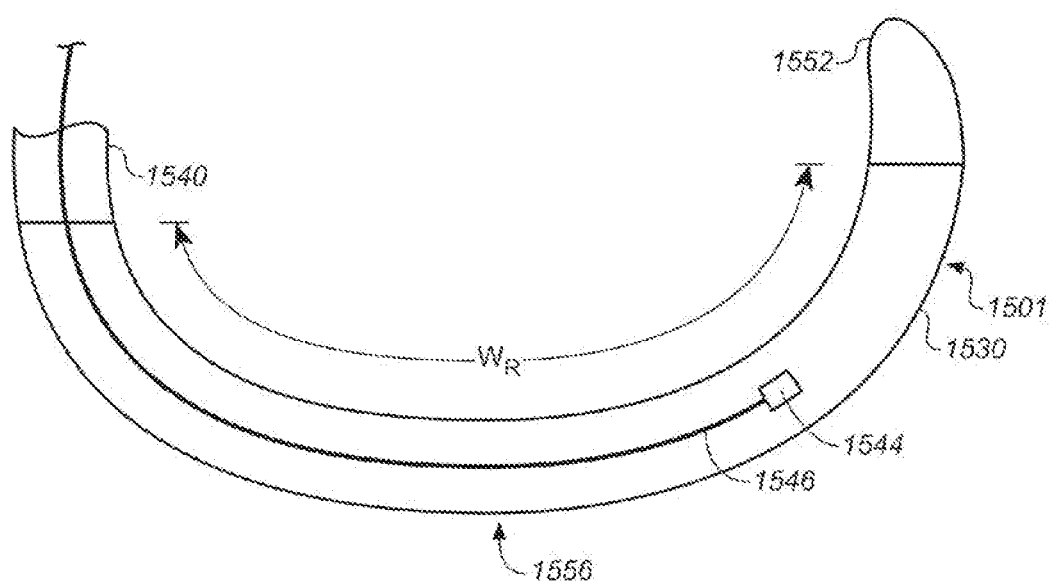
FIG. 15 shows an additional variation of a catheter that may be used to visualize a region of a heart.

FIG. 15 shows a catheter (1501) comprising a distal section (1556) having a window region ($W_R$) extending from the distal boundary of the proximal stiff section (1540) of the catheter to the catheter distal tip (1552). The walls (1530) of the extended window region are at least partially transparent to ultrasonic energy. For example, walls (1530) may be made of a thin polymer film having a thickness of about 0.007 inch or less (e.g., about 0.006 inch, about 0.005 inch, about 0.004 inch, about 0.003 inch, or about 0.002 inch). In some variations, the walls may be formed of one or more polymers, such as nylon, PEBAX® polymer, polyethylene, and/or polyimide. Other suitable materials may also be used. The distal section has a radius of curvature that may be reduced by applying force in a proximal direction via a tensioning element (not shown). Catheter (1501) comprises an ultrasonic transducer (1544) that may be translated along the extended window region ($W_R$) by translation of a connector (1546). Ultrasonic transducer (1544) may enable ultrasonic visualization of anatomy and/or structures, such as the subannular groove, the mitral valve, and/or implants in or near the subannular groove or the mitral valve. Of course, transducer (1544) may also be rotated using connector (1546).

As discussed above, some catheters may be at least partially radiopaque. For example, a catheter may comprise a wall made from a polymer composite comprising one or more radiopaque materials, such as barium sulfate or bismuth trioxide, and/or metal markers (e.g., tungsten markers). Catheters may also be at least partially coated with one or more radiopaque materials. For example, select portions of a catheter may be at least partially coated (e.g., by plating or sputtering) with a biocompatible metal such as gold, silver, titanium, tantalum, or alloys thereof, or coated with a polymer or ink that contains a radiopaque material (e.g., metal markers such as tungsten markers, or barium sulfate or bismuth trioxide). In some variations, catheters may be rendered radiopaque using a polymer with chemically bound radiopaque moieties (e.g., iodine-containing moieties). Catheters that are at least partially radiopaque may be used in methods that combine ultrasonic visualization techniques with fluoroscopic visualization techniques, such as those described earlier, wherein a contrast agent is injected into the subannular groove to visualize the subannular groove.

While certain variations of devices have been described, additional variations of visualization devices may be used. In some variations, a visualization device may comprise at least one scope. The scope(s) may be used, for example, to locate a target site for implant (e.g., anchor) deployment, and/or to evaluate an implant and/or a target site after the implant has been deployed at the target site. In certain variations in which a visualization device comprising a scope is used in a cardiac procedure (e.g., a heart valve repair procedure), the scope may be used to locate and evaluate an annulus, leaflets, and/or commissures of the heart. A scope may also be used to help an operator become oriented as to the environment of a target site, to observe implant deployment and/or orientation during and/or after a procedure, and/or to assess an implant after it has been deployed into tissue. For example, a scope may be used to determine whether a deployed anchor is positioned correctly, or whether an anchor's arms have bent or curved sufficiently upon deployment. A scope may also be used to observe the state of a tether coupling multiple anchors to each other (e.g., whether the tether is damaged), or may be used for any other suitable purpose.

In some variations, a visualization device may comprise a scope, such as a fiber optic scope or a rigid scope, that may be at least partially positioned within a scope housing during use. The scope housing may, for example, help to protect the scope during use, and/or may help to limit the likelihood of the scope causing damage to tissue as the scope is advanced to a target site, or once the scope has reached the target site. Additionally, the scope housing may enhance the scope's visualization of the surrounding area. Housings may have any appropriate size and shape. Furthermore, in variations employing multiple scopes, each scope may be disposed within its own individual housing, or at least two scopes may share a housing.

Figure 50:
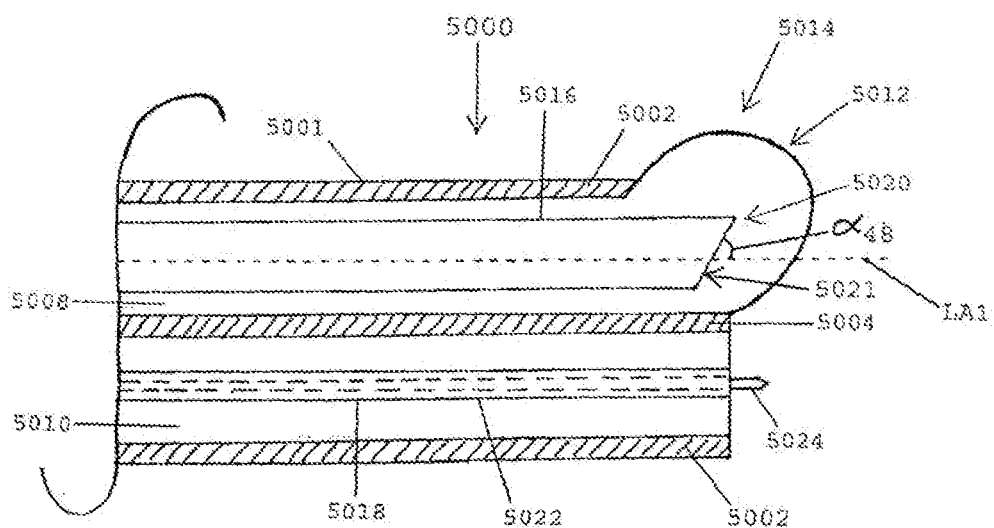
FIG. 50 is a side view in partial cross-section of a variation of a visualization device.

In certain variations, a scope housing may be bubble-shaped. The rounded shape of a bubble housing may, for example, make the housing relatively atraumatic toward tissue, and may also allow for good visualization of tissue surrounding the housing. For example, FIG. 50 shows a visualization device (5000) comprising a housing (5001) including a first outer wall portion (5002) and a second inner wall portion (5004) defining two lumens (5008) and (5010) therebetween. Device (5000) also comprises a scope (5016) located within lumen (5008), as well as an anchor (5018) located within lumen (5010).

In some variations, wall portions (5002) and (5004) may be formed of one or more relatively transparent materials. Non-limiting examples of such materials include polymers, such as polyether-block co-polyamide polymers (e.g., PEBAX® polyether block amide copolymers, including but not limited to PEBAX® 35D polymer, PEBAX® 40D polymer, PEBAX® 55D polymer, PEBAX® 63D polymer, and PEBAX® 72D polymer), copolyester elastomers, thermoset polymers, polyolefins (e.g., polypropylene or polyethylene, including high-density polyethylene (HDPE) and low-density polyethylene (LDPE)), ethylene vinyl acetate copolymers, polyamides, polyimides, polyurethanes (e.g., POLYBLEND™ polymer), polyvinyl chloride (PVC), fluoropolymers (e.g., fluorinated ethylene propylene (FEP), perfluoroalkoxy (PFA) polymer, polyvinylidenefluoride (PVDF), etc.), silicones, and copolymers and combinations (e.g., blends) thereof. Examples of polyamides include nylon 6 (e.g., ZYTEL® HTN high performance polyamides from DuPont™), nylon 11 (e.g., RILSAN® B polyamides from Arkema Inc.), and nylon 12 (e.g., GRILAMID® polyamides from EMS-Grivory, RILSAN® A polyamides from Arkema Inc., and VESTAMID® polyamides from Degussa Corp.). Other polymers and/or non-polymeric materials may also be used. Moreover, in certain variations, one or more materials (e.g., polymers) may be combined (e.g., blended), if it is suitable to do so.

Using one or more relatively transparent materials in wall portions (5002) and (5004) may, for example, allow for scope (5016) to achieve relatively good visualization of the tissue surrounding device (5000), and/or may allow for an operator to determine the location of scope (5016) and/or anchor (5018) relatively easily.

As shown, device (5000) further includes a rounded dome- or bubble-shaped scope housing (5012) in its distal portion (5014), extending from wall portions (5002) and (5004). Scope (5016) partially extends into scope housing (5012), and may in some cases be translatable so that the scope may be further extended into the scope housing, or may be retracted from the scope housing.

Scope (5016) is angled at its distal end (5020), so that it may provide an angled line of sight through scope housing (5012). More specifically, the distal edge (5021) of scope (5016) forms an angle (α48) relative to the longitudinal axis (LA1) of scope (5016). Angle (α48) may be, for example, from about 25° to about 85° (e.g., from about 30° to about 60°). Of course, scope (5016) is only one variation of a scope, and other variations may alternatively or additionally be used with any of the devices described here, as appropriate.

Anchor (5018) comprises an elongated member (5022) and a distal anchoring portion (5024), which is sized and shaped to temporarily anchor into tissue. Distal anchoring portion (5024) is depicted as having a single tissue-piercing tip. However, other variations of devices may use anchoring portions having different configurations, as appropriate. As an example, in some variations, an anchoring portion may comprise multiple tissue-piercing tips. Anchor (5018) may be used, for example, to help stabilize device (5000) while the device is used to visualize a target site.

During use, device (5000) may be advanced toward a target site. Scope (5016) may be actuated prior to, during, and/or after such advancement, to provide a view of the pathway to the target site, and/or to provide a view of the target site itself. Scope housing (5012) may shield scope (5016), so that the scope does not damage tissue (e.g., by snagging the tissue), and so that the scope is less likely to experience any damage itself. In some cases, distal anchoring portion (5024) of anchor (5018) may be temporarily anchored into tissue when device (5000) is in use. This temporary anchoring may, for example, help to stabilize device (5000) with respect to the tissue, allowing the scope to provide a reliable image of its surroundings. In certain variations, anchor (5018) may be deployable from, and retractable into, lumen (5010). This may, for example, allow the distal anchoring portion (5024) to be extended when desired for use, and to otherwise be retracted (e.g., to limit the likelihood of harm to tissue when the distal anchoring portion is not in use). While a visualization device comprising one anchor has been described, it should be noted that some variations of visualization devices comprising one or more scopes may comprise more than one anchor, or may not comprise any anchors at all.

Figure 51:
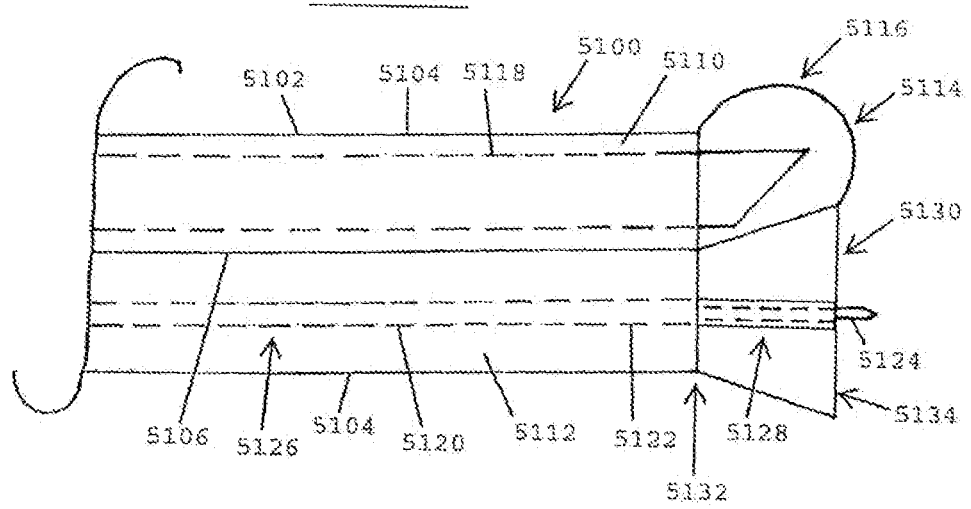
FIG. 51 is an illustrative side view of another variation of a visualization device.

As discussed above, other variations of anchors may be used. The type of anchor that is used in a device may depend, for example, on the nature of the target tissue and/or the desired anchoring time and stability. FIG. 51 shows another variation of a visualization device (5100) comprising an anchor having a different configuration from anchor (5018) above. More specifically, device (5100) comprises a housing (5102) including a first wall portion (5104) and a second wall portion (5106) defining two lumens (5110) and (5112) therebetween. As shown, device (5100) further includes a rounded dome or bubble (5114) in its distal portion (5116), extending from wall portions (5104) and (5106). Additionally, device (5100) comprises a scope (5118) located within lumen (5110), as well as an anchor (5120) located within lumen (5112).

Anchor (5120) comprises an elongated member (5122) and a distal anchoring portion (5124), which is sized and shaped to temporarily anchor into tissue. As shown, a portion (5126) of elongated member (5122) is disposed within lumen (5112), while another portion (5128) of elongated member (5122) is disposed within a funnel-shaped housing (5130) extending from the distal end (5132) of housing (5102), between wall portions (5106) and (5104). Distal anchoring portion (5124) extends distally beyond the distal end (5134) of funnel-shaped housing (5130). Funnel-shaped housing (5130) may be formed of any appropriate material or materials, and in some variations, may be formed of one or more relatively transparent materials, such as one or more of the materials described above with reference to wall portions (5002) and (5004) in FIG. 50. Funnel-shaped housing (5130) may be sized and shaped to temporarily seal against tissue during use. This may, for example, help to provide a more stable anchoring of distal anchoring portion (5124) into tissue. While housing (5130) is funnel-shaped, any other shapes that are suitable for achieving a similar effect may be used. In addition, in certain variations, saline may be flushed through lumen (5112) and into funnel-shaped housing (5130) during use (e.g., to keep lumen (5112) clear and the visualization zone blood-free).

While devices having bubble-shaped scope housings have been described, some variations of devices may comprise scope housings having different shapes or configurations. The size and shape of a scope housing may depend, for example, on the size and shape of the scope being housed (which, in turn, may depend on the characteristics of the target anatomy, such as the size of an atrial opening of a heart, and/or on one or more other factors).

Figure 52:
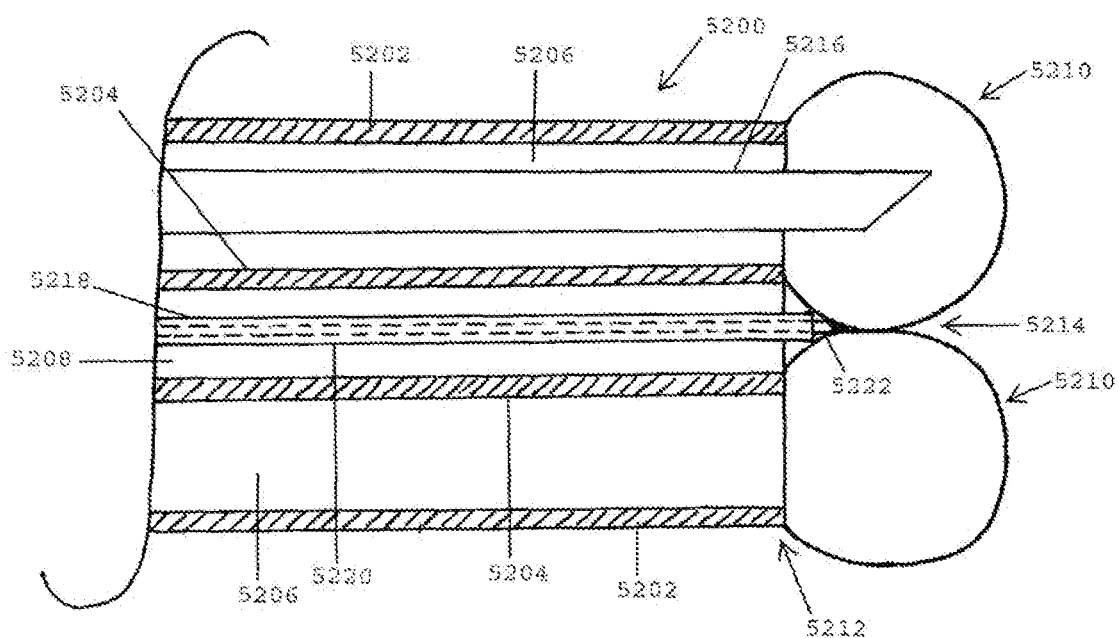
FIG. 52 is a side view in partial cross-section of an additional variation of a visualization device.

Some variations of devices may have other configurations suitable for positioning and/or stabilizing the device and/or an anchor of the device during use. For example, FIG. 52 shows an exemplary visualization device (5200) comprising an outer tubular member (5202) and an inner tubular member (5204) disposed within a lumen (5206) of outer tubular member (5202). Inner tubular member (5204) also has its own lumen (5208). As shown, device (5200) further includes a donut-shaped balloon (5210) at the distal end (5212) of outer tubular member (5202). While balloon (5210) has a small opening (5214) at its center, the opening is effectively sealed together by its various sides contacting each other. As a result, balloon (5210) effectively seals lumen (5208) of inner tubular member (5204). Device (5200) also comprises a scope (5216) located within lumen (5206), as well as an anchor (5218) located within lumen (5208). Anchor (5218) comprises an elongated member (5220) and a distal anchoring portion (5222), which is sized and shaped to temporarily anchor into tissue.

During use, balloon (5210) may be positioned against tissue, and anchor (5218) may be pushed through opening (5214) so that distal anchoring portion (5222) may contact and anchor into the target tissue. Anchor (5218) may be extendible and/or retractable in order to achieve this anchoring. Alternatively or additionally, device (5200) may be capable of allowing distal anchoring portion (5222) to be extended and/or retracted independently of the rest of anchor (5218), so that distal anchoring portion (5222) may push through opening (5214) and into tissue. The presence of balloon (5210) causes anchor (5218) to assume a very specific and intended positioning during use. This may help to limit the likelihood of the anchor damaging target tissue, and may also result in highly targeted and controlled deployment of the anchor.

In some variations, a visualization device may comprise one or more rotatable components. As an example, a visualization device may comprise at least one rotatable scope. In some such variations, the operator may be capable of controlling scope rotation using one or more actuators (e.g., located in a proximal portion of the device). FIGS. 53A-53D provide illustrative cross-sectional views of different variations of visualization devices comprising rotatable scopes. While rotatable scopes are depicted, it should be understood that certain variations of visualization devices may alternatively or additionally comprise one or more other rotatable components, such as rotatable scope housings.

Figure 53A:
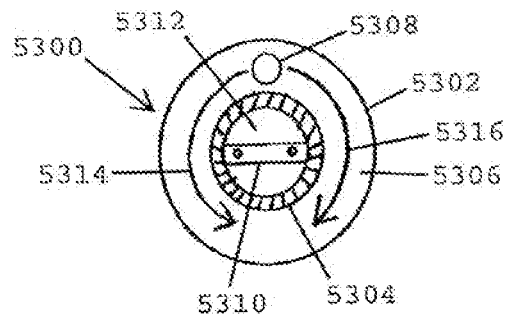
FIGS. 53A-53D are front cross-sectional views of different variations of visualization devices.

Referring specifically now to FIG. 53A, a visualization device (5300) comprises an outer tubular member (5302) and an inner tubular member (5304) disposed within a lumen (5306) of the outer tubular member. Device (5300) further comprises a scope (5308) located within lumen (5306), as well as an anchor (5310) located within a lumen (5312) of inner tubular member (5304). As shown, scope (5308) is capable of rotating within lumen (5306), around inner tubular member (5304), in the direction of arrow (5314) or arrow (5316). Scope (5308) is not restricted in its rotation—in other words, it is capable of rotating around the entirety of inner tubular member (5304). Such rotatability may, for example, allow for a very comprehensive view of the target site.

Figure 53B:
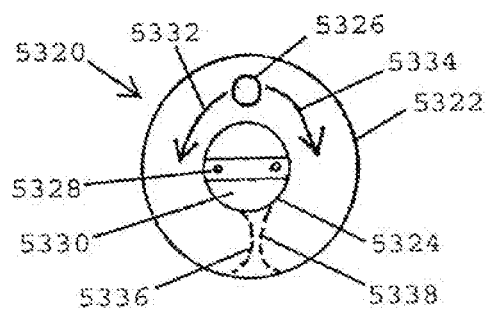

FIG. 53B shows another variation of a visualization device (5320) comprising a scope that, while rotatable, is restricted somewhat in its rotation. As shown there, device (5320) comprises an outer scope housing (5322) surrounding an inner tubular member (5324). Device (5320) further comprises a scope (5326) disposed within outer scope housing (5322), and an anchor (5328) disposed within a lumen (5330) of inner tubular member (5324). Scope (5326) is rotatable within outer scope housing (5322), in the direction of arrow (5332) or arrow (5334). However, outer scope housing (5322) comprises two wall portions (5336) and (5338) that prevent scope (5326) from fully rotating around inner tubular member (5324).

Figure 53C:
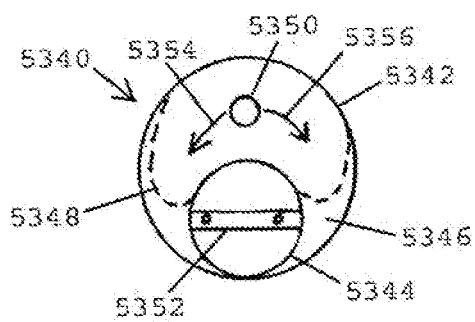

While FIGS. 53A and 53B depict devices comprising centrally located anchors and anchor housings, anchors and anchor housings may be positioned in any appropriate location of a visualization device. For example, FIG. 53C shows a visualization device (5340) comprising an outer tubular member (5342) and an inner tubular member (5344) disposed within a lumen (5346) of the outer tubular member. Device (5340) also comprises a scope housing (5348) disposed within lumen (5346) of outer tubular member (5342), as well as a rotatable scope (5350) disposed within scope housing (5348). Additionally, device (5340) comprises an anchor (5352) disposed within inner tubular member (5344). During use, scope (5350) may rotate within scope housing (5348) in the direction of arrow (5354) or arrow (5356). However, the rotation of scope (5350) is limited by the boundaries of the scope housing. Moreover, given this limitation, as well as the location of inner tubular member (5344) and anchor (5352), scope (5350) is not capable of completing a full 360° rotation within device (5340) (which is also the case with scope (5326) in FIG. 53B above).

Figure 53D:
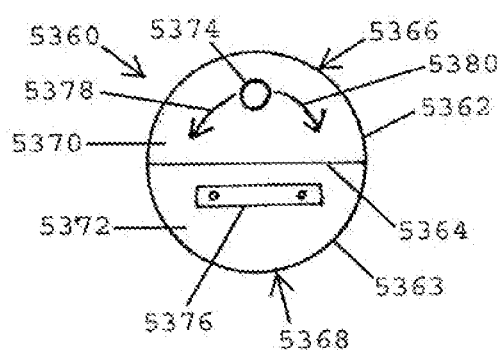

FIG. 53D shows an additional variation of a visualization device (5360). As shown there, device (5360) comprises a tubular member (5362) comprising an outer wall portion (5363) and an inner wall portion (5364) that effectively divides tubular member (5362) into two portions (5366) and (5368). Portions (5366) and (5368) each have their own lumen (5370) and (5372), respectively. Device (5360) also comprises a scope (5374) disposed within lumen (5370), and an anchor (5376) disposed within lumen (5372). As shown in FIG. 53D, scope (5374) is capable of rotating within lumen (5370), in the direction of arrow (5378) or arrow (5380). While scope (5374) is not capable of completing a full (360°) rotation within lumen (5370), some variations of visualization devices may comprise one or more scopes that are capable of such rotation within a lumen of a portion of the device.

In certain variations, a visualization device may comprise multiple (e.g., two, three, four, five, etc.) scopes. In a device comprising multiple scopes, the scopes may all be the same as each other, or at least two of the scopes may be different from each other (e.g., in size, shape, type of scope, etc.). Moreover, each scope may be positioned in its own housing, or at least two scopes may be positioned in the same housing. Additionally, the scopes may be positioned for visualization of different regions of a target site, and in some cases, may be individually actuated (e.g., so that the desired image or images may be achieved by actuating selected scopes).

Figure 54A:
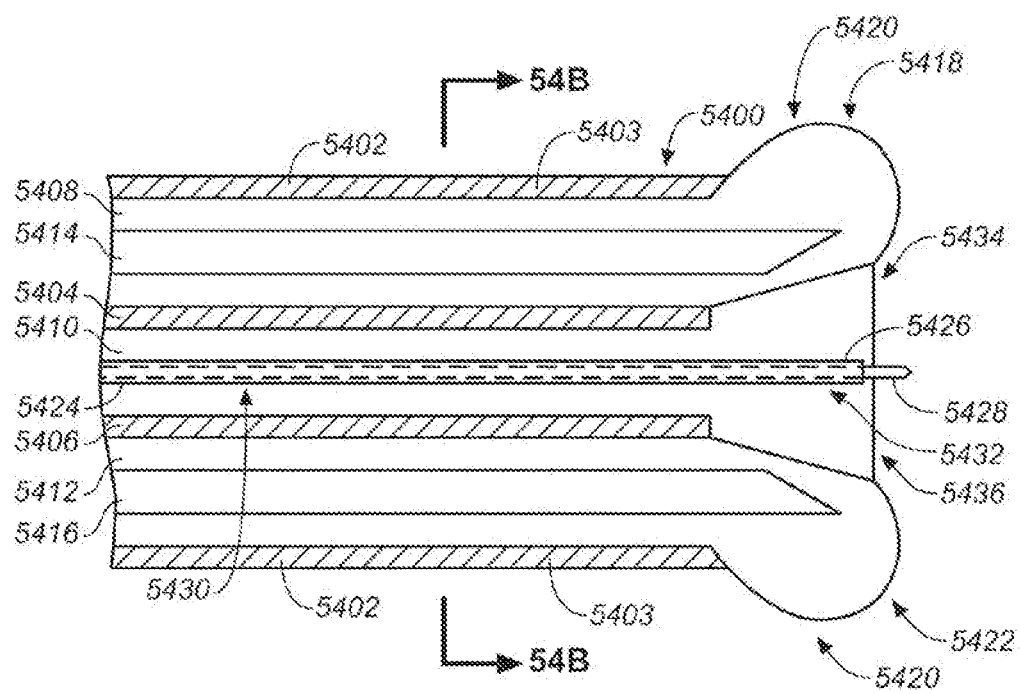
FIG. 54A is a side view in partial cross-section of a variation of a visualization device.
Figure 54B:
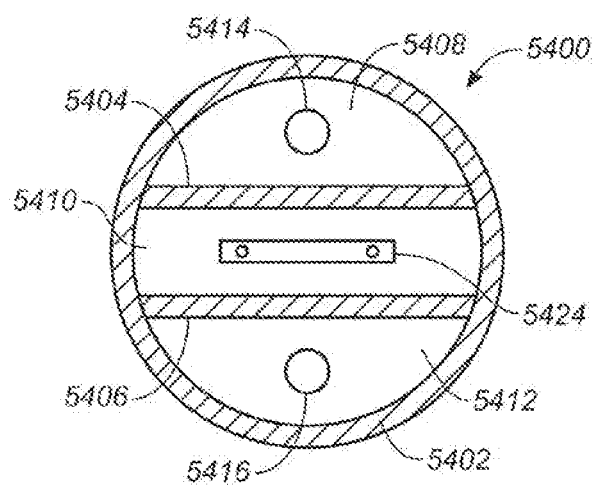
FIG. 54B is a cross-sectional view of the visualization device of FIG. 54A, taken at line 54B-54B.

An exemplary variation of a visualization device comprising multiple scopes is depicted in FIGS. 54A and 54B. As shown there, a visualization device (5400) comprises a tubular member (5402) comprising an outer wall portion (5403) and two inner wall portions (5404) and (5406). Inner wall portions (5404) and (5406) partition outer tubular member (5402) so that device (5400) has three lumens (5408), (5410) and (5412). Device (5400) further comprises a first scope (5414) disposed within lumen (5408), and a second scope (5416) disposed within lumen (5412). Scope (5414) is also partially disposed within a rounded dome- or bubble-shaped scope housing (5418) that is located in a distal portion (5420) of device (5400), and that is in fluid communication with lumen (5408). Similarly, scope (5416) is partially disposed within a rounded dome- or bubble-shaped housing (5422) that is also located in distal portion (5420) of device (5400), but that is in fluid communication with lumen (5412).

Device (5400) further comprises an anchor (5424) disposed within lumen (5410), where the anchor comprises an elongated member (5426) and a distal anchoring portion (5428). As shown in FIG. 54A, a portion (5430) of elongated member (5426) is disposed within lumen (5410), while another portion (5432) of elongated member (5426) is disposed within a funnel-shaped housing (5434) extending from inner wall portions (5404) and (5406). Distal anchoring portion (5428) extends distally beyond the distal end (5436) of funnel-shaped housing (5434). In some cases, and as discussed with respect to funnel-shaped housing (5130) above, funnel-shaped housing (5434) may be sized and shaped to temporarily seal against tissue during use. This may, for example, help to provide a more stable anchoring of distal anchoring portion (5428) into tissue.

Figure 55:
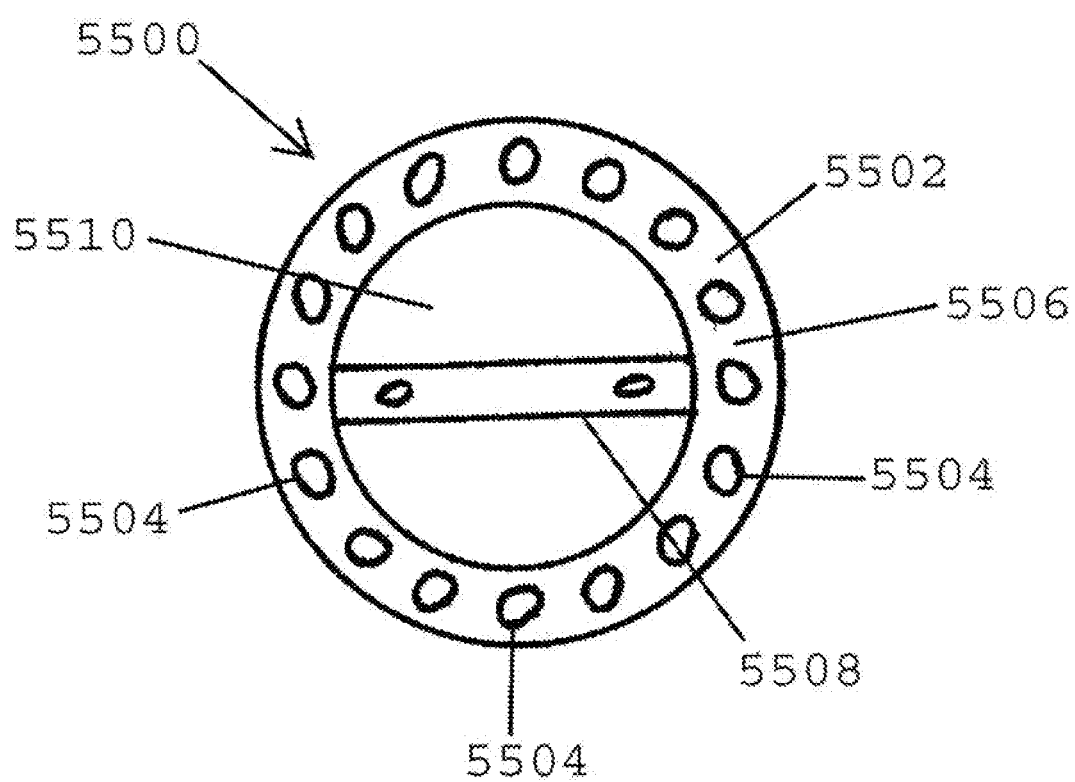
FIG. 55 is a front cross-sectional view of a variation of a visualization device.

Of course, device (5400) is only one variation of a visualization device comprising multiple scopes, and other variations (e.g., having different configurations) may be used, as appropriate. For example, FIG. 55 depicts a variation of a visualization device (5500) comprising a tubular member (5502) and multiple fiber scopes (5504) embedded within a wall portion (5506) of the tubular member. Device (5500) further comprises an anchor (5508) disposed within a lumen (5510) of tubular member (5502). As shown, scopes (5504) are essentially evenly distributed radially around tubular member (5502). However, other variations of visualization devices may comprise scopes that are not evenly distributed or positioned, and/or that form different patterns. The arrangement of scopes in a device may be selected, for example, based on the target site and the desired image or images to be obtained therefrom.

Figure 56A:
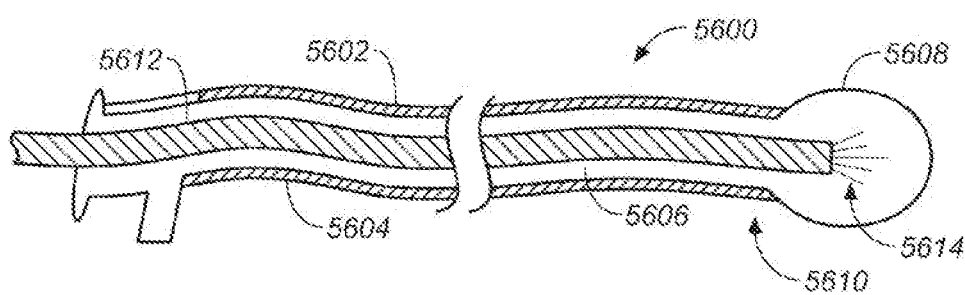
FIG. 56A is an illustrative side view in partial cross-section of a variation of a visualization device.

Still other variations of visualization devices employing scopes may be used. For example, FIG. 56A shows a visualization catheter (5600) comprising a flexible tubular member (5602) including a wall portion (5604) and having a lumen (5606) therethrough. Catheter (5600) also comprises a transparent balloon (5608) at the distal end (5610) of tubular member (5602). In some cases, balloon (5608) may be inflated and/or deflated as desired, or may be capable of a one-time inflation and/or a one-time deflation. During use, and as shown in FIG. 56A, a long flexible endoscope (5612) may be passed through lumen (5606) of tubular member (5602), sliding axially within the tubular member. A distal portion (5614) of the endoscope may be positioned within balloon (5608), as depicted. The endoscope may then be used to view the surrounding area. Endoscope (5612) may, for example, have a length of about 10 centimeters to about 150 centimeters, and/or a diameter of about 1 millimeter to about 3 millimeters. The size of endoscope (5612) and/or catheter (5600) may depend, for example, on the characteristics of the target site.

Figure 56B:
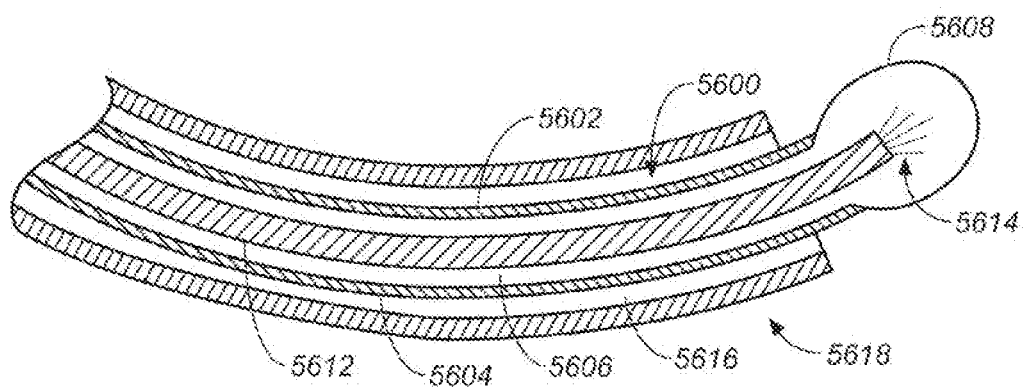
FIG. 56B is an illustrative side view in partial cross-section of the visualization device of FIG. 56A, disposed within a variation of a guide catheter.

In some variations, catheter (5600) may be advanced to a target site by being passed within another catheter, such as a guide catheter or a tunnel catheter. For example, FIG. 56B depicts catheter (5600) disposed within a lumen (5616) of a guide catheter (5618). With distal end (5614) of endoscope (5612) positioned within balloon (5608), catheter (5600) may then be positioned so that balloon (5608) is located at the distal end of the catheter in which catheter (5600) is disposed. In some variations, balloon (5608) may be in a deflated form as catheter (5600) is being positioned, and may later be inflated (e.g., with saline or a saline-contrast solution). The inflation of balloon (5608) may displace blood surrounding distal end (5614) of endoscope (5612). This blood displacement, in turn, may allow the space occupied by optically clear balloon (5608) to be visualized. By being able to visualize the space just distal to the distal end or tip of the guide catheter, tunnel catheter, or other catheter or device in which catheter (5600) is positioned, the operator may be able to navigate the catheter or device successfully to the target site (e.g., the subannular space).

As discussed above, balloon (5608) is optically transparent or clear. Balloon (5608) may comprise one or more materials, such as one or more polymers. Non-limiting examples of polymers which may be appropriate include polyurethanes, nylon, polyesters (e.g., polyethylene terephthalate or PET), neoprene, silicone, and polyethylene. Combinations (e.g., blends) of polymers and/or other materials may also be used. In certain variations, balloon (5608) may comprise latex. In some variations, balloon (5608) may comprise isoprene. Balloon (5608) may be relatively elastic, and in use may conform to surrounding anatomical structures, such as the ventricular wall, chordae tendineae, and/or heart valve leaflets. This conformational characteristic of the balloon surface may enhance the ability of balloon (5608) to displace blood surrounding anatomical structures, so that catheter (5600) may be used to provide relatively high optical visibility of the anatomical structures.

Catheter (5600) (e.g., tubular member (5602)) may comprise one or more materials. Exemplary materials include polymers, such as nylon, polyurethane, PEBAX® polyether block amide copolymers, polyolefins (e.g., polyethylene), polyetheretherketone (PEEK), polyimides, and fluoropolymers. Combinations of polymers and/or other materials may also be used. For example, in some variations, catheter (5600) may comprise a metal wire braid or coil disposed within a polymer matrix.

Figure 57:
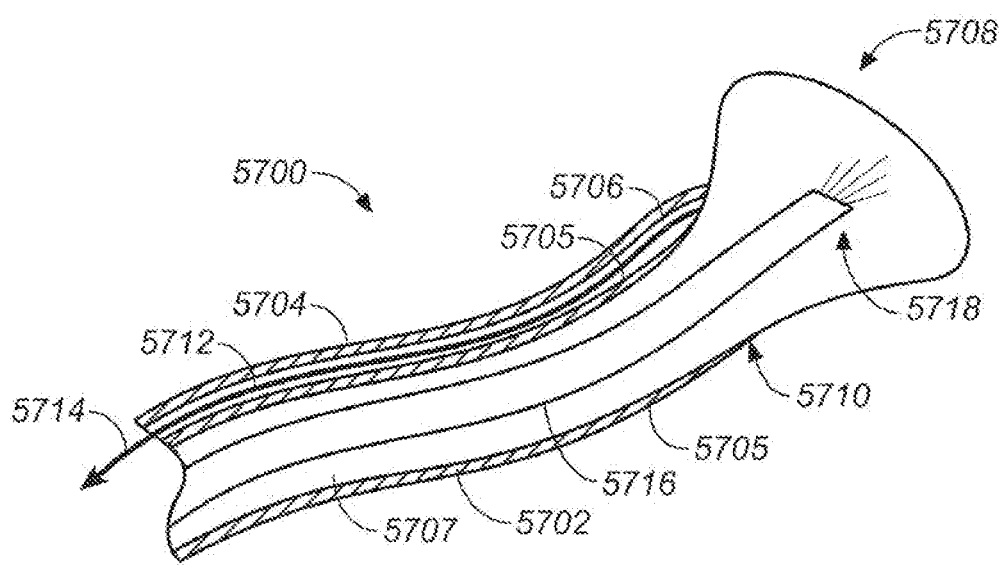
FIG. 57 is an illustrative side view in partial cross-section of another variation of a visualization device.

In certain variations, a catheter comprising at least one scope may also comprise a tendon or other tensioning member that may be tensioned to maneuver the catheter. For example, FIG. 57 depicts a visualization catheter (5700) comprising a flexible elongated member (5702) including first and second wall portions (5704) and (5705), as well as first and second lumens (5706) and (5707). Catheter (5700) also comprises a transparent balloon (5708) at the distal end (5710) of elongated member (5702), which is in fluid communication with second lumen (5707). Catheter (5700) further comprises a tensioning member (5712) disposed within first lumen (5706), where the tensioning member is configured to be tensioned in the direction of arrow (5714), to flex elongated member (5702). As shown, a long flexible endoscope (5716) may be passed through second lumen (5707), and its distal portion (5718) may be positioned within balloon (5708). While catheter (5700) is depicted as comprising one tensioning member (5712), other variations of catheters may comprise multiple (i.e., at least two) tensioning members. The tensioning members may all be disposed within a single lumen of the catheter, or at least two tensioning members may be disposed in different lumens of the catheter. Moreover, in some variations, a visualization catheter may comprise at least one tensioning member that is not disposed within any lumens of the catheter.

As described above, in certain variations, a visualization device and/or method may be used in conjunction with a chord manipulation catheter, diagnostic catheter and/or guide catheter. Moreover, a visualization device and/or method may be used in conjunction with any other appropriate catheter. Furthermore, in some variations, a chord manipulation catheter, diagnostic catheter and/or guide catheter may also be capable of functioning as a visualization catheter. Of course, in certain variations, a chord manipulation catheter, diagnostic catheter and/or guide catheter may be used independently of any of the visualization devices and/or methods described here.

Catheter Configurations

In some variations, a catheter, such as a diagnostic catheter, chord manipulation catheter, guide catheter or visualization catheter, may comprise one or more curve regions. The curve regions may, for example, help the catheter to be successfully navigated to, and/or positioned within, a target site. In certain variations, the curvature of a catheter may be designed to cause the catheter to automatically register with the subannular groove region of a heart, and/or to automatically cannulate the subannular groove. This may, for example, allow for highly predictable and accurate positioning of the catheter within the subannular groove region of the heart. Additionally, it may be relatively easy for an operator to accurately deliver such a catheter to a subannular groove region of a heart.

An exemplary curved catheter is shown in FIGS. 16A-16D. As shown there, a guide catheter (1650) comprises a proximal operating portion (1652) and a shaft (1670) (e.g., which may be braided) comprising a distal portion (1672) having a compound curve (1673). Compound curve (1673) may be used, for example, to help access a target site, such as a subannular groove of a heart. For example, the compound curve may be configured to allow the catheter to automatically register in the subannular groove. Proximal operating portion (1652) includes a hemostatic valve (1654), a port (1656), a hub cap (1658), and a pullwire tensioning knob (1660). A pullwire (1674) is connected to pullwire tensioning knob (1660), and extends through shaft (1670) to distal portion (1672), where the pullwire is connected to a pullwire ring (1676). Pullwire (1674) may be used to deflect a deflectable section (1678) of distal portion (1672). As shown in FIG. 16D, guide catheter (1650) also comprises an atraumatic or soft tip (1680). While guide catheter (1650) includes curves and a deflectable section, some variations of guide catheters or other types of catheters may include one or more curves without including any deflectable sections. Additionally, certain variations of catheters may comprise a deflectable section that may be deflected into a curved shape, but may not comprise any other curve regions.

Figure 16E:
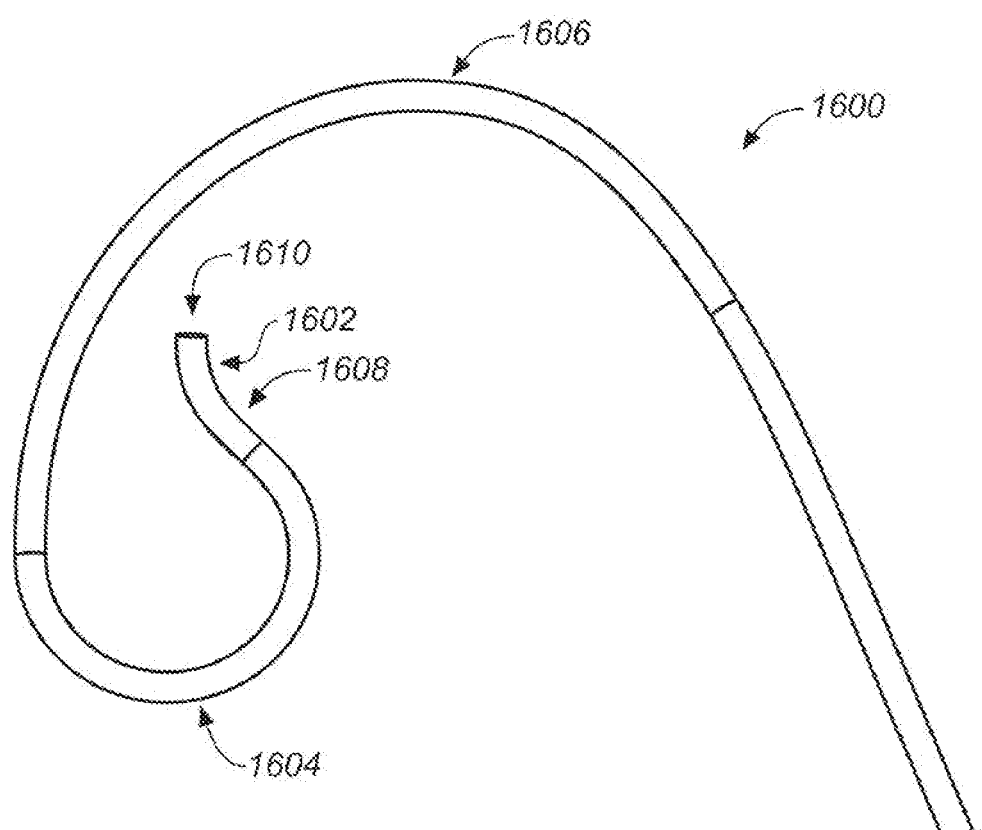
FIG. 16E is a perspective view of a variation of a diagnostic catheter.

While a curved guide catheter has been described, other types of catheters may also have one or more curve regions. Moreover, it should be understood that curve regions and features discussed herein with respect to one type of catheter may be applied to other types of catheters, as appropriate. FIG. 16E shows a portion of a diagnostic catheter (1600) having three curve regions: a valve curve region (1602), a transition curve region (1604), and an arch curve region (1606). The geometry of diagnostic catheter (1600) may, for example, allow specific anatomical landmarks to be targeted during use. The geometry of a catheter such as diagnostic catheter (1600) may also allow for automatic positioning of the catheter at a target site, such as automatic cannulation of the subannular groove. Each of the curve regions will now be discussed in further detail below.

Arch curve region (1606) typically may be sized and shaped to fit within (e.g., to conform to the curve of) the aortic arch of a heart. The geometry of arch curve region (1606) may cause diagnostic catheter (1600) to automatically orient toward the endocardial surface and away from the center of the ventricular cavity during use. In some variations, arch curve region (1606) may form an arc having an arc diameter of about 3.5 inches to about 5 inches (e.g., about 4 inches) and/or defining a central angle of about 60° to about 270° (e.g., about 60° to about 180°, or about 100° to about 170°, such as about 150°).

Transition curve region (1604) generally may be sized and shaped for positioning the distal portion (1608) of catheter (1600) (including distal end (1610)) within the mitral valve region. Transition curve region (1604) typically may be shaped such that when diagnostic catheter (1600) has been delivered to a target subvalvular space of a heart, transition curve region (1604) spans from the aortic root to the entrance of the subannular groove, pointing toward the anterior side of the left ventricle. The diameter of the arc of transition curve region (1604) may be selected so that diagnostic catheter (1600) presses up against the septal wall of the heart when distal portion (1608) of diagnostic catheter (1600) is positioned in a subannular groove region of a mitral valve. In certain variations, transition curve region (1604) may form an arc having an arc diameter of about 1 inch to about 3 inches (e.g., about 1 inch to about 2 inches, such as about 1.2 inches) and/or defining a central angle of about 90° to about 270° (e.g., about 120° to about 270°, about 180° to about 270°, about 200° to about 270°, or about 220° to about 250°, such as about 230°).

Finally, valve curve region (1602) typically may be sized and shaped to fit within a subannular groove region of a mitral valve. In some cases, valve curve region (1602) may automatically conform to the shape of the subannular groove region during positioning, without requiring any adjustment thereafter. In certain variations, valve curve region (1602) may be positioned at an angle of about 45° with respect to transition curve region (1604). However, upon insertion of the guide tunnel, valve curve region (1602) may become planar relative to the subannular groove of the mitral valve. In some variations, the length (or arc length) of valve curve region (1602) may be selected such that when diagnostic catheter (1600) is withdrawn, there is sufficient length at the distal portion (1608) of diagnostic catheter (1600) to force diagnostic catheter (1600) up against the septal wall of the heart without distal portion (1608) dislodging from the subannular groove. In some variations, valve curve region (1602) may form an arc having an arc diameter of about 0.75 inch to about 1.5 inches (e.g., about 0.75 inch to about 1.2 inches, or about 0.9 inch) and/or defining a central angle of about 60° to about 80° (e.g., about 70° or about 77°), or about 75° to about 120° (e.g., about 100° to about 120°, such as about 115°).

Diagnostic catheter (1600) has three curve regions. However, in certain variations, a diagnostic catheter may have one or two curve regions, or may have more than three curve regions (e.g., four, five, six, etc.). As an example, in some variations, a diagnostic catheter may have a transition curve region and a valve curve region, but may not have an arch curve region. In some such variations, the diagnostic catheter may be sufficiently flexible to be easily routed through the aortic arch, without being pre-curved to fit the aortic arch. As another example, in certain variations, a diagnostic catheter may have a valve curve region, a transition curve region, and an arch curve region such as those described above with reference to FIG. 16E, and may also have a fourth curve region. The fourth curve region may, for example, serve to brace the diagnostic catheter up against the septal wall of the left ventricle of the heart. In some variations, a guide catheter may include a fourth curve region that may brace the guide catheter up against the septal wall of the left ventricle of a heart when the guide catheter is being advanced to a subvalvular space of the heart. This bracing may, for example, help to prevent backward movement of the guide catheter when another device is being advanced through and out of the guide catheter.

While one variation of a diagnostic catheter is described with reference to FIG. 16E, and additional variations of diagnostic catheters are described below, it should be understood that the sizes and/or shapes (and/or other appropriate characteristics) of the diagnostic catheters described herein may be applied to guide catheters, as well, and vice-versa. For example, in some variations, a diagnostic catheter and guide catheter may have the same curves with the same shapes, with the guide catheter having scaled-up dimensions relative to the diagnostic catheter. Thus, it should be understood that the descriptions herein with respect to diagnostic catheters may also be applied to guide catheters or other types of catheters (e.g., chord manipulation catheters, anchor deployment catheters) as appropriate, and vice versa.

FIG. 16E shows only one example of a diagnostic catheter variation. However, any number of different variations may be used. For example, FIGS. 17A-17G depict another variation of a diagnostic catheter having a different curvature from the diagnostic catheter of FIG. 16E.

Figures 17A, 17B:
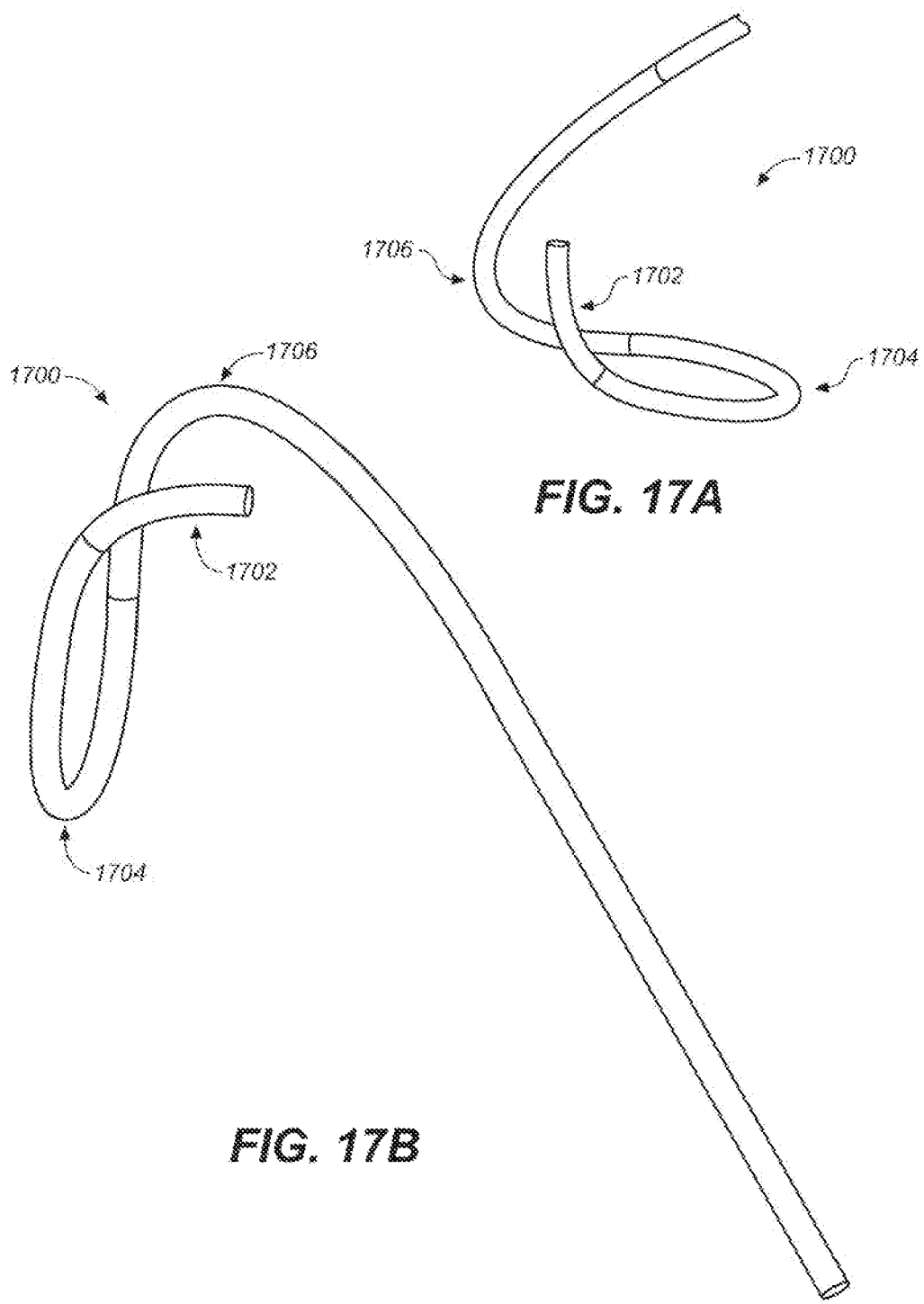
FIGS. 17A and 17B are perspective views of another variation of a diagnostic catheter.

As shown in FIGS. 17A-17C, a diagnostic catheter (1700) comprises a valve curve region (1702), a transition curve region (1704), and an arch curve region (1706). Referring specifically to FIG. 17C, diagnostic catheter (1700) also comprises a region (1708) that is proximal to valve curve region (1702), transition curve region (1704), and arch curve region (1706). Region (1708) has a length (L1) that may be, for example, from about 25 inches to about 40 inches (e.g., from about 30 inches to about 40 inches, or from about 30 inches to about 35 inches, such as 32.715 inches). A proximal portion (1710) of region (1708) has a length (L2) that may be, for example, from about 1 inch to about 4 inches (e.g., from about 2 inches to about 3 inches, such as 2.473 inches). Additionally, and referring still to FIG. 17C, arch curve region (1706) forms an arc having an arc diameter (AD1) that may be, for example, from about 3 inches to about 5 inches (e.g., from about 3.5 inches to about 4.5 inches, such as 3.5 inches). The arc also defines a central angle ($\alpha 1$) that may be, for example, from about 60° to about 180° (e.g., from about 60° to about 160°, from about 100° to about 160°, or from about 100° to about 140°, such as 120°).

Additionally, and referring now to FIG. 17D, diagnostic catheter (1700) comprises a tubular member (1712) having an outer diameter (OD1) and an inner diameter (ID1). In some variations, inner diameter (ID1) may be from about 1.33 millimeters to about 3 millimeters. Alternatively or additionally, outer diameter (OD1) may be from about 1.67 millimeters to about 3.33 millimeters.

As will be explained in further detail below, in a diagnostic catheter comprising a valve curve region, a transition curve region, and/or an arch curve region, each region may define a different plane. For example, FIG. 17E shows that arch curve region (1706) defines an arch plane (1716), while transition curve region (1704) defines a transition plane (1718). In certain variations, the angle ($\alpha 2$) between arch plane (1716) and transition plane (1718) may be from about 20° to about 60° (e.g., from about 30° to about 60°, or from about 40° to about 60°, such as 50°).

Figure 17F:
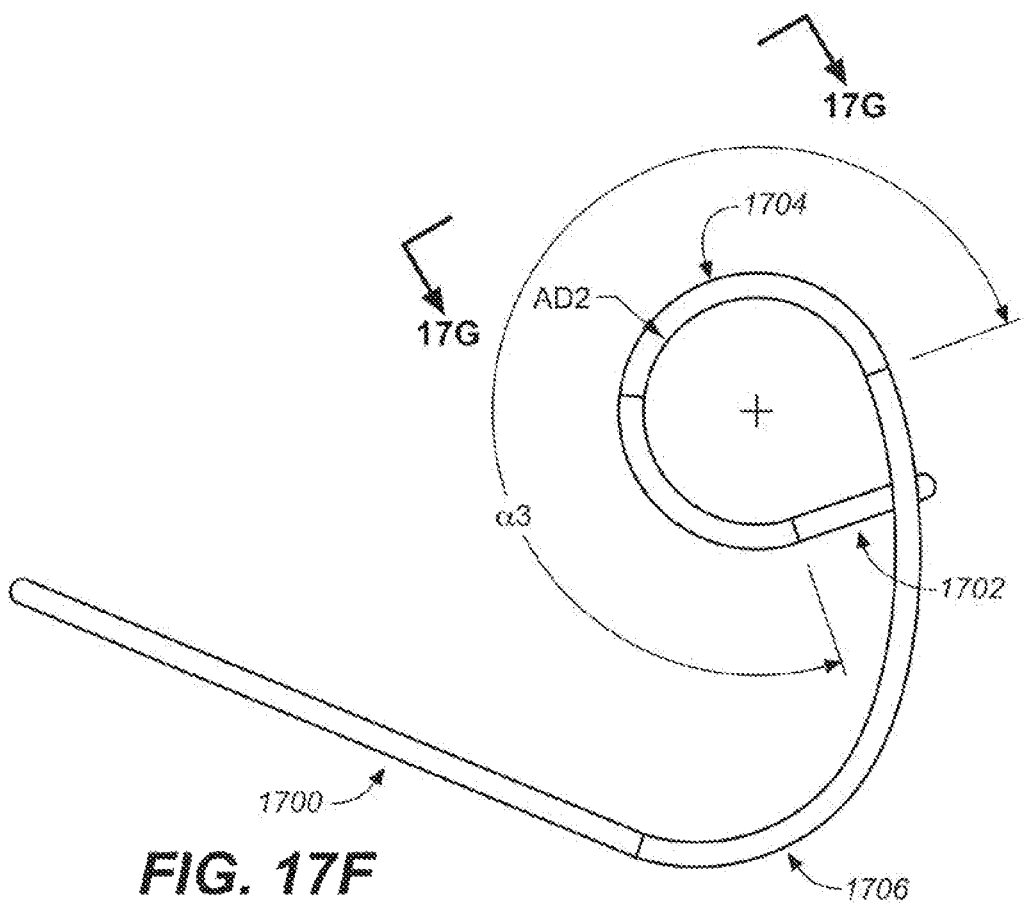
FIG. 17F is a view of the diagnostic catheter as shown in FIG. 17E, taken along line 17F-17F.
Figure 17G:
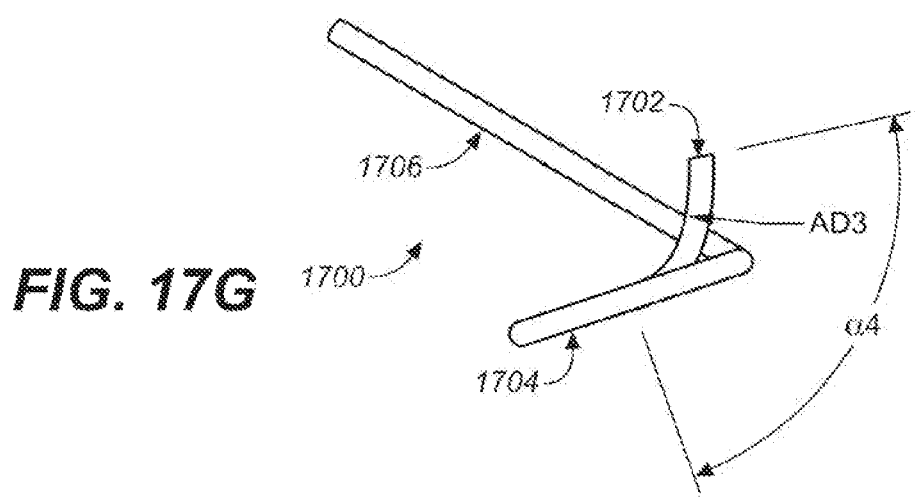
FIG. 17G is a view of the diagnostic catheter as shown in FIG. 17F, taken along line 17G-17G.

As shown in FIG. 17F, transition curve region (1704) forms an arc having an arc diameter (AD2) that may be, for example, from about 1 inch to about 3 inches (e.g., from about 1 inch to about 2 inches, such as 1 inch). The arc also defines a central angle ($\alpha 3$) that may be, for example, from about 90° to about 270° (e.g., from about 120° to about 270°, from about 180° to about 270°, or from about 200° to about 270°, such as 270°). Additionally, and referring now to FIG. 17G, valve curve region (1702) forms an arc having an arc diameter (AD3) that may be, for example, from about 0.75 inch to about 1.5 inches (e.g., from about 0.8 inch to about 1.3 inches, or from about 0.8 inch to about 1.1 inches, such as 1 inch), and defining a central angle ($\alpha 4$) that may be, for example, from about 60° to about 120° (e.g., from about 75° to about 120°, from about 100° to about 120°, or from about 75° to about 105°, such as 90°).

In some variations, a catheter such as a diagnostic catheter, chord manipulation catheter, guide catheter, and/or visualization catheter, may have a high degree of flexion that allows a flexible distal section of the catheter to be formed into a tighter curve. This may, for example, provide the catheter with enhanced ability to navigate and, in some cases, to visualize, complex spaces such as a subannular groove of a mitral valve.

Figure 18A:
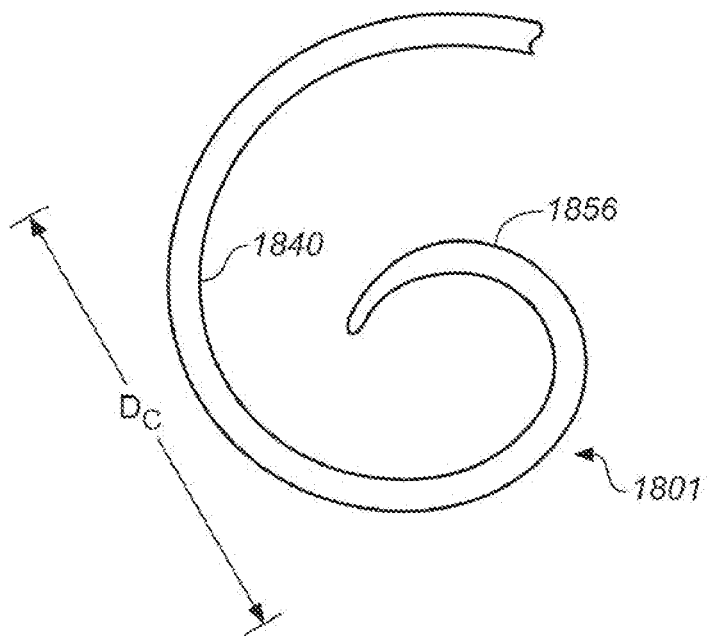
FIGS. 18A and 18B illustrate flexed and extended configurations, respectively, of a variation of a catheter.
Figure 18B:
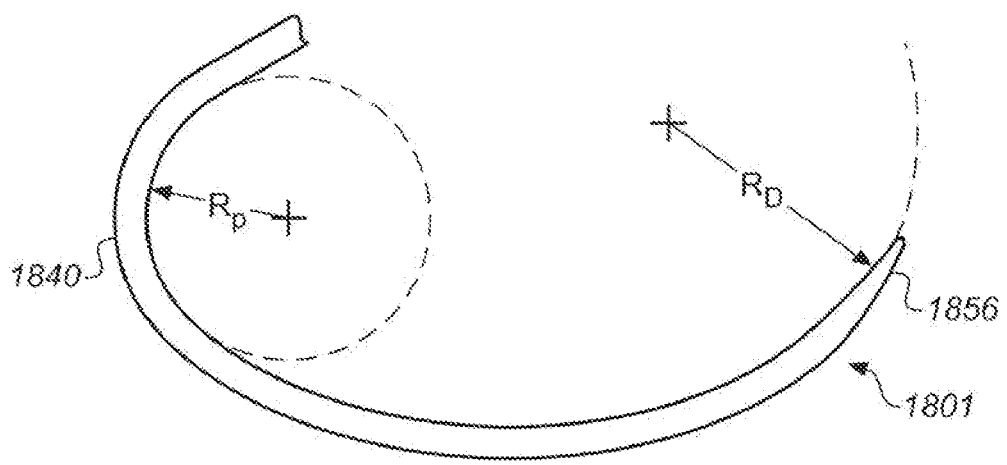

A variation of such a catheter with a high degree of flexion is shown in FIGS. 18A and 18B. FIG. 18A shows the catheter (1801), which comprises a proximal section (1840) and a distal section (1856) in a configuration having a high degree of flexion due to tension applied to a tensioning element (not shown) in catheter (1801). FIG. 18B shows catheter (1801) in an extended configuration. When catheter (1801) is in an extended configuration, at least a portion of proximal section (1840) may have a radius of curvature ($R_P$) of at most about 1.6 inches (e.g., about 0.75 inch, about 0.8 inch, about 0.85 inch, about 0.9 inch, about 0.95 inch, about 1.0 inch, about 1.05 inches, about 1.1 inches, about 1.15 inches, about 1.2 inches, about 1.25 inches, about 1.3 inches, about 1.35 inches, about 1.4 inches, about 1.45 inches, or about 1.5 inches). Alternatively or additionally, at least a portion of distal section (1856) may have a radius of curvature ($R_D$) of at most about 1.6 inches (e.g., about 0.75 inch, about 0.8 inch, about 0.85 inch, about 0.9 inch, about 0.95 inch, about 1.0 inch, about 1.05 inches, about 1.1 inches, about 1.15 inches, about 1.2 inches, about 1.25 inches, about 1.3 inches, about 1.35 inches, about 1.4 inches, about 1.45 inches, or about 1.5 inches).

The curvature of distal section (1856) may define a plane that is distinct from the plane defined by the curvature of proximal section (1840). In some variations, the planes may be oriented at about 90° relative to each other, while in other variations, the planes may be oriented at a different angle relative to each other (e.g., about 60° or about 30° relative to each other). The relative orientation of the planes may be selected, for example, based on the anatomy or structure to be visualized.

As shown in FIG. 18A, when catheter (1801) is flexed (e.g., to a configuration of maximum flexion by applying maximum tension to a tensioning element of the catheter), the flexed portion of the catheter has a dimension ($D_c$). In some variations, dimension ($D_c$) may be from about 1.0 inch to about 1.5 inches (e.g., about 1.1 inches, about 1.2 inches, about 1.3 inches, or about 1.4 inches).

Figure 19A:
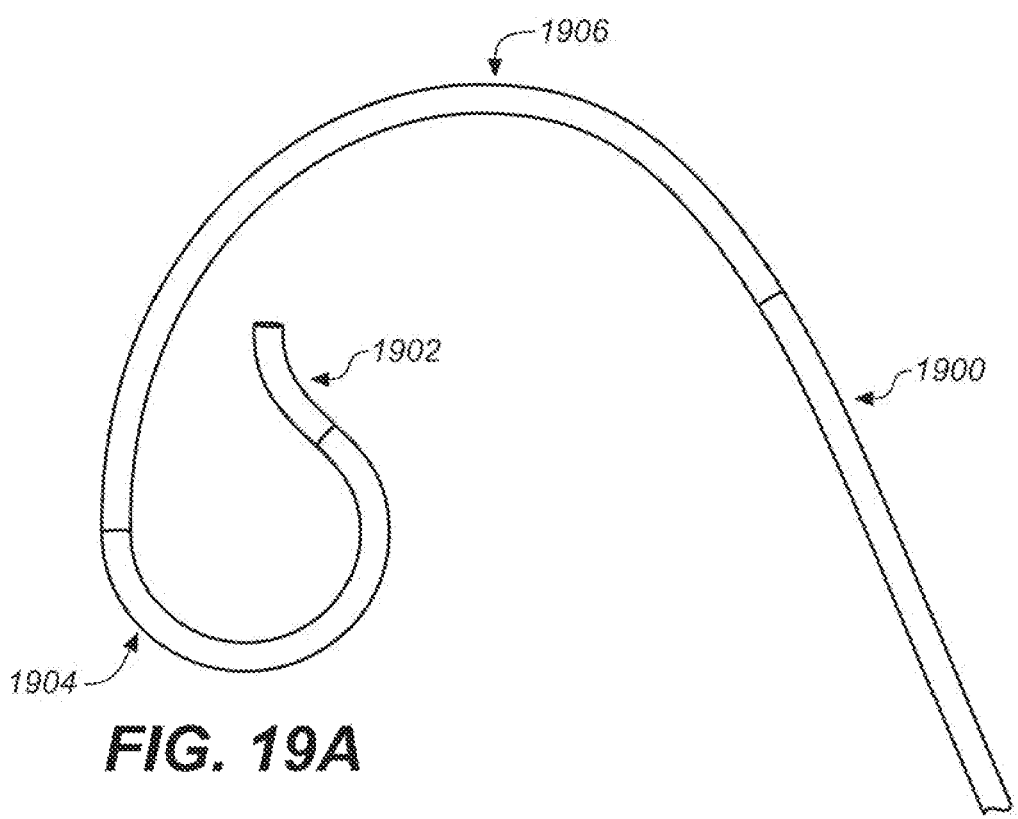
FIG. 19A is a perspective view of an additional variation of a diagnostic catheter.
Figure 19B:
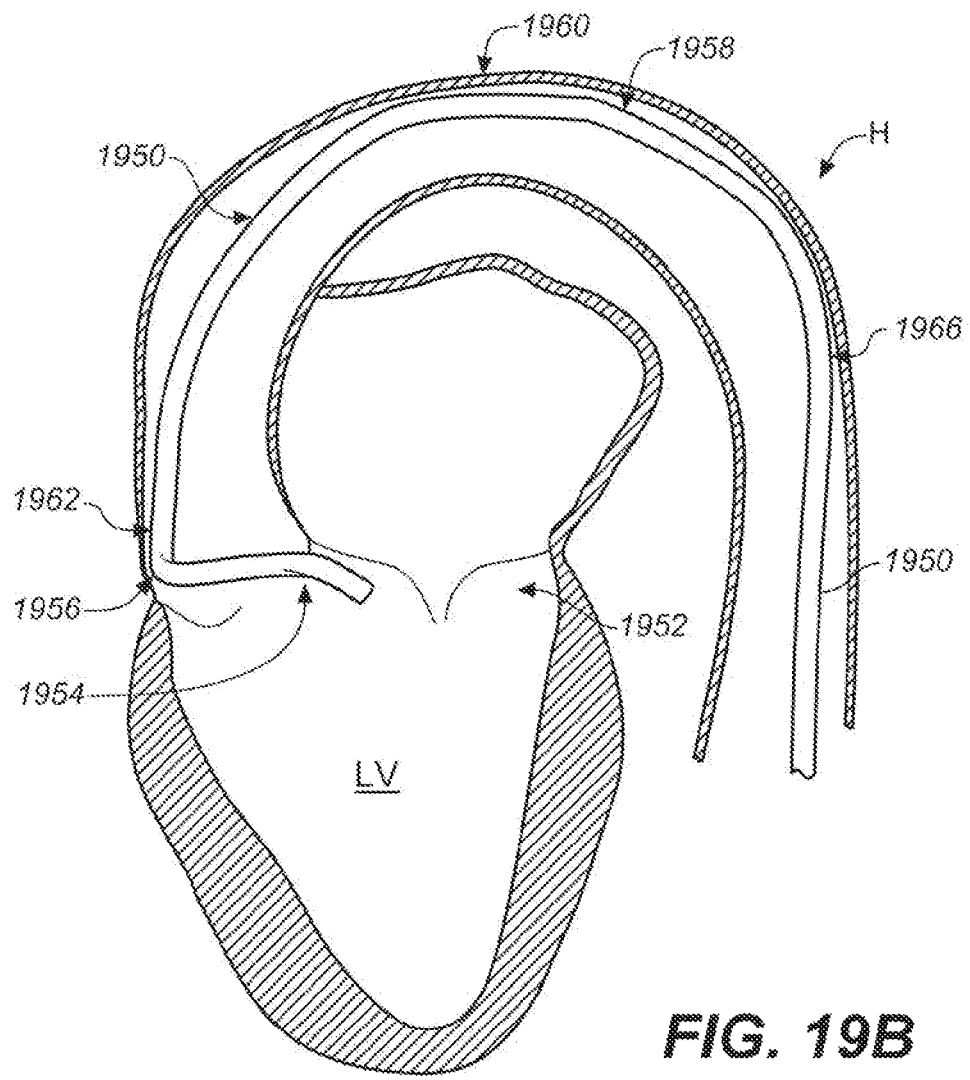
FIG. 19B is an illustrative view of the advancement of a variation of a diagnostic catheter into a subvalvular space of a heart.

As described above, a diagnostic catheter may comprise different regions having different curvatures. As another example of this type of configuration, FIG. 19A shows a diagnostic catheter (1900) comprising a valve curve region (1902), a transition curve region (1904), and an arch curve region (1906). The curvature and size of each of these regions may depend, for example, on the characteristics of the targeted anatomy. For example, FIG. 19B shows a diagnostic catheter (1950) being advanced into the subvalvular space (1952) of a left ventricle (LV) of a heart (H), where the diagnostic catheter comprises a valve curve region (1954), a transition curve region (1956), and an arch curve region (1958). These three curve regions are designed to correspond to the path that the catheter takes to access subvalvular space (1952). Diagnostic catheter (1950) is configured such that, when disposed within the aortic arch (1960) of the heart, the diagnostic catheter has certain bracing points (1962) and (1966) that may help to stabilize its position. Of course, diagnostic catheter (1950) is only one variation of a diagnostic catheter, and other variations of diagnostic catheters may include different numbers or locations or bracing points, or may not include any bracing points.

Figure 20:
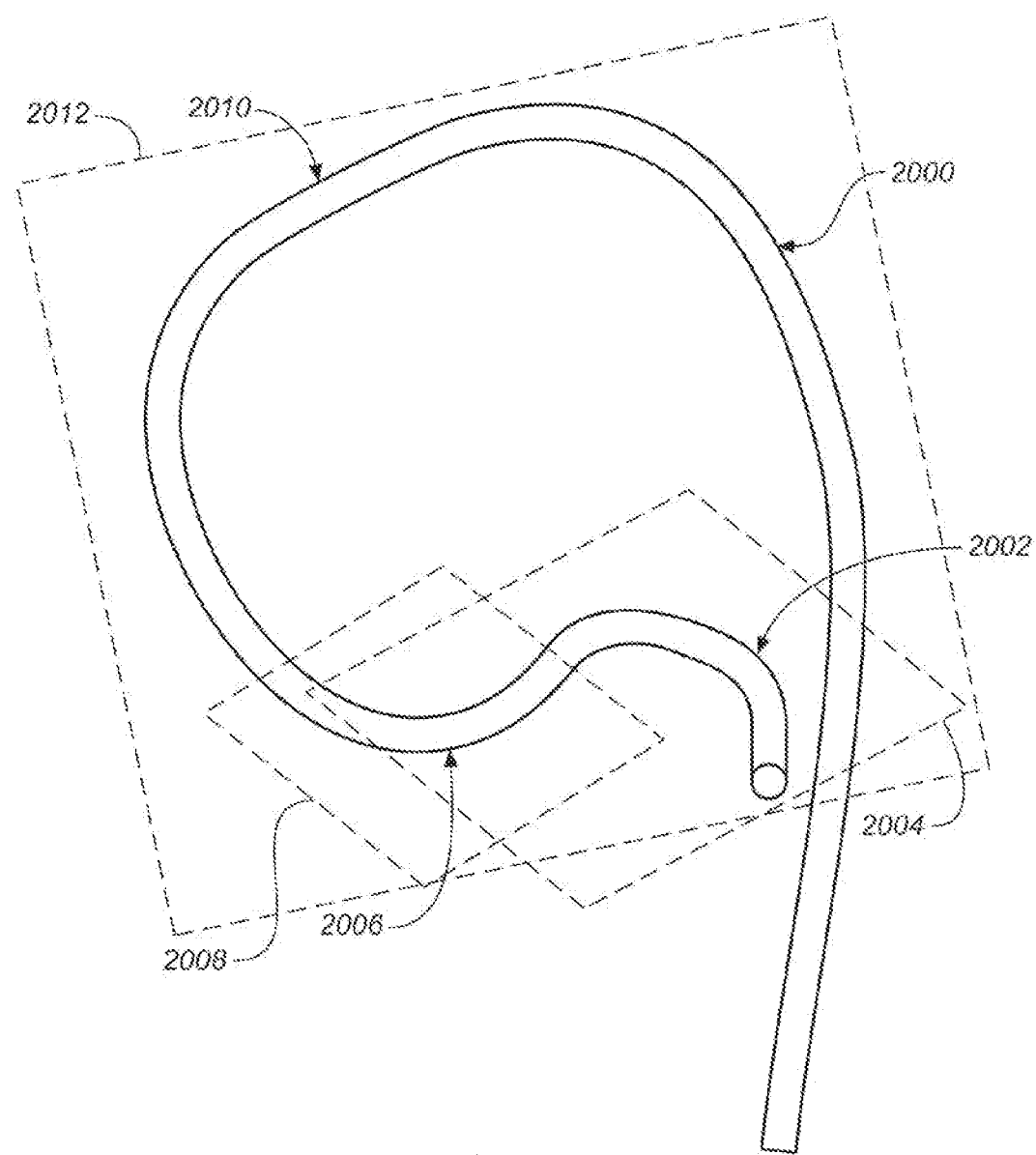
FIG. 20 is an illustrative depiction of a variation of a diagnostic catheter and three planes defined by three different regions of the diagnostic catheter.

As also described above, in a diagnostic catheter comprising a valve curve region, a transition curve region, and/or an arch curve region, each region may define a different plane. For example, FIG. 20 shows a diagnostic catheter (2000) comprising a valve curve region (2002) defining a valve plane (2004), a transition curve region (2006) defining a transition plane (2008), and an arch curve region (2010) defining an arch plane (2012). In some cases, the relationships of two or more of these regions and/or planes to each other may be used to help define the curved configuration of a diagnostic catheter (or any other appropriate catheter). Additionally, while FIG. 20 shows a diagnostic catheter having three curve regions defining three different planes, diagnostic catheters having different configurations may also be used. As an example, a diagnostic catheter may comprise only two curve regions defining two different planes (e.g., a valve curve region defining a valve plane and a transition curve region defining a transition plane), or may comprise more than three curve regions defining more than three different planes. As another example, in some variations, a diagnostic catheter may comprise multiple curve regions, with at least two of the curve regions defining different planes, and at least two of the curve regions defining the same plane.

Figure 21A:
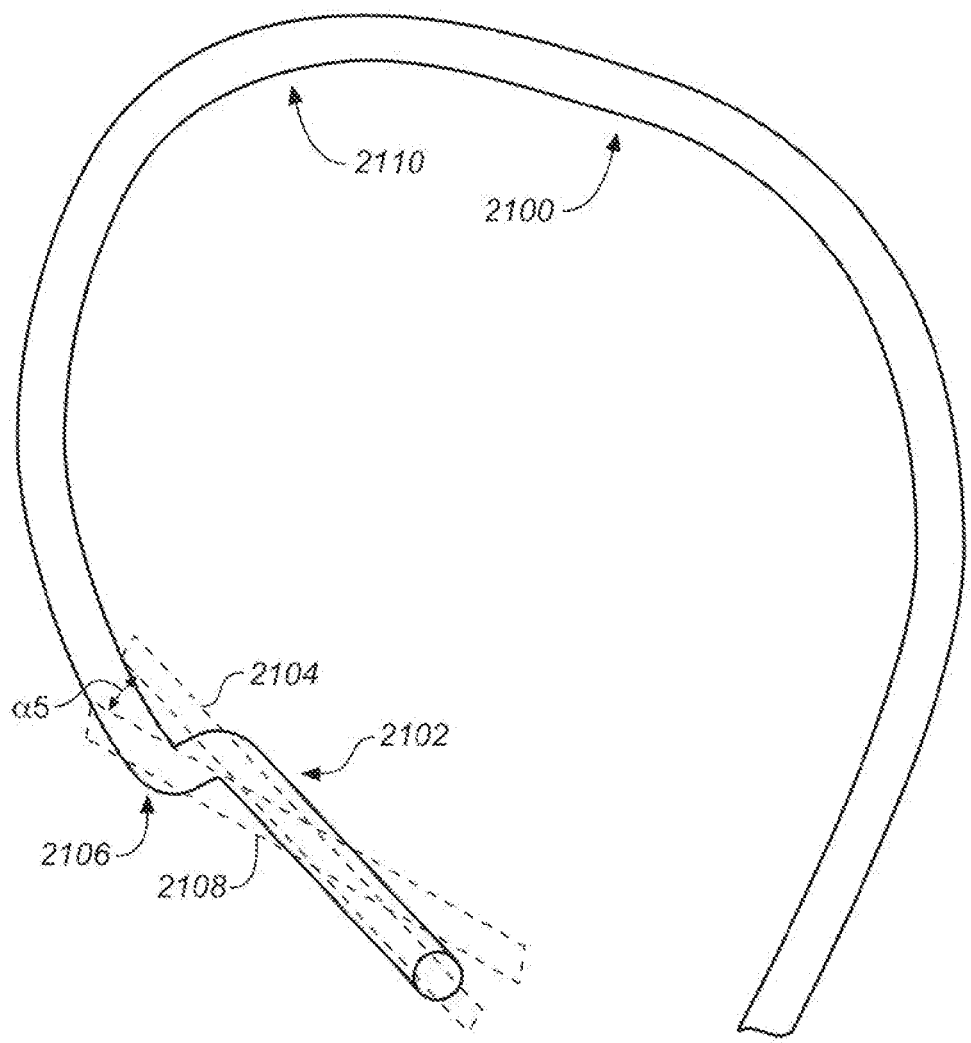
FIG. 21A is an illustrative depiction of another variation of a diagnostic catheter and two planes defined by two different regions of the diagnostic catheter.
Figure 21B:
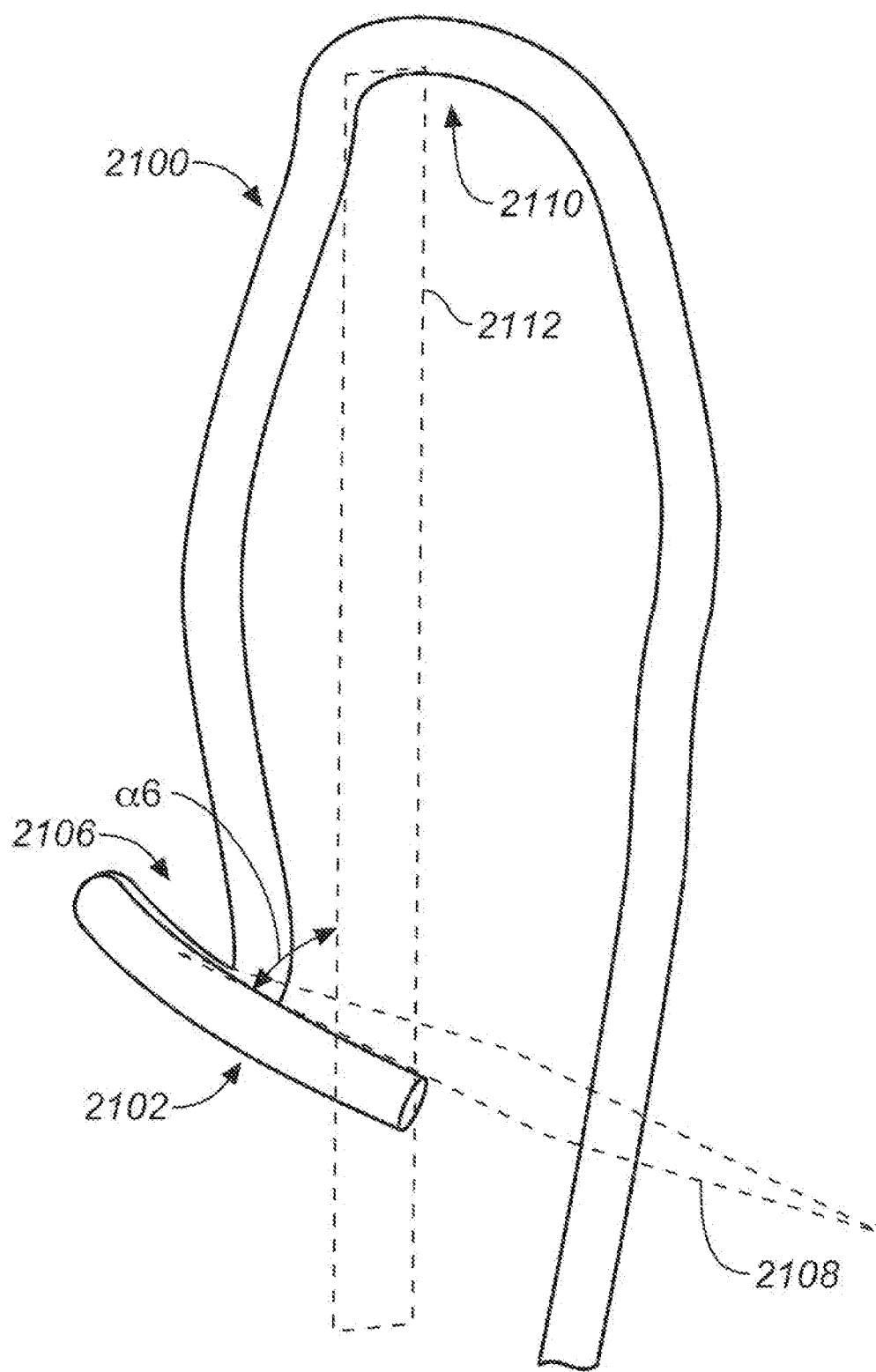
FIG. 21B is another illustrative depiction of the diagnostic catheter of FIG. 21A and two planes defined by two different regions of the diagnostic catheter.
Figure 21C:
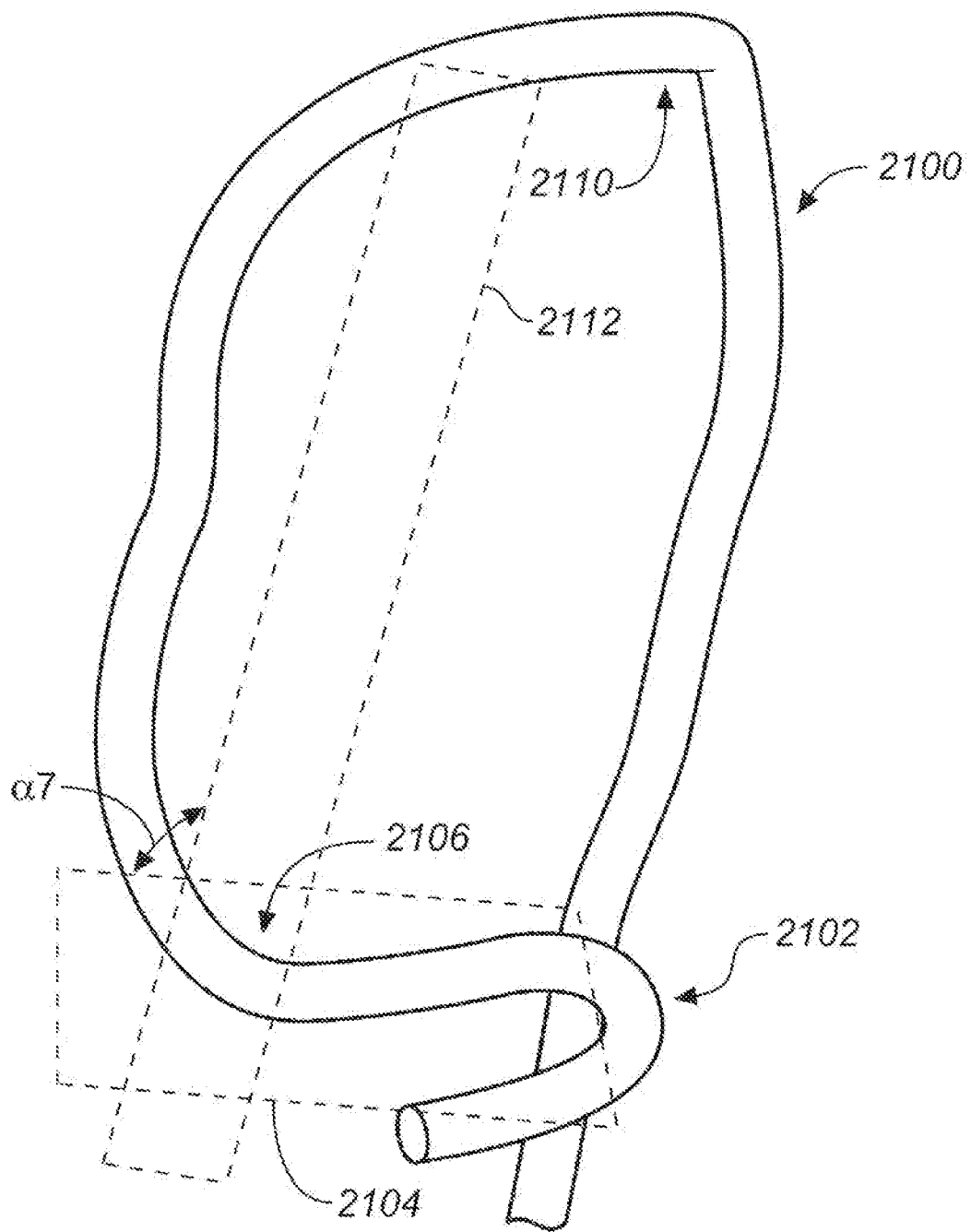
FIG. 21C is an additional illustrative depiction of the diagnostic catheter of FIG. 21A and two planes defined by two different regions of the diagnostic catheter.

FIGS. 21A-21C depict another variation of a diagnostic catheter comprising three curve regions defining three planes. As shown there, a diagnostic catheter (2100) comprises a valve curve region (2102) defining a valve plane (2104), a transition curve region (2106) defining a transition plane (2108), and an arch curve region (2110) defining an arch plane (2112). Referring first to FIG. 21A, valve plane (2104) and transition plane (2108) are positioned at an angle ($\alpha 5$) with respect to each other. In some variations, angle ($\alpha 5$) may be from about 0° to about 90° (e.g., from about 20° to about 90°, from about 20° to about 65°). Referring next to FIG. 21B, transition plane (2108) and arch plane (2112) are positioned at an angle ($\alpha 6$) with respect to each other. In certain variations, angle ($\alpha 6$) may be from about 15° to about 90° (e.g., from about 30° to about 90° or from about 15° to about 45°). Finally, and referring to FIG. 21C, valve plane (2104) and arch plane (2112) are positioned at an angle ($\alpha 7$) with respect to each other.

Figure 22A:
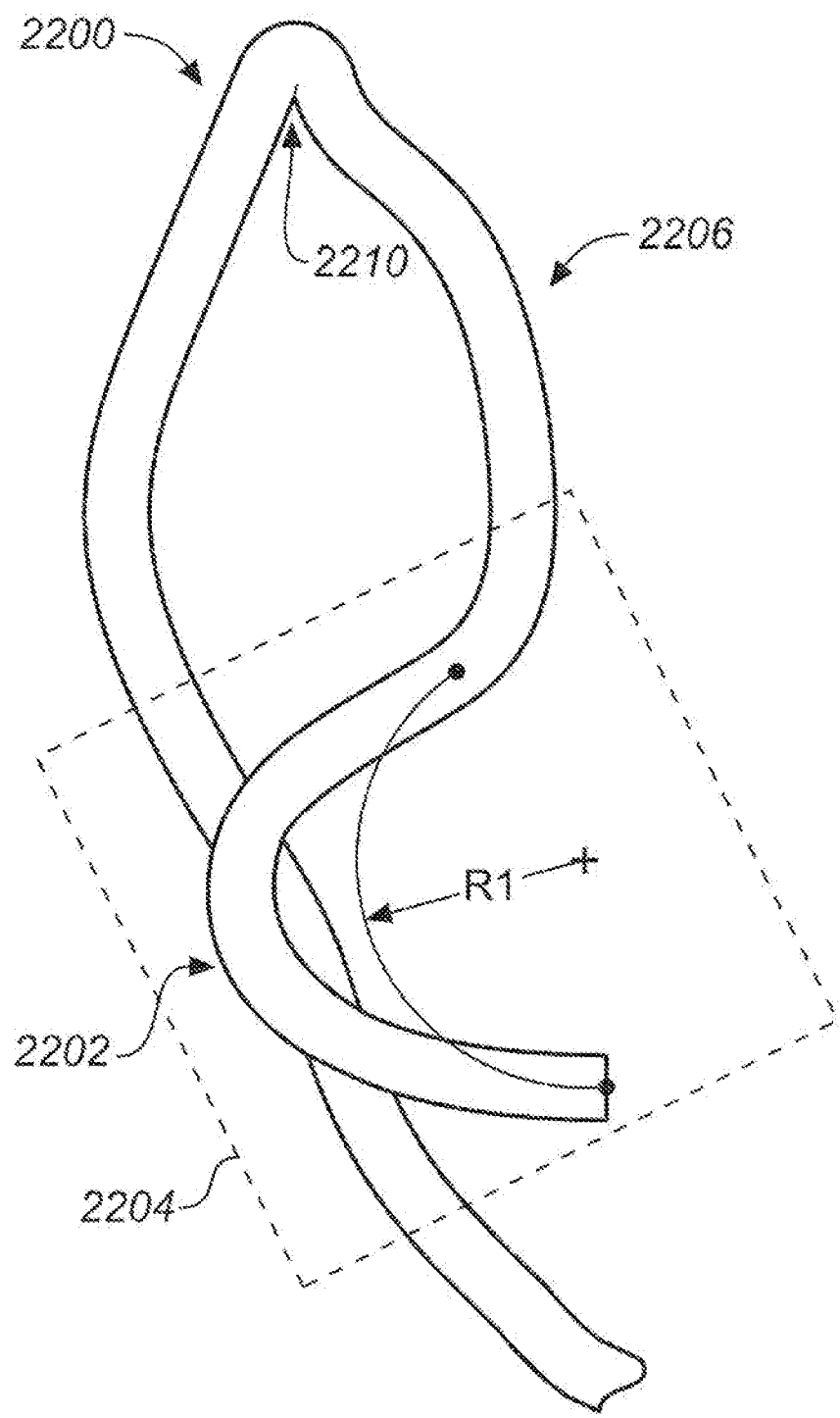
FIG. 22A is an illustrative depiction of an additional variation of a diagnostic catheter, showing the radius of curvature of a first region of the diagnostic catheter that defines a first plane.
Figure 22B:
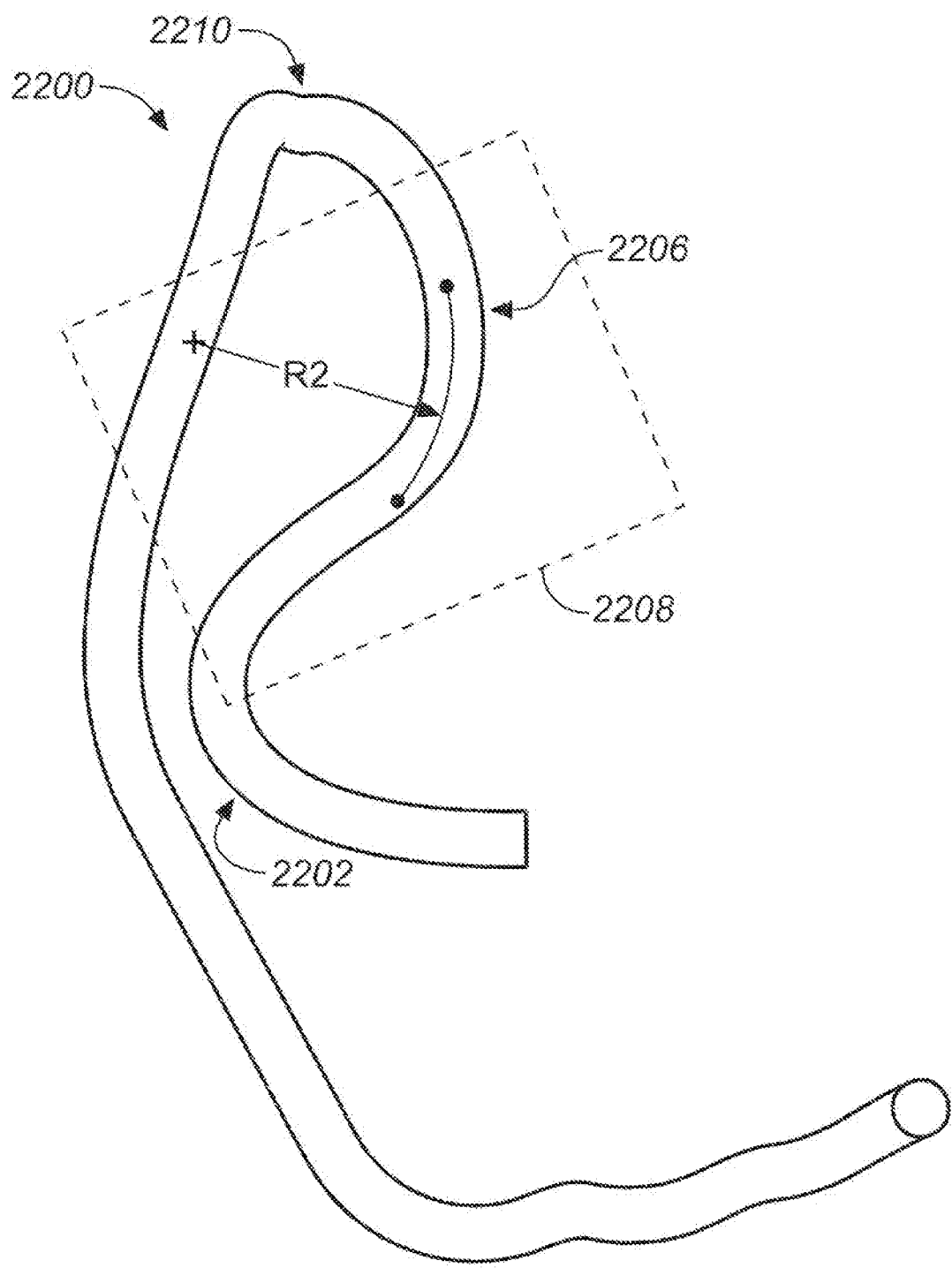
FIG. 22B is an illustrative depiction of the diagnostic catheter of FIG. 22A, showing the radius of curvature of a second region of the diagnostic catheter that defines a second plane.
Figure 22C:
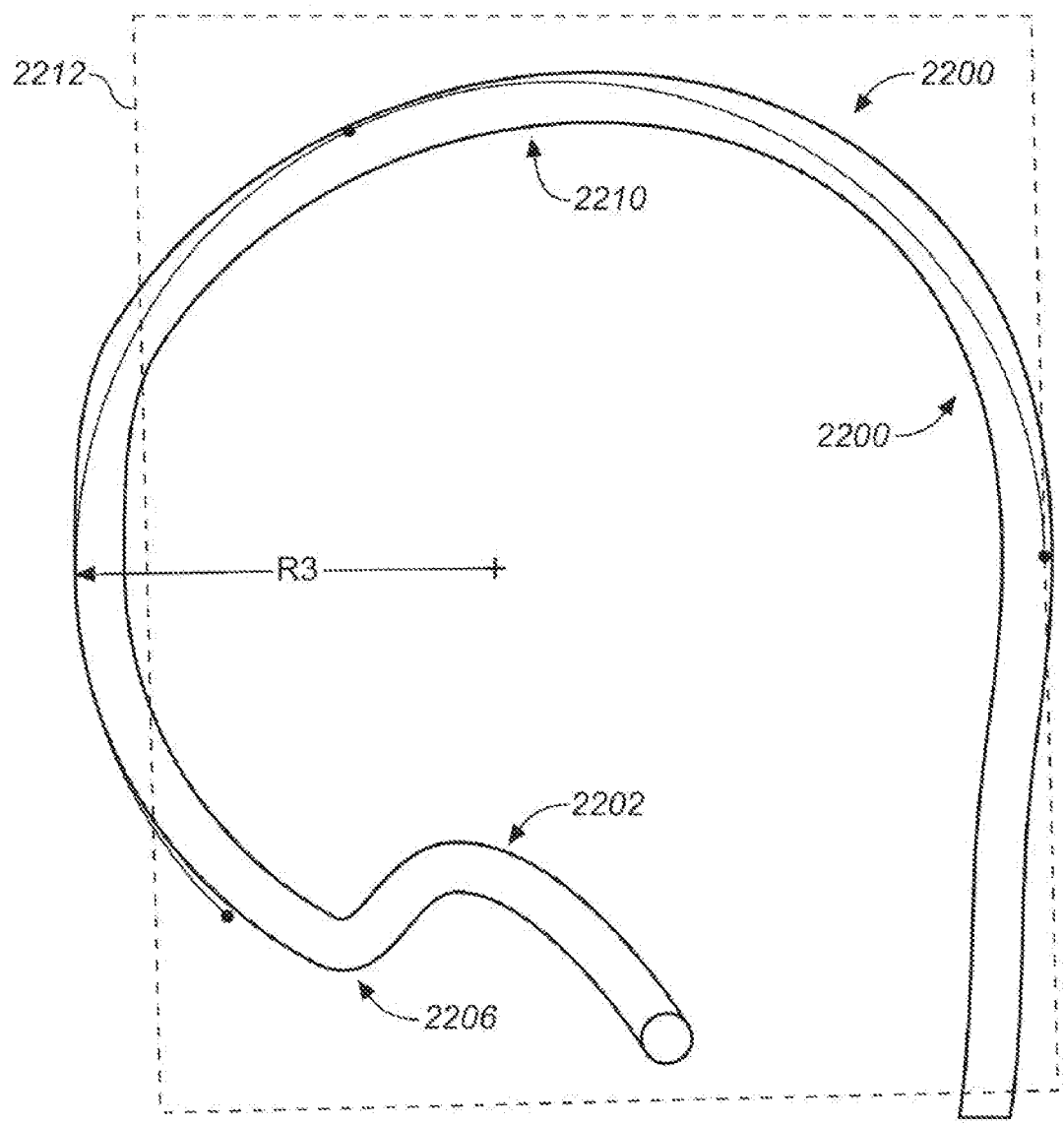
FIG. 22C is an illustrative depiction of the diagnostic catheter of FIG. 22A, showing the radius of curvature of a third region of the diagnostic catheter that defines a third plane.

FIGS. 22A-22C illustrate another way in which the curves of a diagnostic catheter may be defined. As shown there, a diagnostic catheter (2200) comprises a valve curve region (2202) defining a valve plane (2204), a transition curve region (2206) defining a transition plane (2208), and an arch curve region (2210) defining an arch plane (2212). As shown in FIG. 22A, valve curve region (2202) has a radius of curvature (R1) that may be, for example, from about 10 millimeters to about 25 millimeters (e.g., from about 10 millimeters to about 20 millimeters, or from about 15 millimeters to about 25 millimeters). As shown in FIG. 22B, transition curve region (2206) has a radius of curvature (R2) that may be, for example, from about 20 millimeters to about 40 millimeters (e.g., from about 20 millimeters to about 35 millimeters, or from about 25 millimeters to about 40 millimeters). Finally, and as shown in FIG. 22C, arch curve region (2210) has a radius of curvature (R3) that may be, for example, from about 25 millimeters to about 50 millimeters (e.g., from about 25 millimeters to about 40 millimeters, or from about 35 millimeters to about 50 millimeters).

Figure 23D:
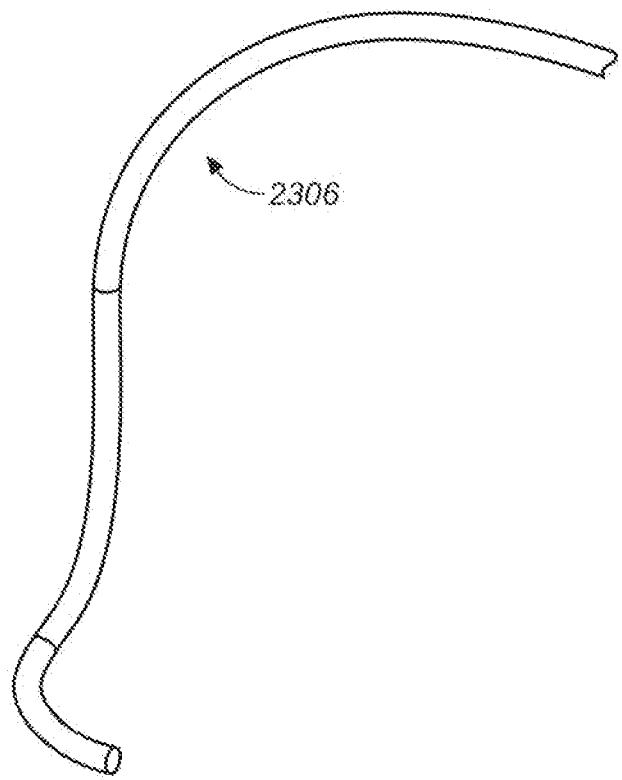
Figure 23E:
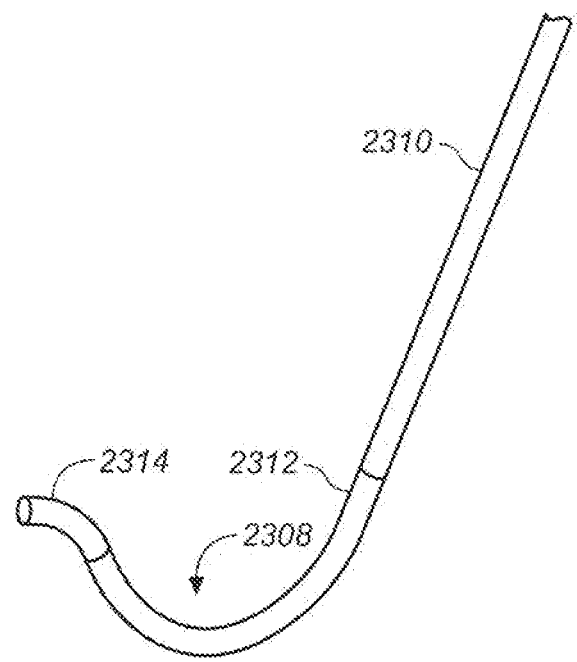
Figure 23F:
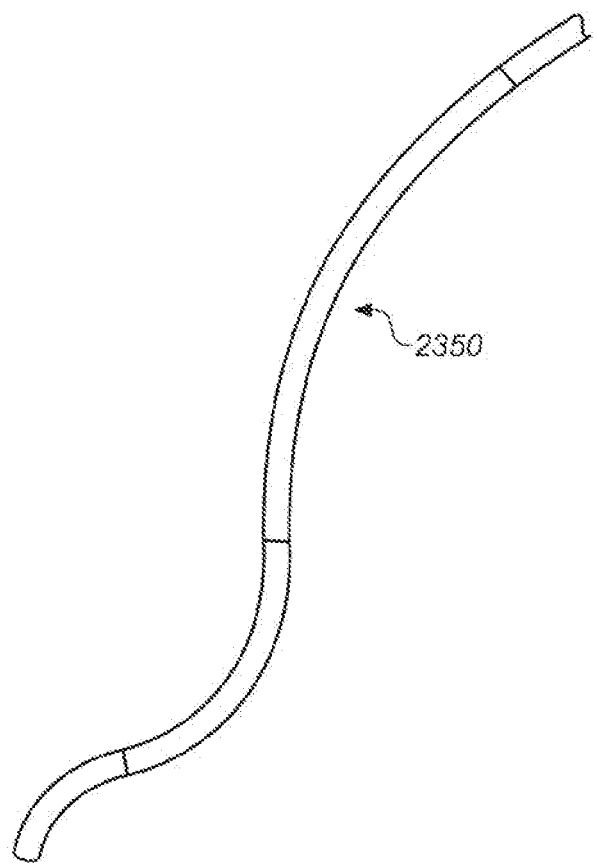
Figure 23G:
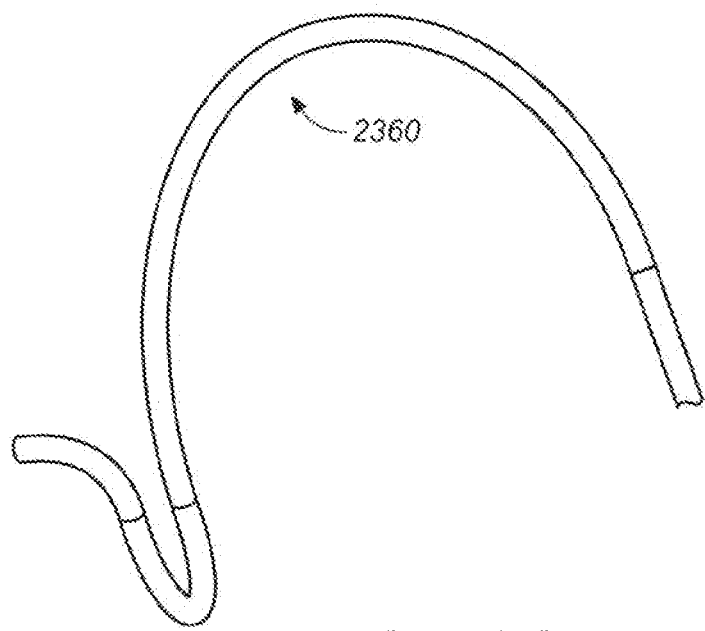
Figure 23H:
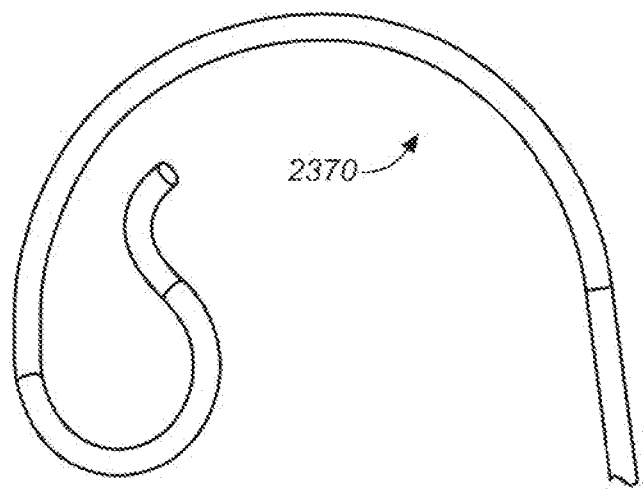
Figure 23I:
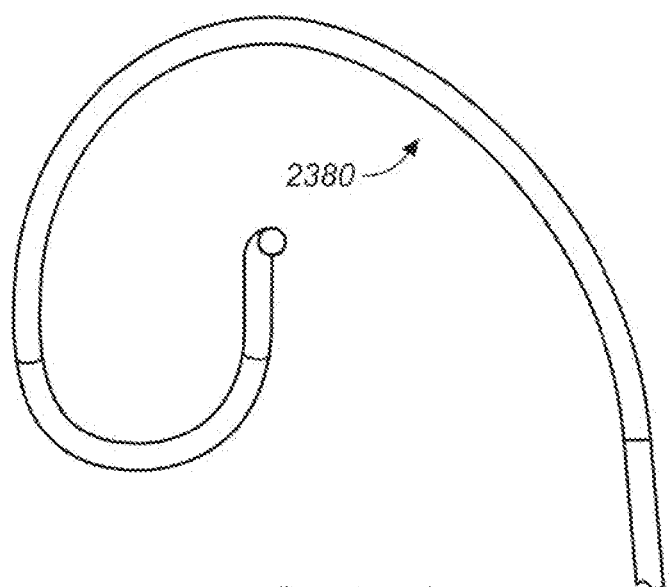
Figure 23J:
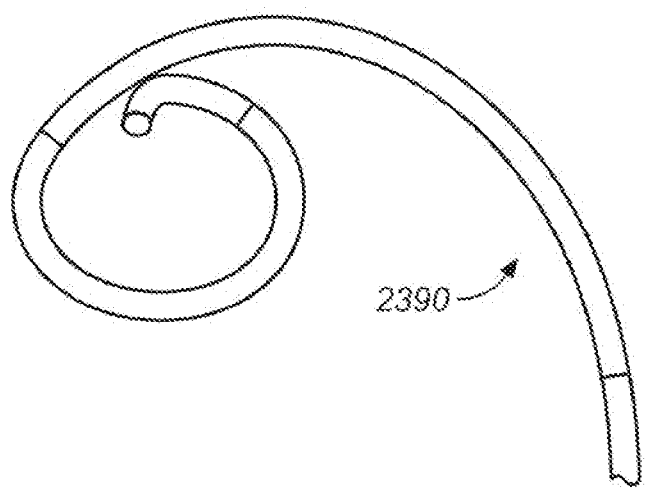
Figure 23K:
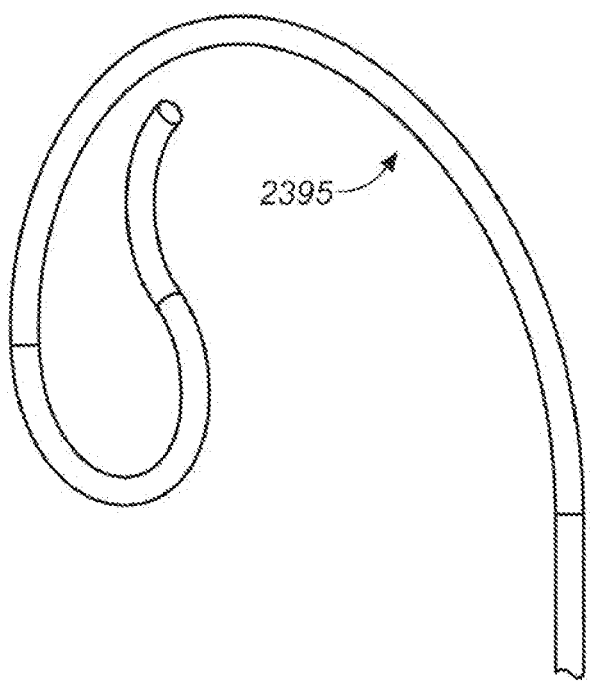

Certain variations of diagnostic catheters having particular shapes have been described. However, other variations of diagnostic catheters having other shapes may be used. The shape of a diagnostic catheter (e.g., the number, size, and shape of its curves, etc.) may be at least partially determined, for example, based on the characteristics of the target site and/or the subject to be treated. FIGS. 23A-23K illustrate different examples of curved diagnostic catheters. More specifically, FIG. 23A shows a diagnostic catheter (2300) including a few wide curves, FIG. 23B shows a diagnostic catheter (2302) having a couple of curves that are a little steeper, FIG. 23C shows a diagnostic catheter (2304) having a helical shape, FIG. 23D shows a diagnostic catheter (2306) that is very similar to diagnostic catheter (2300) of FIG. 23A but that has slight differences in the positioning of its curves, and FIG. 23E shows a diagnostic catheter (2308) having somewhat of a golf club-type shape, with a relatively straight region (2310), a rounded curve region (2312) distal of relatively straight region (2310), and a small curved tip region (2314) distal of rounded curve region (2312). FIGS. 23F-23K show different variations of diagnostic catheters (2350), (2360), (2370), (2380), (2390), and (2395), respectively, all having different curvatures.

Methods of Making Catheters

Catheters, such as diagnostic catheters, chord manipulation catheters, guide catheters, visualization catheters, and anchor deployment catheters, may be made using any suitable method. In some variations, a catheter may be formed using a laying-up or building-up process, in which two or more tubular members (e.g., comprising different materials) are combined together to form a catheter. For example, in certain variations, a catheter may be assembled by providing a liner (e.g., a polytetrafluoroethylene liner), positioning one or more tubular members over the liner (adjacent to each other and/or over each other), and fusing the various layers together (e.g., by heating the combination). In some variations, one or more braids, coils, etc. may be added into the layering. Other methods that may be used to form catheters include, but are not limited to, extrusion methods.

In certain variations, a catheter may be placed in a fixture which may be used to shape the catheter so that it includes one or more curve regions. Such a fixture may be used, for example, to form a diagnostic catheter, chord manipulation catheter, guide catheter, visualization catheter or anchor deployment catheter described here. The fixture may be used to shape a commercially available catheter, or to shape a custom-made catheter (e.g., assembled using the laying-up process described in the preceding paragraph). In certain variations, the catheter and fixture may be heated once the catheter has been molded around the fixture, to help set the curvature into the catheter. For example, the catheter and the fixture may be heated to a temperature of about 120° C. to about 140° C. (e.g., about 125° C. to about 135° C., such as about 130° C.). In some variations, the catheter and the fixture may be heated for a period of about one hour. The catheter may also be cooled for a period of time (e.g., one hour) after heating. It should be noted that in some cases, the dimensions of the catheter may change somewhat as a result of relaxation during the cooling period. In such cases, the dimensions of the catheter when it is initially shaped on the fixture may be selected taking this change into account.

In some instances, at least one mandrel or other elongated member may be positioned within the lumen of the catheter during the shaping process. The mandrel or other elongated member may, for example, help to prevent the lumen of the catheter from losing its patency while the catheter is being molded.

Figure 24A:
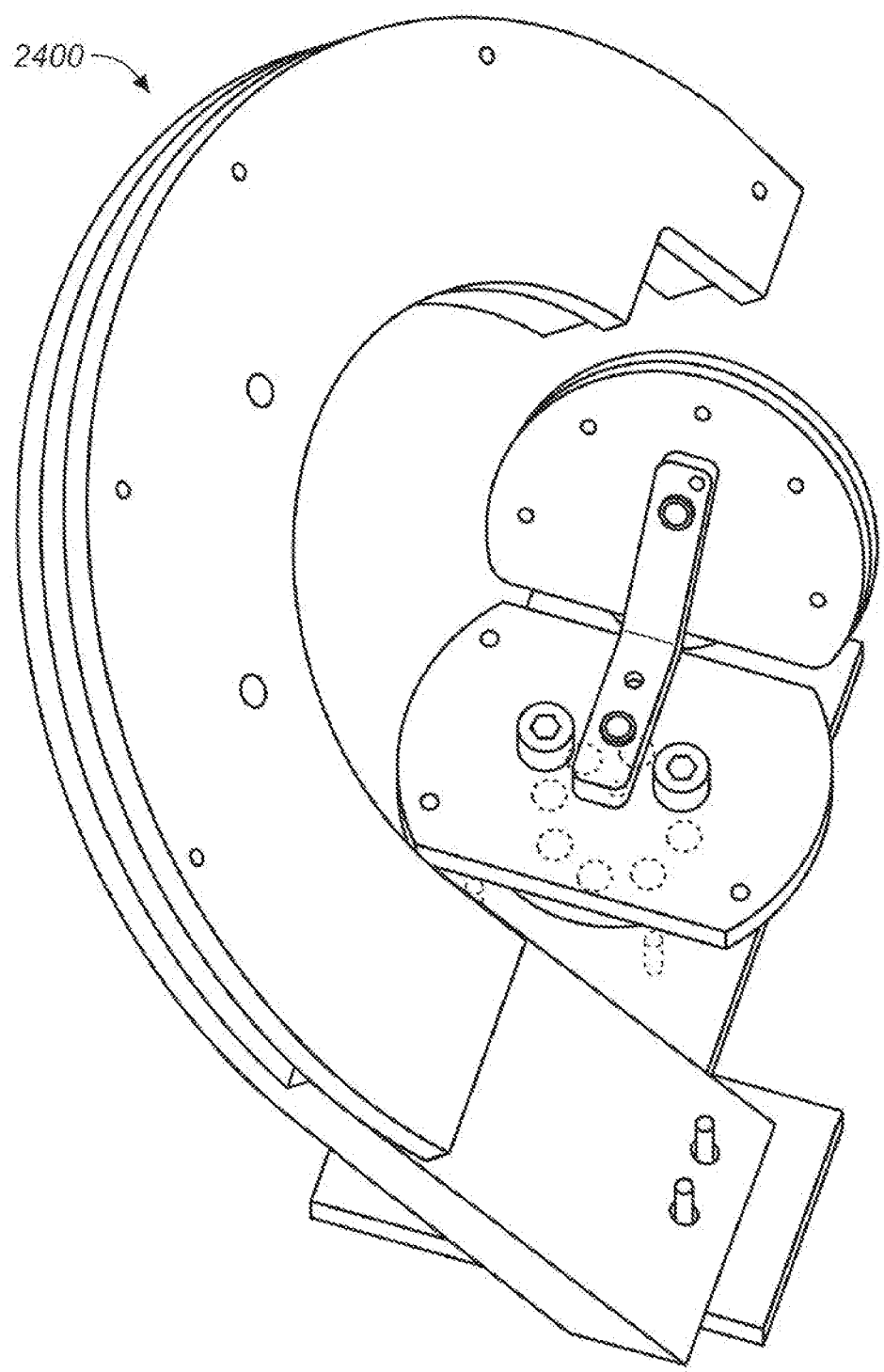
FIG. 24A is a perspective view of a variation of a fixture for shaping a catheter.
Figure 24B:
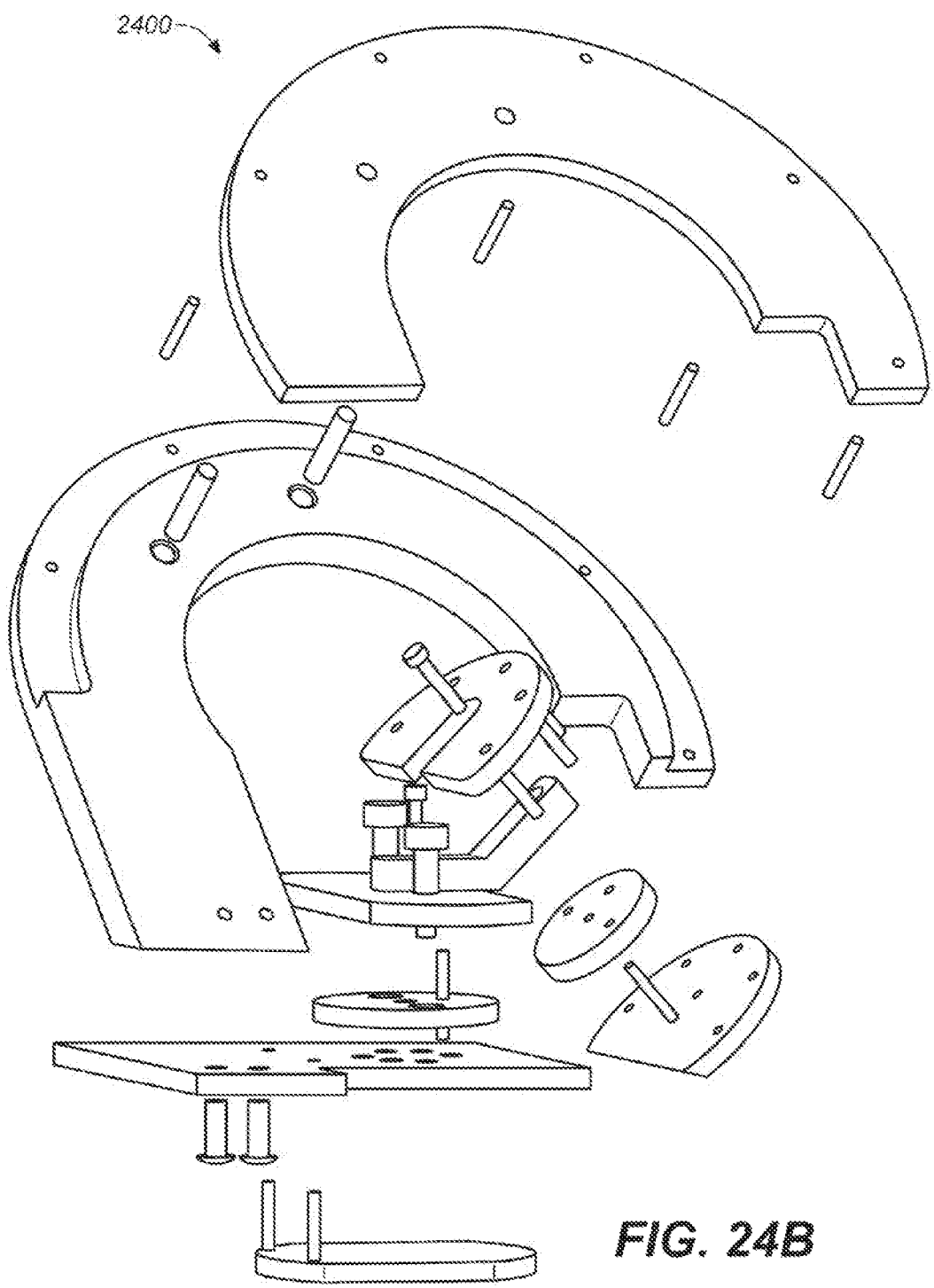
FIG. 24B is an exploded view of the fixture of FIG. 24A.
Figure 24C:
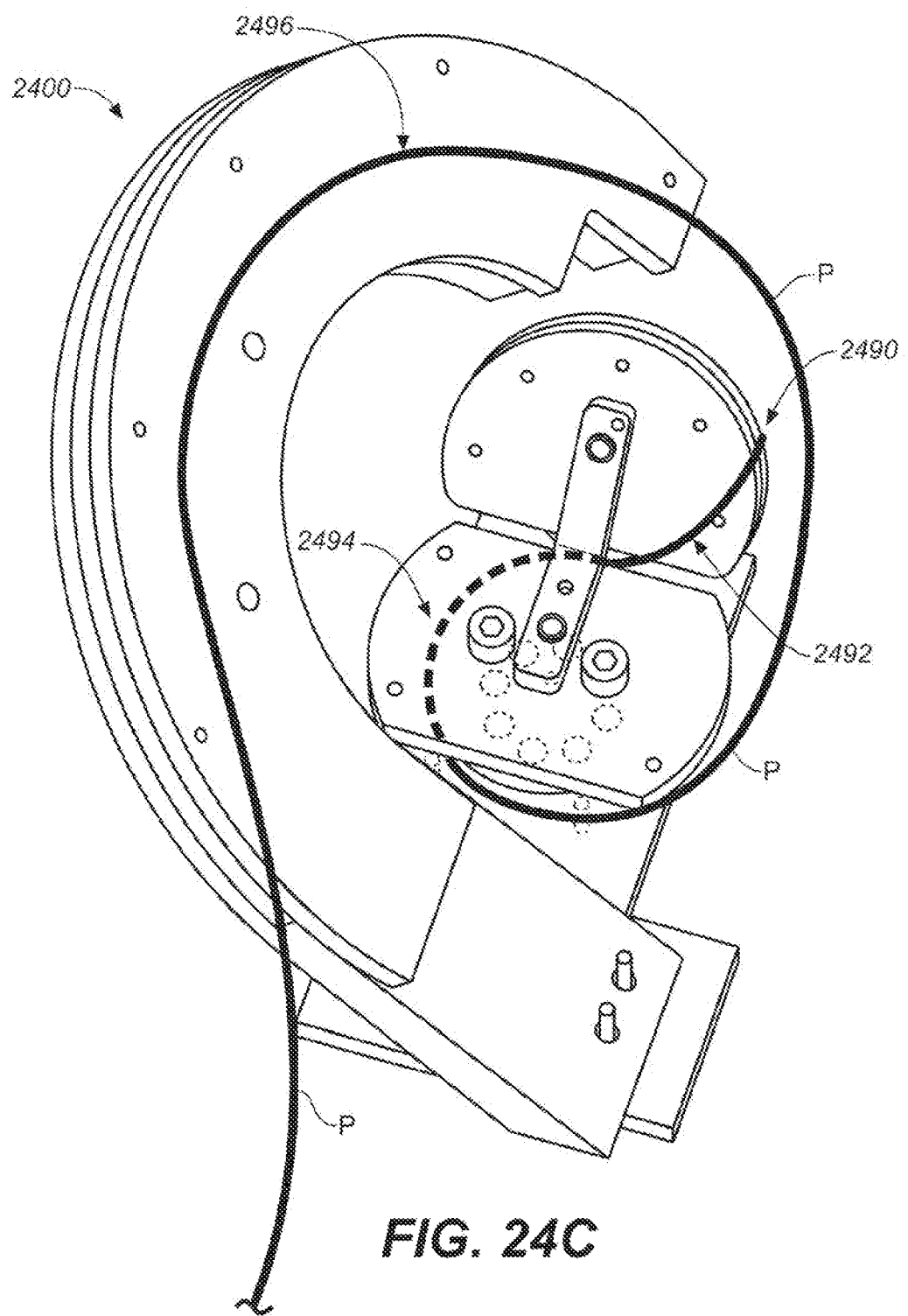
FIG. 24C depicts the positioning of a catheter on the fixture of FIGS. 24A and 24B, where the fixture will be used to shape the catheter.

FIGS. 24A and 24B depict a variation of a fixture (2400) that may be used to mold a catheter, such as a 9 Fr diagnostic catheter (i.e., a diagnostic catheter having an outer diameter of 3 millimeters). FIG. 24A provides a perspective view of the fixture, while FIG. 24B provides an exploded view of the fixture. One or more components of the fixture (e.g., the entire fixture) may be made of, for example, one or more polymers, such as ULTEM® polyimide thermoplastic resin. Other appropriate materials may alternatively or additionally be used. FIG. 24C illustrates how a catheter may be wound around fixture (2400) so that the catheter is shaped to have a valve curve region, a transition curve region, and an arch curve region, for example. More specifically, FIG. 24C shows a pathway (P) along which a catheter may be positioned on fixture (2400), so that curves may be molded into the catheter. The dashed lines that form part of pathway (P) are intended to depict that portion of pathway (P) that is located beneath that region of fixture (2400). During use of fixture (2400), a catheter may be attached to the fixture (e.g., held in place by pins) at a point (2490). Alternatively or additionally, the catheter may be stabilized with respect to the fixture in one or more other ways. The catheter may then be wound around fixture (2400), along pathway (P). Region (2492) of pathway (P) corresponds to the valve curve region of the resulting catheter, region (2494) corresponds to the transition curve region of the resulting catheter, and region (2496) corresponds to the arch curve region of the resulting catheter. To form these curves, the catheter may be maintained on the fixture for an appropriate amount of time, and then may be removed from the fixture once the curves have set into the catheter.

While fixture (2400) depicts one variation of a catheter-shaping fixture, other variations may be used. Alternatively or additionally, other variations of pathways may be used. For example, FIGS. 24D-24G depict additional non-limiting variations of fixtures that may be used to mold or shape a catheter (e.g., according to the method described above).

Figure 24D:
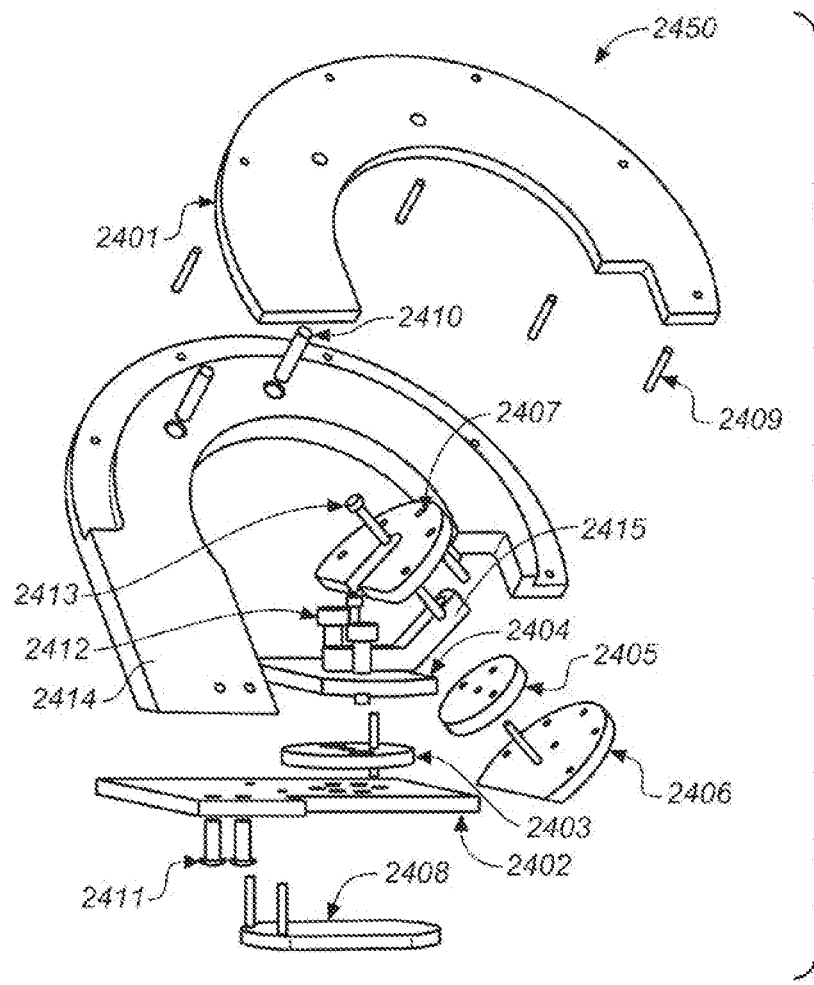
FIG. 24D is an exploded view of another variation of a fixture for shaping a catheter.

First, FIG. 24D shows a fixture (2450) that may be used to form a catheter (e.g., a 9 Fr catheter, or a catheter having an outer diameter of 3 millimeters) including an arch curve region, a transition curve region, and a valve curve region. Fixture (2450) comprises an arch clamshell portion (2401), dowel pins (2409) and (2410) (e.g., formed of stainless steel), and an arch portion (2414). Fixture (2450) also comprises a round clamshell portion (2407) (e.g., 0.75 inch) and a round back portion (2406) (e.g., 0.75 inch), as well as a round portion (2405) (e.g., 0.75 inch), a transition cap portion (2404) (e.g., 1 inch), a transition base portion (2402) (e.g., 1 inch), and socket head cap screws (2412) and (2413). Additionally, fixture (2450) comprises a round portion (2403) (e.g., 1 inch), a socket button head cap screw (2411), a transition cap clamshell portion (2408) (e.g., 1 inch), and an angle block portion (2415). Fixture (2450) is configured such that when the catheter is being shaped on the fixture, the catheter has an arch curve region and a transition curve region defining planes at an angle of about 45° relative to each other, and a valve curve region defining a plane that is at an angle of about 135° with respect to the transition curve region. However, after the catheter is removed from the fixture, the catheter may relax somewhat, so that these angles may change.

Figure 24E:
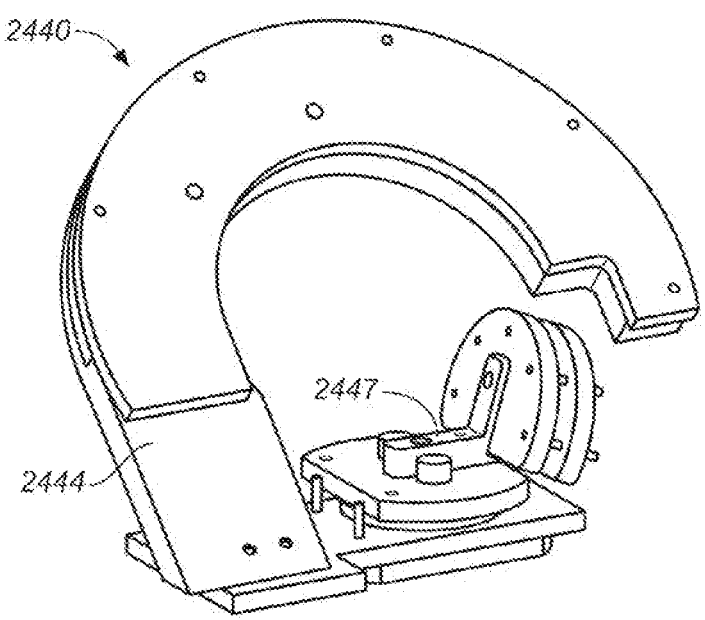
FIGS. 24E-24G are illustrative views of additional variations of fixtures for shaping a catheter.

FIG. 24E shows a fixture (2440) that may be used, for example, to form a catheter (e.g., a 9 Fr catheter, or a catheter having an outer diameter of 3 millimeters). While being shaped by the fixture, the catheter may have an arch curve region and a transition curve region defining planes at an angle of about 45° relative to each other, and/or a valve curve region defining a plane that is at an angle of about 110° with respect to the transition curve region. Of course, while a catheter being shaped in the fixture may have these 45° and 110° angles, after being removed from the fixture, the catheter may relax somewhat and these angles may change. Fixture (2440) comprises an arch portion (2444) and an angle block portion (2447).

Figure 24F:
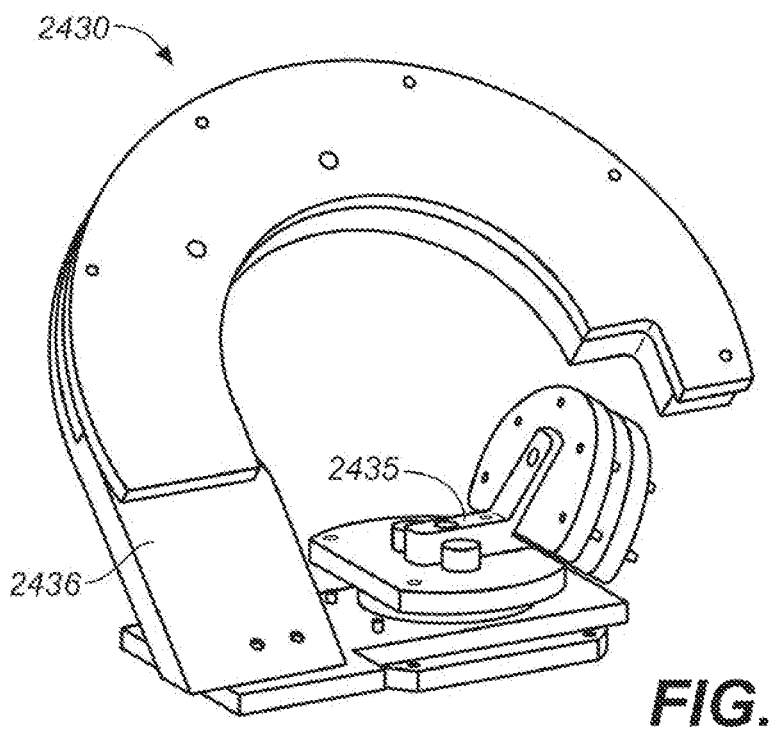

Another variation of a fixture (2430) that may be used, for example, to form a catheter (e.g., a 9 Fr catheter, or a catheter having an outer diameter of 3 millimeters) is depicted in FIG. 24F. While being shaped by the fixture, the catheter may have an arch curve region and a transition curve region defining planes at an angle of about 35° relative to each other, and/or a valve curve region defining a plane that is at an angle of about 135° with respect to the transition curve region. As described above, however, while a catheter being shaped in the fixture may have these 35° and 135° angles, after being removed from the fixture, the catheter may relax somewhat and these angles may change. Fixture (2430) comprises an angle block portion (2435) and an arch portion (2436).

Figure 24G:
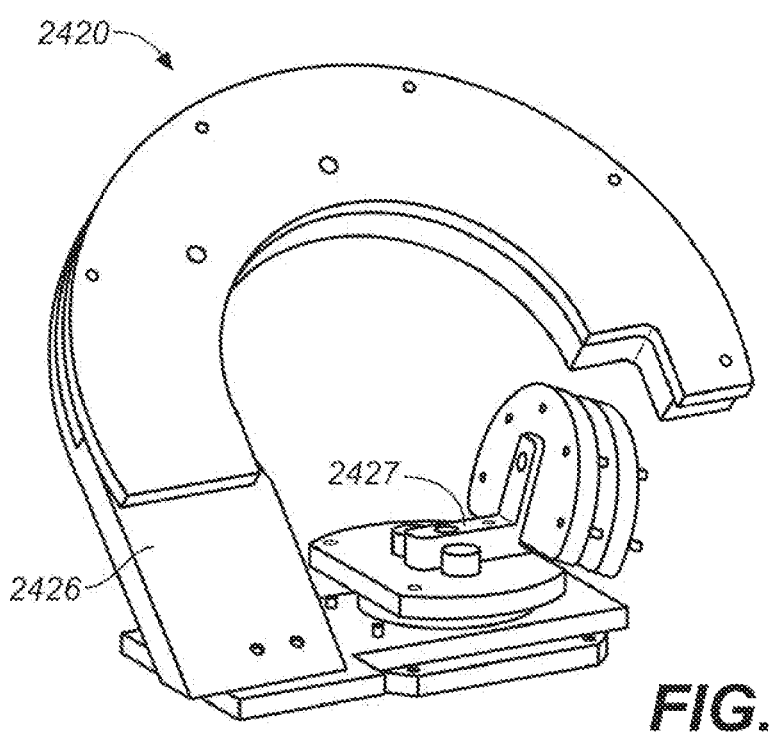

FIG. 24G shows an additional variation of a fixture (2420) that may be used, for example, to form a catheter (e.g., a 9 Fr catheter, or a catheter having an outer diameter of 3 millimeters). While being shaped by the fixture, the catheter may have an arch curve region and a transition curve region defining planes at an angle of about 35° relative to each other, and/or a valve curve region defining a plane that is at an angle of about 110° with respect to the transition curve region. However, and as described above, while a catheter being shaped in the fixture may have these 35° and 110° angles, after being removed from the fixture, the catheter may relax somewhat and these angles may change. As shown in FIG. 24G, fixture (2420) comprises an arch portion (2426) and an angle block portion (2427).

While the fixtures described above may be used to form a catheter with three curve regions, in some variations a fixture (including, but not limited to, one of the above-described fixtures) may be used to form a catheter with only one or two curve regions, or with more than three curve regions (e.g., by winding the catheter along the fixture in a different manner). Alternatively or additionally, a fixture may be used to form a catheter having one or more other features. Furthermore, in certain variations, multiple fixtures (e.g., 2, 3, 5) may be used to form multiple curves in a catheter.

Chord Manipulation Devices and Methods

In some cases, a catheter may confront one or more obstacles as it is being delivered to a target site. The obstacle(s) may make it relatively difficult or even impossible to access the target site with the catheter. For example, in a mitral valve repair procedure, it may be difficult or impossible to access the subannular groove region because of the presence of one or more interfering chords in and/or near the region. In some such cases, the chord or chords may be manipulated to make the subannular groove region more accessible. Any of a number of different devices and methods may be used to manipulate chords, non-limiting examples of which will now be discussed in more detail.

Certain variations of chord manipulation devices may be in the form of chord-cutting devices. The chord-cutting devices may be used, for example, to cut one or more chords to provide access to a subvalvular space (e.g., a subannular groove region) in a heart. Chord-cutting devices, as well as other chord manipulation devices described here, may be used with any type of chord, as appropriate. In certain variations, such devices may at least be used to cut one or more tertiary or third-order chords. As discussed above, it may not be necessary for a heart to have all of its tertiary or third-order chords in order for the mitral valve and the overall heart to function sufficiently.

Figure 58A:
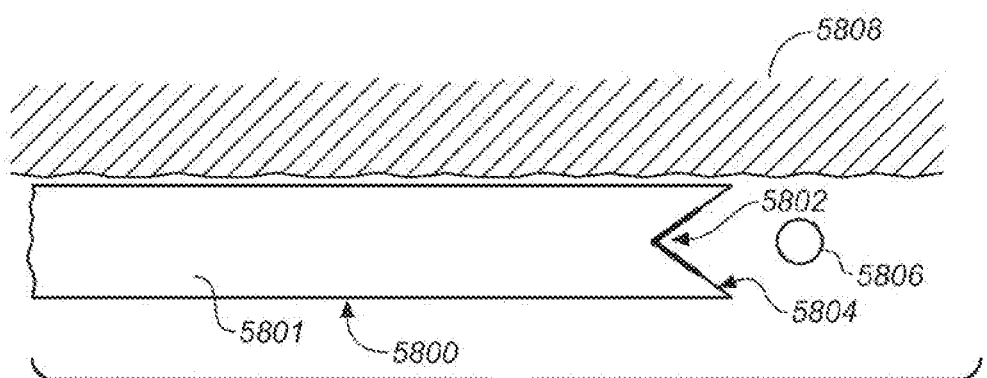
FIGS. 58A-58C illustrate variations of a device and method for cutting one or more chords.
Figure 58B:
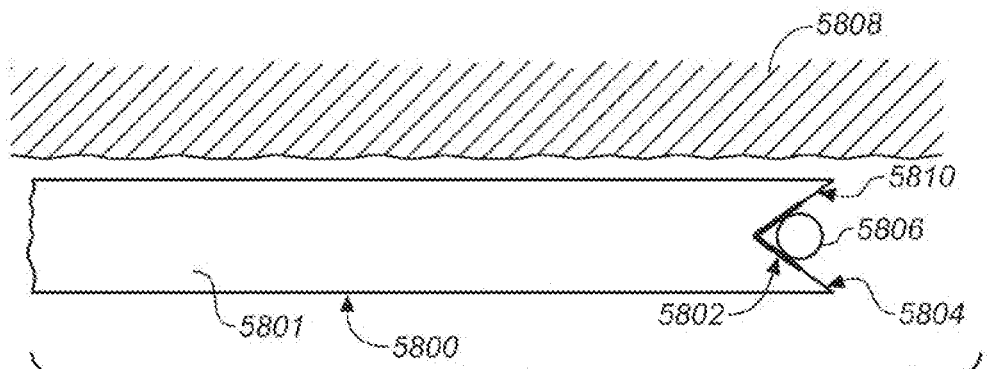
Figure 58C:
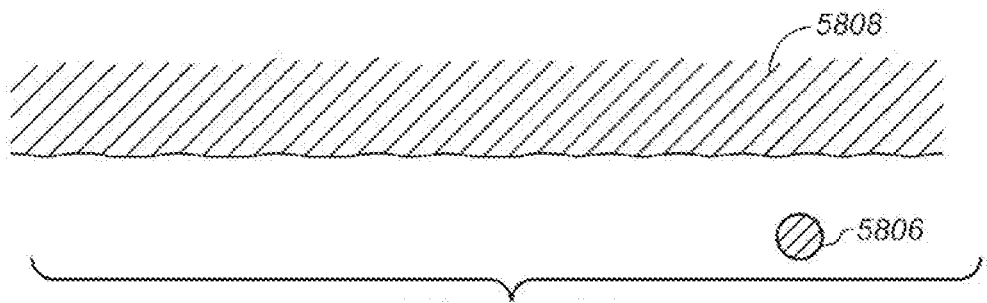

Chord-cutting devices may have any appropriate size, shape, and/or configuration, and in some cases, may be tailored for use with a particular subject's anatomy. FIGS. 58A-58C show one example of a variation of a device and related method for cutting one or more chords. As shown there, a chord-cutting device (5800) comprises an elongated member (5801) having a V-shaped blade (5802) in its distal section (5804). In FIGS. 58A-58C, chord-cutting device (5800) is used to sever a chord (5806) in the region of a ventricular wall (5808) of a heart. First, and referring to FIG. 58A, chord-cutting device (5800) is advanced along ventricular wall (5808), toward chord (5806). If chord-cutting device (5800) is able to pass between chord (5806) and ventricular wall (5808), then chord-cutting device (5800) will not sever chord (5806). However, and as shown in FIG. 58B, here chord (5806) is too close to ventricular wall (5808) to allow for passage of chord-cutting device (5800) therebetween. Instead, chord (5806) falls into a notch (5810) in distal section (5804) of elongated member (5801) (FIG. 58B), and is severed by blade (5802). The result is a severed chord (5806), as shown in FIG. 58C. After the operator has used chord-cutting device (5800) to sever chord (5806), the operator may, for example, continue to advance chord-cutting device (5800) along its original path (e.g., to sever more interfering chords), or may simply withdraw chord-cutting device (5800) from the body of the subject. In some cases, after the chord has been severed (and, e.g., after the chord-cutting device has been withdrawn from the body), a catheter may be routed past the severed chord and to a target site in the heart (e.g., to perform a procedure at the target site).

Figure 58D:
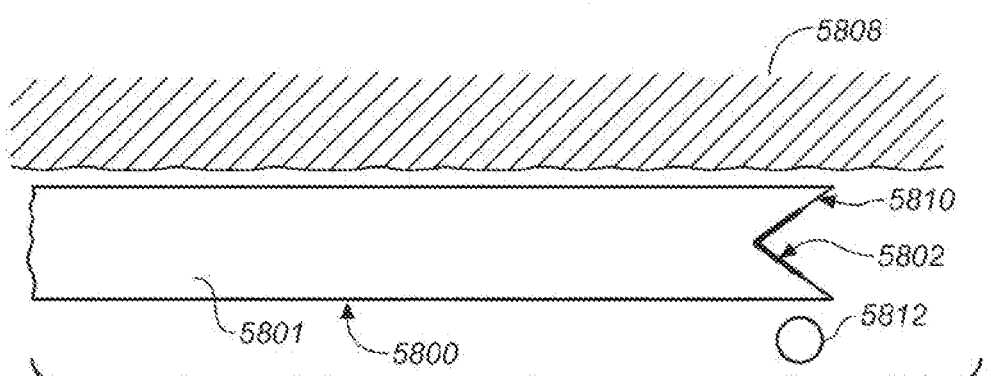
FIG. 58D shows the device of FIGS. 58A-58C passing a chord without cutting the chord.

As noted above, in some cases, the space between a chord and a ventricular wall may be sufficiently large to allow for passage of chord-cutting device (5800), such that chord-cutting device (5800) will not sever the chord. FIG. 58D depicts an example of such a situation, in which a chord-cutting device (5800) passes between a chord (5812) and ventricular wall (5808). Because there is sufficient room between chord (5812) and ventricular wall (5808) to allow for clear passage of chord-cutting device (5800) therethrough, chord-cutting device (5800) passes by chord (5812) without severing it.

Chord-cutting devices such as chord-cutting device (5000) may be made of any suitable material or materials, and may have any dimensions that are appropriate for delivery of the devices to, and use of the devices within, a heart ventricle.

Figure 59A:
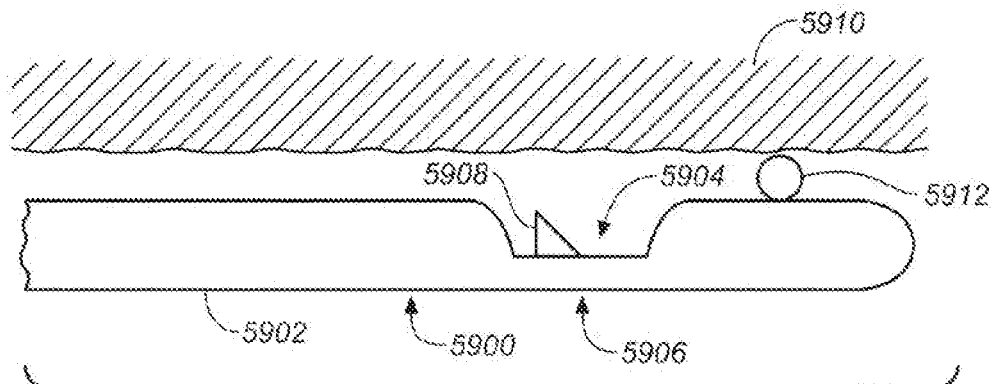
FIGS. 59A-59C illustrate additional variations of a device and method for cutting one or more chords.
Figure 59B:
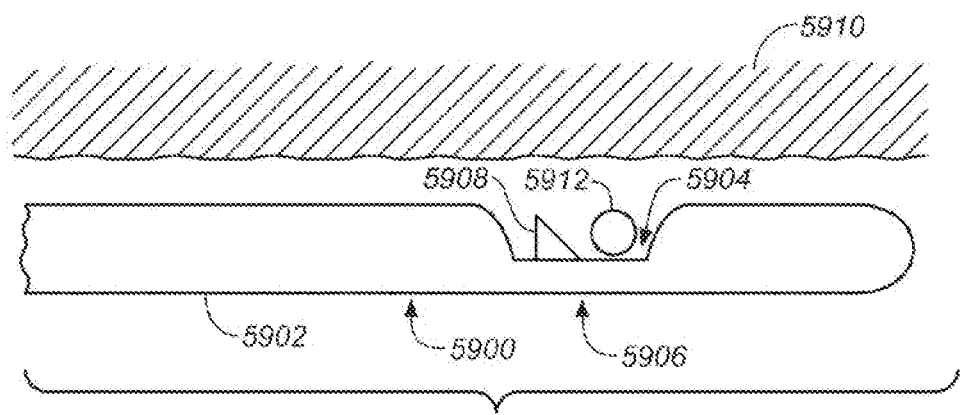
Figure 59C:
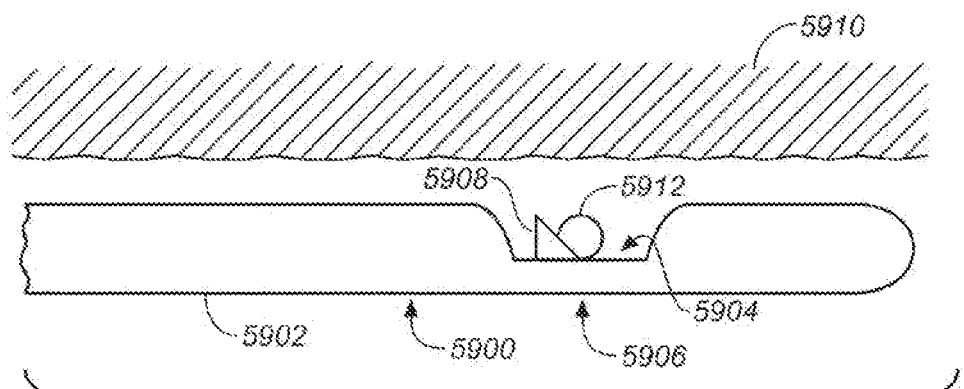

Of course, while FIGS. 58A-58D show one variation of a chord-cutting device, others suitable variations of chord-cutting devices may be used. For example, FIGS. 59A-59C depict a different variation of a chord-cutting device. As shown there, a chord-cutting device (5900) comprises an elongated member (5902) having a groove (5904) in its distal portion (5906). A cutting blade (5908) is disposed within groove (5904), and is slidable along a track (not shown) in the groove (e.g., by actuating a mechanism, such as a slide actuator, in a proximal portion of chord-cutting device (5900)).

FIG. 59A depicts chord-cutting device (5900) as it is advanced along a ventricular wall (5910) of a heart, where it confronts a chord (5912). Chord-cutting device (5900) is too large to be able to pass through the space between chord (5912) and ventricular wall (5910). As a result, during the continued advancement of chord-cutting device (5900), chord (5912) becomes positioned between ventricular wall (5910) and chord-cutting device (5900). As shown in FIGS. 59B and 59C, chord (5912) then slides into groove (5904), and the continued advancement of chord-cutting device (5900) causes cutting blade (5908) to contact and thereby sever chord (5912). While chord-severing via the continued advancement of chord-cutting device (5900) has been described, in some variations, chord-cutting device (5900) may alternatively or additionally be used to sever a chord by slidably advancing cutting blade (5908) along the track in groove (5904), until the cutting blade contacts and severs the chord. The position of cutting blade (5908) in groove (5904) may cause cutting blade (5908) to be sheltered, such that chord-cutting device (5900) is relatively unlikely to cut or damage non-target tissue. Other blade protection mechanisms or shields may alternatively or additionally be used. Additionally, in some variations, the dimensions of blade (5908) may be selected so that the blade fits within the dimensions of groove (5904).

Figure 59D:
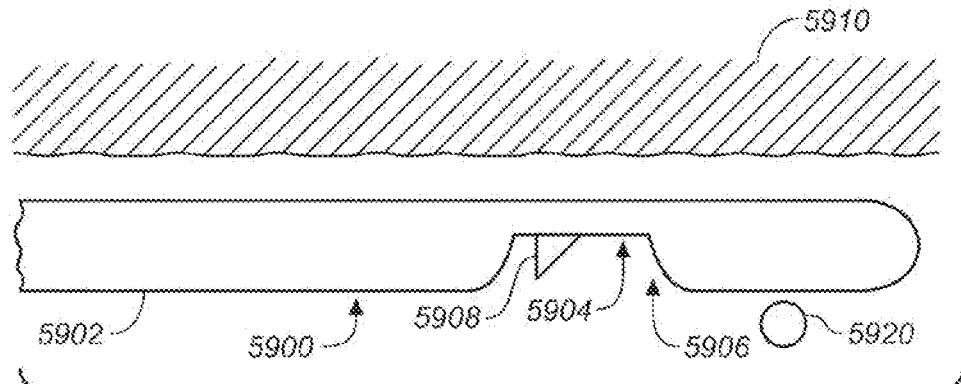
FIGS. 59D-59F depict the device of FIGS. 59A-59C being used with a different variation of a method for cutting one or more chords.
Figure 59E:
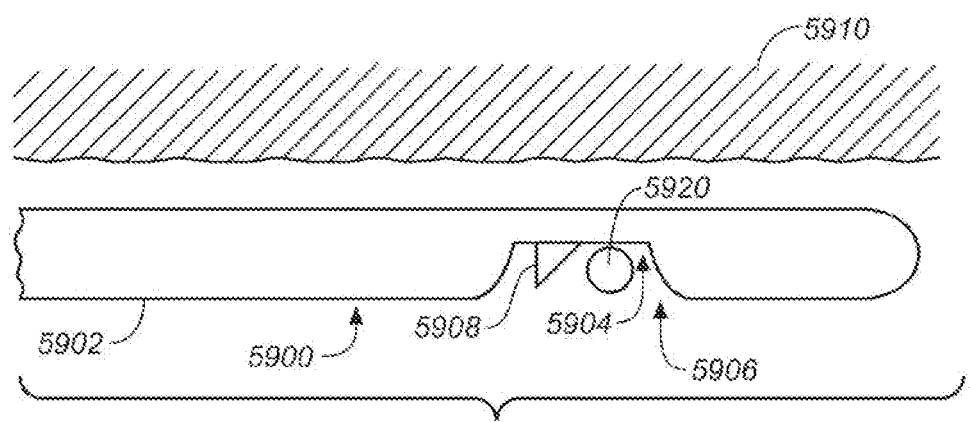
Figure 59F:
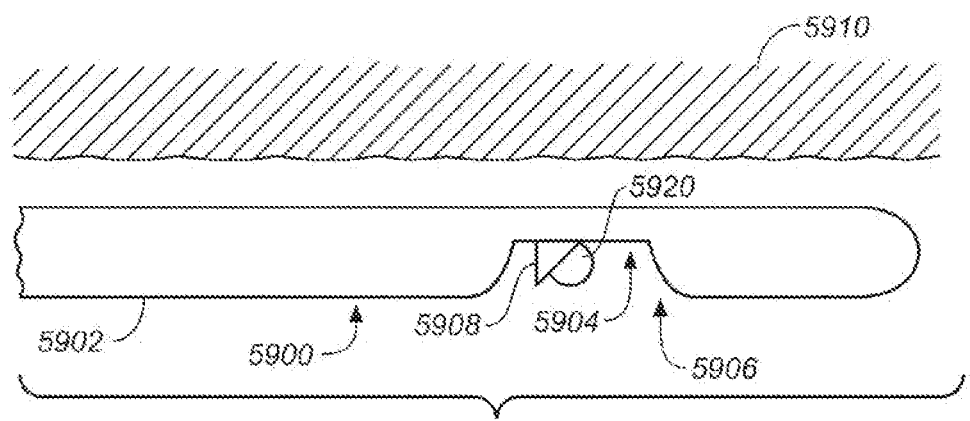

FIGS. 59A-59C show just one orientation of chord-cutting device (5900) with respect to ventricular wall (5910). However, other chord-cutting device orientations may also be used, as appropriate. For example, FIGS. 59D-59F show chord-cutting device (5900) after it has been rotated 180° with respect to ventricular wall (5910) (relative to its orientation in FIGS. 59A-59C). Additionally, as shown there, a chord (5920) is relatively close to ventricular wall (5910), but still is able to pass over the distal-most part of distal portion (5906) as chord-cutting device (5900) is advanced along ventricular wall (5910). As shown, once groove (5904) is positioned in the vicinity of chord (5920), chord (5920) slides into groove (5904). In some cases, this may occur because chord (5920) is relatively close to ventricular wall (5910), such that chord-cutting device (5900) just fits between the chord and the ventricular wall. By contrast, a chord that is relatively spaced apart from a ventricular wall may not slide into groove (5904), and instead may simply pass over chord-cutting device (5900) as it is advanced. After chord (5920) has slid into groove (5904), the operator may continue to advance chord-cutting device (5900) (and/or may slidably advance cutting blade (5908) along the track in groove (5904)), until cutting blade (5908) contacts and severs chord (5920), as shown in FIG. 59F.

Figure 60A:
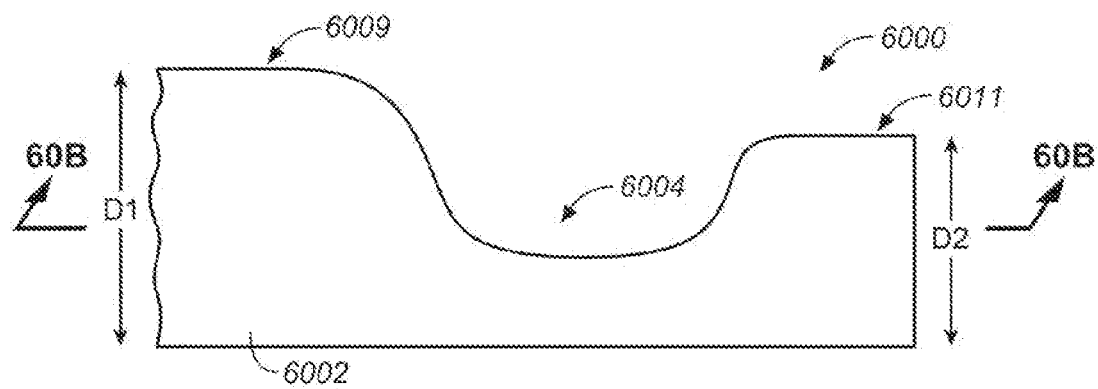
FIG. 60A is a side view of a variation of a device for cutting one or more chords.
Figure 60B:
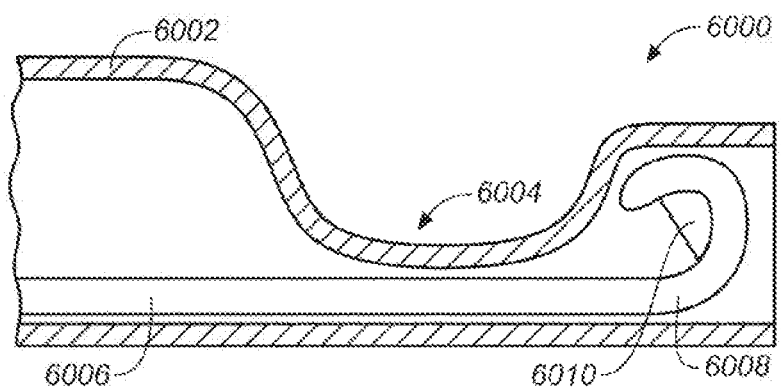
FIG. 60B is a cross-sectional view of the device of FIG. 60A, taken along line 60B-60B.
Figure 60C:
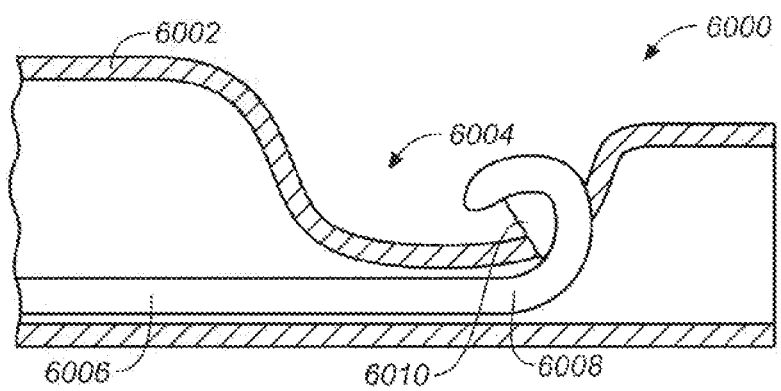
FIG. 60C depicts the cross-sectional view of FIG. 60B, after the position of one of the components of the device has changed.

Other variations of chord-cutting devices may be used. For example, FIGS. 60A-60J depict additional variations of a device and method for cutting one or more chords. Referring first to FIG. 60A, a chord-cutting device (6000) comprises a housing (6002) having a grooved portion (6004). As shown in FIG. 60B, which provides a cross-sectional view of chord-cutting device (6000), the device also comprises a cutting member (6006) slidably disposed within housing (6002), where the cutting member (6006) comprises a curved elongated body (6008) and a cutting blade (6010) coupled to the body. Referring again to FIG. 60A, housing (6002) comprises a more proximal portion (6009) having a dimension (D1) and a more distal portion (6011) having a corresponding dimension (D2) that is smaller than dimension (D1). While not shown, housing (6002) includes a slot within the region of grooved portion (6004), such that cutting member (6006) can pass through a grooved portion (6004), as shown in FIG. 60C. When cutting member (6006) passes through grooved portion (6004), a portion of cutting member (6006) extends outside of housing (6002), such that it can contact chords positioned within grooved portion (6004). It should be noted, of course, that this is just one possible configuration of a cutting member, and other configurations may be employed. As an example, in some variations, an entire cutting member may extend outside of a chord-cutting device housing during at least a portion of a chord-cutting process. As another example, in certain variations, a chord-cutting device may comprise a housing having multiple grooved portions.

Figure 60D:
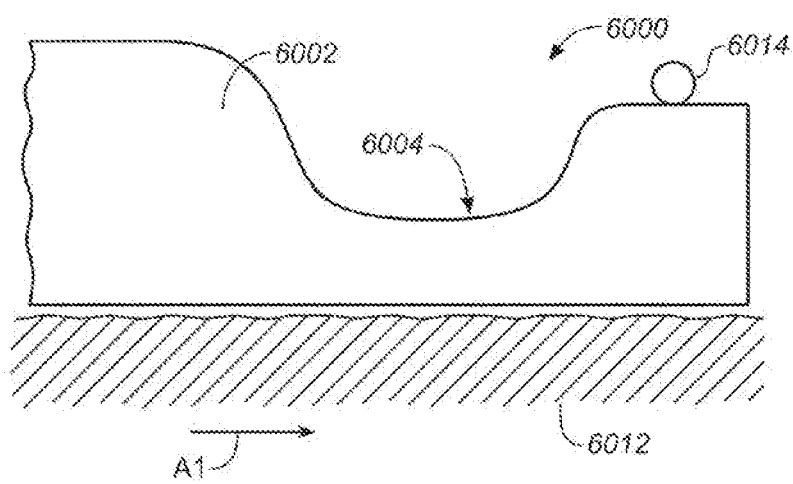
FIGS. 60D-60J depict a variation of a method for cutting one or more chords using the device of FIGS. 60A-60C.
Figure 60E:
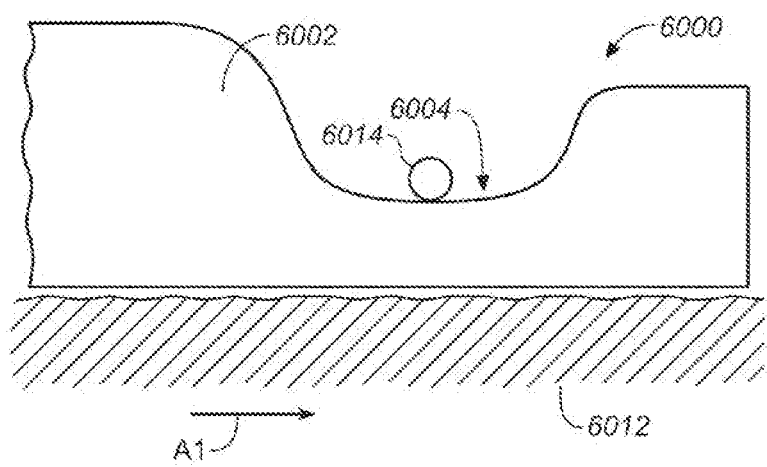
Figure 60F:
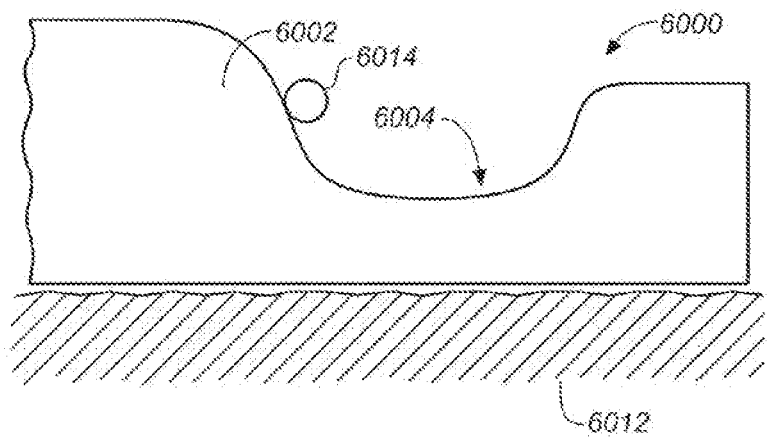

Referring now to FIG. 60D, during use an operator may position chord-cutting device (6000) between a ventricular wall (6012) and a chord (6014). The operator may then advance chord-cutting device (6000) in the direction of arrow (A1), such that chord (6014) becomes positioned within grooved portion (6004) (FIG. 60E). As the operator continues to advance chord-cutting device (6000) in the direction of arrow (A1), chord (6014) begins to travel up the other side of grooved portion (6004). However, in this case, while chord (6014) was able to pass over distal portion (6011) of chord-cutting device (6000), chord (6014) is not able to pass over the larger proximal portion (6009). As a result, chord-cutting device (6000) is no longer capable of being advanced in the direction of arrow (A1). When this occurs, the operator may experience the resistance to further advancement as a tactile indication of the presence of an obstacle in the path of chord-cutting device (6000). Such a tactile indication may also be provided by other variations of chord-cutting devices. Alternatively or additionally, a chord-cutting device may comprise one or more sensors and/or other indicators that may notify the operator of the presence of an obstructing chord. Moreover, in some variations, the location of a chord in the path of a device may be determined using one or more visualization methods, such as echocardiography (e.g., 3D echocardiography), magnetic resonance imaging (MRI), and/or computed tomography (CT). In some variations, the location of a chord manipulation device with respect to a heart wall may be verified using, for example, contrast agent and X-ray fluoroscopy.

Figure 60G:
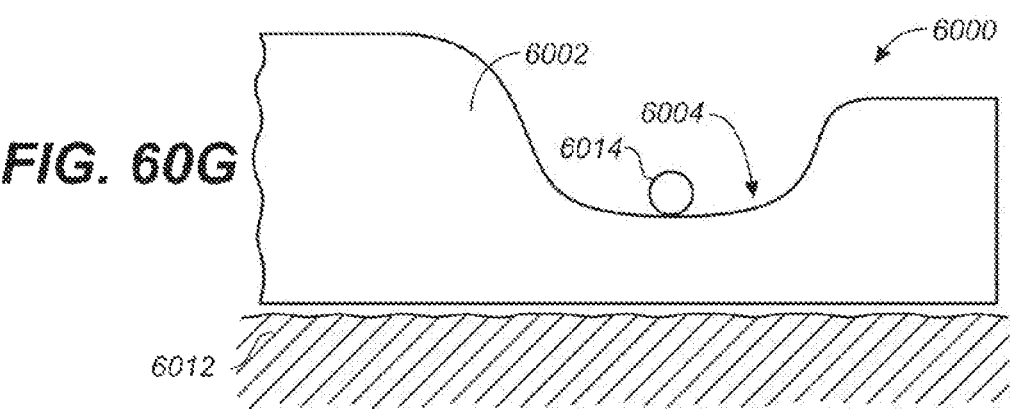
Figure 60H:
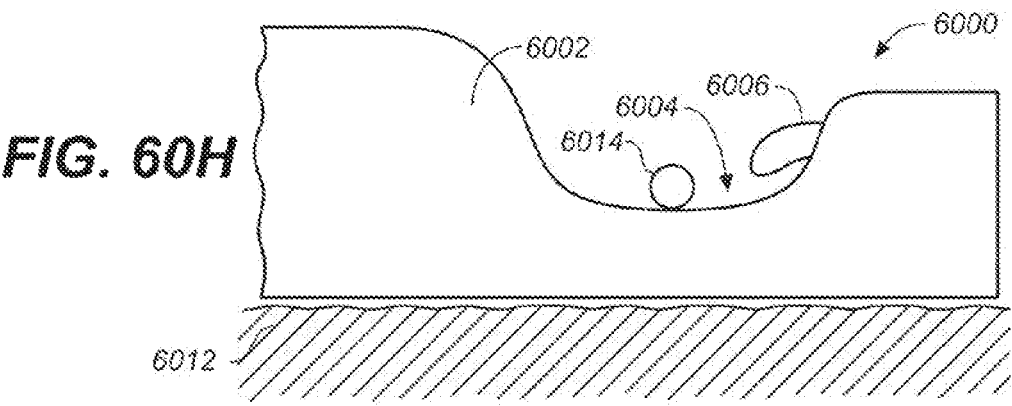
Figure 60I:
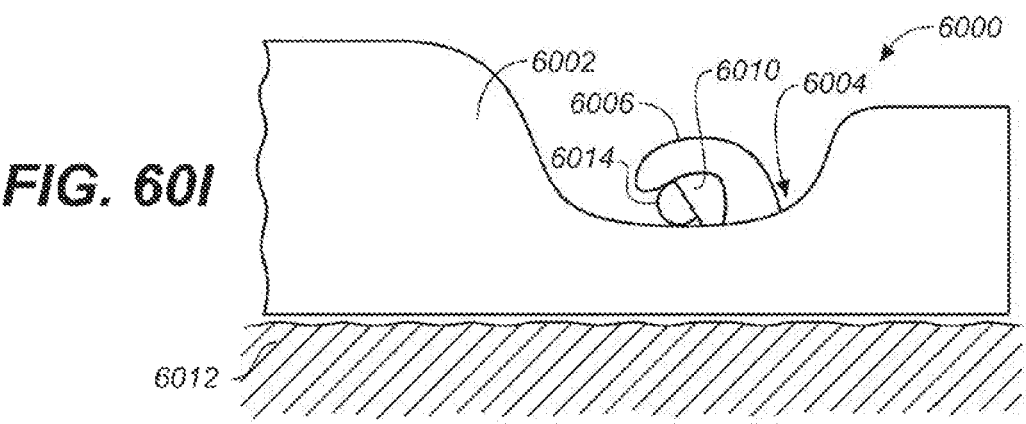
Figure 60J:
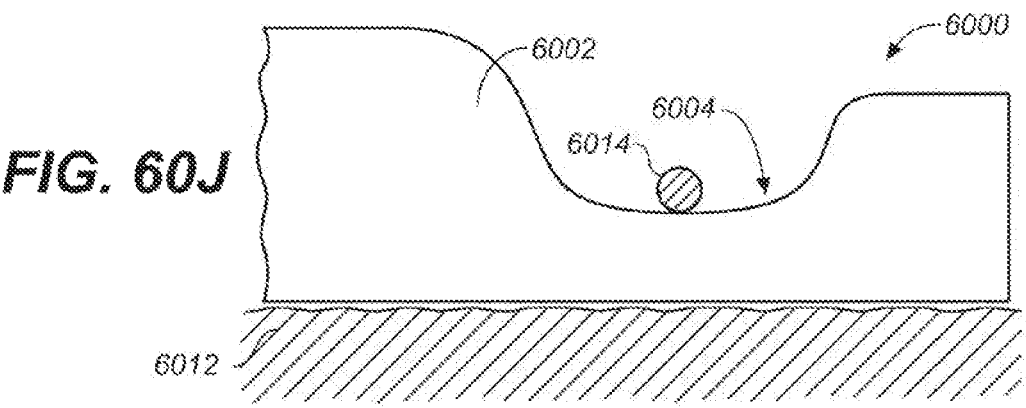

Upon becoming aware of the presence of an obstacle in the path of chord-cutting device (6000), the operator may proximally withdraw chord-cutting device (6000), so that chord (6014) becomes positioned within grooved portion (6004), as shown in FIG. 60G. Then, and as shown in FIG. 60H, the operator may actuate cutting member (6006) to translate it across grooved portion (6004), where cutting blade (6010) contacts and cuts chord (6014) (FIG. 60I). The result is a severed chord (6014), as shown in FIG. 60J. Of course, as with all chord manipulation devices and methods described here, the operator may simply elect to withdraw the entire device when it comes into contact with a chord, rather than manipulating (e.g., cutting) the chord, if it is appropriate to do so.

Because cutting member (6006) is disposed within housing (6002) when not in use, inadvertent tissue cutting or damage may be avoided. Moreover, in some cases, chord-cutting device (6000) may include one or more safety mechanisms to prevent inadvertent advancement of cutting member (6006). For example, a button or switch may be activated to deploy a barrier in the slot (not shown) in groove portion (6004), and to thereby prevent advancement of cutting member (6006) within the slot. Additionally, the design of cutting device (6000) may help to control the cutting of a chord. For example, the design may allow for chords to be positioned within grooved portion (6004) in a particular way, such that the chords are stabilized prior to cutting.

Figure 60K:
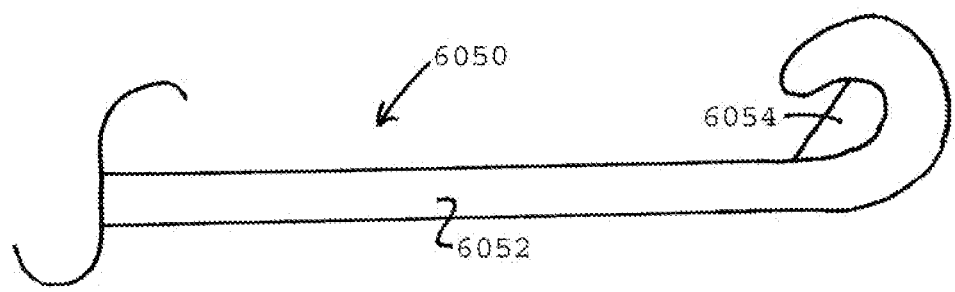
FIGS. 60K-60M show different variations of cutters that may be used in devices for cutting one or more chords.
Figure 60L:
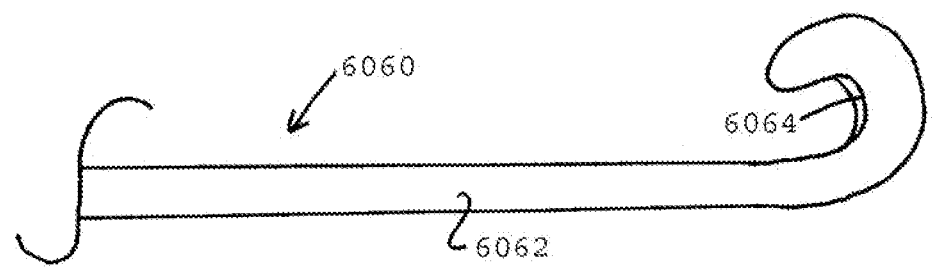
Figure 60M:
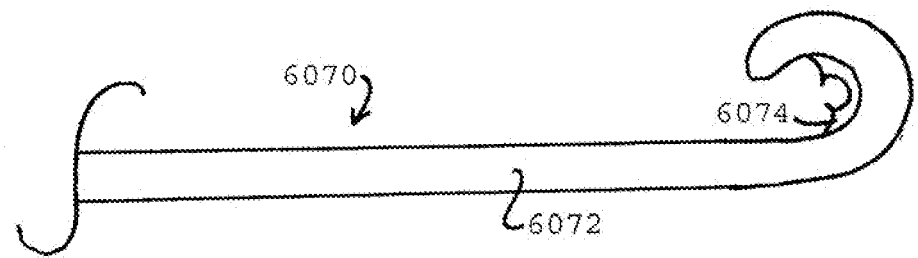
Figure 60N:
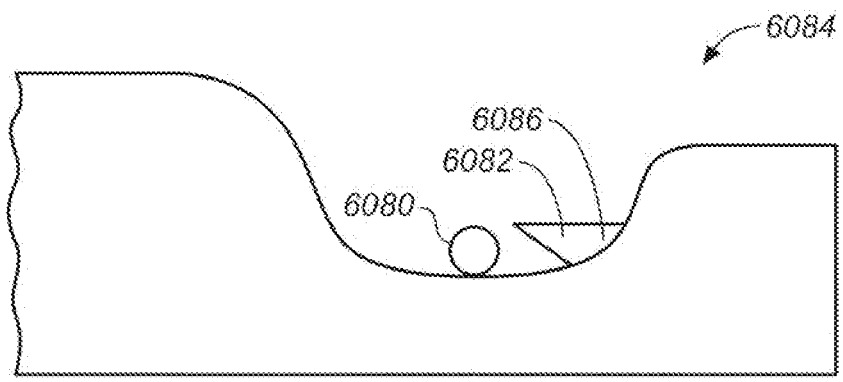
FIGS. 60N and 60O depict additional variations of a device and method for cutting one or more chords.
Figure 60O:
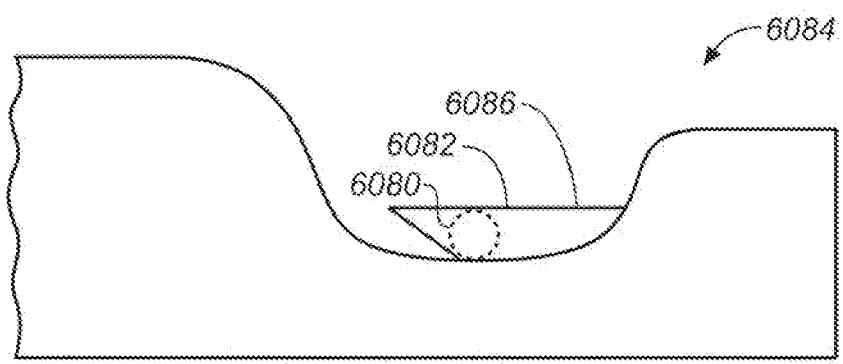

Of course, cutting member (6006) is only one variation of a cutting member, and other suitable variations may be used. For example, cutting members having different sizes and/or shapes may be used, and in some variations, multiple cutting members may be used. As an example, FIG. 60K shows another variation of a cutting member (6050). As shown there, cutting member (6050) comprises a curved elongated body (6052) and a cutting blade (6054) coupled to the curved elongated body, where cutting blade (6054) is sloped in a direction opposite that of cutting blade (6010) described above. As another example, FIG. 60L shows a cutting member (6060) comprising a curved elongated body (6062) and a curved cutting blade (6064). Curved cutting blade (6064) may, for example, provide highly controlled chord cutting. For example, the blade's position at the very end of cutting member (6060), and within the contour of its curve, may make it highly unlikely that the blade will prematurely cut a chord. As an additional example, FIG. 60M shows a cutting member (6070) comprising a curved elongated body (6072) and a cutting blade (6074) that is both curved and notched. While FIGS. 60K-60M show specific exemplary variations of cutting members, other appropriate cutting members may alternatively or additionally be used in a chord-cutting device. For example, in some variations, a chord-cutting device may comprise a cutting member that does not comprise a curved elongated member, and/or that just comprises one or more blades. As an example, FIGS. 60N and 60O illustrate a method that comprises severing a chord (6080) with a chord-cutting device (6084). As shown there, chord-cutting device (6084) comprises a cutting member (6082) slidably disposed within a track (not shown) of chord-cutting device (6084). Cutting member (6082) is in the form of a cutting blade (6086).

Figure 61:
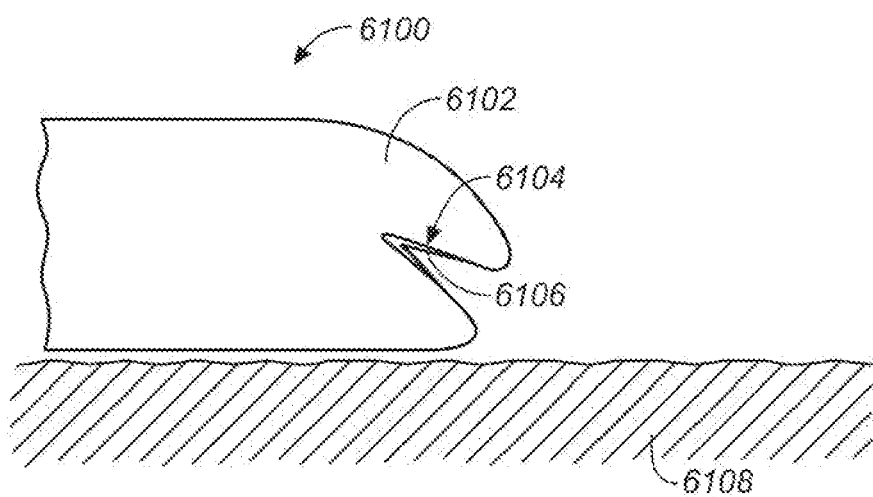
FIG. 61 shows another variation of a device for cutting one or more chords.

Additional variations of chord-cutting devices are contemplated. As an example, FIG. 61 shows a chord-cutting device (6100) comprising a body (6102) having a V-shaped opening (6104) formed therein, and a cutting blade (6106) disposed within the opening. During use, an operator may advance chord-cutting device (6100) adjacent a ventricular wall (6108), and use it to sever chords that prevent chord-cutting device (6100) from passing between them and the ventricular wall. The obstructing chords may be swept into V-shaped opening (6104), where they may be severed by coming into contact with cutting blade (6106).

In some variations, a chord-cutting device may comprise one or more expandable members. In some such variations, the expandable members may comprise inflatable members, such as balloons. The expandable members may be used, for example, to assess whether it is necessary to sever one or more chords to provide a target site with enhanced accessibility.

Figure 62A:
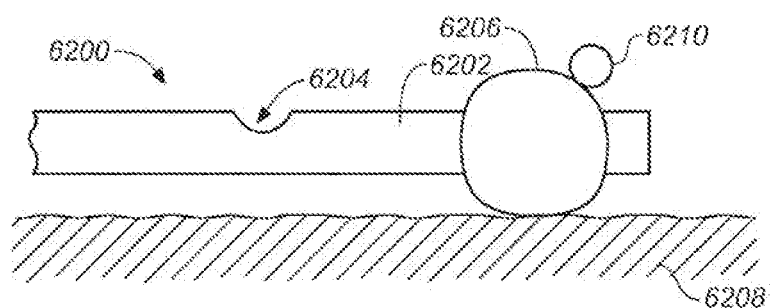
FIGS. 62A-62E show variations of a device and method for cutting one or more chords.
Figure 62B:
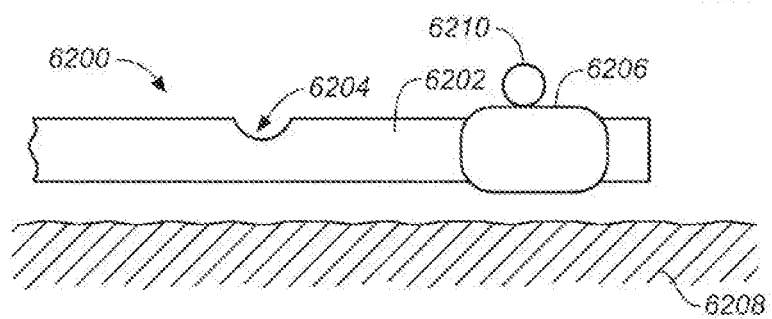
Figure 62C:
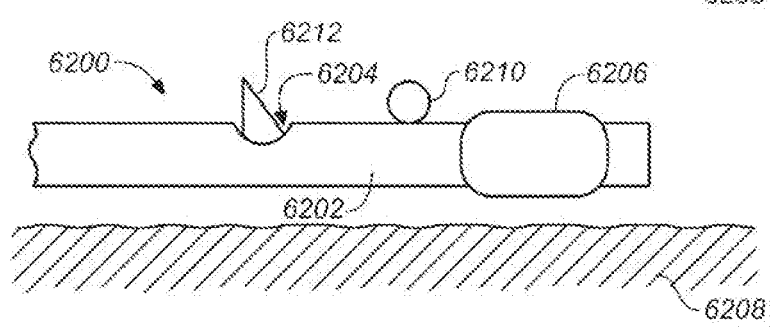
Figures 62D, 62E:
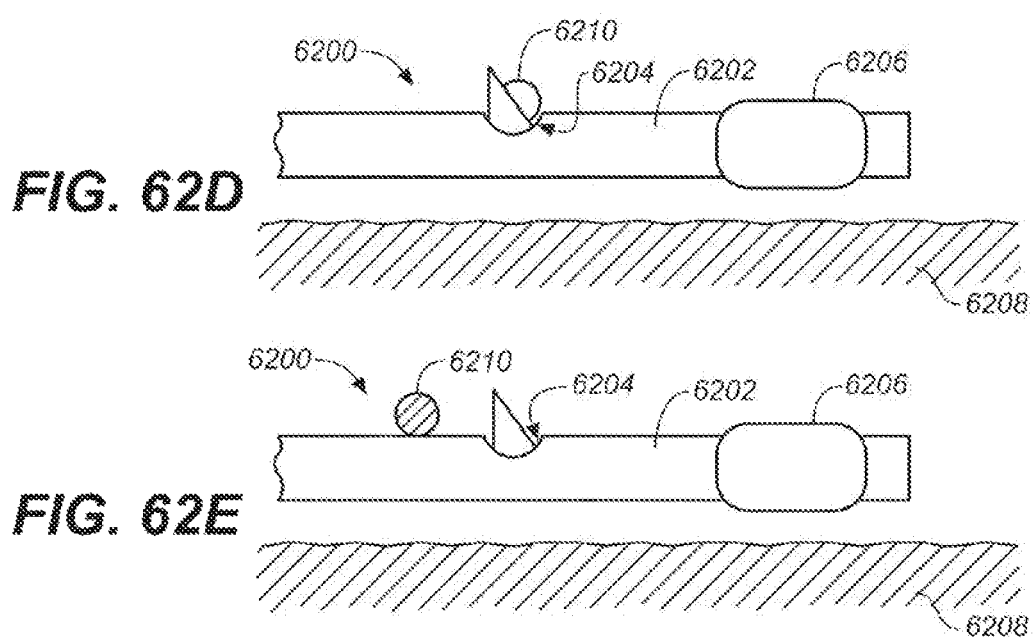

As an example, FIG. 62A show a chord-cutting device (6200) comprising an elongated member (6202) having a notch (6204) formed therein, and an inflatable member (6206) disposed at the distal end of the elongated member. In FIG. 62A, inflatable member (6206) is inflated. During use, chord-cutting device (6200) may be advanced through a subvalvular space of a heart with inflatable member (6206) in its inflated state. The inflatable member may be fully inflated, or may be inflated to less than its full inflation capacity. FIG. 62A shows chord-cutting device (6200) when inflatable member (6206) is unable to pass between a chord (6210) and a ventricular wall of the heart. When this occurs, the operator generally will not be able to advance chord-cutting device (6200) any further, and may experience a tactile sensation indicating that the chord-cutting device is stuck. In response, and referring now to FIG. 62B, the operator may at least partially deflate inflatable member (6206), so that chord-cutting device (6200) is able to pass between chord (6210) and ventricular wall (6208). As shown in FIG. 62C, the operator may then actuate a cutting blade (6212) of chord-cutting device (6200), such that the cutting blade appears through notch (6204). Chord-cutting device (6200) may then be advanced toward chord (6210) so that cutting blade (6212) contacts and cuts the chord (as shown in FIG. 62D), thereby resulting in a severed chord (6210) (FIG. 62E). In some cases, after the chord has been severed, cutting blade (6212) may be retracted back into notch (6204) and/or chord-cutting device (6200) may be further advanced through the subvalvular space of the heart (e.g., to sever any additional chords that may present obstacles to catheter advancement).

Figure 63D:
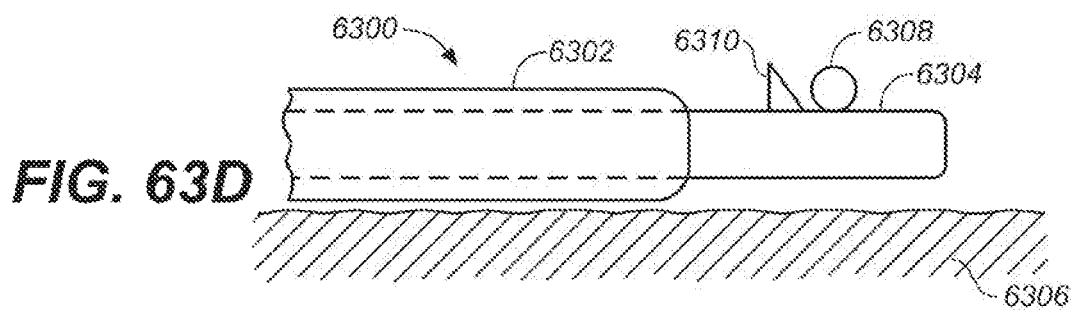
Figure 63E:
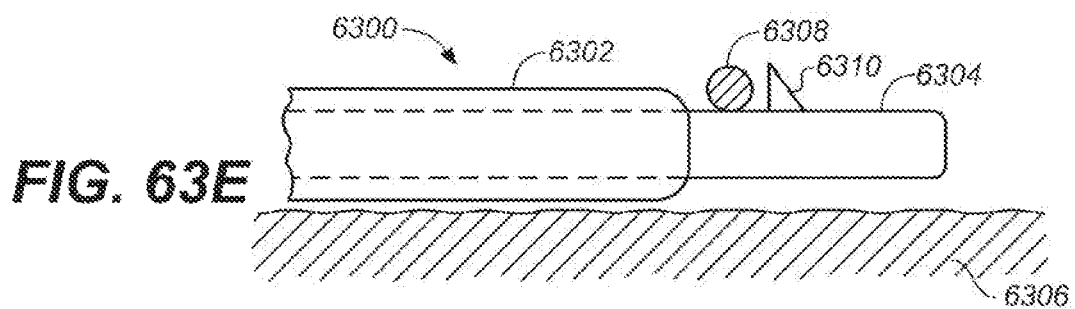

FIGS. 63A-63E depict another variation of a chord-cutting device (6300). As shown there, chord-cutting device (6300) comprises an outer tubular member (6302) and an inner elongated member (6304) disposed within a lumen of outer tubular member (6302). During use, an operator may position chord-cutting device (6300) so that outer tubular member (6302) is adjacent a heart tissue wall (6306), and may advance chord-cutting device (6300) along the heart tissue wall. During this advancement, chord-cutting device (6300) may approach one or more chords, such as chord (6308) in FIG. 63A. As shown in FIG. 63A, the space (S) between chord (6308) and heart tissue wall (6306) is not large enough for chord-cutting device (6300) to pass therethrough. In response, and referring now to FIG. 63B, the operator may proximally withdraw outer tubular member (6302), and may attempt to push inner elongated member (6304) between chord (6308) and heart tissue wall (6306). As shown in FIG. 63C, here there is sufficient space for inner elongated member (6304) to pass between the chord and the heart tissue wall. Referring now to FIG. 63D, the operator may actuate a blade (6310) or other cutting member from chord-cutting device (6300) and, as shown in FIG. 63E, may continue to advance chord-cutting device (6300) until blade (6310) severs chord (6308). In cases in which there is insufficient space for inner elongated member (6304) to pass between a chord and a heart tissue wall, the operator may, for example, advance a smaller chord-cutting device to the obstructed location and use that smaller chord-cutting device to cut the chord.

Figure 64A:
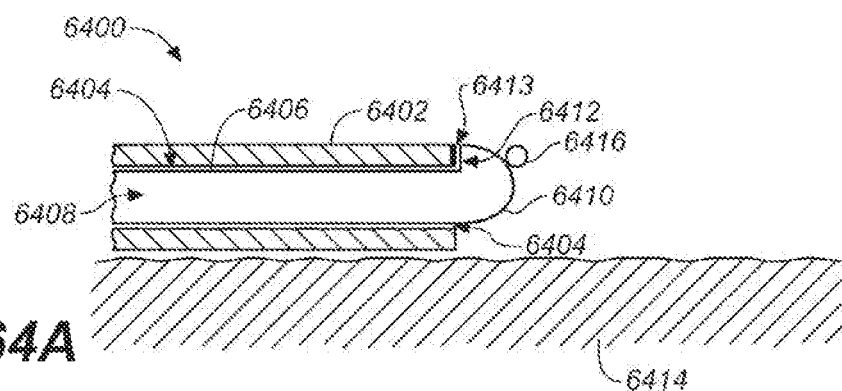
FIGS. 64A-64D depict additional variations of a device and method for cutting one or more chords.

Still other variations of chord-cutting devices may be used. As an example, FIG. 64A depicts another variation of a chord-cutting device (6400) comprising an outer tubular member (6402) having a lumen (6404), and an inner rotatable member (6406) disposed within lumen (6404). Inner rotatable member (6406) comprises an elongated body portion (6408) and a rounded asymmetrical head portion (6410). The rounded shape of head portion (6410) may, for example, cause chord-cutting device (6400) to be relatively atraumatic and unlikely to harm body tissue during use. Head portion (6410) comprises a shelf (6412) configured to align with a sharpened edge (6413) of outer tubular member (6402). During use, an operator may elect to cover sharpened edge (6413) with shelf (6412), or to expose sharpened edge (6413). For example, sharpened edge (6413) may be covered by shelf (6412) during initial advancement of chord-cutting device (6400) within the body, and then uncovered when sharpened edge (6413) is needed to sever a chord.

Figure 64B:
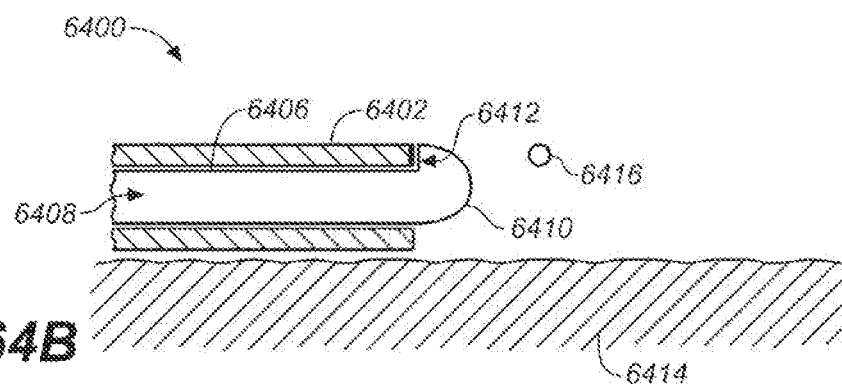
Figure 64C:
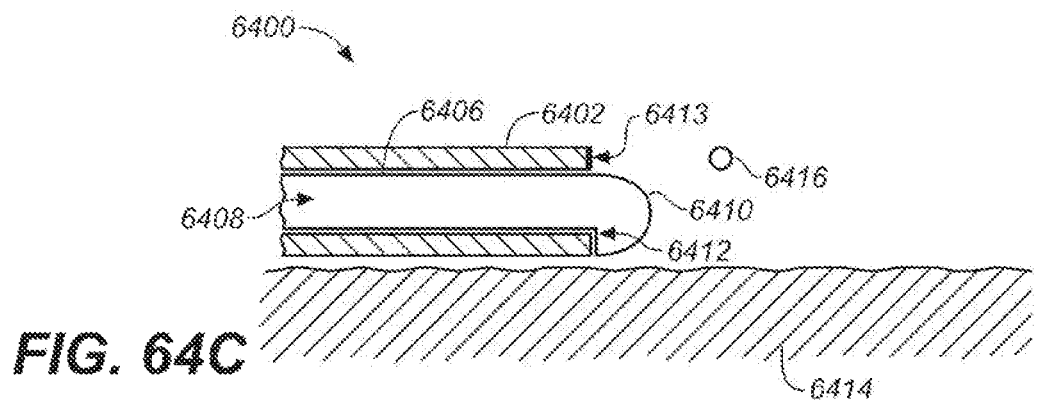
Figure 64D:
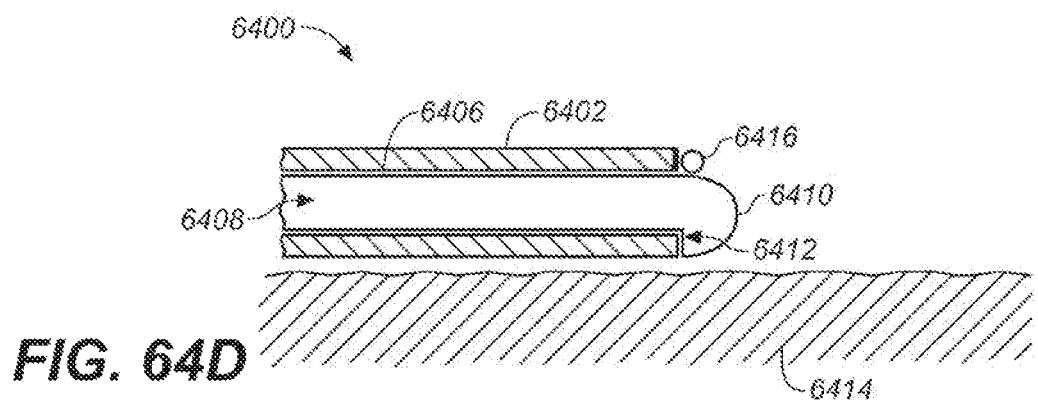

As an example, FIG. 64A shows chord-cutting device (6400) being advanced along a heart tissue wall (6414) and toward a chord (6416). During this advancement, shelf (6412) covers sharpened edge (6413). As shown in FIG. 64A, chord-cutting device (6400) is too large to fit between heart tissue wall (6414) and chord (6416). Upon determining that this is the case, the operator may partially proximally withdraw chord-cutting device (6400), as shown in FIG. 64B. Referring now to FIG. 64C, the operator may then rotate inner rotatable member (6406), so that shelf (6412) no longer covers sharpened edge (6413). Then, and as shown in FIG. 64D, chord-cutting device (6400) may once again be advanced toward chord (6416), so that sharpened edge (6413) contacts and thereby severs chord (6416). While one variation of an inner member is shown, it should be understood that other variations (e.g., having different shapes) may be used, as appropriate. As an example, in some variations, an inner member may itself be tubular. This may, for example, allow an operator to deliver one or more therapeutic agents through the inner member and into the body during use.

Figure 65A:
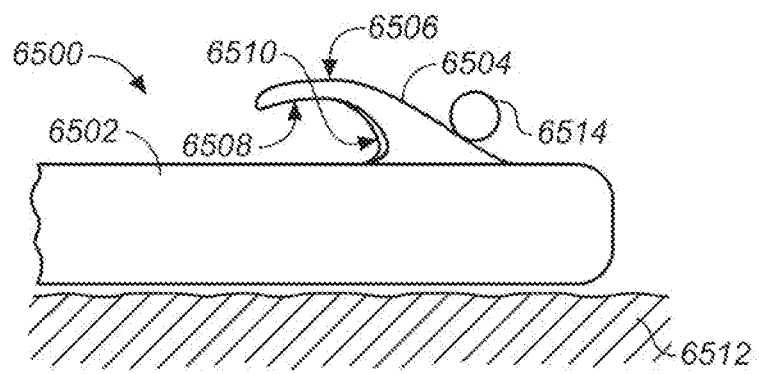
FIGS. 65A-65E are illustrative depictions of further variations of a device and method for cutting one or more chords.
Figure 65B:
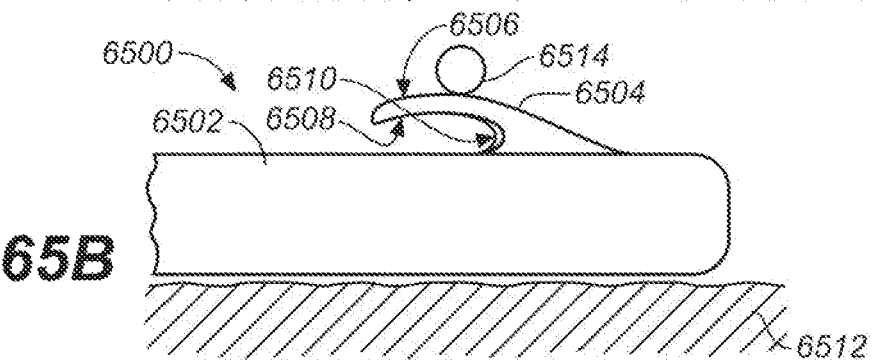
Figure 65C:
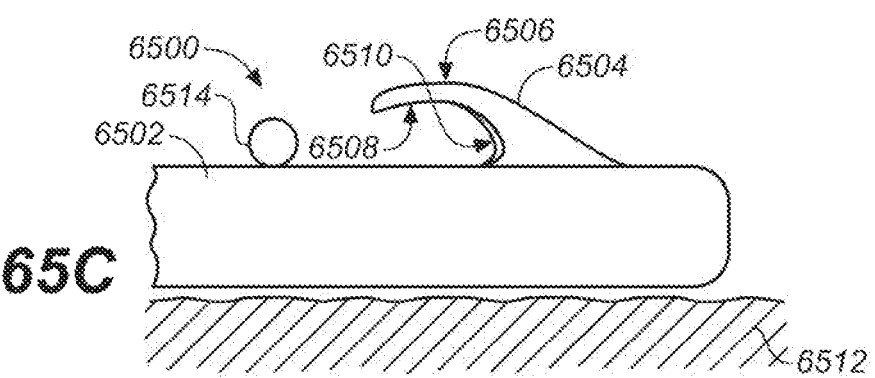
Figure 65D:
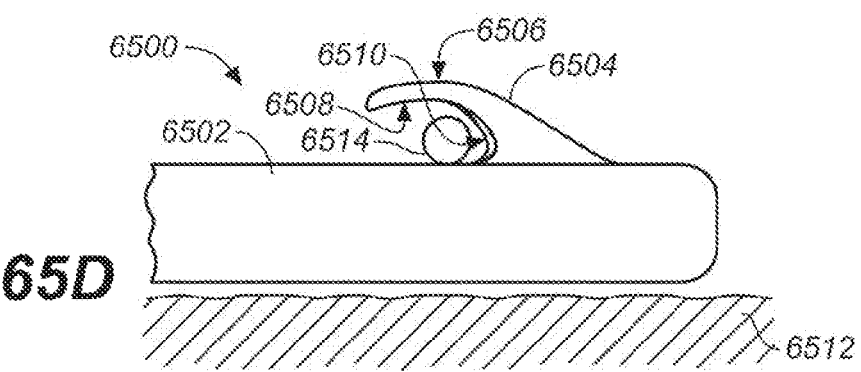
Figure 65E:
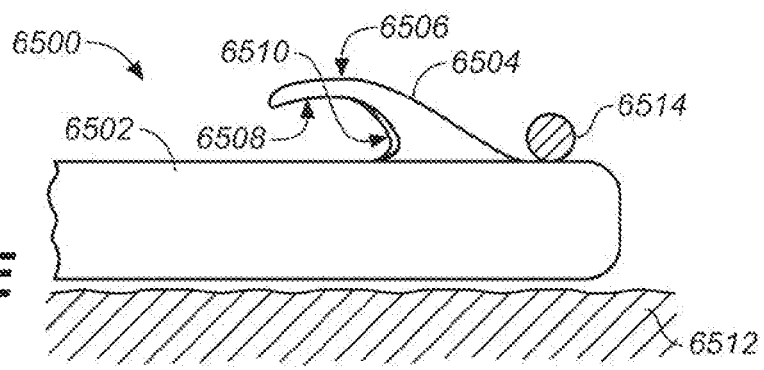

FIGS. 65A-65E illustrate additional variations of a chord-cutting device and related method for cutting one or more chords. As shown there, a chord-cutting device (6500) comprises an elongated member (6502) and a curved cutting member (6504) projecting from an outer surface of the elongated member. Curved cutting member (6504) comprises an outer rounded surface (6506) and an inner surface (6508) including a cutting blade (6510). Referring now specifically to FIG. 65A, during use chord-cutting device (6500) may be advanced along a heart tissue wall (6512) and toward a chord (6514). As shown in FIG. 65A, chord-cutting device (6500) may become stuck between chord (6514) and heart tissue wall (6512) when cutting member (6504) is in its fully projected state. However, the operator may continue to push chord-cutting device (6500), until the portion of chord-cutting device (6500) comprising curved cutting member (6504) squeezes between chord (6514) and heart tissue wall (6512), as shown in FIG. 65B. In some cases, cutting member (6504) may have some flexibility or springiness that allows it to be pushed downward (i.e., closer to elongated body portion (6502)), and to fit between chords and heart tissue wall (6512) in this way. Referring now to FIG. 65C, eventually the portion of cutting device (6500) comprising curved cutting member (6504) passes by chord (6514). Since cutting member (6504) is no longer restrained by chord (6514), it may assume its original position. Next, and as shown in FIG. 65D, the operator may proximally withdraw chord-cutting device (6500) until cutting member (6504) contacts chord (6514) and cutting blade (6510) severs chord (6514). FIG. 65E shows chord (6514) after it has been severed. While not shown here, in some variations, chord-cutting device (6500) may be delivered to a target site in a delivery device (e.g., a tubular member such as a catheter) that temporarily covers curved cutting member (6504) (e.g., preventing inadvertent tissue-snagging or other tissue damage by the cutting member during delivery).

Figure 66A:
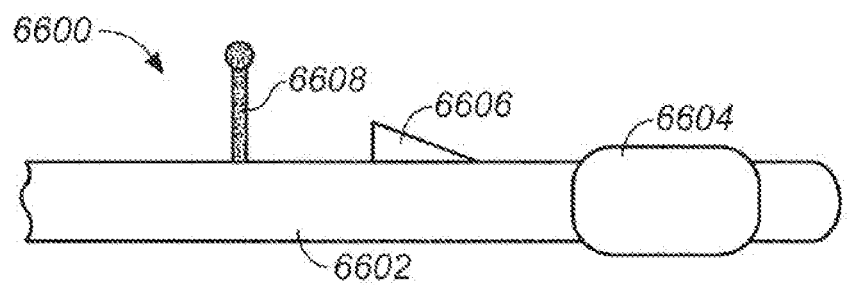
FIGS. 66A-66C depict different variations of devices that may be used to cut one or more chords.

In some variations, a chord-cutting device may comprise one or more radiopaque markers and/or markings. These markers and/or markings may be used, for example, to help align the device properly within the heart during use. For example, FIG. 66A shows a chord-cutting device (6600) comprising an elongated member (6602), an inflatable member (6604), and a cutting blade (6606). Chord-cutting device (6600) further comprises a radiopaque projection (6608). Radiopaque projection (6608) may be used, for example, to help determine the orientation of chord-cutting device (6600) under X-ray fluoroscopy during use, and/or to let the operator know the approximate positioning of cutting blade (6606) during use. While one variation of a radiopaque projection has been depicted, it should be understood that other variations of radiopaque projections may alternatively or additionally be employed. Moreover, while a radiopaque projection has been shown, some variations of chord-cutting devices may alternatively or additionally comprise other forms of radiopaque markers or markings. Additionally, in some cases multiple radiopaque markers and/or markings may be used.

Figure 66B:
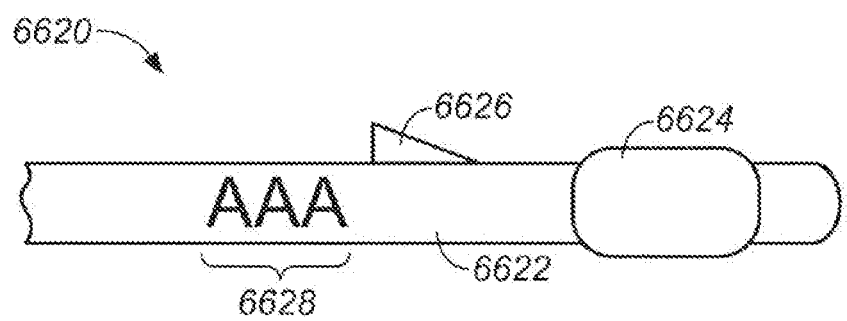
Figure 66C:
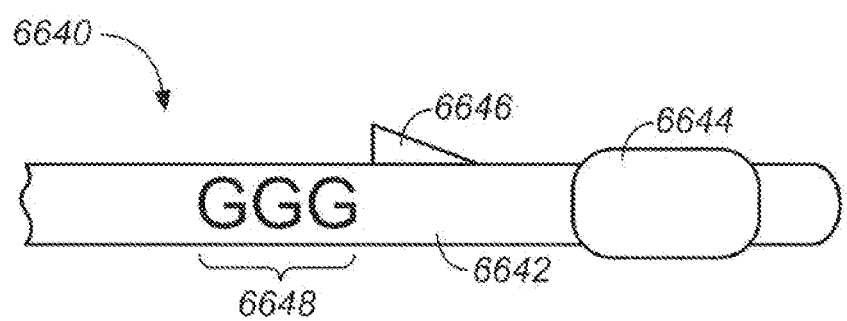

FIG. 66B shows a chord-cutting device (6620) comprising an elongated member (6622), an inflatable member (6624), and a cutting blade (6626). Chord-cutting device (6620) also includes a number of radiopaque markings (6628), each in the form of an "A," along elongated member (6622). As another example, FIG. 66C shows a cutting device (6640) comprising an elongated member (6642), an inflatable member (6644), and a cutting blade (6646), where elongated member (6642) includes three radiopaque markings (6648), each in the form of a "G." Of course, while certain letters have been shown, other letters, numbers, designs, and the like may be used, and any suitable combination of markings (e.g., combinations of letters and numbers) may be used. Radiopaque markers or markings may be employed with any of the devices described herein as appropriate, and are not limited to use with chord-cutting devices.

Figure 67A:
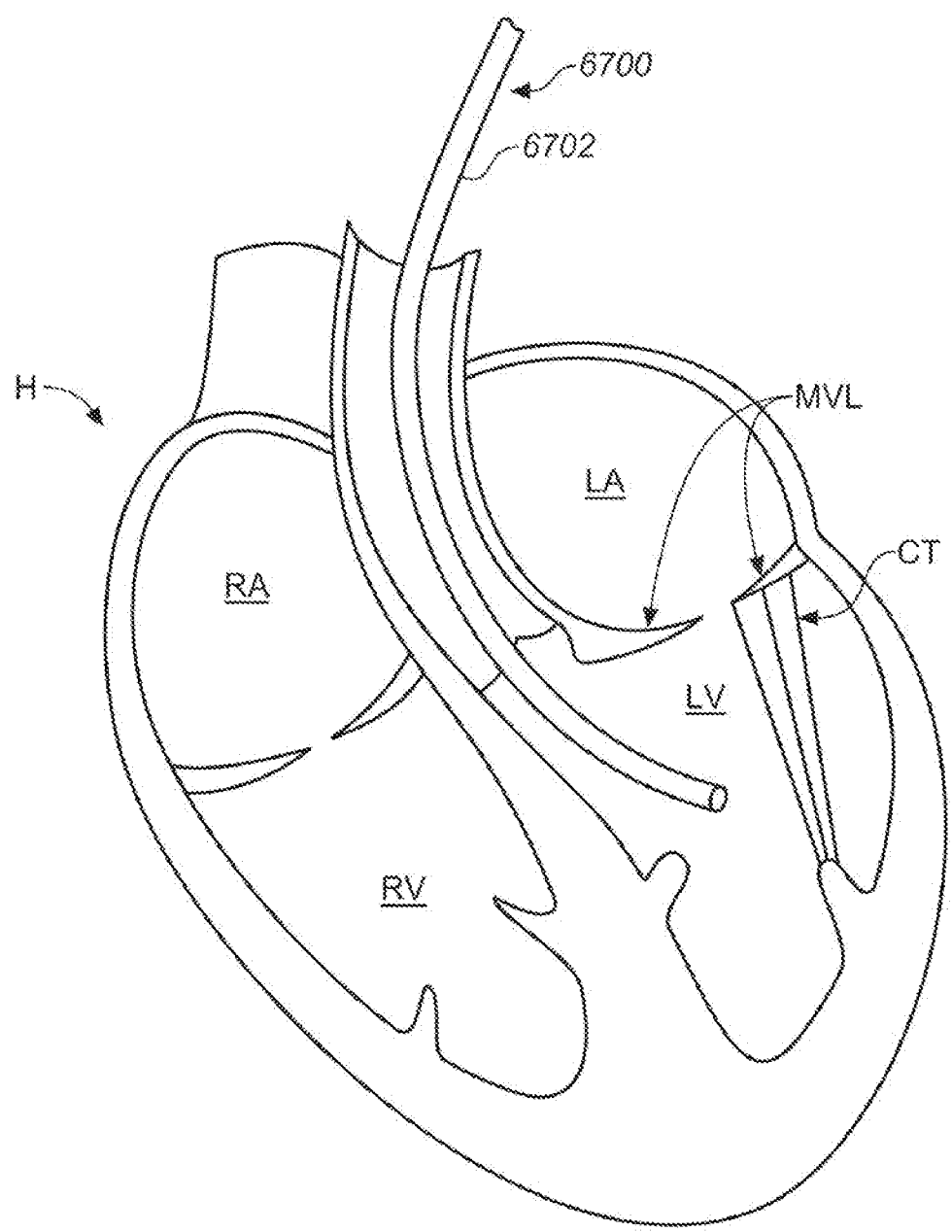
FIGS. 67A-67D are illustrative views of variations of a device and method for manipulating one or more chords.
Figure 67B:
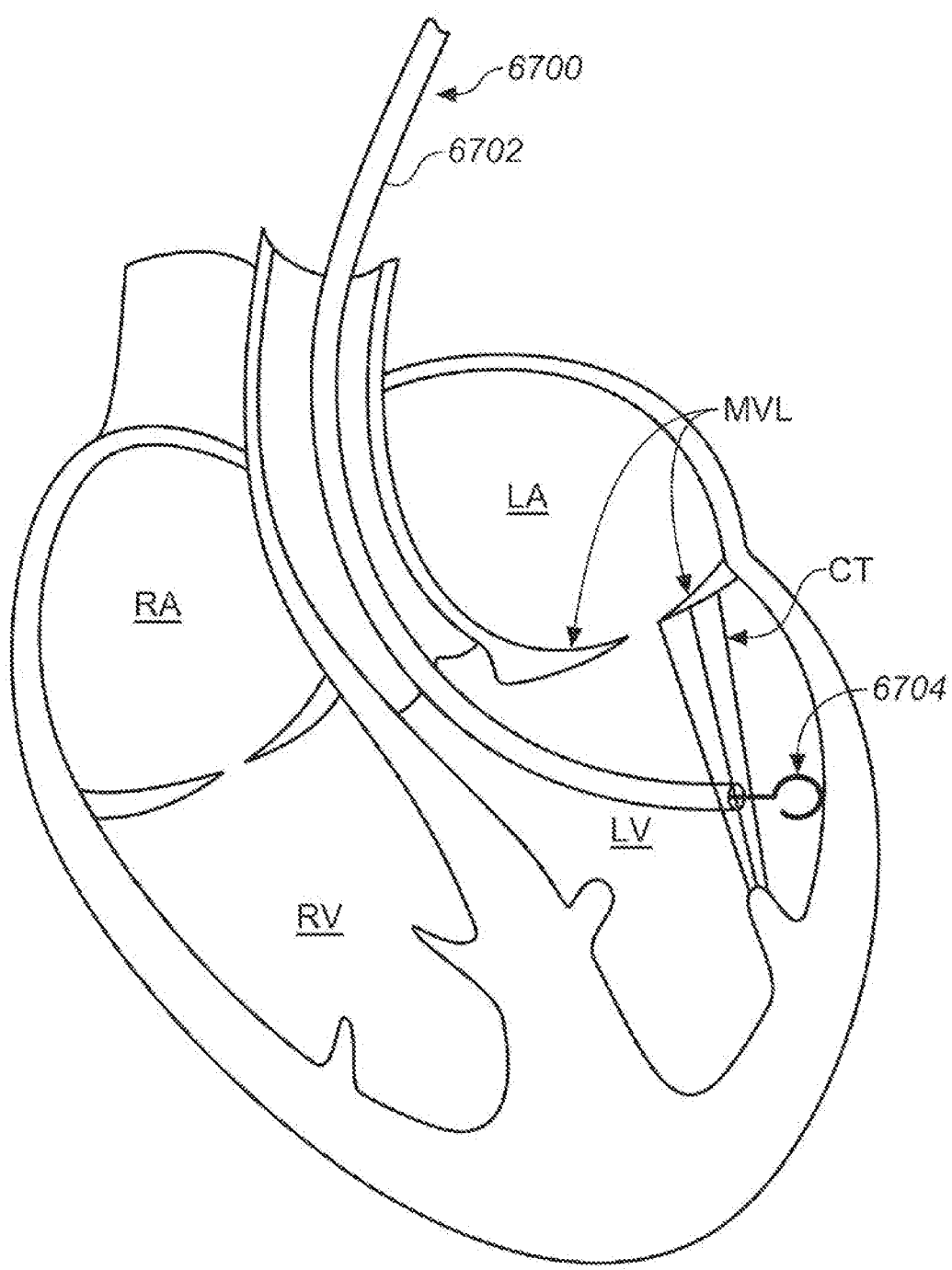
Figure 67C:
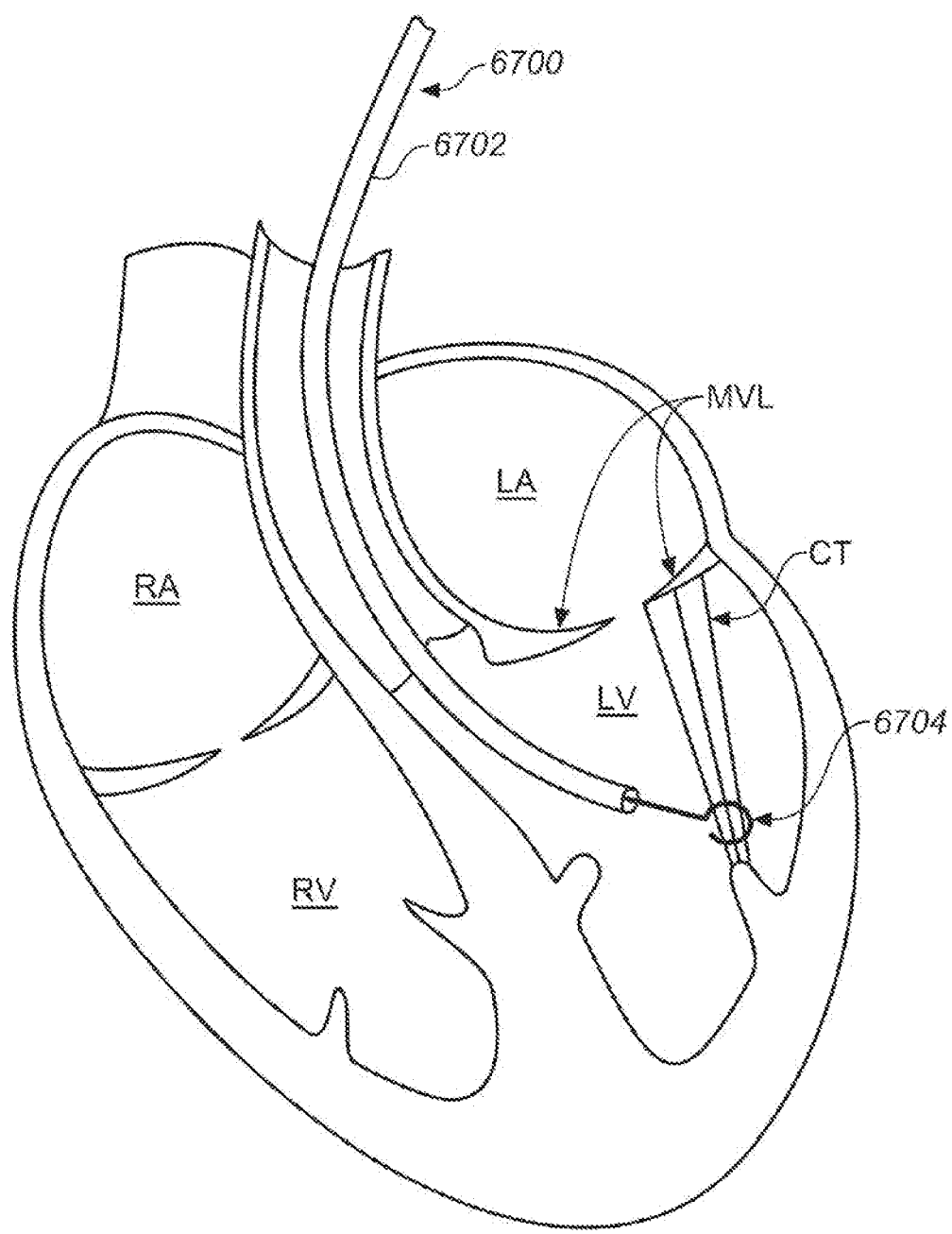
Figure 67D:
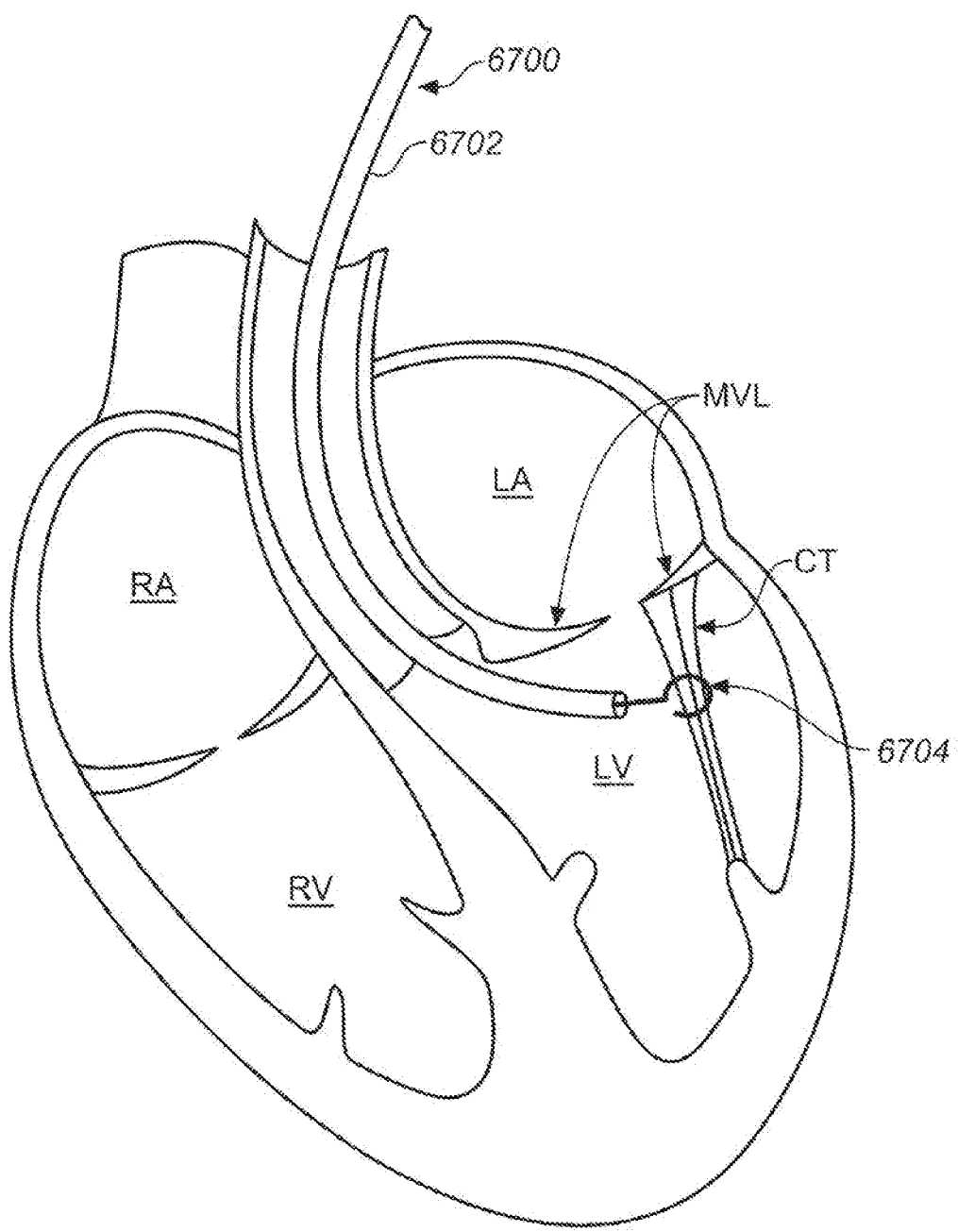

While chord-cutting devices and methods have been described, in some variations, chords may alternatively or additionally be manipulated in one or more other ways. For example, FIGS. 67A-67D show a device and method for manipulating one or more chords by gathering the chords (e.g., to move them out of the way of a catheter being tracked along a subannular groove region). Referring now to FIG. 67A, a chord-gathering device (6700) comprising an elongated member (6702) may be advanced into a left ventricle (LV) of a heart (H). As shown in FIGS. 67B and 67C, a hook (6704) may be advanced from elongated member (6702) and may be hooked around chordae tendineae (CT) in left ventricle (LV) (FIG. 67C). In some variations, the chords may be visualized (e.g., using one or more of the visualization methods described above) prior to, during, and/or after such hooking. Once the chords have been hooked, and referring now to FIG. 67D, hook (6704) may be drawn up toward mitral valve leaflets (MVL), thereby gathering the chords (and, e.g., providing additional space for advancement of a catheter within left ventricle (LV)). Of course, while a hook has been described, other variations of chord manipulation devices may alternatively or additionally comprise one or more different mechanisms for manipulating chords. Additionally, in certain variations, a device may be able to serve more than one chord manipulation function. For example, a device may be capable of both cutting and gathering chords to move and/or re-position the chords.

Anchor Deployment Methods

As described above, in certain variations, after a diagnostic catheter has been used to assess the accessibility of a mitral valve region, a procedure may be performed to deploy coupled anchors (e.g., tethered anchors) to the region. FIGS. 25A-25D illustrate a variation of an anchor deployment method.

Figure 25A:
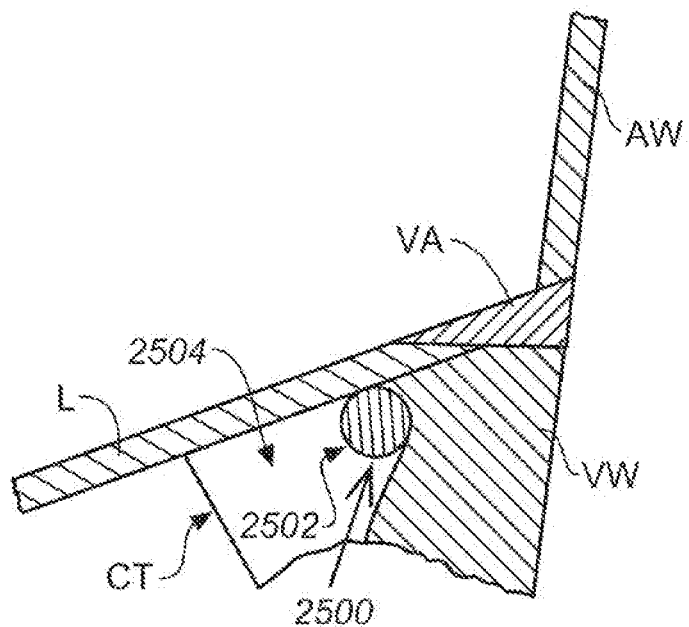
FIGS. 25A-25D are cross-sectional views of a portion of a heart, schematically illustrating a variation of a method for deploying an anchor into a region of a mitral valve annulus of the heart.

As shown in FIG. 25A, in one variation, a distal portion (2502) of a guide catheter (2500) may be positioned in a desired location under a valve leaflet (L) and adjacent a ventricular wall (VW) in a heart ventricle having a chorda tendinea (CT). The valve annulus (VA) generally comprises an area of heart wall tissue at the junction of the ventricular wall (VW) and the atrial wall (AW) that is relatively fibrous and, thus, significantly stronger than leaflet tissue and other heart wall tissue. It is noted, however, that considerable structural variations of the annulus exist within patient populations, and that an attempted delivery of an implant to the valve annulus (VA) may instead result in the implant contacting or attaching to the tissue adjacent to the valve annulus. The term "annular tissue" as used herein shall include the valve annulus and the tissue adjacent to or surrounding the valve annulus.

Distal portion (2502) of guide catheter (2500) may be advanced into position generally under valve annulus (VA) by any suitable technique, some of which are described below. Distal portion (2502) of guide catheter (2500) may be used to deliver one or more anchors to the valve annular tissue, to stabilize and/or expose the annulus, or both. In one variation, using guide catheter (2500) having a flexible elongate body, flexible distal portion (2502) may be positioned in the heart ventricle at the level of valve leaflet (L) using any of a variety of access routes described herein. Distal portion (2502) may be advanced under the posterior valve leaflet into a space such as subannular groove region (2504) or in subvalvular space (2506). It has been found that when guide catheter (2500) is passed, for example, under the mitral valve via an intravascular approach, guide catheter (2500) may be inserted into subannular groove region (2504) or subvalvular space (2506) and advanced either partially or completely around the circumference of the valve. Once in subannular groove region (2504) or subvalvular space (2506), distal portion (2502) of guide catheter (2500) may be positioned proximate to the intersection of the valve leaflet(s) and ventricular wall (VW), which is near valve annulus (VA). These are but examples of possible access routes of a guide catheter to a valve annulus, and any other appropriate access routes may be used.

In some variations, it may be advantageous to provide guide catheter (2500) with a curvable portion having a radius in an expanded/curved state that is greater than a radius of the valve annulus, the subannular groove region or the ventricular chamber. The relative size of this portion of guide catheter (2500), when positioned within the smaller sized ventricle, may exert a radially outward force that may improve the surface contact between guide catheter (2500) and left ventricle (LV). For example, in one variation, guide catheter (2500) in the expanded state may have a radius that is about 25% to about 50% larger than the valve annulus. Additionally, certain variations of guide catheters may further include one or more expandable members (e.g., balloons) that may expand to urge or press or wedge the guide catheter into a target site (e.g., in the subvalvular space).

Figure 25B:
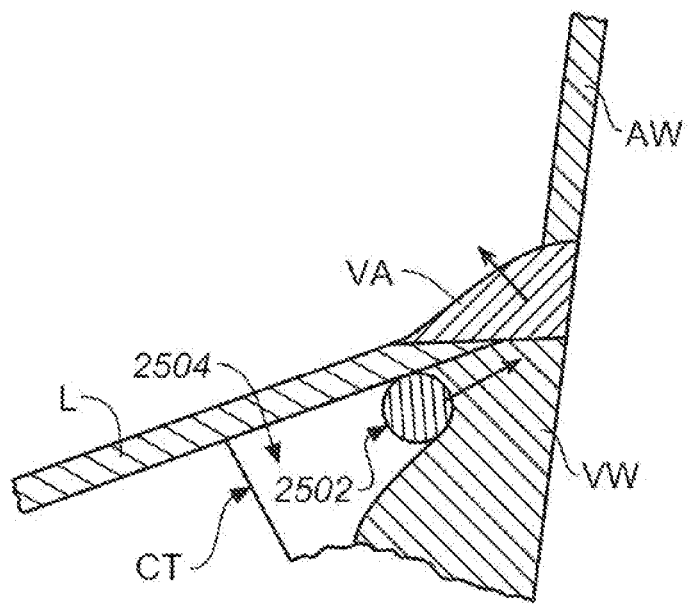

In some variations, guide catheter (2500) (and specifically distal portion (2502)) may be used to stabilize and/or expose the valve annulus or annular tissue. Other catheters may alternatively or additionally be used to stabilize and/or expose the valve annulus or annular tissue. Such stabilization and exposure are described, for example, in U.S. patent application Ser. No. 10/656,797 (published as US 2005/0055087 A1), which is incorporated herein by reference in its entirety. For example, distal portion (2502) may be positioned generally under the annular tissue, and force may be applied to distal portion (2502) to stabilize valve annulus (VA) or the annular tissue, as shown in FIG. 25B. Such force may be directed in any suitable direction to expose, position and/or stabilize the annulus or annular tissue. In another example, an upward and lateral force is shown in FIG. 25B by the solid-headed arrow drawn from the center of distal portion (2502). In other examples, only upward, only lateral, or any other suitable force(s) may be applied. With application of force to distal portion (2502), the annular tissue may rise or project outwardly, thus exposing the annulus for easier viewing or access. The applied force may also stabilize valve annulus (VA) or the valve annular tissue, thereby facilitating surgical procedures and visualization.

Figure 25C:
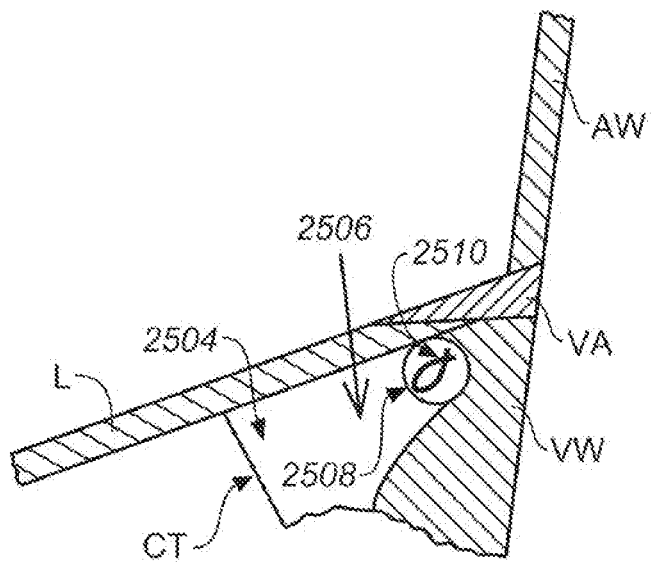
Figure 25D:
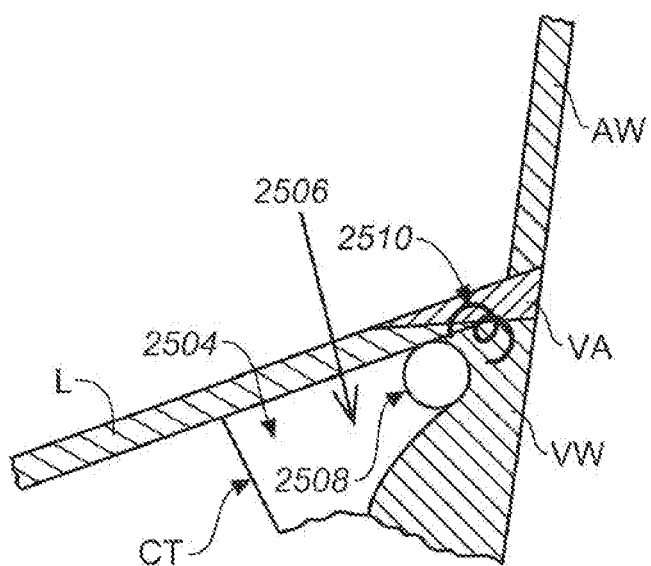

In some variations, an anchor deployment catheter may exert additional force after the first anchor is engaged to body tissue. The first anchor may provide additional leverage and stability for manipulating the anchor deployment catheter. Referring to FIGS. 25C and 25D, an anchor deployment catheter (2508) is schematically shown deploying an anchor (2510) to a valve annulus (VA) or annular tissue. Variations of anchor deployment catheters are described, for example, in U.S. patent application Ser. No. 12/366,553 (published as US 2009/0222083 A1), U.S. Provisional Application Ser. No. 61/160,230, filed on Mar. 13, 2009, and U.S. Provisional Application Ser. No. 61/178,910, filed on May 15, 2009, all of which are incorporated herein by reference in their entirety. Anchor (2510) is shown first housed within anchor deployment catheter (2508) in FIG. 25C, and then deployed to valve annulus (VA) or to annular tissue, as depicted in FIG. 25D. Of course, although the deployment and position of anchor (2510) is described with respect to valve annulus (VA), one or more anchors (2510) may miss valve annulus (VA) and attach to other structures or tissues accessible from subannular groove region (2504) or generally from subvalvular space (2506).

As shown, in some variations, anchors (2510) may have a relatively straight configuration when housed in anchor deployment catheter (2508), with two penetrating tips and a loop in between the tips. Upon deployment from anchor deployment catheter (2508), the tips of an anchor (2510) may curve in opposite directions to form two semi-circles, circles, ovals, overlapping helices or the like. This is but one example of a type of self-securing anchor which may be deployed to annular tissue. Additional anchor variations are described, for example, in U.S. patent application Ser. No. 11/202,474 (published as US 2005/0273138 A1), which is incorporated herein by reference in its entirety. In certain variations, multiple coupled anchors (2510) may be deployed, and the anchors (2510) may be drawn together to reduce the annular dimensions.

Figure 26A:
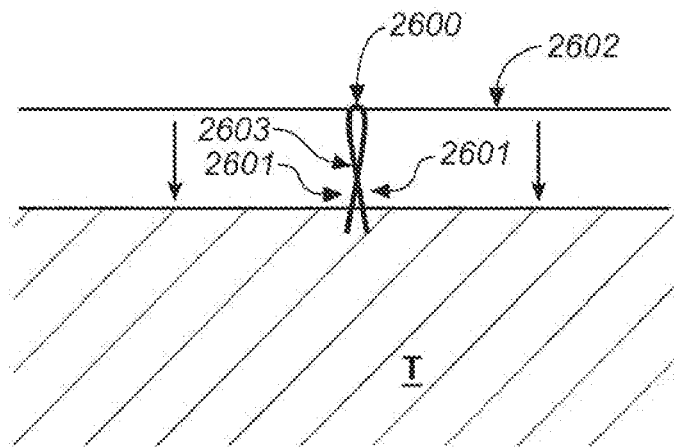
FIGS. 26A-26C are schematic cross-sectional views of a variation of a self-forming anchor attaching to body tissue.
Figure 26B:
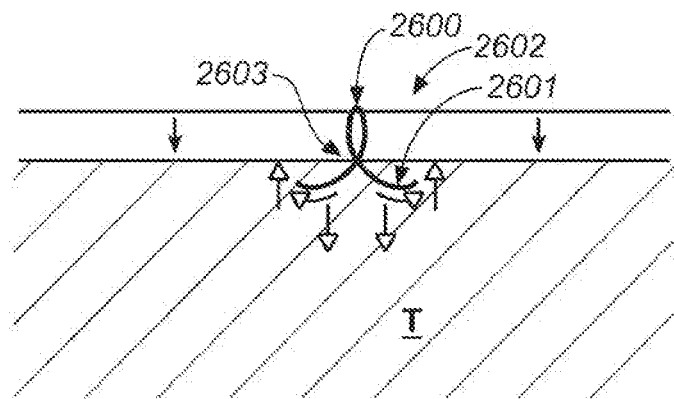
Figure 26C:
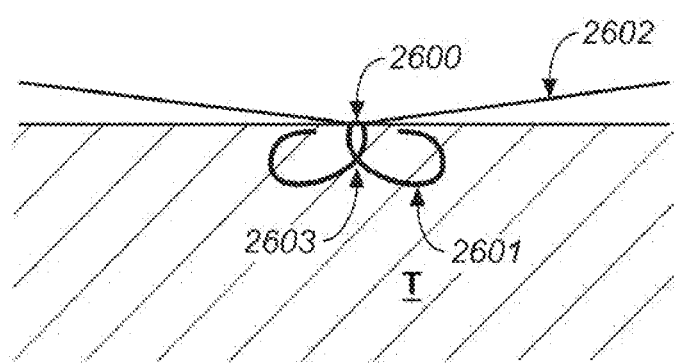

In some variations, one or more self-forming anchors (2600) may be stored in an anchor deployment device in a straightened configuration, coupled with a tether (2602), as shown in FIG. 26A. Anchors (2600) may be held or restrained in that straightened state, while their deployed configuration is non-linear or curved. Arms (2601) meet at a junction section (2603), which is slidably coupled to tether (2602). In certain variations, junction section (2603) may comprise an open or closed loop configuration and may change in size or configuration when arms (2601) are deployed. In this particular variation, as arms (2601) of anchor (2600) are released from the delivery system, arms (2601) are permitted to resume their deployed configuration, penetrating the tissue (T) along a penetration pathway. As the distal portions of arms (2601) regain their deployed configurations, arms (2601) will generally separate and reorient toward the tissue surface (depicted as open-headed arrows). In some variations, the penetration pathways may be curved, so that as anchor (2600) further penetrates into tissue (T), junctional section (2603) of anchor (2600) will continue along a similar pathway as the arms (2601). This may reduce the degree of tissue compression or stretching as anchor (2600) is deployed, which in turn may also reduce the resulting arrythmogenic risk, if any, from anchor deployment. The horizontal and vertical forces generated (depicted as open-headed arrows) by arms (2601) may also result in a counterforce which causes junction section (2603) to be brought toward the tissue surface (downward-pointing open arrows) and may even pull portions of junction section (2603) into tissue (T), as shown in FIG. 26B. Once anchor (2600) is fully deployed (FIG. 26C), anchor (2600) may be substantially embedded in tissue (T).

Portions of tether (2602) coupled to junction section (2603) are also brought closer to the surface of tissue (T). Bringing tether (2602) closer to tissue (T) may be beneficial because a greater proportion of the cross-sectional blood flow path, as bordered by tether (2602), is preserved. As a result, the risk that any subsequent catheters or implanted components inserted into the heart chamber or valve will snag or damage tether (2602) may be reduced. Additionally, the degree of hemolysis, as compared to a tether that crosses the mitral flow pathway farther from the tissue surface, may be reduced as well.

Figure 26D:
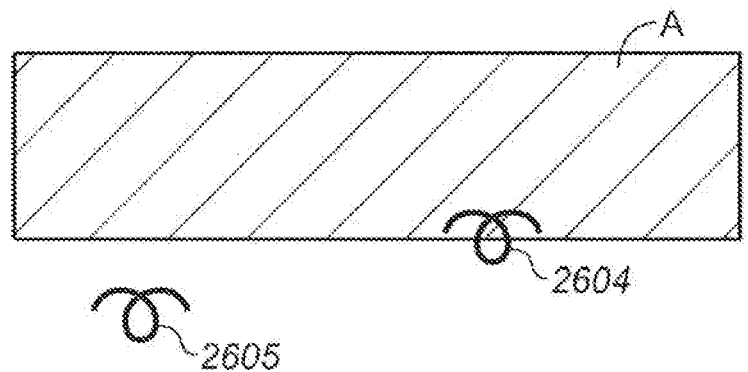
FIGS. 26D-26F are cross-sectional views of variations of anchors attaching to body tissue.
Figure 26E:
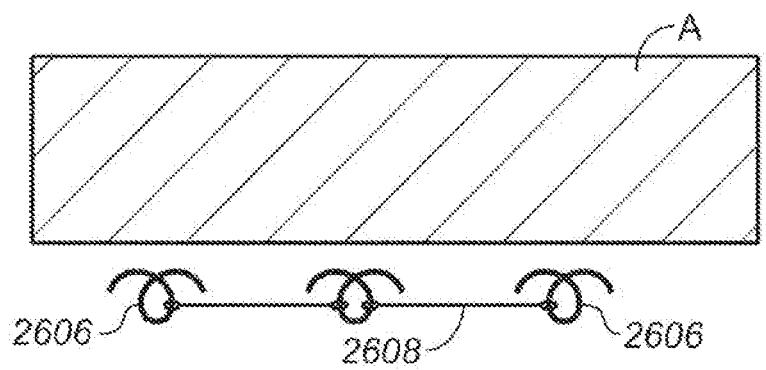
Figure 26F:
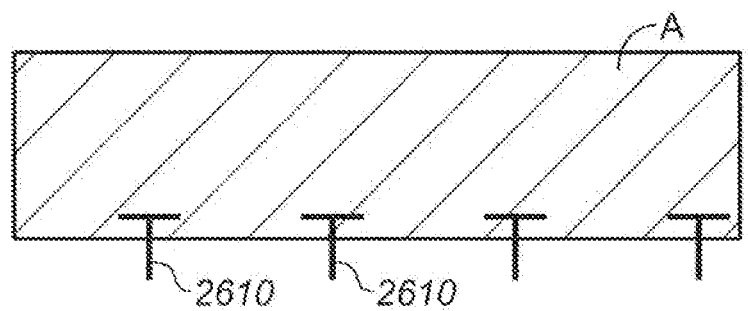

FIGS. 26D-26F depict different variations of anchor deployments into annular tissue. For example, FIG. 26D shows one variation where one anchor (2604) has been deployed into an annulus (A), while another anchor (2605) has been deployed slightly below annulus (A), in the subannular groove. The implant shown in FIG. 26E comprises a series of anchors (2606) that have been deployed into the subannular groove, slightly below annulus (A). In this variation, the anchors (2606) are coupled by a tether (2608). In the variation depicted in FIG. 26F, each anchor (2610) has been deployed into annulus (A). Here the anchors are shown as T-tags, although other types of anchors may alternatively or additionally be used, as appropriate. It should be understood that when reference is made to "annular tissue," it is meant to encompass the annulus itself, as well as tissue in close proximity to the annulus, such that implant (or anchor) deployment into the annular tissue can accomplish a change in the annulus anatomy (e.g., a reduction in annulus circumference). Consequently, deployment of anchors into "annular tissue" includes at least each of the variations depicted in FIGS. 26D-26F.

Various anchor designs and deployment methods are disclosed, for example, in U.S. patent application Ser. No. 10/741,130 (published as US 2004/0193191 A1); Ser. No. 10/792,681 (published as US 2004/0243227 A1); Ser. No. 10/900,980 (published as US 2005/0107811 A1); Ser. No. 11/255,400 (published as US 2006/0129188 A1); and Ser. No. 10/901,555 (published as US 2006/0058817 A1), all of which are incorporated herein by reference in their entirety. Various anchor designs and deployment methods are also disclosed, for example, in U.S. patent application Ser. No. 11/202,474 (published as US 2005/0273138 A1), which was previously incorporated by reference in its entirety. It should also be noted that in addition to one or more anchors, an implant may comprise a fabric or mesh, or an annuloplasty device or prosthesis, such as a ring, partial ring, or band, alone or in combination with one or more anchors. For example, the implant may be any of those implants described in U.S. patent application Ser. No. 10/461,043 (issued as U.S. Pat. No. 6,986,775); Ser. No. 10/656,797 (published as US 2005/0055087 A1); Ser. No. 10/741,130 (published as US 2004/0193191 A1); Ser. No. 10/776,682

(published as US 2005/0107810 A1); Ser. No. 10/792,681 (published as US 2004/0243227 A1); Ser. No. 10/901,019 (published as US 2005/0065550 A1); Ser. No. 10/901,444 (published as US 2006/0025784 A1); Ser. No. 10/901,455 (published as US 2006/0025750 A1); Ser. No. 10/901,554 (published as US 2005/0107812 A1); and Ser. No. 10/901,555 (published as US 2006/0058817 A1), all of which are incorporated herein by reference in their entirety.

Figure 27A:
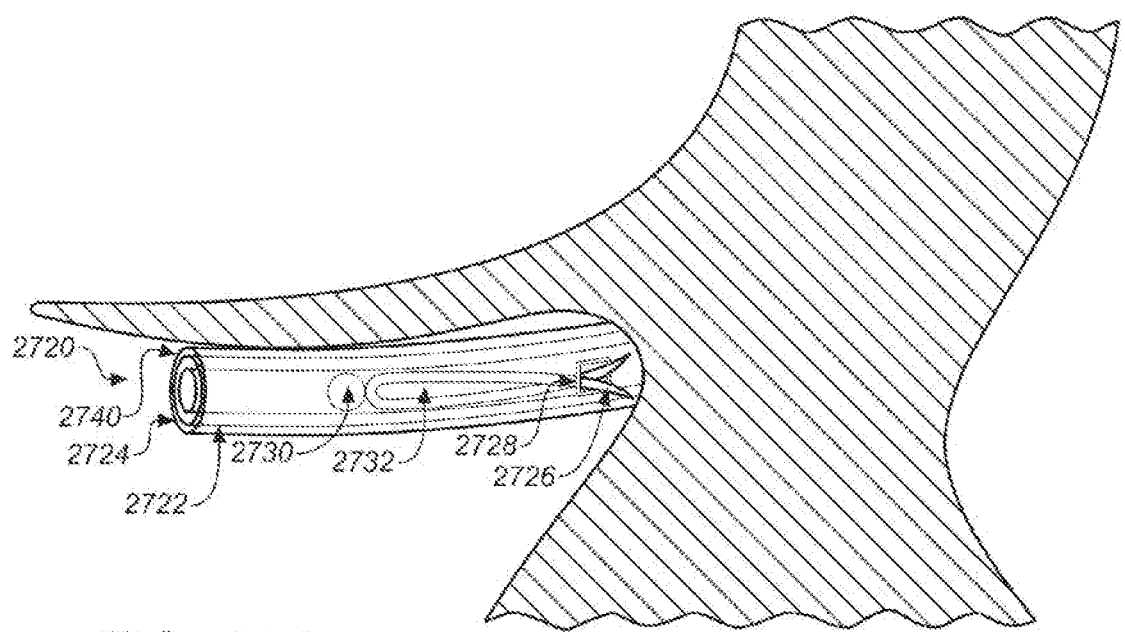
FIGS. 27A-27F schematically demonstrate a variation of a method for applying anchors from the subvalvular space of a heart.

Another variation of a method for applying a plurality of tethered anchors (2726) to the annular tissue of a heart is shown in FIGS. 27A-27F. As shown in FIG. 27A, an anchor deployment catheter (2720) is first contacted with valve annulus (VA) or annular tissue such that openings (2728) are oriented to deploy anchors (2726) into the tissue. Such orientation may be achieved by any suitable technique. In one variation, for example, a housing (2722) having an elliptical cross-sectional shape may be used to orient openings (2728). Alternatively or additionally, various radiopaque markings may be included on anchor deployment catheter (2720), so that anchor deployment catheter (2720) may be oriented using X-ray fluoroscopy. Contact between housing (2722) and the annular tissue may be enhanced by expanding an expandable member (2724) to wedge housing (2722) within the deepest portion of the subannular groove region.

Generally, anchor deployment catheter (2720) may be advanced into any suitable location for treating any valve or body tissue by any suitable advancement or device placement method. For example, in one variation a guide member may first be advanced in a retrograde fashion through an aorta, typically via access from a femoral artery. It should be noted, however, that access may be obtained through other suitable vessels as well (e.g., the jugular artery). Similarly, other suitable methods of accessing the subannular groove may also be used, including minimally invasive thoracotomy techniques (e.g., mini-thoracotomy) and/or minimally invasive sternotomy techniques (e.g., mini-sternotomy).

The guide member may be passed into the left ventricle of the heart and thus into the space formed by the mitral valve leaflets, the left ventricular wall and chordae tendineae of the left ventricle. Once in this space, the guide member may be advanced along a portion (or all) of the circumference of the mitral valve. A sheath (2740) may be advanced over the guide member within the space below the valve leaflets, and the guide member may be removed through sheath (2740). In some variations, the guide member may comprise a steerable guide catheter. Anchor deployment catheter (2720) may then be advanced through the sheath to a desired position within the space, and sheath (2740) may be removed. In other variations, a guide tunnel (not shown) may be passed through the sheath to provide additional stability and to facilitate positioning of anchor deployment catheter (2720).

Figure 27B:
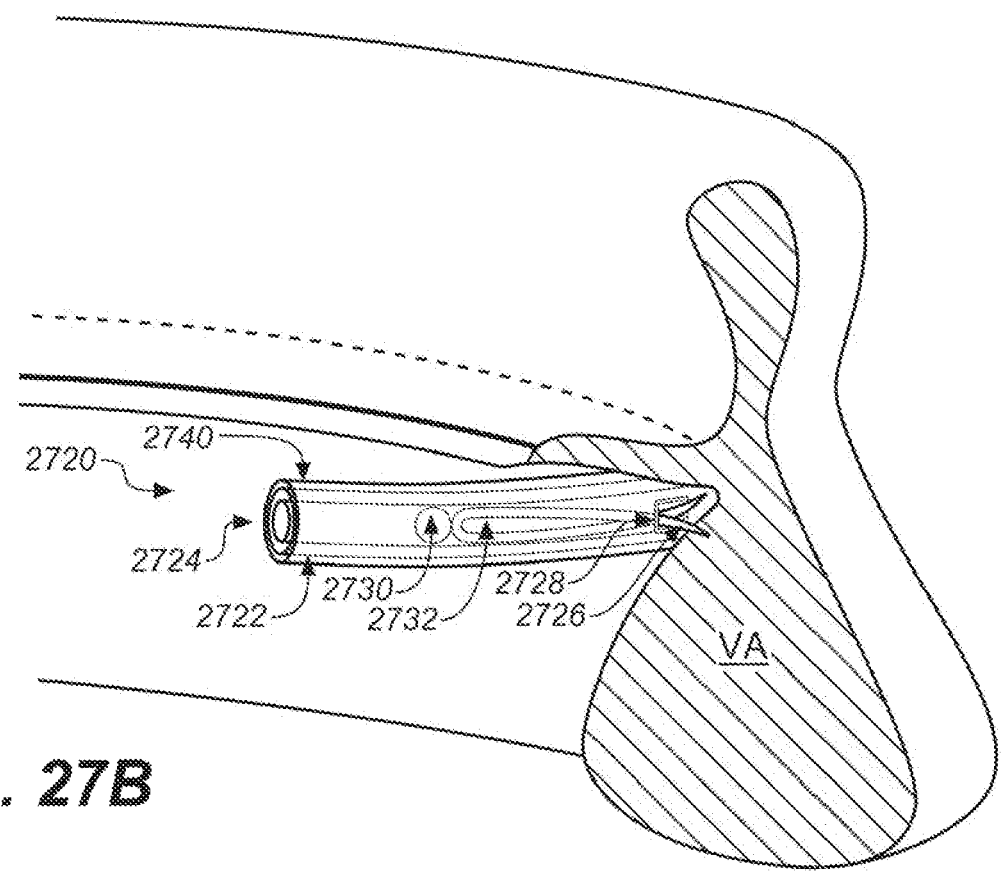
Figure 27C:
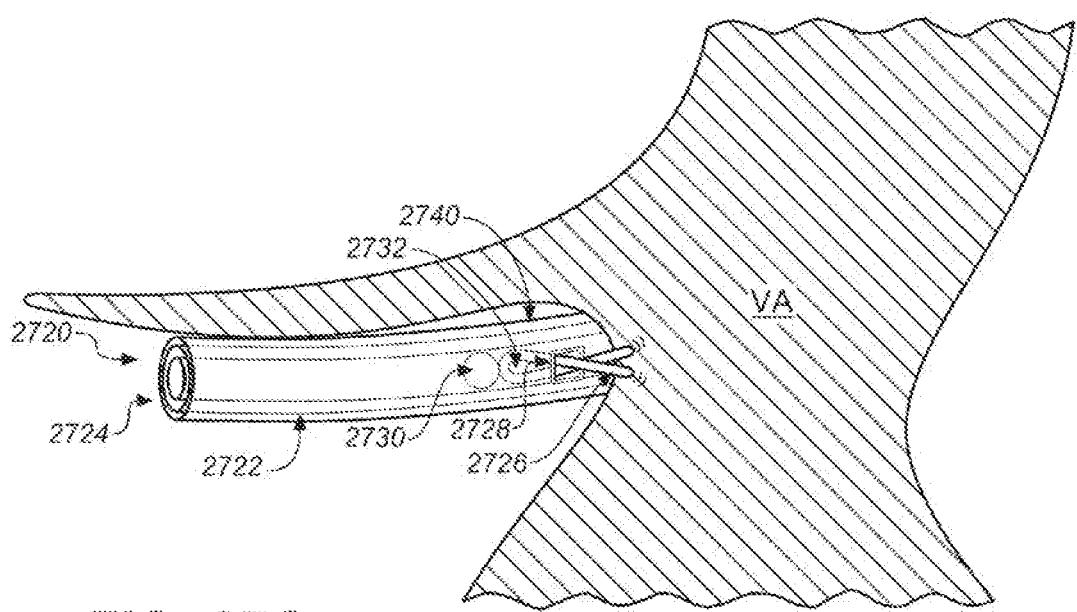
Figure 27D:
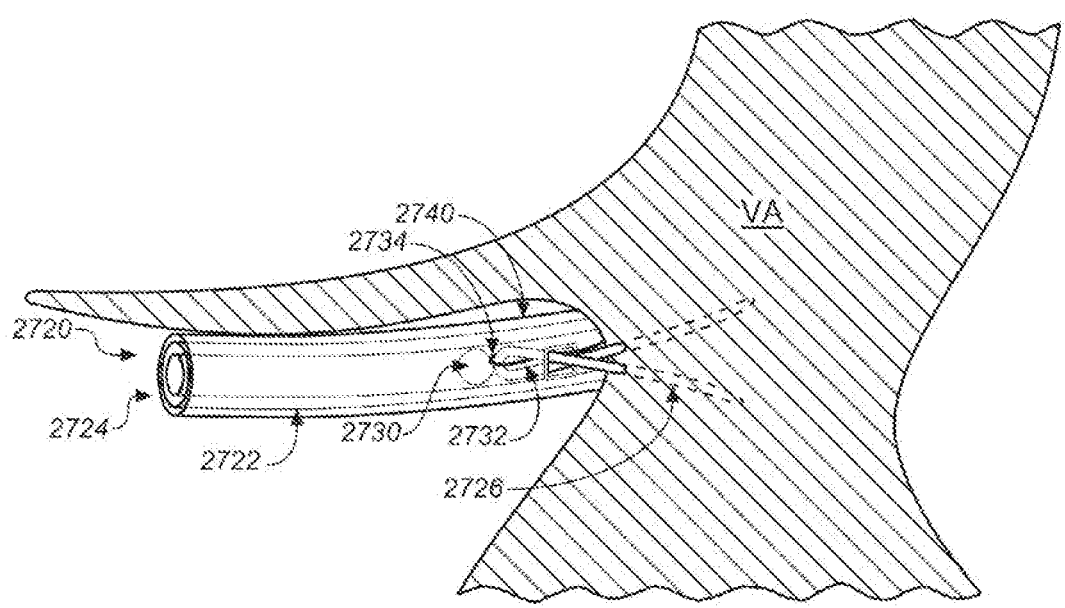

As shown in FIG. 27B, when anchor deployment catheter (2720) is positioned in a desired location for deploying anchors (2726), an anchor contacting member (2730) disposed within the anchor deployment member may be retracted (e.g., using pull cord (2732), FIG. 27A) to contact and apply force to a most-distal anchor (2726). This force may cause anchor (2726) to deploy through an opening (2728) and into valve annulus (VA) or annular tissue. FIG. 27C shows anchor (2726) further deployed out of opening (2728) and into valve annulus (VA) or annular tissue. FIG. 27D shows valve annulus (VA) transparently, so that further deployment of anchors (2726) can be seen. As shown, in one variation, anchors (2726) include two tips that move in opposite directions upon release from housing (2722) and upon contacting valve annulus (VA) or annular tissue. Between the two tips, an anchor (2726) may be looped or may have any other suitable eyelet or other device for allowing slidable coupling with a tether (2734).

Figure 27E:
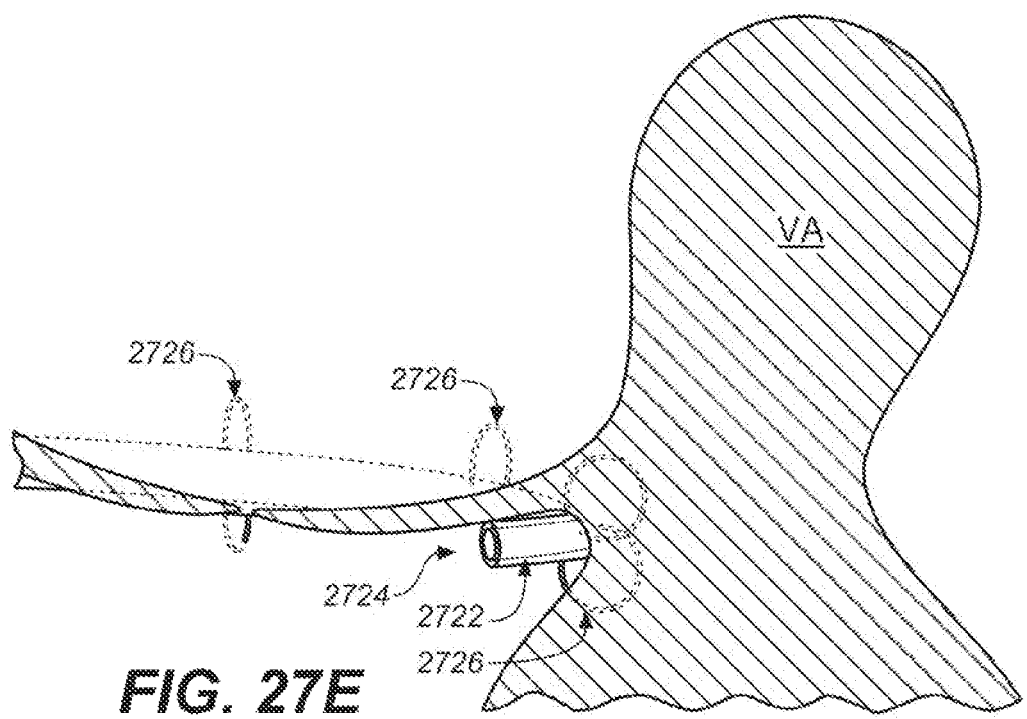
Figure 27F:
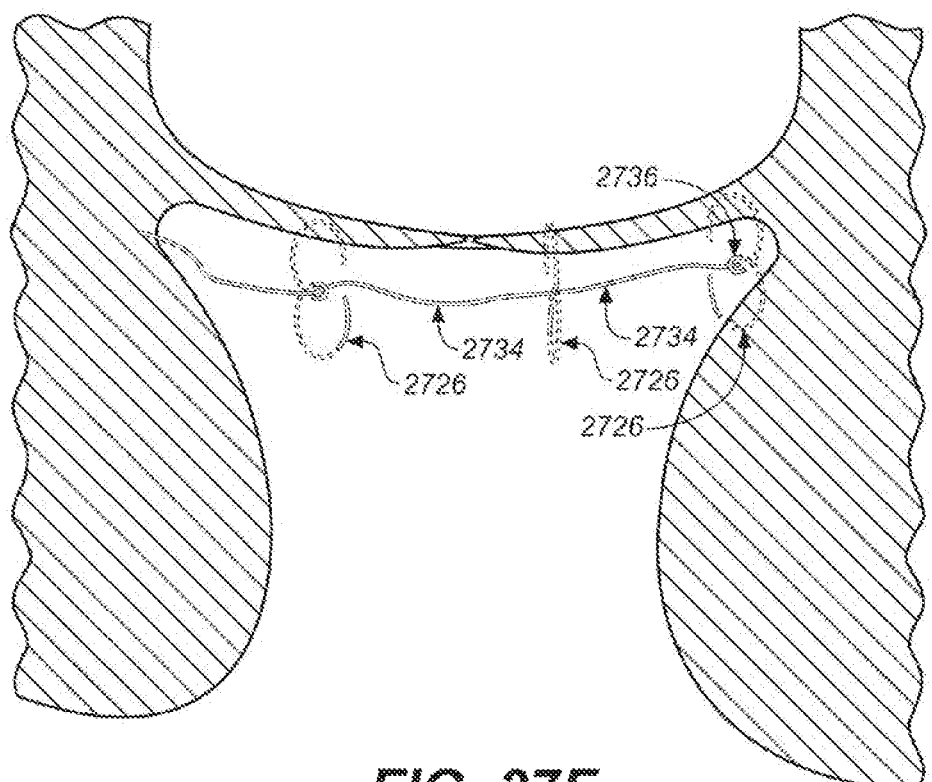

Referring now to FIG. 27E, anchors (2726) are seen in their fully deployed or nearly fully deployed shape, with each tip (or "arm") of each anchor (2726) having curved to form a circle or semi-circle. In some variations anchors (2726) may have any other suitable deployed and undeployed shapes, as described more fully above. FIG. 27F shows anchors (2726) deployed into valve annulus (VA) or annular tissue and coupled to tether (2734), with the distal-most anchor (2726) coupled to tether (2734) at an attachment point (2736). At this stage, tether (2734) may be tensioned to reduce the annular dimensions, and may thereby reduce valve regurgitation. In some variations, valve function may be monitored by means such as echocardiogram and/or fluoroscopy, and tether (2734) may be tensioned, loosened, and adjusted to achieve a desired amount of annular reduction as evident via the employed visualization technique(s). When a desired amount of annular reduction is achieved, the implant may be fixed using any of a variety of termination devices and methods.

For example, in one variation, tensioning tether (2734), attaching tether (2734) to most-proximal anchor (2726), and cutting tether (2734) may be achieved using a termination device (not shown). The termination device may comprise, for example, a catheter advanceable over tether (2734), where the catheter includes a cutting member and a knot (e.g., formed of a nickel-titanium alloy such as Nitinol) or other attachment member for attaching tether (2734) to the most proximal anchor. In some variations, the termination catheter may be advanced over tether (2734) to a location at or near the proximal end of the tethered anchors (2726). It may then be used to apply opposing force to the most proximal anchor (2726) while tether (2734) is tensioned. Attachment and cutting members may then be used to attach tether (2734) to the most proximal anchor (2726), and to cut tether (2734) just proximal to the most proximal anchor (2726). Such a termination device is only one possible way of accomplishing the cinching, attachment and cutting steps, and any other suitable devices and/or techniques may be used. Additional devices and methods for terminating (e.g., cinching and fastening) are described, for example, in U.S. patent application Ser. No. 11/232,190 (published as US 2006/0190030 A1) and Ser. No. 11/270,034 (published as US 2006/0122633 A1), both of which are incorporated herein by reference in their entirety. Additional devices and methods for terminating (e.g., cinching and fastening) are also described, for example, in U.S. patent application Ser. No. 12/480,568, filed on Jun. 8, 2009, which is incorporated herein by reference in its entirety. In some variations, the termination device may be located in the same heart chamber as the remaining portions of the implant, which may permit the implant to be wholly implanted in a single heart chamber. In other variations, however, a portion of the implant may pass transmurally through a septal wall or an outer wall of a heart chamber. In these variations, the termination member and optionally one or more anchors may be located in a different heart chamber.

In some variations, it may be advantageous to deploy a first number of anchors (2726) along a first portion of annular tissue, cinch the first anchors to achieve a desired reduction in annular dimensions in that portion of the annular tissue, move the anchor deployment catheter (2720) to another portion of the annular tissue, and deploy and cinch a second number of anchors (2726) along a second portion of the annular tissue. Such a method may be more convenient, in some cases, than extending anchor deployment catheter (2720) around all or most of the circumference of the annular tissue, and may allow a shorter, more maneuverable housing (2722) to be used.

Although a preferred access route to the subannular groove region or subvalvular space is a retrograde route through the aorta to the heart, other access routes may also be used. Access to the heart may also be transthoracic, with a delivery device being introduced into the heart via an incision or port in the heart wall. Even open heart surgical procedures may benefit from the methods and devices described herein. In some variations, hybrid access involving a combination of access methods described herein may be used. In one specific example, dual access to a valve may be achieved with a combination of venous and arterial access sites. User manipulation of both ends of a guidewire placed across a valve may improve positioning and control of the catheter and the implants. In other examples of hybrid access, both minimally invasive and surgical access may be used to implant one or more cardiac devices.

Other variations of methods may also include treatment of the tricuspid valve annulus, tissue adjacent the tricuspid valve leaflets, or any other cardiac or vascular valve. Thus, although the description herein discloses specific examples of devices and methods for mitral valve repair, the devices and methods may be used in any suitable procedure, both cardiac and non-cardiac. For example, in certain variations, the mitral valve reshaping devices and procedures may be used with the tricuspid valves also, and some variations may also be adapted for use with the pulmonary and aortic valves. Likewise, the other examples provided below are directed to the left ventricle, but the devices and methods may also be adapted by one of ordinary skill in the art for use in the right ventricle or either atrium. Additionally, in some variations the devices and methods may be used with the great vessels of the cardiovascular system, for example, to treat aortic root dilatation.

Figure 28:
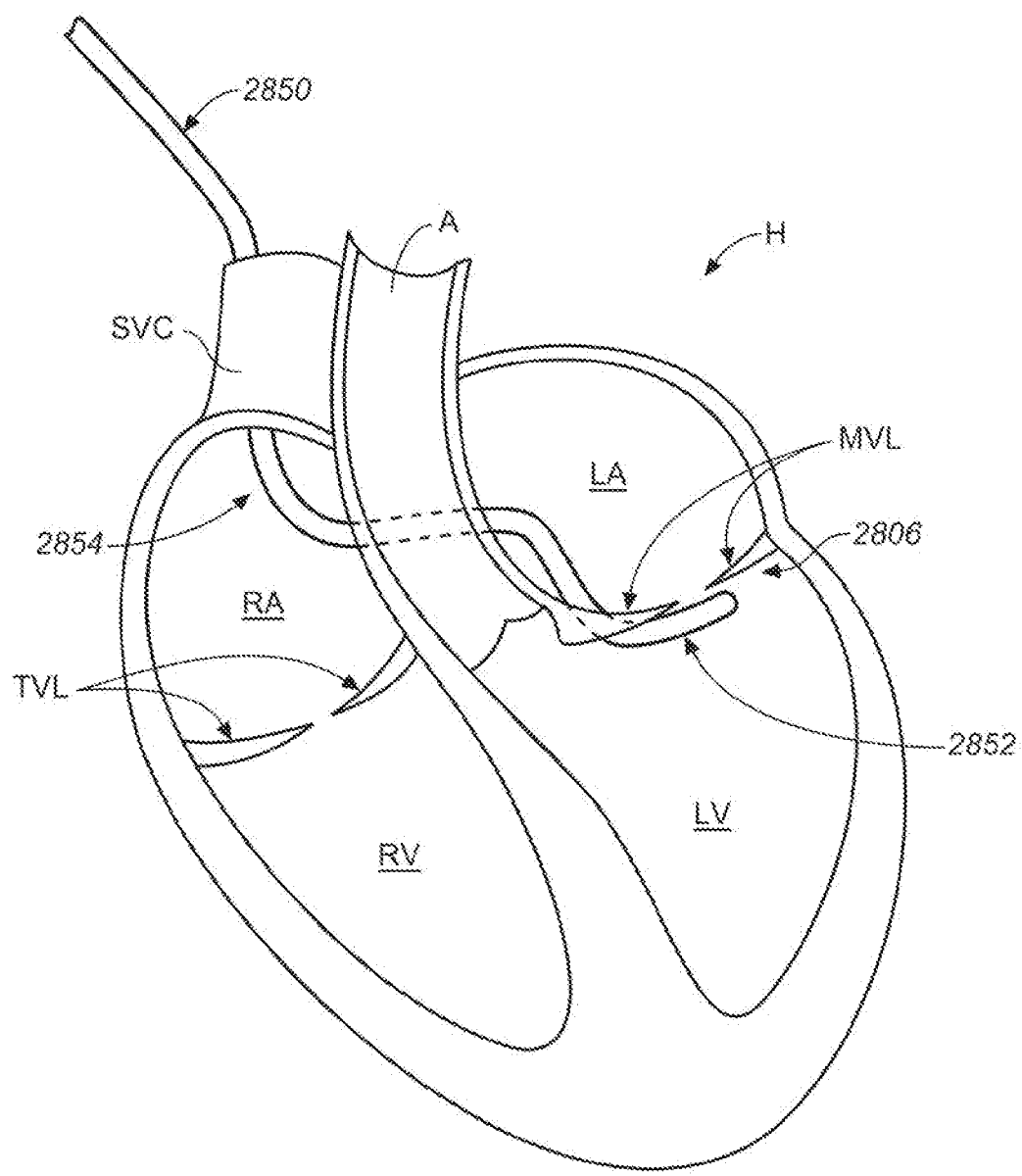
FIG. 28 shows a transseptal approach to a left ventricle of a heart.

Access to the other chambers of the heart may be performed through percutaneous or venous cut-down access, including but not limited to transjugular, subclavicular and femoral vein access routes. When venous access is established, access to the right atrium, the right ventricle, the tricuspid valve and other right-sided cardiac structures can occur. Furthermore, access to left-sided heart structures, such as the left atrium, left ventricle, mitral valve and aortic valve, may be subsequently achieved by performing a transseptal puncture procedure. Referring to FIG. 28 with a heart (H) shown in cross-section, a transseptal puncture is traditionally performed using a Mullins introducer sheath with a Brockenbrough curved needle through the interatrial septum to access the left atrium (LA), but any of a variety of other transseptal puncture devices or kits may also be used. After puncturing through left atrium (LA), supravalvular access to the mitral valve may be achieved by a guide catheter (2850) having a tubular body (2854), with the distal portion (2852) of the guide catheter entering the subvalvular space (2806). Antegrade access to the left ventricle (LV) may also occur by crossing the mitral valve. Similarly, access from the right ventricle (RV) to left ventricle (LV) may be obtained by transseptal puncture of the ventricular septum. In still other variations, a catheter device may access the coronary sinus and a valve procedure may be performed directly from the sinus.

Figure 29:
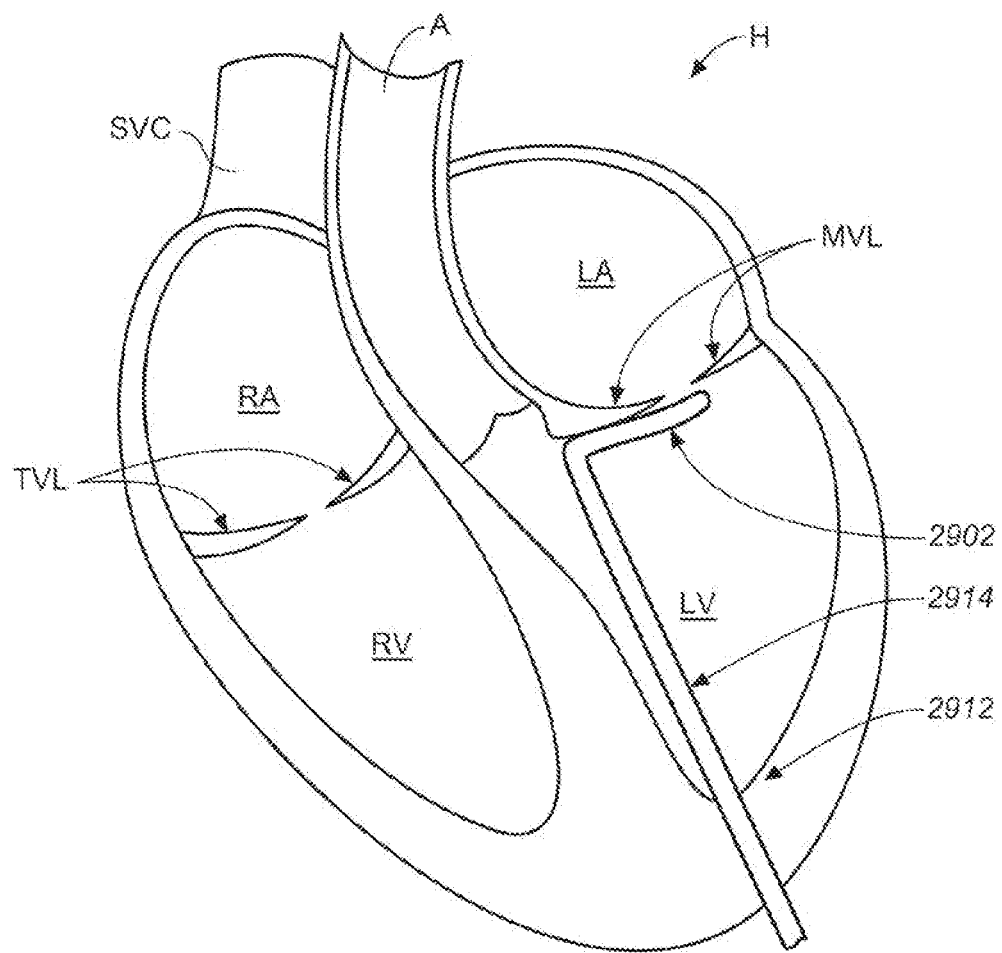
FIG. 29 shows a transapical approach to a left ventricle of a heart.

Surgical approaches that may be used include, but are not limited to, transcatheter procedures made through surgical incisions in the aorta or myocardium. In one particular variation, depicted in FIG. 29, a transapical approach with a surgical delivery device (2914) is utilized, to provide a guide catheter (2902) with a more linear route to the subvalvular space. The transapical approach also reduces potential effects of a myocardial incision on cardiac output, as the apical wall (2912) typically contributes less mechanical effect on left ventricular ejection fraction compared to other sections of the myocardial wall.

Kits are also described here. In some variations, the kits may include at least one diagnostic catheter, at least one chord manipulation device, at least one guide catheter, and/or at least one visualization catheter. In certain variations, the kit may further include at least one pigtail catheter, at least one guidewire, at least one sheath, at least one guide tunnel, and/or at least one anchor deployment catheter. In some variations, a kit may include multiple (e.g., 2, 3, 4, 5) different diagnostic catheters, such as diagnostic catheters having different shapes and/or sizes. Alternatively or additionally, a kit may include multiple (e.g., 2, 3, 4, 5) different guide catheters, such as guide catheters having different shapes and/or sizes, and/or may include multiple different visualization devices, such as visualization catheters having different shapes and/or sizes, and/or may include multiple different anchor deployment catheters, such as anchor deployment catheters having different sizes and/or shapes. In some variations, a kit may include multiple different chord manipulation devices, such as different types of chord manipulation devices and/or chord manipulation devices having different sizes. In certain variations, a kit may include one or more cinching devices and/or one or more termination devices (e.g., locking devices, cutting devices, or combination locking and cutting devices). Of course, instructions for use may also be provided with the kits.

EXAMPLES

The following examples are intended to be illustrative and not to be limiting.

Example 1

Figure 30A:
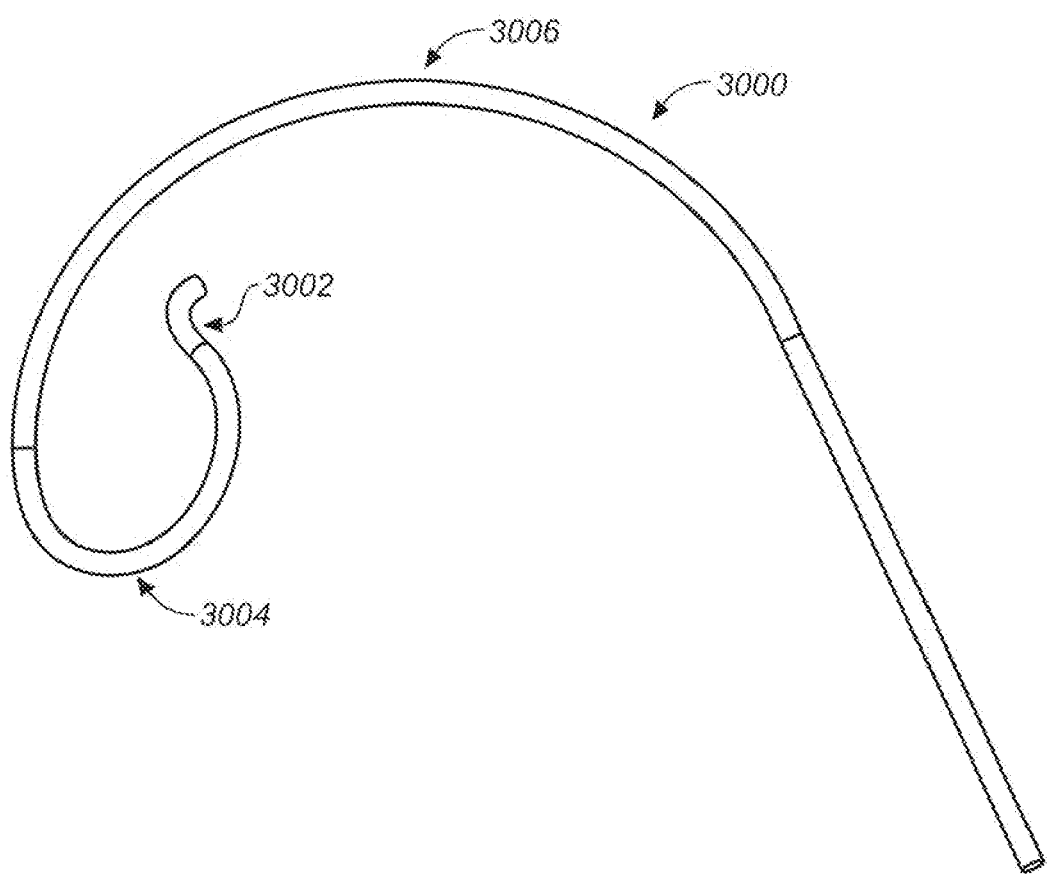
FIG. 30A is a perspective view of a variation of a diagnostic catheter.

FIG. 30A shows a computer illustration of a diagnostic catheter (3000). As shown there, diagnostic catheter (3000) comprises a valve curve region (3002), a transition curve region (3004), and an arch curve region (3006).

Referring now to FIG. 30B, diagnostic catheter (3000) also comprises a region (3008) that is proximal to arch curve region (3006). Region (3008) has a length (L3) that may be, for example, from about 25 inches to about 40 inches (e.g., from about 30 inches to about 40 inches, or from about 35 inches to about 38 inches, such as 36.828 inches). A proximal portion (3010) of region (3008) has a length (L4) that may be, for example, from about 1 inch to about 4 inches (e.g., from about 2 inches to about 3 inches, such as 2.473 inches). Additionally, and referring still to FIG. 30B, arch curve region (3006) forms an arc having an arc diameter (AD4) that may be, for example, from about 3.5 inches to about 5 inches (e.g., from about 3.5 inches to about 4.5 inches, such as 4.045 inches), and defining a central angle ($\alpha 8$) that may be, for example, from about 60° to about 180° (e.g., from about 120° to about 180°, or from about 140° to about 160°, such as 153°). If a fixture is used to form arch curve region (3006), the fixture may have a corresponding arch curve region comprising an arc with an arc diameter of, for example, 3.438 inches, and/or defining a central angle of, for example, 180°.

Additionally, and referring now to FIG. 30C, diagnostic catheter (3000) comprises a tubular member (3012) having an outer diameter (OD2) and an inner diameter (ID2). In some variations, inner diameter (ID2) may be from about 1.33 millimeters to about 3 millimeters. Alternatively or additionally, outer diameter (OD2) may be from about 1.67 millimeters to about 3.33 millimeters.

Referring now to FIG. 30D, arch curve region (3006) defines an arch plane (3016), while transition curve region (3004) defines a transition plane (3018). In certain variations, the angle ($\alpha 9$) between arch plane (3016) and transition plane (3018) may be from about 15° to about 35° (e.g., from about 20° to about 35°, such as 35°). If a fixture is used to form transition curve region (3004) and arch curve region (3006), the fixture may have corresponding transition and arch curve regions defining transition and arch planes having an angle therebetween of, for example, 35°.

As shown in FIG. 30E, transition curve region (3004) forms an arc having an arc diameter (AD5) that may be, for example, from about 1 inch to about 3 inches (e.g., from about 1 inch to about 2 inches, such as 1.176 inches), and defining a central angle ($\alpha 10$) that may be, for example, from about 90° to about 270° (e.g., from about 180° to about 270°, from about 180° to about 250°, or from about 210° to about 250°, such as 229.5°). If a fixture is used to form transition curve region (3004), the fixture may have a corresponding transition curve region comprising an arc with an arc diameter of, for example, 1 inch, and/or defining a central angle of, for example, 270°.

Additionally, and referring now to FIG. 30F, valve curve region (3002) defines a valve plane (3020). In certain variations, the angle ($\alpha 11$) between transition plane (3018) and valve plane (3020) may be from about 100° to about 125° (e.g., from about 105° to about 120°, such as 110°). If a fixture is used to form valve curve region (3002) and transition curve region (3004), the fixture may have corresponding valve and transition curve regions defining valve and transition planes having an angle therebetween of, for example, 110°.

Finally, and referring now to FIG. 30G, valve curve region (3002) forms an arc having an arc diameter (AD6) that may be, for example, from about 0.75 inch to about 1.5 inches (e.g., from about 0.75 inch to about 1 inch, such as 0.88 inch), and defining a central angle ($\alpha 12$) that may be, for example, from about 60° to about 80° (e.g., from about 70° to about 80°, such as 76.5°). If a fixture is used to form valve curve region (3002), the fixture may have a corresponding valve curve region comprising an arc with an arc diameter of, for example, 0.75 inch, and/or defining a central angle of, for example, 90°.

Example 2

Figure 31A:
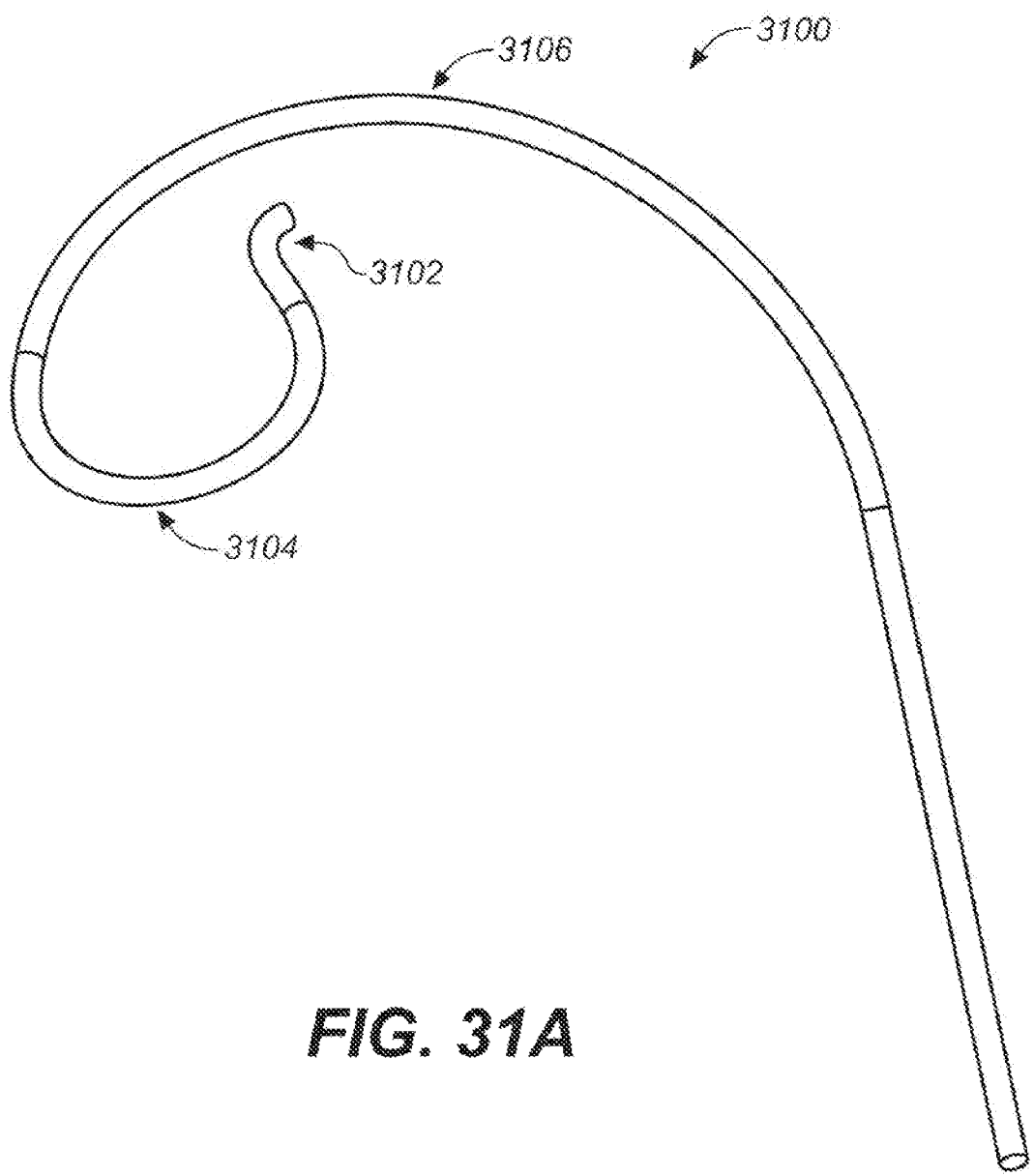
FIG. 31A is a perspective view of a variation of a diagnostic catheter.

FIG. 31A shows a computer illustration of a diagnostic catheter (3100). As shown there, diagnostic catheter (3100) comprises a valve curve region (3102), a transition curve region (3104), and an arch curve region (3106).

Referring now to FIG. 31B, diagnostic catheter (3100) also comprises a region (3108) that is proximal to arch curve region (3106). Region (3108) has a length (L5) that may be, for example, from about 25 inches to about 40 inches (e.g., from about 25 inches to about 35 inches, such as 32.752 inches). A proximal portion (3110) of region (3108) has a length (L6) that may be, for example, from about 1 inch to about 4 inches (e.g., from about 2 inches to about 3 inches, such as 2.473 inches). Additionally, and referring still to FIG. 31B, arch curve region (3106) forms an arc having an arc diameter (AD7) that may be, for example, from about 3.5 inches to about 5 inches (e.g., from about 3.5 inches to about 4.5 inches, such as 4.045 inches), and defining a central angle ($\alpha 13$) that may be, for example, from about 60° to about 180° (e.g., from about 120° to about 180°, or from about 140° to about 160°, such as 153°). If a fixture is used to form arch curve region (3106), the fixture may have a corresponding arch curve region comprising an arc with an arc diameter of, for example, 3.438 inches, and/or defining a central angle of, for example, 180°.

Additionally, and referring now to FIG. 31C, diagnostic catheter (3100) comprises a tubular member (3112) having an outer diameter (OD3) and an inner diameter (ID3). In some variations, inner diameter (ID3) may be from about 1.33 millimeters to about 3 millimeters. Alternatively or additionally, outer diameter (OD3) may be from about 1.67 millimeters to about 3.33 millimeters.

Referring now to FIG. 31D, arch curve region (3106) defines an arch plane (3116), while transition curve region (3104) defines a transition plane (3118). In certain variations, the angle ($\alpha 14$) between arch plane (3116) and transition plane (3118) may be from about 15° to about 35° (e.g., from about 20° to about 35°, such as 35°). If a fixture is used to form transition curve region (3104) and arch curve region (3106), the fixture may have corresponding transition and arch curve regions defining transition and arch planes having an angle therebetween of, for example, 35°.

As shown in FIG. 31E, transition curve region (3104) forms an arc having an arc diameter (AD8) that may be, for example, from about 1 inch to about 3 inches (e.g., from about 1 inch to about 2 inches, such as 1.176 inches), and defining a central angle ($\alpha 15$) that may be, for example, from about 90° to about 270° (e.g., from about 180° to about 270°, from about 180° to about 250°, or from about 210° to about 250°, such as 229.5°). If a fixture is used to form transition curve region (3104), the fixture may have a corresponding transition curve region comprising an arc with an arc diameter of, for example, 1 inch, and/or defining a central angle of, for example, 270°.

Additionally, and referring now to FIG. 31F, valve curve region (3102) defines a valve plane (3120). In certain variations, the angle ($\alpha 16$) between transition plane (3118) and valve plane (3120) may be from about 115° to about 150° (e.g., from about 125° to about 145°, such as 135°). If a fixture is used to form valve curve region (3102) and transition curve region (3104), the fixture may have corresponding valve and transition curve regions defining valve and transition planes having an angle therebetween of, for example, 135°.

Finally, and referring now to FIG. 31G, valve curve region (3102) forms an arc having an arc diameter (AD9) that may be, for example, from about 0.75 inch to about 1.5 inches (e.g., from about 0.75 inch to about 1 inch, such as 0.88 inch), and defining a central angle ($\alpha 17$) that may be, for example, from about 60° to about 80° (e.g., from about 70° to about 80°, such as 76.5°). If a fixture is used to form valve curve region (3102), the fixture may have a corresponding valve curve region comprising an arc with an arc diameter of, for example, 0.75 inch, and/or defining a central angle of, for example, 90°.

Example 3

Figure 32A:
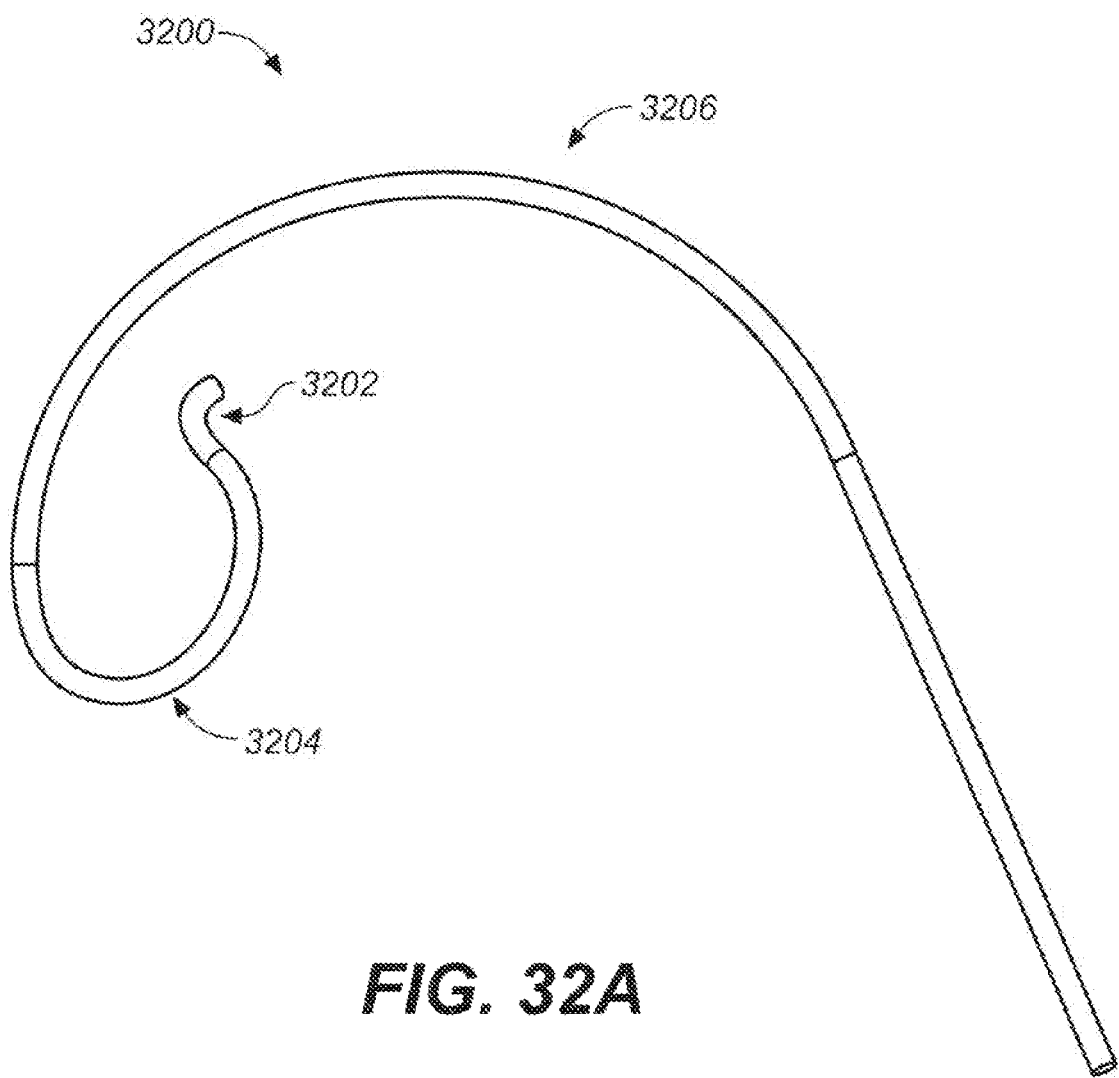
FIG. 32A is a perspective view of a variation of a diagnostic catheter.

FIG. 32A shows a computer illustration of a diagnostic catheter (3200). As shown there, diagnostic catheter (3200) comprises a valve curve region (3202), a transition curve region (3204), and an arch curve region (3206).

Referring now to FIG. 32B, diagnostic catheter (3200) also comprises a region (3208) that is proximal to arch curve region (3206). Region (3208) has a length (L7) that may be, for example, from about 25 inches to about 40 inches (e.g., from about 25 inches to about 35 inches, such as 32.752 inches). A proximal portion (3210) of region (3208) has a length (L8) that may be, for example, from about 1 inch to about 4 inches (e.g., from about 2 inches to about 3 inches, such as 2.473 inches). Additionally, and referring still to FIG. 32B, arch curve region (3206) forms an arc having an arc diameter (AD10) that may be, for example, from about 3.5 inches to about 5 inches (e.g., from about 3.5 inches to about 4.5 inches, such as 4.045 inches), and defining a central angle ($\alpha 18$) that may be, for example, from about 60° to about 180° (e.g., from about 120° to about 180°, or from about 140° to about 160°, such as 153°). If a fixture is used to form arch curve region (3206), the fixture may have a corresponding arch curve region comprising an arc with an arc diameter of, for example, 3.438 inches, and/or defining a central angle of, for example, 180°.

Additionally, and referring now to FIG. 32C, diagnostic catheter (3200) comprises a tubular member (3212) having an outer diameter (OD4) and an inner diameter (ID4). In some variations, inner diameter (ID4) may be from about 1.33 millimeters to about 3 millimeters. Alternatively or additionally, outer diameter (OD4) may be from about 1.67 millimeters to about 3.33 millimeters.

Referring now to FIG. 32D, arch curve region (3206) defines an arch plane (3216), while transition curve region (3204) defines a transition plane (3218). In certain variations, the angle ($\alpha 19$) between arch plane (3216) and transition plane (3218) may be from about 20° to about 45° (e.g., from about 35° to about 45°, such as 45°). If a fixture is used to form transition curve region (3204) and arch curve region (3206), the fixture may have corresponding transition and arch curve regions defining transition and arch planes having an angle therebetween of, for example, 45°.

Figure 32E:
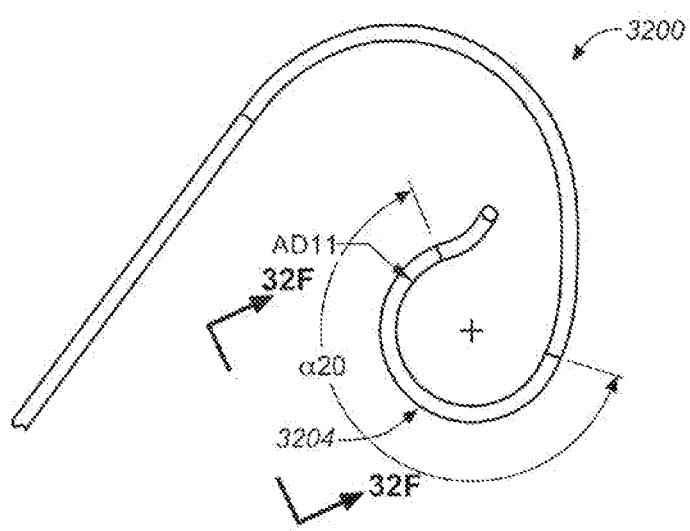
FIG. 32E is a view of the diagnostic catheter as shown in FIG. 32D, taken along line 32E-32E.

As shown in FIG. 32E, transition curve region (3204) forms an arc having an arc diameter (AD11) that may be, for example, from about 1 inch to about 3 inches (e.g., from about 1 inch to about 2 inches, such as 1.176 inches), and defining a central angle ($\alpha 20$) that may be, for example, from about 90° to about 270° (e.g., from about 180° to about 270°, from about 180° to about 250°, or from about 210° to about 250°, such as 229.5°). If a fixture is used to form transition curve region (3204), the fixture may have a corresponding transition curve region comprising an arc with an arc diameter of, for example, 1 inch, and/or defining a central angle of, for example, 270°.

Figure 32F:
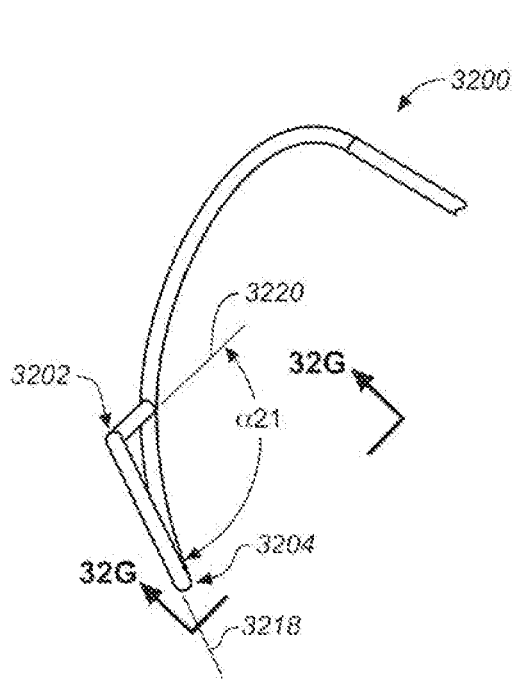
FIG. 32F is a view of the diagnostic catheter as shown in FIG. 32E, taken along line 32F-32F.

Additionally, and referring now to FIG. 32F, valve curve region (3202) defines a valve plane (3220). In certain variations, the angle ($\alpha 21$) between transition plane (3218) and valve plane (3220) may be from about 100° to about 125° (e.g., from about 105° to about 120°, such as 110°). If a fixture is used to form valve curve region (3202) and transition curve region (3204), the fixture may have corresponding valve and transition curve regions defining valve and transition planes having an angle therebetween of, for example, 110°.

Figure 32G:
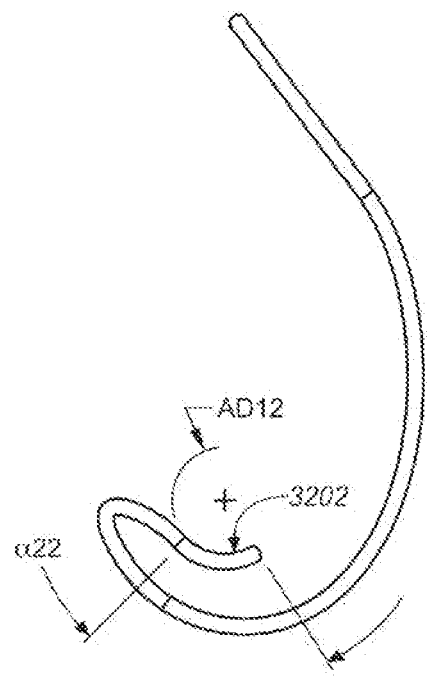
FIG. 32G is a view of the diagnostic catheter as shown in FIG. 32F, taken along line 32G-32G.

Finally, and referring now to FIG. 32G, valve curve region (3202) forms an arc having an arc diameter (AD12) that may be, for example, from about 0.75 inch to about 1.5 inches (e.g., from about 0.75 inch to about 1 inch, such as 0.882 inch), and defining a central angle ($\alpha 22$) that may be, for example, from about 60° to about 80° (e.g., from about 70° to about 80°, such as 76.5°). If a fixture is used to form valve curve region (3202), the fixture may have a corresponding valve curve region comprising an arc with an arc diameter of, for example, 0.75 inch, and/or defining a central angle of, for example, 90°.

Example 4

Figure 33A:
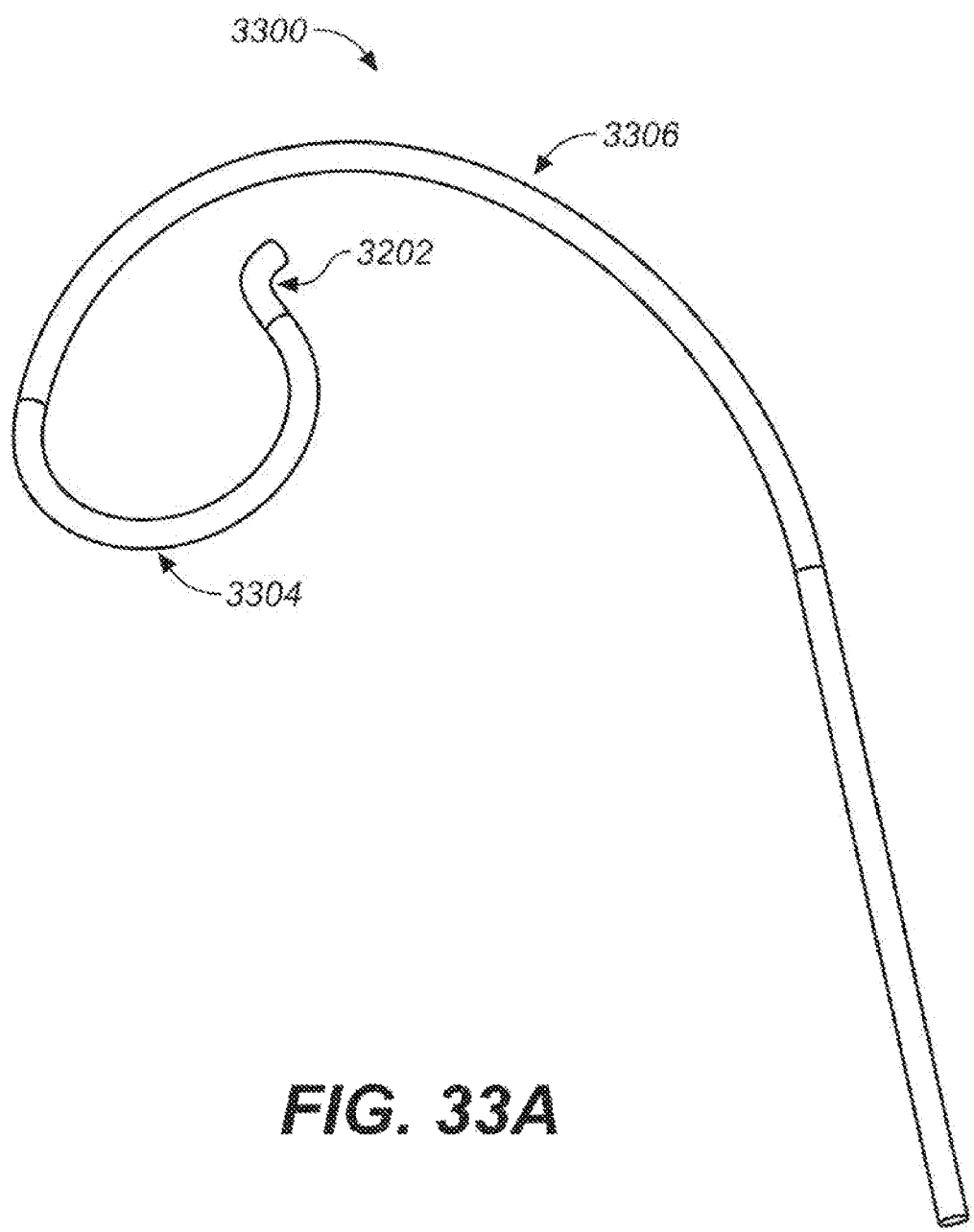
FIG. 33A is a perspective view of a variation of a diagnostic catheter.

FIG. 33A shows a computer illustration of a diagnostic catheter (3300). As shown there, diagnostic catheter (3300) comprises a valve curve region (3302), a transition curve region (3304), and an arch curve region (3306).

Referring now to FIG. 33B, diagnostic catheter (3300) also comprises a region (3308) that is proximal to arch curve region (3306). Region (3308) has a length (L9) that may be, for example, from about 25 inches to about 40 inches (e.g., from about 25 inches to about 35 inches, such as 32.752 inches). A proximal portion (3310) of region (3308) has a length (L10) that may be, for example, from about 1 inch to about 4 inches (e.g., from about 2 inches to about 3 inches, such as 2.473 inches). Additionally, and referring still to FIG. 33B, arch curve region (3306) forms an arc having an arc diameter (AD13) that may be, for example, from about 3.5 inches to about 5 inches (e.g., from about 3.5 inches to about 4.5 inches, such as 4.045 inches), and defining a central angle ($\alpha 23$) that may be, for example, from about 60° to about 180° (e.g., from about 120° to about 180°, or from about 140° to about 160°, such as 153°). If a fixture is used to form arch curve region (3306), the fixture may have a corresponding arch curve region comprising an arc with an arc diameter of, for example, 3.438 inches, and/or defining a central angle of, for example, 180°.

Additionally, and referring now to FIG. 33C, diagnostic catheter (3300) comprises a tubular member (3312) having an outer diameter (OD5) and an inner diameter (ID5). In some variations, inner diameter (ID5) may be from about 1.33 millimeters to about 3 millimeters. Alternatively or additionally, outer diameter (OD5) may be from about 1.67 millimeters to about 3.33 millimeters.

Referring now to FIG. 33D, arch curve region (3306) defines an arch plane (3316), while transition curve region (3304) defines a transition plane (3318). In certain variations, the angle ($\alpha 24$) between arch plane (3316) and transition plane (3318) may be from about 20° to about 45° (e.g., from about 35° to about 45°, such as 45°). If a fixture is used to form transition curve region (3304) and arch curve region (3306), the fixture may have corresponding transition and arch curve regions defining transition and arch planes having an angle therebetween of, for example, 45°.

As shown in FIG. 33E, transition curve region (3304) forms an arc having an arc diameter (AD14) that may be, for example, from about 1 inch to about 3 inches (e.g., from about 1 inch to about 2 inches, such as 1.176 inches), and defining a central angle ($\alpha 25$) that may be, for example, from about 90° to about 270° (e.g., from about 180° to about 270°, from about 180° to about 250°, or from about 210° to about 250°, such as 229.5°). If a fixture is used to form transition curve region (3304), the fixture may have a corresponding transition curve region comprising an arc with an arc diameter of, for example, 1 inch, and/or defining a central angle of, for example, 270°.

Additionally, and referring now to FIG. 33F, valve curve region (3302) defines a valve plane (3320). In certain variations, the angle ($\alpha 26$) between transition plane (3318) and valve plane (3320) may be from about 115° to about 150° (e.g., from about 125° to about 145°, such as 135°). If a fixture is used to form valve curve region (3302) and transition curve region (3304), the fixture may have corresponding valve and transition curve regions defining valve and transition planes having an angle therebetween of, for example, 135°.

Finally, and referring now to FIG. 33G, valve curve region (3302) forms an arc having an arc diameter (AD15) that may be, for example, from about 0.75 inch to about 1.5 inches (e.g., from about 0.75 inch to about 1 inch, such as 0.882 inch), and defining a central angle ($\alpha 27$) that may be, for example, from about 60° to about 80° (e.g., from about 70° to about 80°, such as 76.5°). If a fixture is used to form valve curve region (3302), the fixture may have a corresponding valve curve region comprising an arc with an arc diameter of, for example, 0.75 inch, and/or defining a central angle of, for example, 90°.

Example 5

Figure 34A:
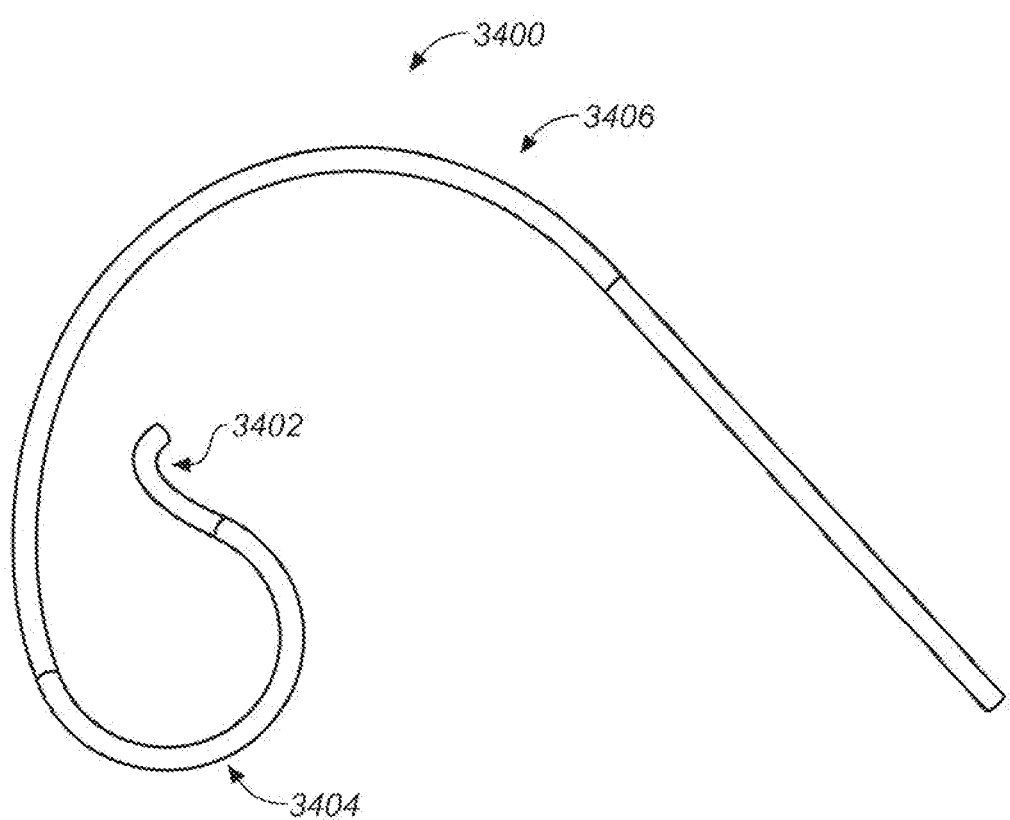
FIG. 34A is a perspective view of a variation of a diagnostic catheter.

FIG. 34A shows a computer illustration of a diagnostic catheter (3400). As shown there, diagnostic catheter (3400) comprises a valve curve region (3402), a transition curve region (3404), and an arch curve region (3406).

Referring now to FIG. 34B, diagnostic catheter (3400) also comprises a region (3408) that is proximal to arch curve region (3406). Region (3408) has a length (L11) that may be, for example, from about 25 inches to about 40 inches (e.g., from about 25 inches to about 35 inches, such as 32.752 inches). A proximal portion (3410) of region (3408) has a length (L12) that may be, for example, from about 1 inch to about 4 inches (e.g., from about 2 inches to about 3 inches, such as 2.473 inches). Additionally, and referring still to FIG. 34B, arch curve region (3406) forms an arc having an arc diameter (AD16) that may be, for example, from about 3.5 inches to about 5 inches (e.g., from about 3.5 inches to about 4.5 inches, such as 4.045 inches), and defining a central angle ($\alpha 28$) that may be, for example, from about 60° to about 180° (e.g., from about 120° to about 180°, or from about 140° to about 160°, such as 153°). If a fixture is used to form arch curve region (3406), the fixture may have a corresponding arch curve region comprising an arc with an arc diameter of, for example, 3.438 inches, and/or defining a central angle of, for example, 180°.

Additionally, and referring now to FIG. 34C, diagnostic catheter (3400) comprises a tubular member (3412) having an outer diameter (OD6) and an inner diameter (ID6). In some variations, inner diameter (ID6) may be from about 1.33 millimeters to about 3 millimeters. Alternatively or additionally, outer diameter (OD6) may be from about 1.67 millimeters to about 3.33 millimeters.

Referring now to FIG. 34D, arch curve region (3406) defines an arch plane (3416), while transition curve region (3404) defines a transition plane (3418). In certain variations, the angle ($\alpha 29$) between arch plane (3416) and transition plane (3418) may be from about 15° to about 35° (e.g., from about 20° to about 35°, such as 35°). If a fixture is used to form transition curve region (3404) and arch curve region (3406), the fixture may have corresponding transition and arch curve regions defining transition and arch planes having an angle therebetween of, for example, 35°.

As shown in FIG. 34E, transition curve region (3404) forms an arc having an arc diameter (AD17) that may be, for example, from about 1 inch to about 3 inches (e.g., from about 1 inch to about 2 inches, such as 1.176 inches), and defining a central angle ($\alpha 30$) that may be, for example, from about 90° to about 270° (e.g., from about 180° to about 270°, from about 180° to about 250°, or from about 210° to about 250°, such as 229.5°). If a fixture is used to form transition curve region (3404), the fixture may have a corresponding transition curve region comprising an arc with an arc diameter of, for example, 1 inch, and/or defining a central angle of, for example, 270°.

Additionally, and referring now to FIG. 34F, valve curve region (3402) defines a valve plane (3420). In certain variations, the angle ($\alpha 31$) between transition plane (3418) and valve plane (3420) may be from about 100° to about 125° (e.g., from about 105° to about 120°, such as 110°). If a fixture is used to form valve curve region (3402) and transition curve region (3404), the fixture may have corresponding valve and transition curve regions defining valve and transition planes having an angle therebetween of, for example, 110°.

Finally, and referring now to FIG. 34G, valve curve region (3402) forms an arc having an arc diameter (AD18) that may be, for example, from about 0.75 inch to about 1.5 inches (e.g., from about 0.75 inch to about 1 inch, such as 0.882 inch), and defining a central angle ($\alpha 32$) that may be, for example, from about 75° to about 120° (e.g., from about 100° to about 120°, such as 114.75°). If a fixture is used to form valve curve region (3402), the fixture may have a corresponding valve curve region comprising an arc with an arc diameter of, for example, 0.75 inch, and/or defining a central angle of, for example, 135°.

Example 6

Figure 35A:
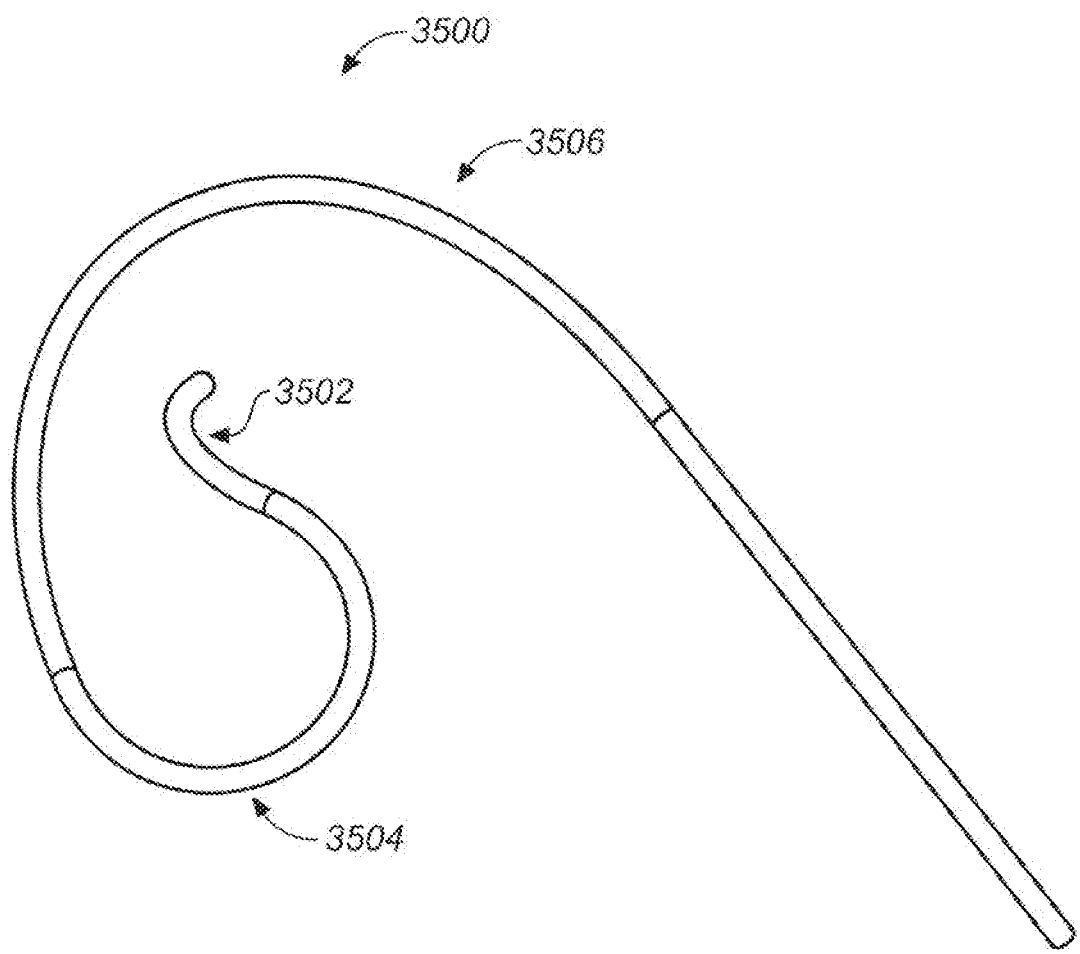
FIG. 35A is a perspective view of a variation of a diagnostic catheter.

FIG. 35A shows a computer illustration of a diagnostic catheter (3500). As shown there, diagnostic catheter (3500) comprises a valve curve region (3502), a transition curve region (3504), and an arch curve region (3506).

Referring now to FIG. 35B, diagnostic catheter (3500) also comprises a region (3508) that is proximal to arch curve region (3506). Region (3508) has a length (L13) that may be, for example, from about 25 inches to about 40 inches (e.g., from about 25 inches to about 35 inches, such as 32.752 inches). A proximal portion (3510) of region (3508) has a length (L14) that may be, for example, from about 1 inch to about 4 inches (e.g., from about 2 inches to about 3 inches, such as 2.473 inches). Additionally, and referring still to FIG. 35B, arch curve region (3506) forms an arc having an arc diameter (AD19) that may be, for example, from about 3.5 inches to about 5 inches (e.g., from about 3.5 inches to about 4.5 inches, such as 4.045 inches), and defining a central angle ($\alpha 33$) that may be, for example, from about 60° to about 180° (e.g., from about 120° to about 180°, or from about 140° to about 160°, such as 153°). If a fixture is used to form arch curve region (3506), the fixture may have a corresponding arch curve region comprising an arc with an arc diameter of, for example, 3.438 inches, and/or defining a central angle of, for example, 180°.

Additionally, and referring now to FIG. 35C, diagnostic catheter (3500) comprises a tubular member (3512) having an outer diameter (OD7) and an inner diameter (ID7). In some variations, inner diameter (ID7) may be from about 1.33 millimeters to about 3 millimeters. Alternatively or additionally, outer diameter (OD7) may be from about 1.67 millimeters to about 3.33 millimeters.

Referring now to FIG. 35D, arch curve region (3506) defines an arch plane (3516), while transition curve region (3504) defines a transition plane (3518). In certain variations, the angle ($\alpha 34$) between arch plane (3516) and transition plane (3518) may be from about 15° to about 35° (e.g., from about 20° to about 35°, such as 35°). If a fixture is used to form transition curve region (3504) and arch curve region (3506), the fixture may have corresponding transition and arch curve regions defining transition and arch planes having an angle therebetween of, for example, 35°.

Figure 35E:
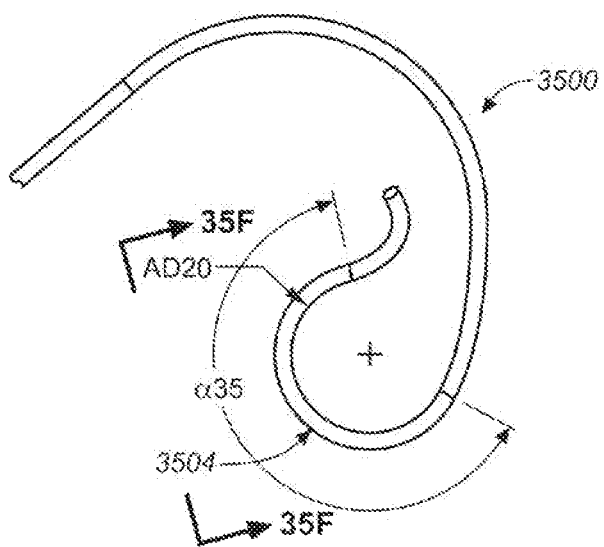
FIG. 35E is a view of the diagnostic catheter as shown in FIG. 35D, taken along line 35E-35E.

As shown in FIG. 35E, transition curve region (3504) forms an arc having an arc diameter (AD20) that may be, for example, from about 1 inch to about 3 inches (e.g., from about 1 inch to about 2 inches, such as 1.176 inches), and defining a central angle ($\alpha$35) that may be, for example, from about 90° to about 270° (e.g., from about 180° to about 270°, from about 180° to about 250°, or from about 210° to about 250°, such as 229.5°). If a fixture is used to form transition curve region (3504), the fixture may have a corresponding transition curve region comprising an arc with an arc diameter of, for example, 1 inch, and/or defining a central angle of, for example, 270°.

Figures 35F, 35G:
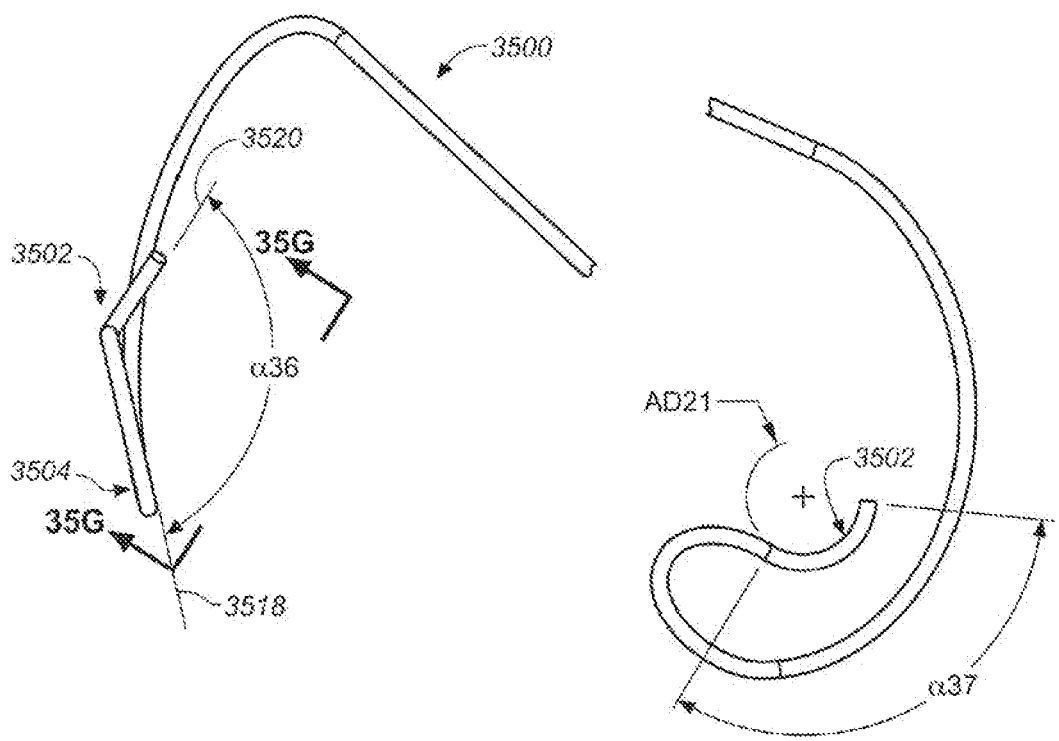
FIG. 35F is a view of the diagnostic catheter as shown in FIG. 35E, taken along line 35F-35F.
FIG. 35G is a view of the diagnostic catheter as shown in FIG. 35F, taken along line 35G-35G.

Additionally, and referring now to FIG. 35F, valve curve region (3502) defines a valve plane (3520). In certain variations, the angle ($\alpha$36) between transition plane (3518) and valve plane (3520) may be from about 115° to about 150° (e.g., from about 125° to about 145°, such as 135°). If a fixture is used to form valve curve region (3502) and transition curve region (3504), the fixture may have corresponding valve and transition curve regions defining valve and transition planes having an angle therebetween of, for example, 135°.

Finally, and referring now to FIG. 35G, valve curve region (3502) forms an arc having an arc diameter (AD21) that may be, for example, from about 0.75 inch to about 1.5 inches (e.g., from about 0.75 inch to about 1 inch, such as 0.882 inch), and defining a central angle ($\alpha$37) that may be, for example, from about 75° to about 120° (e.g., from about 100° to about 120°, such as 114.75°). If a fixture is used to form valve curve region (3502), the fixture may have a corresponding valve curve region comprising an arc with an arc diameter of, for example, 0.75 inch, and/or defining a central angle of, for example, 135°.

Example 7

Figure 36A:
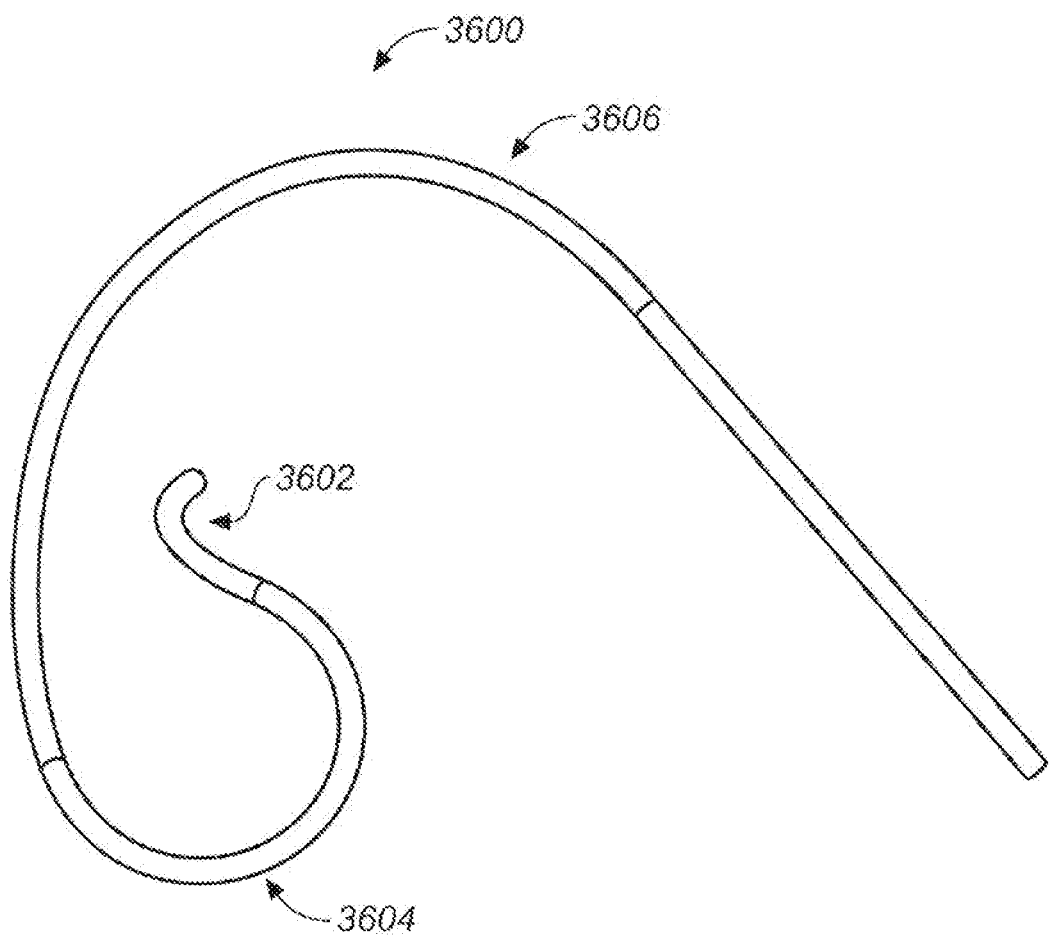
FIG. 36A is a perspective view of a variation of a diagnostic catheter.

FIG. 36A shows a computer illustration of a diagnostic catheter (3600). As shown there, diagnostic catheter (3600) comprises a valve curve region (3602), a transition curve region (3604), and an arch curve region (3606).

Referring now to FIG. 36B, diagnostic catheter (3600) also comprises a region (3608) that is proximal to arch curve region (3606). Region (3608) has a length (L15) that may be, for example, from about 25 inches to about 40 inches (e.g., from about 25 inches to about 35 inches, such as 32.752 inches). A proximal portion (3610) of region (3608) has a length (L16) that may be, for example, from about 1 inch to about 4 inches (e.g., from about 2 inches to about 3 inches, such as 2.473 inches). Additionally, and referring still to FIG. 36B, arch curve region (3606) forms an arc having an arc diameter (AD22) that may be, for example, from about 3.5 inches to about 5 inches (e.g., from about 3.5 inches to about 4.5 inches, such as 4.045 inches), and defining a central angle ($\alpha$38) that may be, for example, from about 60° to about 180° (e.g., from about 120° to about 180°, or from about 140° to about 160°, such as 153°). If a fixture is used to form arch curve region (3606), the fixture may have a corresponding arch curve region comprising an arc with an arc diameter of, for example, 3.438 inches, and/or defining a central angle of, for example, 180°.

Additionally, and referring now to FIG. 36C, diagnostic catheter (3600) comprises a tubular member (3612) having an outer diameter (OD8) and an inner diameter (ID8). In some variations, inner diameter (ID8) may be from about 1.33 millimeters to about 3 millimeters. Alternatively or additionally, outer diameter (OD8) may be from about 1.67 millimeters to about 3.33 millimeters.

Referring now to FIG. 36D, arch curve region (3606) defines an arch plane (3616), while transition curve region (3604) defines a transition plane (3618). In certain variations, the angle ($\alpha$39) between arch plane (3616) and transition plane (3618) may be from about 20° to about 45° (e.g., from about 35° to about 45°, such as 45°). If a fixture is used to form transition curve region (3604) and arch curve region (3606), the fixture may have corresponding transition and arch curve regions defining transition and arch planes having an angle therebetween of, for example, 45°.

Figure 36E:
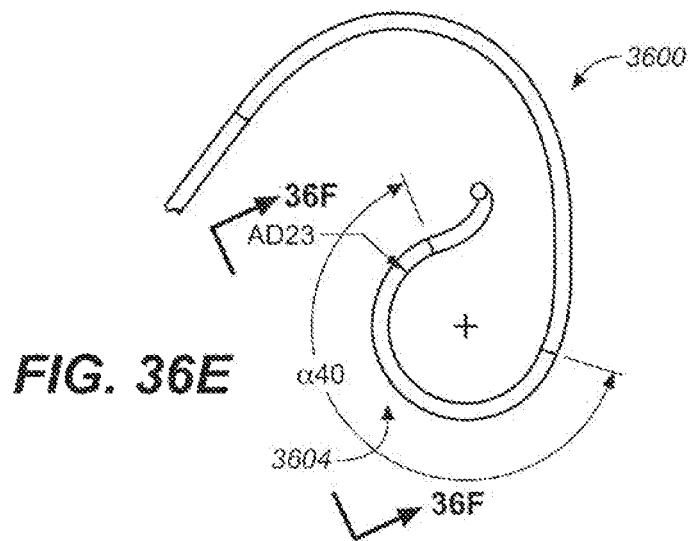
FIG. 36E is a view of the diagnostic catheter as shown in FIG. 36D, taken along line 36E-36E.

As shown in FIG. 36E, transition curve region (3604) forms an arc having an arc diameter (AD23) that may be, for example, from about 1 inch to about 3 inches (e.g., from about 1 inch to about 2 inches, such as 1.176 inches), and defining a central angle ($\alpha$40) that may be, for example, from about 90° to about 270° (e.g., from about 180° to about 270°, from about 180° to about 250°, or from about 210° to about 250°, such as 229.5°). If a fixture is used to form transition curve region (3604), the fixture may have a corresponding transition curve region comprising an arc with an arc diameter of, for example, 1 inch, and/or defining a central angle of, for example, 270°.

Figure 36F:
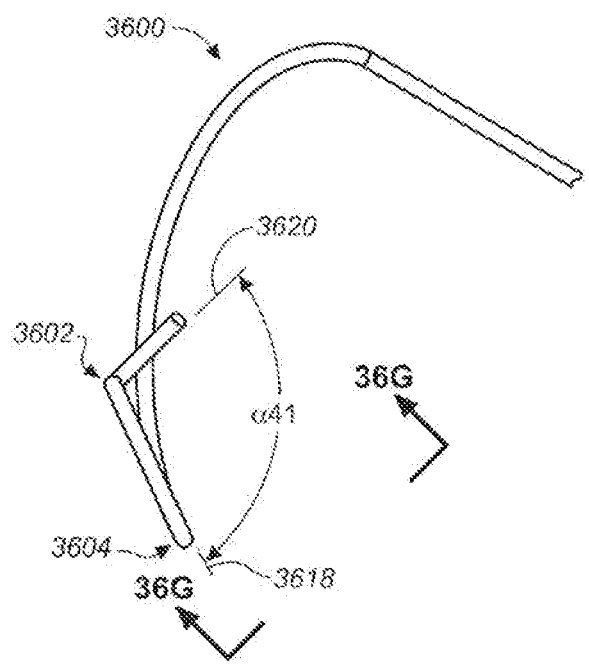
FIG. 36F is a view of the diagnostic catheter as shown in FIG. 36E, taken along line 36F-36F.

Additionally, and referring now to FIG. 36F, valve curve region (3602) defines a valve plane (3620). In certain variations, the angle ($\alpha$41) between transition plane (3618) and valve plane (3620) may be from about 100° to about 125° (e.g., from about 105° to about 120°, such as 110°). If a fixture is used to form valve curve region (3602) and transition curve region (3604), the fixture may have corresponding valve and transition curve regions defining valve and transition planes having an angle therebetween of, for example, 110°.

Figure 36G:
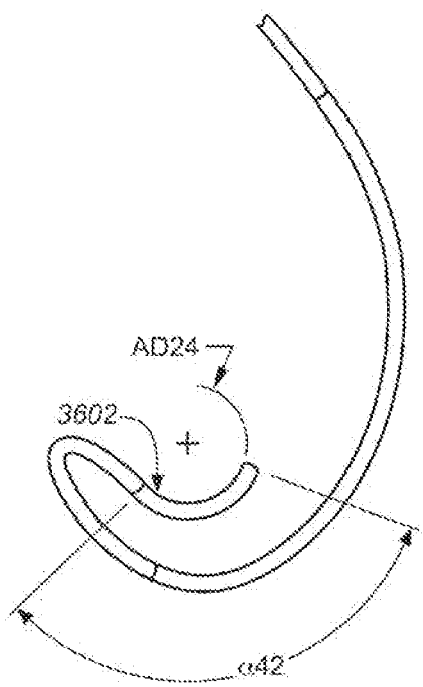
FIG. 36G is a view of the diagnostic catheter as shown in FIG. 36F, taken along line 36G-36G.

Finally, and referring now to FIG. 36G, valve curve region (3602) forms an arc having an arc diameter (AD24) that may be, for example, from about 0.75 inch to about 1.5 inches (e.g., from about 0.75 inch to about 1 inch, such as 0.882 inch), and defining a central angle ($\alpha$42) that may be, for example, from about 75° to about 120° (e.g., from about 100° to about 120°, such as 114.75°). If a fixture is used to form valve curve region (3602), the fixture may have a corresponding valve curve region comprising an arc with an arc diameter of, for example, 0.75 inch, and/or defining a central angle of, for example, 135°.

Example 8

Figure 37A:
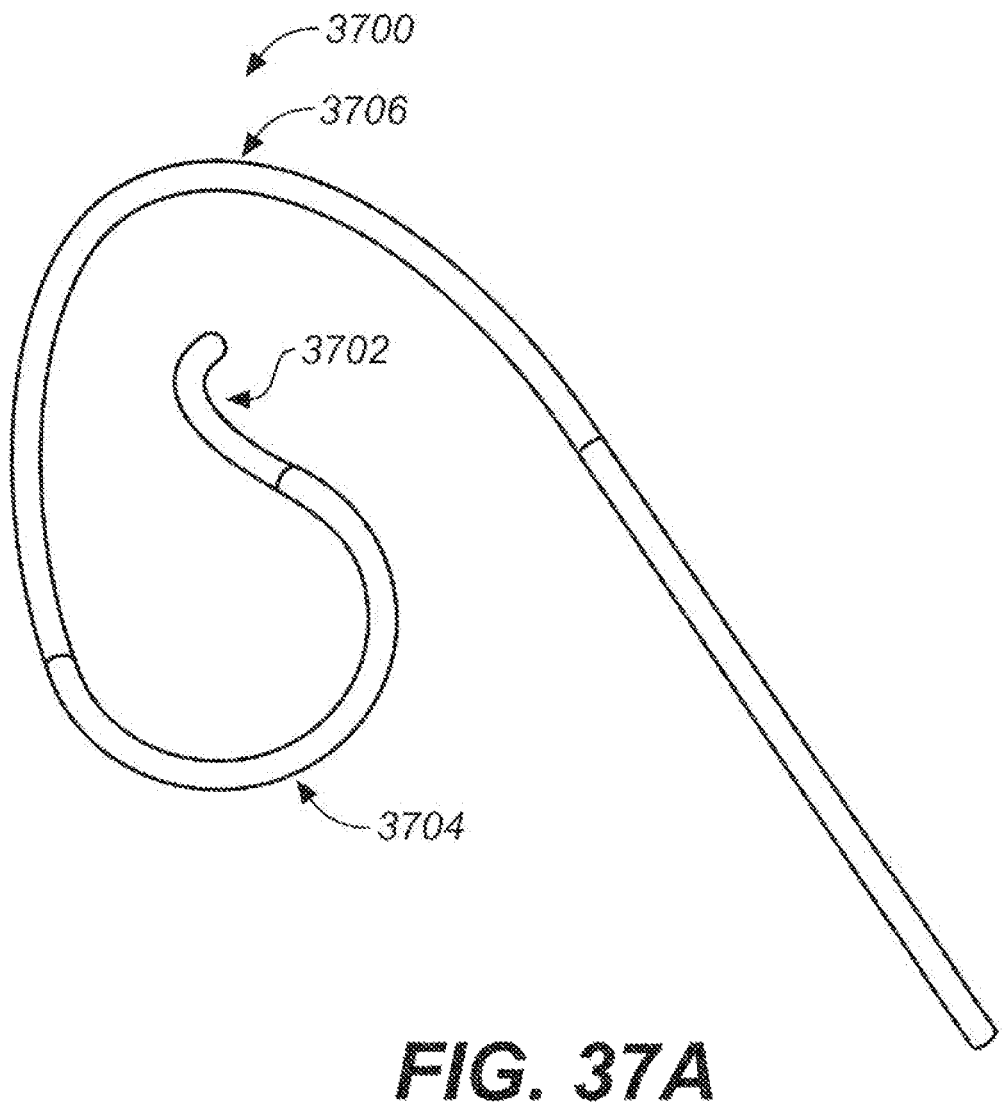
FIG. 37A is a perspective view of a variation of a diagnostic catheter.

FIG. 37A shows a computer illustration of a diagnostic catheter (3700). As shown there, diagnostic catheter (3700) comprises a valve curve region (3702), a transition curve region (3704), and an arch curve region (3706).

Referring now to FIG. 37B, diagnostic catheter (3700) also comprises a region (3708) that is proximal to arch curve region (3706). Region (3708) has a length (L17) that may be, for example, from about 25 inches to about 40 inches (e.g., from about 25 inches to about 35 inches, such as 32.752 inches). A proximal portion (3710) of region (3708) has a length (L18) that may be, for example, from about 1 inch to about 4 inches (e.g., from about 2 inches to about 3 inches, such as 2.473 inches). Additionally, and referring still to FIG. 37B, arch curve region (3706) forms an arc having an arc diameter (AD25) that may be, for example, from about 3.5 inches to about 5 inches (e.g., from about 3.5 inches to about 4.5 inches, such as 4.045 inches), and defining a central angle ($\alpha$43) that may be, for example, from about 60° to about 180° (e.g., from about 120° to about 180°, or from about 140° to about 160°, such as 153°). If a fixture is used to form arch curve region (3706), the fixture may have a corresponding arch curve region comprising an arc with an arc diameter of, for example, 3.438 inches, and/or defining a central angle of, for example, 180°.

Additionally, and referring now to FIG. 37C, diagnostic catheter (3700) comprises a tubular member (3712) having an outer diameter (OD9) and an inner diameter (ID9). In some variations, inner diameter (ID9) may be from about 1.33 millimeters to about 3 millimeters. Alternatively or additionally, outer diameter (OD9) may be from about 1.67 millimeters to about 3.33 millimeters.

Referring now to FIG. 37D, arch curve region (3706) defines an arch plane (3716), while transition curve region (3704) defines a transition plane (3718). In certain variations, the angle (α44) between arch plane (3716) and transition plane (3718) may be from about 20° to about 45° (e.g., from about 35° to about 45°, such as 45°). If a fixture is used to form transition curve region (3704) and arch curve region (3706), the fixture may have corresponding transition and arch curve regions defining transition and arch planes having an angle therebetween of, for example, 45°.

As shown in FIG. 37E, transition curve region (3704) forms an arc having an arc diameter (AD26) that may be, for example, from about 1 inch to about 3 inches (e.g., from about 1 inch to about 2 inches, such as 1.176 inches), and defining a central angle (α45) that may be, for example, from about 90° to about 270° (e.g., from about 180° to about 270°, from about 180° to about 250°, or from about 210° to about 250°, such as 229.5°). If a fixture is used to form transition curve region (3704), the fixture may have a corresponding transition curve region comprising an arc with an arc diameter of, for example, 1 inch, and/or defining a central angle of, for example, 270°.

Additionally, and referring now to FIG. 37F, valve curve region (3702) defines a valve plane (3720). In certain variations, the angle (α46) between transition plane (3718) and valve plane (3720) may be from about 115° to about 150° (e.g., from about 125° to about 145°, such as 135°). If a fixture is used to form valve curve region (3702) and transition curve region (3704), the fixture may have corresponding valve and transition curve regions defining valve and transition planes having an angle therebetween of, for example, 135°.

Finally, and referring now to FIG. 37G, valve curve region (3702) forms an arc having an arc diameter (AD27) that may be, for example, from about 0.75 inch to about 1.5 inches (e.g., from about 0.75 inch to about 1 inch, such as 0.882 inch), and defining a central angle (α47) that may be, for example, from about 75° to about 120° (e.g., from about 100° to about 120°, such as 114.75°). If a fixture is used to form valve curve region (3702), the fixture may have a corresponding valve curve region comprising an arc with an arc diameter of, for example, 0.75 inch, and/or defining a central angle of, for example, 135°.

Example 9

A study is conducted to provide three-dimensional support for development of catheter shapes. The study aims to define a catheter shape that achieves desired positioning of the catheter in the subannular groove of a heart from an anterior approach, with appropriate bracing points against the greater curvature of the aortic arch and within the ascending aorta contralateral to the entrance of the subannular groove.

Eight subjects of varying age (50±16 years) and sex (5 male, 3 female) are analyzed with SimVascular, a specialized imaging software that may be used to build custom geometric models from medical image data. By visualizing the medical image data directly, the user may be able to isolate specific parts of the anatomy and build-up shapes in three-dimensional space based on these images. For this study, cardiac-gated CT image data (i.e., data based on the optimized acquisition of images during moments in time when the heart is quiescent) is used. An image volume representing one-tenth of the cardiac cycle is analyzed for each patient, and an idealized path of a catheter is drawn in three-dimensional space.

Several visualization options are available in SimVascular, including point cloud and isosurface. The point cloud visualization renders the image data with varying densities of white dots, based on the image intensity at that location. The user can choose the range of intensities to visualize, providing flexibility in the level of detail. The point cloud visualization may be appropriate, for example, for checking the overall position of the catheter (e.g., because the point cloud visualization can provide some transparency). Another visualization modality is the isosurface, which allows the user to create a solid surface with detailed features based on the image intensity. The isosurface visualization may be appropriate, for example, for checking the positioning of the catheter along the mitral annulus (e.g., because the isosurface visualization may allow for a more detailed view of the edges of the anatomy).

The path generated in SimVascular is extracted into SolidWorks as the basis for the catheter model. For each patient, two catheter models are created. The first model strictly follows the path extracted from SimVascular, while the second model is an idealized catheter created by confining the catheter to three distinct planes. The first plane (MVPlane) represents the segment of the catheter which lies solely below the mitral annulus, extrapolating an extension of the catheter path from commissure to commissure. The second plane (TransitionPlane) represents the segment of the catheter spanning from the mitral valve to the ascending aorta. Finally, the third plane (ArchPlane) represents the length of the catheter resting along the aortic arch. All planes and curves are created as a best-fit approximation by the user. In some variations, a catheter model may be created using a least-squares approximation or may be manually created (e.g., by tracing an optimized path with a computer mouse).

Several measurements are taken on the models of all eight subjects. The MVPlane-TransitionPlane measurement represents the angle between the idealized mitral valve plane and the idealized transition plane, the TransitionPlane-ArchPlane measurement represents the angle between the idealized transition plane and the idealized arch plane, and the MVPlane-ArchPlane measurement represents the angle between the idealized mitral valve plane and the idealized arch plane, according to the anatomy of the particular subject.

The length of the curve drawn onto each of the three planes is also measured (MVCurve, TransitionCurve, ArchCurve). In addition, the radius of curvature for the three curves (MVRadius, TransitionRadius, ArchRadius) is reported. In some cases, several curves are used to construct an arch. In Tables 1-3 below, only the first curve (directly adjacent to the transition curve) is measured.

TABLE 1

Measured Angle (Degrees) Between the Three Planes.

|  | MVPlane-TransitionPlane | TrarasitionPlane-ArchPlane | MVPlane-ArchPlane |
|---|---|---|---|
| Subject1 | 0 | 0 | 0 |
| Subject2 | 0 | 0 | 0 |
| Subject3 | 0 | 67 | 67 |
| Subject4 | 10 | 0 | 10 |
| Subject5 | 35 | 27 | 62 |
| Subject6 | 49 | 69 | 20 |
| Subject7 | 12 | 24 | 12 |
| Subject8 | 1 | 61 | 60 |

TABLE 2

Measured Lengths (mm) of the Three Segments of an Idealized Catheter.

|  | MVCurve | TransitionCurve | ArchCurve |
|---|---|---|---|
| Subject1 | 42 | 21 | 65 |
| Subject2 | 60 | 82 | 110 |
| Subject3 | 46 | 20 | 89 |
| Subject4 | 53 | 51 | 38 |
| Subject5 | 64 | 54 | 51 |
| Subject6 | 50 | 45 | 50 |
| Subject7 | 57 | 45 | 86 |
| Subject8 | 62 | 42 | 86 |

TABLE 3

Measured Radius of Curvature (mm) of the Three Segments of an Idealized Catheter.

|  | MVRadius | TransitionRadius | ArchRadius |
|---|---|---|---|
| Subject1 | 13 | 36 | 39 |
| Subject2 | 22 | 31 | 35 |
| Subject3 | 17 | 22 | 43 |
| Subject4 | 16 | 32 | 56 |
| Subject5 | 20 | 24 | 28 |
| Subject6 | 17 | 23 | 34 |
| Subject7 | 19 | 35 | 38 |
| Subject8 | 21 | 27 | 42 |

In Table 1 above, the angle between the transition plane and the mitral valve plane ranges from 0° to 49°, with the mean angle at 13°. This implies that this dimension should be varied in the final catheter design to accommodate various patient anatomies, with more incremental changes closer to the lower range of the measurements. Additionally, the angle between the transition plane and the arch plane ranges from 0° to 69°, with the mean angle at 31°. Any variations in this dimension may be equally incremented over the range. Finally, the angle between the mitral valve plane and the arch plane ranges from 0° to 67°, with the mean angle at 29°.

The length of the catheter in contact with the mitral valve annulus has a range from 42 millimeters to 64 millimeters, with the mean at 54 millimeters. The length of the transition curve varies from 20 millimeters to 82 millimeters, with the mean at 45 millimeters. Finally, the length of the arch curve has a broad range from 38 millimeters to 110 millimeters, with the mean at 72 millimeters.

The radius of curvature for the mitral valve ranges from 13 millimeters to 22 millimeters, with the average at 18 millimeters. This range may not require variation from patient to patient. The transition curve has a radius of curvature ranging from 22 millimeters to 36 millimeters, with the mean at 29 millimeters. Because of the important role the transition curve plays in bracing the catheter, it may be preferable to vary this parameter to accommodate patient variability. Finally, the arch radius of curvature varies from 28 millimeters to 56 millimeters, with the mean at 39 millimeters. This dimension likely may be held constant across all patient groups.

Example 10

A catheter suitable for probing the subannular groove of a mitral valve and the anatomy surrounding the subannular groove using ultrasound is constructed. The catheter includes the following segments.

First, the catheter includes a distal window formed of 70D PEBAX® polymer. The window, which is cylindrical, has a length of about 0.5 centimeter to about 1 centimeter, and a wall thickness of about 0.007 inch. The catheter also includes an ultrasonic transducer disposed within the distal window.

Additionally, the catheter includes a flexible distal segment that is proximal to the distal window. The flexible distal segment has a bi-lumen construction, and includes an inner layer formed of high-density polyethylene (HDPE), an intermediate layer formed of 35D PEBAX® polymer, and an outer jacket formed of 40D PEBAX® polymer including 20% by weight barium sulfate. The smaller lumen has an inner diameter of about 0.01 inch to about 0.012 inch, and the larger lumen has an inner diameter of about 0.045 inch to about 0.056 inch. The flexible distal segment has an outer diameter of about 0.07 inch, and a length of about 2 inches to 4 inches.

The catheter further includes a proximal segment that is stiffer than the distal segment. The proximal segment has a bi-lumen construction, and comprises 70D PEBAX® polymer and stainless steel braid. The smaller lumen of the proximal segment has an inner diameter of about 0.012 inch to about 0.016 inch, and the larger lumen has an inner diameter of about 0.05 inch to about 0.06 inch. The proximal segment has an outer diameter of about 0.089 inch, and a length of about 60 inches to 70 inches.

Example 11

Figure 38:
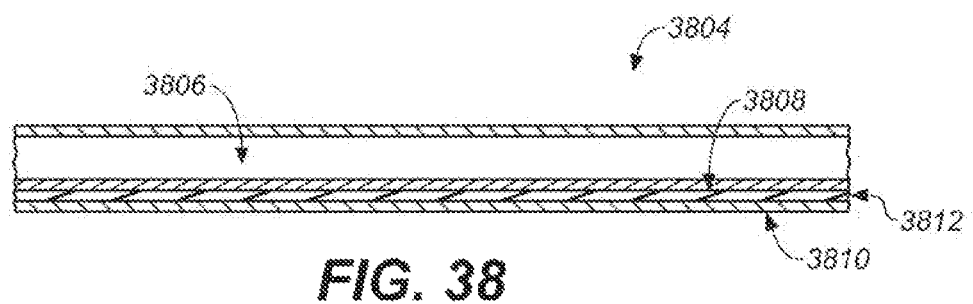
FIG. 38 is a schematic cross-sectional view of a variation of a steerable catheter with a pull wire.
Figure 39A:
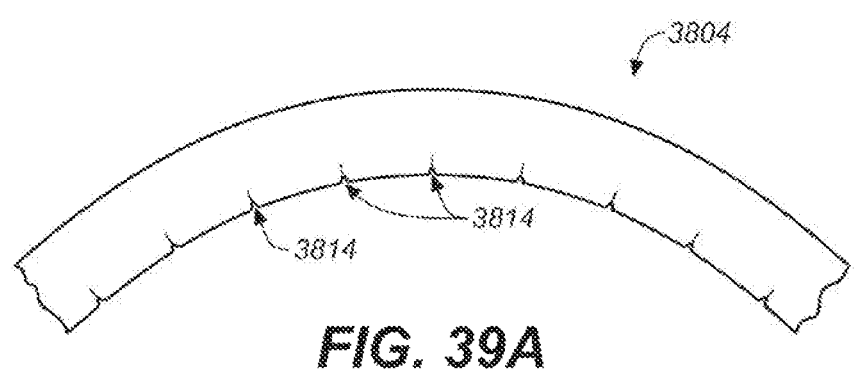
FIGS. 39A and 39B are schematic side elevation and cross-sectional views, respectively, of the steerable catheter of FIG. 38 in a bent orientation.
Figure 39B:
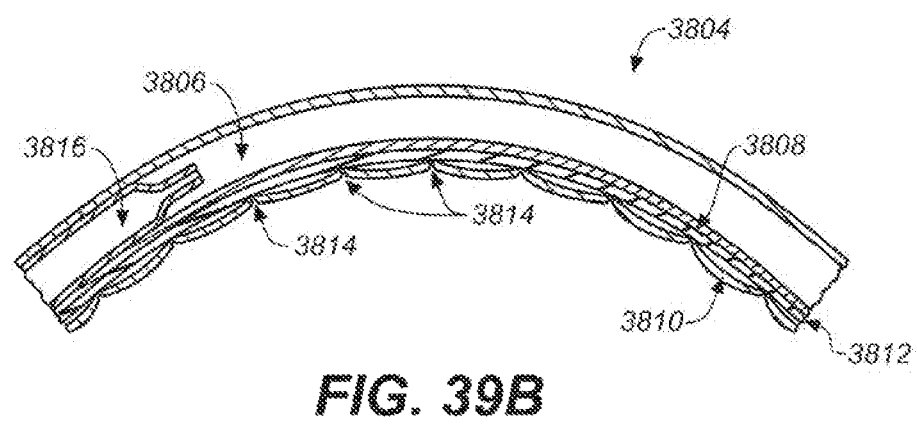

The ease of inserting a catheter to a body location may be influenced by a number of catheter characteristics. While a catheter made from stiffer materials may exhibit improved user responsiveness relating torqueability and/or pushability over longer insertion distances, stiffer catheter materials may also affect the catheter's maneuverability through tight anatomical bends. In some cases, catheter maneuverability may be improved by using a steering mechanism to position the catheter tip in the desired orientation or direction. FIG. 38 illustrates one example of a steerable catheter segment, comprising a tubular catheter body (3804) with one or more conduits (3806) and a pull lumen (3808) containing a pull member (3810). Pull member (3810) may be attached distally to catheter body (3804) such that, when pulled proximally, pull member (3810) will asymmetrically compress catheter body (3804) to cause bending, as shown in FIG. 39A. While a steering mechanism (3812) may facilitate the bending of stiffer catheter materials, such materials may sometimes cause creases (3814) or other discontinuities in catheter body (3804) when bent, as illustrated in FIG. 39A. In some examples, creases (3814) may impair the ability to pass instruments (3816) or components through conduit (3806), as is apparent in FIG. 39B.

In some instances, a catheter may be configured with a higher durometer segment that may provide torqueability and/or pushability, along with a lower durometer segment that may provide flexibility and/or compressibility, which may reduce the kinking and/or creasing that may affect the conduct. In some further variations, the materials with different durometers may comprise two or more partially tubular segments of material with a generally semi-circular or other arcuate cross-sectional shape. The two segments may be joined along their longitudinal edges or otherwise oriented to form the tubular structure. A catheter configured with multiple durometer materials along its circumference or perimeter may facilitate flexion or compression of the catheter in at least one direction while also providing sufficient column strength along the same longitudinal segment of the catheter.

Figure 40A:
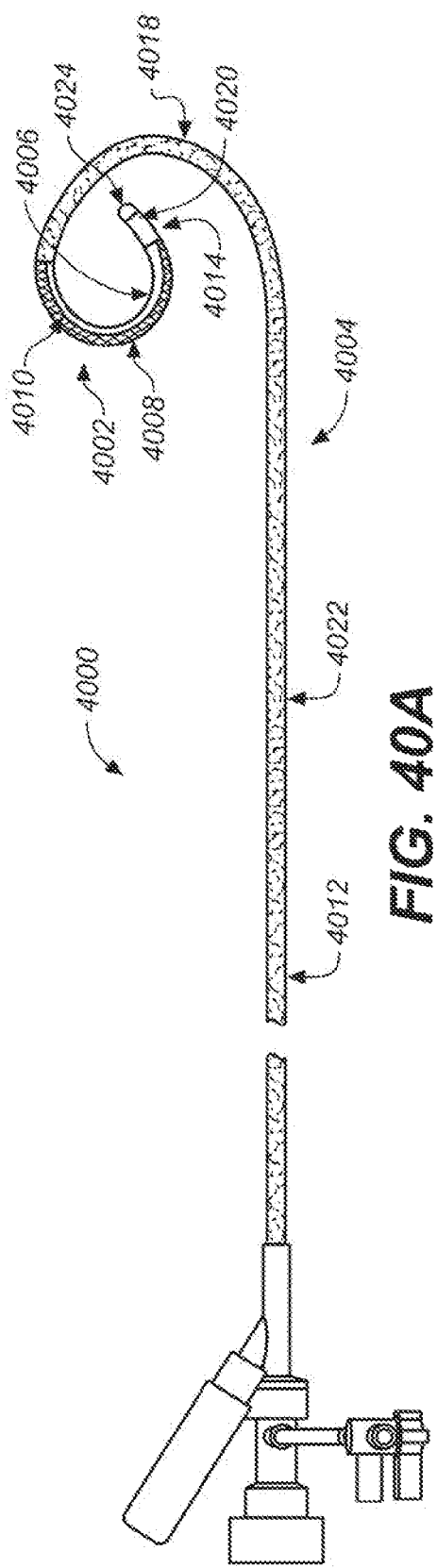
FIG. 40A is a superior elevational view of a variation of a steerable guide catheter.
Figure 40C:
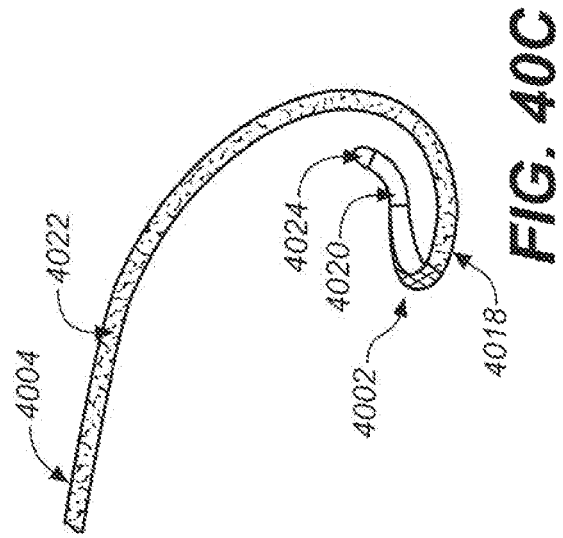
FIG. 40C is a side elevational view of the distal end of the guide catheter.
Figure 40B:
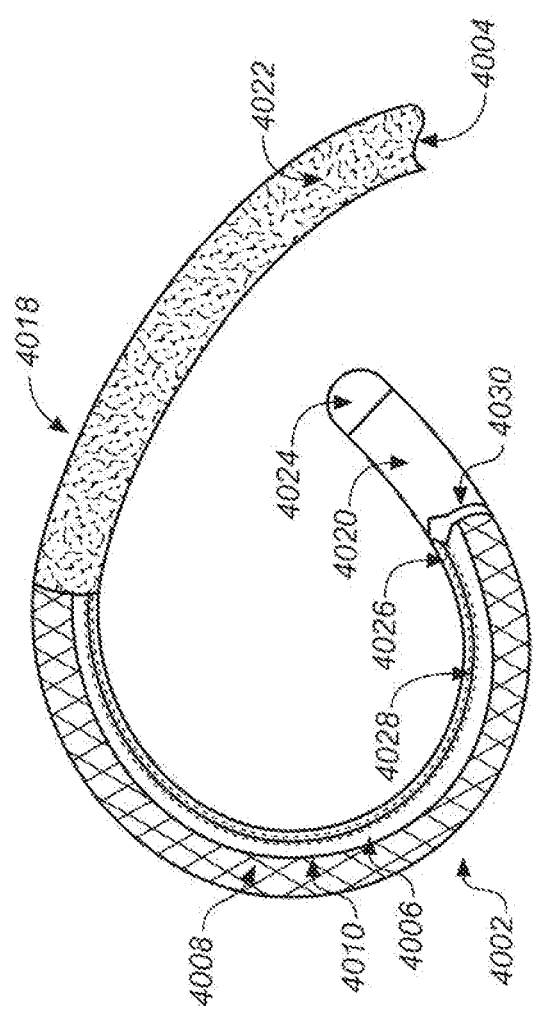
FIG. 40B is a detailed superior elevational view of the distal end of the guide catheter.

In one example, shown in FIG. 40A, a steerable catheter (4000) with one or more deformation regions (4002) is provided. Referring to FIG. 40B, deformation region (4002) may comprise a segment of the catheter body (4004) having a first layer segment (4006) and a second layer segment (4008) with a longitudinal interface (4010) therebetween. First layer segment (4006) and second layer segment (4008) comprise different physical characteristics such that first layer segment (4006) is able to compress or stretch when flexed. In some variations, first layer segment (4006) comprises a material having a lower durometer than the material of second layer segment (4008). In examples where deformation region (4002) is formed by two layer segments, two longitudinal interfaces are formed where the two lateral borders of each layer segment form a longitudinal interface with the complementary lateral border of the other layer segment. Longitudinal interface (4010) may have a linear or simple curve configuration, which may be oriented similar to the longitudinal axis of catheter body (4004). In other variations described below, the deformation region may alternatively comprise non-curvilinear interfaces. Also, although first layer segment (4006) and second layer segment (4008) in this specific example have generally semi-circular configurations, longitudinal interfaces (4010) have generally 180° opposite locations. In other variations, however, deformation region interfaces may be angularly closer together, and/or a deformation region may comprise three or more interfaces.

In some variations, deformation region (4002) may correspond to at least a portion of (e.g., the entirety of) the transition curve region of the other exemplary catheters described herein. In other variations, the deformation region may correspond to the other portions of the exemplary catheters, including but not limited to the valve curve regions, arch curve regions, or combinations of any of the valve curve, transition curve and arch curve regions. Deformation region (4002) may be configured to bend from about 180° to about 30°, about 180° to about 45° in some variations, and about 180° to about 90° in other examples. In certain variations, deformation region (4002) may be configured to bend in two or more directions and/or two or more planes from its straight or base configurations. The range of bending in two or more directions or planes need not be symmetrical with respect to a linear configuration or other base configuration, which may not be linear. Catheter body (4004) may be formed from any of a variety of materials, as described above. In some further variations, first layer segment (4006) and second layer segment (4008) may comprise different materials or the same general type of material but with different durometers. For example, first layer segment (4006) may comprise PEBAX® 35D polymer and second layer segment (4008) may comprise PEBAX® 72D polymer. In other variations, the durometer of the material may range from about 5D to about 72D, in some variations about 35D to about 72D, and in other variations about 35D to about 55D, or about 55D to about 72D. Catheter body (4004) may comprise one or more layers, and sometimes two or more layers. Although FIG. 40B depicts first layer segment (4006) and second layer segment (4008) as forming the outermost layer of deformation region (4002), in other examples, these layer segments (4006) and (4008) may be covered by one or more other layers or reinforcing structures. Catheter body (4004) need not comprise the same number of layers along its entire length. In still other examples, the deformation region may comprise a tubular body that is asymmetrically reinforced with respect to different angular regions, such that the tubular body functionally has a region of increased stiffness and a region of increased compressibility or flexibility.

Figure 40D:
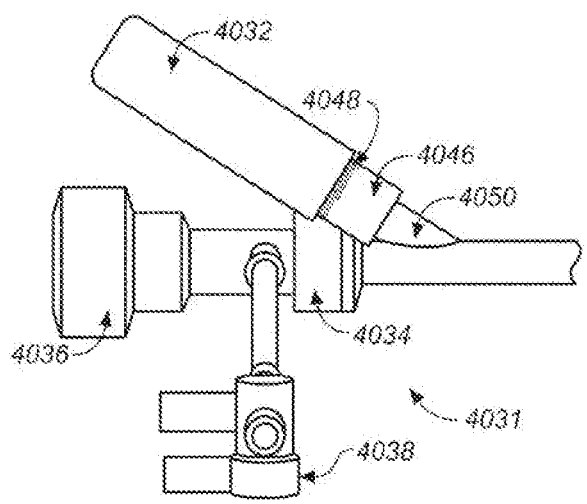
FIG. 40D is a detailed superior elevational view of the proximal end of the guide catheter.

Referring back to FIG. 40A, catheter body (4004) may further comprise a proximal shaft (4012) and a distal shaft (4014) with respect to deformation region (4002). Proximal shaft (4012) may comprise a tubular configuration with at least one inner lumen (not shown) that may be optionally lined with a coating. Proximal shaft (4012) may have a generally linear configuration, but in other variations, proximal shaft (4012) may have a non-linear configuration, including angled and curved sections or combinations thereof, such as the arch curve region (4018). Distal shaft (4014) may also have a linear or curved configuration, such as valve curve region (4020) depicted in FIGS. 40B and 40C. In some variations, proximal shaft (4012) may comprise one or more reinforcement structures (4022), such as tubular or arcuate braiding or interweaving, circular loops, helical structures, or longitudinal supports. The reinforcement structure may comprise one or more metallic and/or non-metallic materials. In one example, proximal shaft (4012) may comprise an outer layer of PEBAX® 72D polymer, and reinforcement structure (4022) may comprise a tubular stainless steel wire braid, which in turn may have an inner coating of PTFE. Distal shaft (4014) may comprise the same material(s) as proximal shaft (4012) or deformation region (4002), or may comprise one or more different materials. In the example of FIG. 40A, distal shaft (4014) comprises a material having a durometer between the durometer of first and second segments (4006) and (4008), but in other examples, the durometer may be generally equal to, less than or greater than first and second segments (4006) and (4008), respectively. Distal shaft (4014) may also comprise an atraumatic tip (4024), which may comprise a material having a lower durometer than the rest of distal shaft (4014), or may be tapered or otherwise shaped to be more flexible or deformable. Distal shaft (4014) may comprise a linear or non-linear configuration, and may be oriented in the same or a different plane with respect to the deformation region (4002) and/or proximal shaft (4012), as shown in FIG. 40D.

In some variations, deformation region (4002) may have an angular orientation of about 0°, about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345°. The bending plane of deformation region (4002), however, need not be the same plane as its curved configuration and may have an angular orientation from about 0° to about 359° to the plane of its curved configuration. In some variations, the bending plane of deformation region has an angular orientation of about 0°, about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345° with respect to the plane of its curved configuration.

In certain variations, deformation region (4002) may have a longitudinal length of about 0.75 inch to about 10 inches, some variations about 1 inch to about 4 inches or more, and in other variations about 1.5 inches to about 2 inches in length. In some variations, deformation region (4002) may have similar inner and outer diameters as described for catheter body (4004), but in other variations of deformation region (4002), the inner diameter and/or outer diameter may be smaller or larger.

Although several variations depicted and described herein have a single inner lumen, in other variations, two or more lumens may be provided along part or all of the catheter body. Variations with multiple lumens need not have lumens with the same diameter, shape or cross-sectional area. Furthermore, any one lumen need not have the same diameter, shape or cross-sectional area along its entire length. Thus, some lumens may comprise a circular shape, but in other variations, the lumens may be oval, square, rectangular or any other shape.

Referring to FIG. 40B, proximal shaft (4012) may further comprise a pull lumen (4026) and pull member (4028) within the wall of proximal shaft (4012). Pull lumen (4026) and/or pull member (4028) may also be coated with a reduced friction coating, such as PTFE. In further variations, pull lumen (4026) may be reinforced with a material such as polyimide. Pull member (4028) may comprise any of a variety of materials, including but not limited to stainless steel, nylon, polyimide, and the like.

In variations comprising a single deformation region and/or steering mechanism, pull lumen (4026) and/or pull member (4028) may terminate within deformation region (4002) or distal shaft (4014). To facilitate the exertion of force in distal shaft (4014) of catheter body (4004), pull member (4028) may comprise a distal pull structure (4030). Pull member (4028) may be welded or twisted around distal pull structure (4030) or may be contiguous with distal pull structure (4030). In the variation illustrated in FIG. 40B, distal pull structure (4030) may comprise a ring-like structure embedded in distal shaft (4014). In alternate variations, distal pull structure (4030) may comprise a helical winding of pull member (4028) or some other wire-based configuration. Pull member (4028) may comprise any of a variety of materials and structures sufficient to transmit longitudinal forces along a length of catheter body (4004). Pull member (4028) and distal pull structure (4030) may be metallic, non-metallic or a combination thereof, comprising one or more materials including but not limited to stainless steel, Nitinol, nylon and/or other polymeric materials. In some variations, pull member (4028) may be coated, for example, to facilitate sliding in pull lumen (4026). In certain variations, such coatings may include polytetrafluoroethylene (PTFE).

In some variations, pull member (4028) may comprise a structure and a material whereby pull member (4028) can exert force on catheter body (4004) only when pulled. In such variations, catheter body (4004) may have a preconfigured shape such that when the force acting on pull member (4028) is released, catheter body (4004) is biased to return to its preconfigured shape. In other variations, pull member (4028) has a sufficient stiffness such that pull member (4028) may also be pushed to facilitate bending of catheter body (4004) in a direction generally different or opposite from the bending that occurs when pull member (4028) is pulled. In other variations, distal pull structure (4030) may be located within deformation region (4002).

Figure 40E:
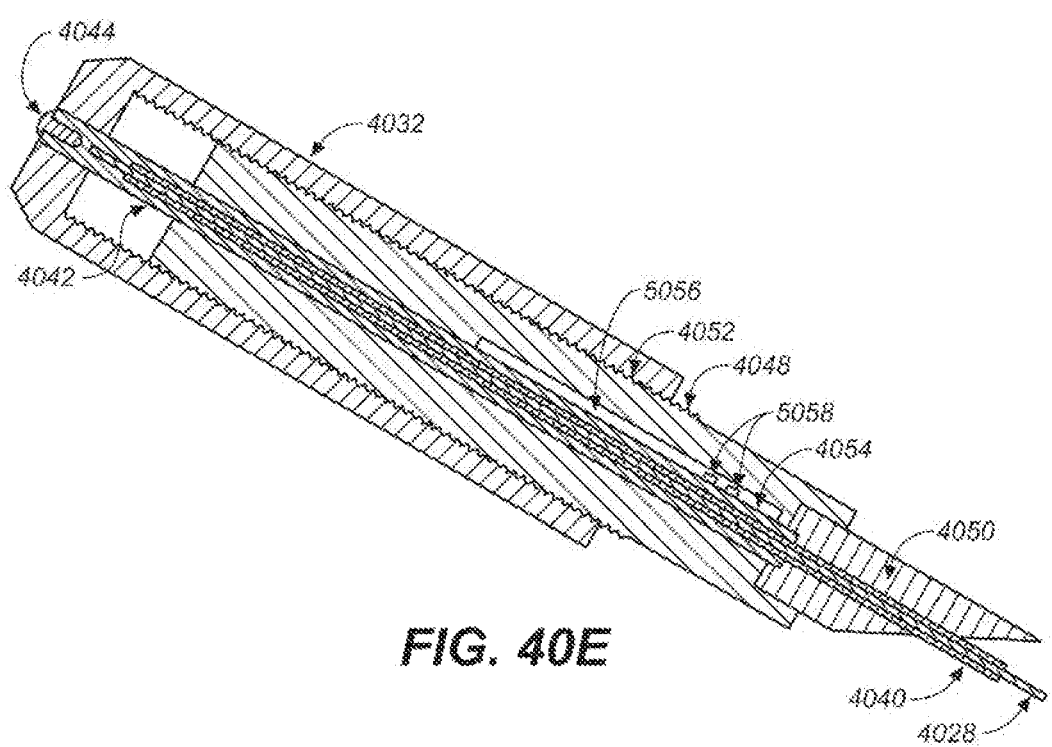
FIG. 40E is a longitudinal cross-sectional view of the steering mechanism of the guide catheter.

Tensioning of pull member (4028) may be controlled by any of a variety of steering mechanisms, including but not limited a pull tab, lever, slider, or knob mechanism, for example. FIG. 40D depicts the proximal end (4031) of steerable catheter (4000), comprising a rotatable knob (4032), a guide hub interface (4034), a hemostatic valve (4036) and a stopcock (4038). Knob (4032) is configured to adjust the tension in pull member (4028) by knob rotation, but in other variations, tension adjustment may occur by pulling the knob. Referring to FIG. 40E, pull member (4028) is attached to a hypotube (4040) by crimping, welding, adhesives or the like. Hypotube (4040) may be attached to a key structure (4042) which forms a complementary interfit with knob (4032) to axially displace pull member (4028) while permitting relative rotational movement between knob (4032) and key structure (4042). Key structure (4042) may also be axially secured to knob (4032) using a screw (4044) or other attachment structure which permits relative rotational movement. In other variations, the knob may be configured to transmit rotational movement to the pull member.

An inner sleeve (4046) with an outer threaded surface (4048) is attached to the base (4050) of the steering assembly. Outer threaded surface (4048) interfaces with the inner threaded surface (4052) of knob (4032). In some variations, to permit axial movement while restricting rotational movement of pull member (4028), hypotube (4040) or key structure (4042) may be configured with a non-circular shape and/or one or more side protrusions which may resist rotational movement along an inner lumen (4054) of inner sleeve (4046). For example, FIG. 40E depicts inner lumen (4054) comprising an elongate groove (5056) which accommodates axial movement of set screws (5058) attached to and protruding from key structure (4042) while restricting rotational displacement of screws (5058).

Figure 41A:
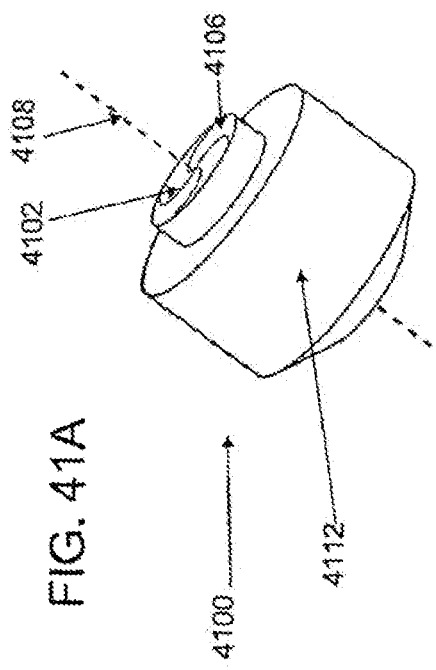
FIG. 41A is a perspective view of a variation of a hemostatic seal.
Figure 41B:
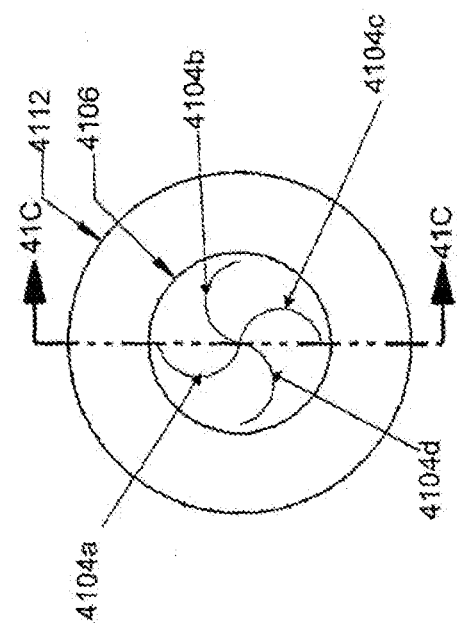
FIG. 41B is a posterior elevational view of the seal.
Figure 41C:
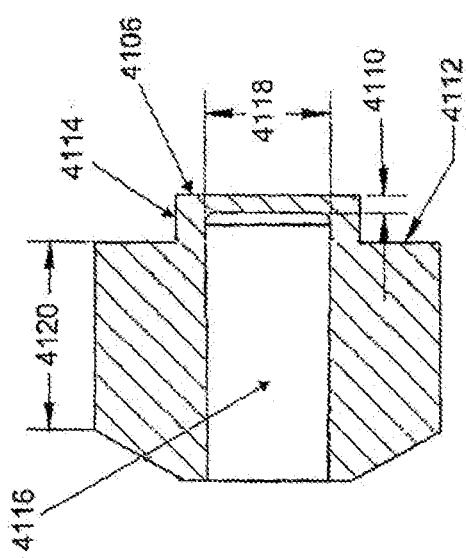
FIG. 41C is a cross-sectional view of the seal.
Figure 42:
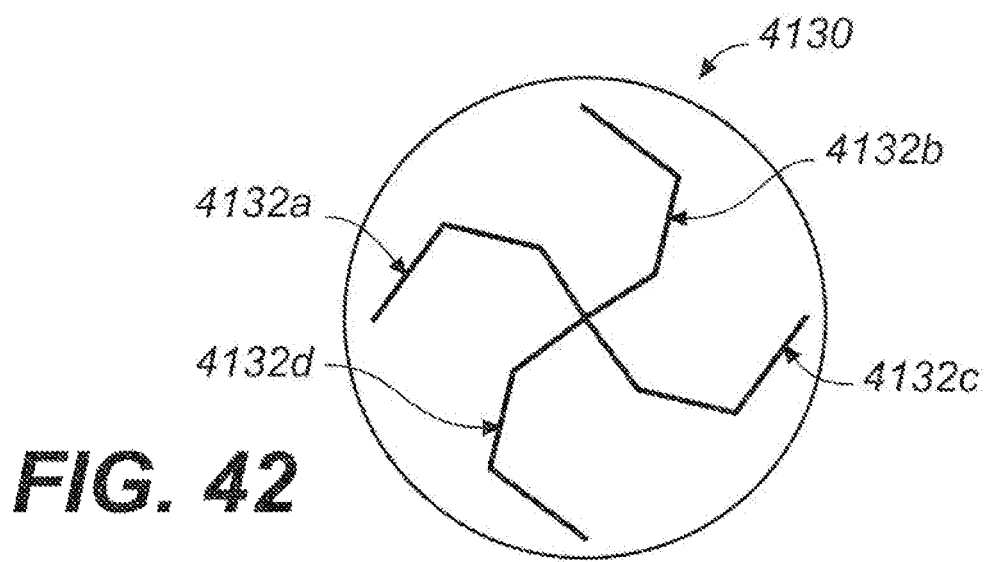
FIG. 42 is a posterior elevational view of another variation of a hemostatic seal.

To reduce the risk of blood or fluid leakage from catheter (4000) during a procedure, proximal end (4031) may comprise hemostatic valve or seal (4036) through which instruments may be inserted or withdrawn. The hemostatic seal may comprise any of a variety of configurations known in the art. In some examples, the hemostatic seal may comprise one or more slits on a septum or sealing member which forms one or more seal flaps. Upon insertion of an instrument or device through the sealing member, the seal flaps may deform or deflect to permit passage of the device while exerting force around a perimeter of the device to substantially resist passage of fluid or gas through the sealing member. Referring to FIGS. 41A-41C, in some examples, the sealing member (4100) has a seal opening (4102) comprising at least one non-linear slit (4104a)-(4104d) with respect to the seal face (4106) or a transverse plane of the seal axis (4108). In the depicted example, the sealing opening (4102) comprises four arcuate or spiral-shaped slits (4104a)-(4104d) arranged about the seal axis (4108). Each of the slits (4104a)-(4104d) has the same relative shape and size as the other slits (4104a)-(4104d), and the slits are uniformly spaced around the axis (4108). However, in other examples, a different number of slits may be provided, one or more slits may have a different size and/or shape, the slits may be non-uniformly spaced or non-symmetrically arranged, and/or the slits may intersect at a location different from the center of the seal face (4106). In FIG. 42, for example, the sealing member (4130) comprises a plurality of multi-angled slits (4132a)-(4132d). Referring back to FIG. 40D, hemostatic valve (4036) and stopcock (4038) may be detached from guide hub (4034) to permit direct insertion of instruments into catheter (4000), or to attach other configurations of hemostatic seals, valves, connectors, sensors and the like.

Referring back to FIGS. 41A-41C, slits (4104a)-(4104d) may have a generally orthogonal orientation through seal face (4106), or may be angled or skewed. In some examples, slits (4104a)-(4104d) may be generally angled with respect to seal face (4106) in the range of about 5° to about 85°, in certain configurations about 10° to about 60°, and in other configurations about 20° to about 45°. Seal face (4106) or sealing member (4100) may comprise any of a variety of elastic or flexible materials, including any of a variety of silicones such as NuSil Med-4035, Med-4820, and/or MED50-5338, may have a durometer in the range of about 20 to about 80 or about 15 to about 60 (e.g., about 20 to about 40). The thickness (4110) of seal face (4106) may be in the range of about 0.01 inch to about 0.1 inch, in some examples about 0.02 inch to about 0.05 inch, and in other examples about 0.025 inch to about 0.03 inch. As illustrated in FIG. 41C, seal face (4106) may be raised or offset from body (4112) of sealing member (4100). The raised distance (4114) of raised seal face (4106) may be in the range of about 0.01 inch to about 0.2 inch, in some configurations about 0.02 inch to about 0.1 inch and in other configurations about 0.04 inch to about 0.06 inch.

Body (4112) of sealing member (4100) comprises a lumen (4116) in communication with sealing opening (4102). Lumen (4116) may have a uniform or non-uniform diameter, cross-sectional area and/or cross-sectional shape. Lumens with non-uniform diameters may taper toward or away from sealing opening (4102), and the taper may be linear or non-linear. In some examples, lumen (4116) may have an average diameter (4118) in the range of about 0.05 inch to about 0.5 inch or more, in some configurations about 0.1 inch to about 0.3 inch, and in other configurations about 0.15 inch to about 0.2 inch. Lumen (4116) may have a length (4120) anywhere in the range of about 0.1 inch to about 1 inch or more, in some configurations about 0.2 inch to about 0.5 inch, and in other configurations about 0.25 inch to about 0.4 inch. Body (4112) may have any of a variety of shapes, including cylindrical, frustoconical, box-like or other shapes, and may be coupled to the guide tunnel by a frame or housing.

Example 12

Although the example depicted in FIG. 40A comprises a steerable catheter (4000) with a deformation region (4002) with a longitudinal linear interface (4010) between the first layer segment (4006) and the second layer segment (4008), in other examples, a catheter may be configured differently. As an example, a catheter may have a non-linear interface between the sections of material, such as a zig-zag or sinusoidal interface. In some variations, a non-linear interface may permit controlled deformation of the lower durometer material between portions of higher durometer material. This deformation may include stretching and/or compression. In certain variations, the deformation region may reduce the buckling of higher durometer material that may interfere with insertion or withdrawal of catheters or instruments from the lumen of the guide catheter.

Figure 43:
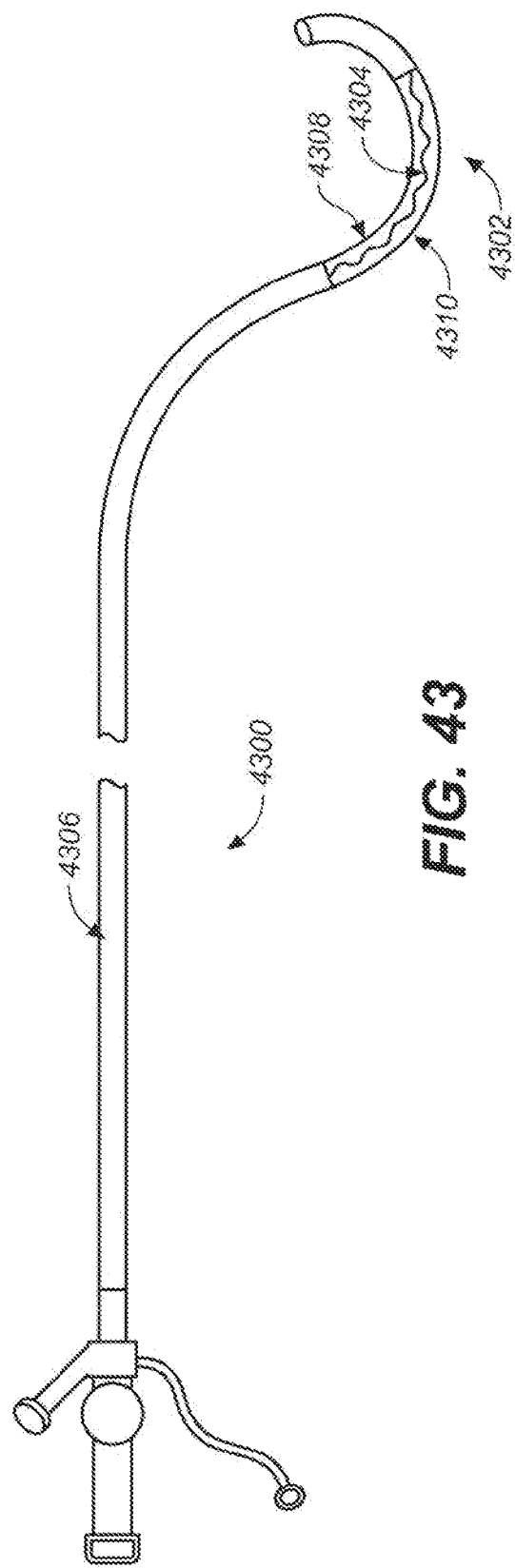
FIG. 43 is a superior elevational view of another variation of a steerable guide catheter.
Figure 44A:
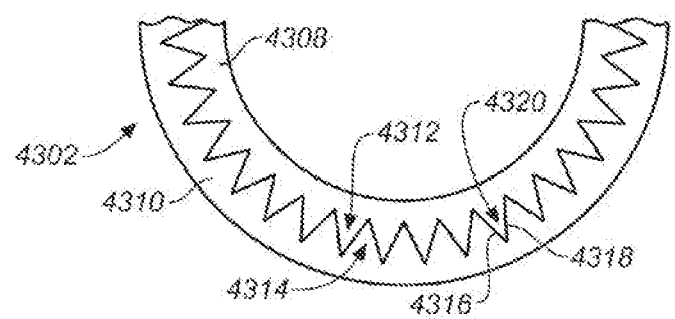
FIGS. 44A-44C are schematic elevational views of a deformation region of a catheter in various configurations.
Figure 44B:
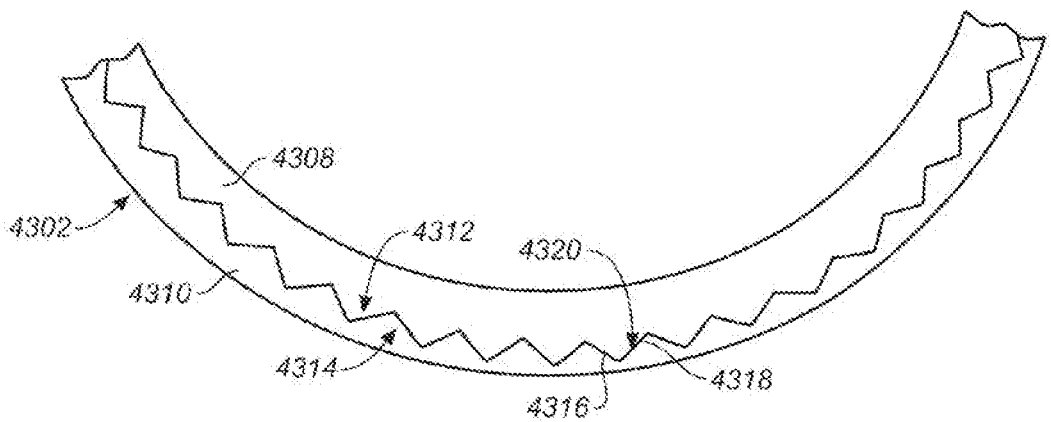
Figure 44C:
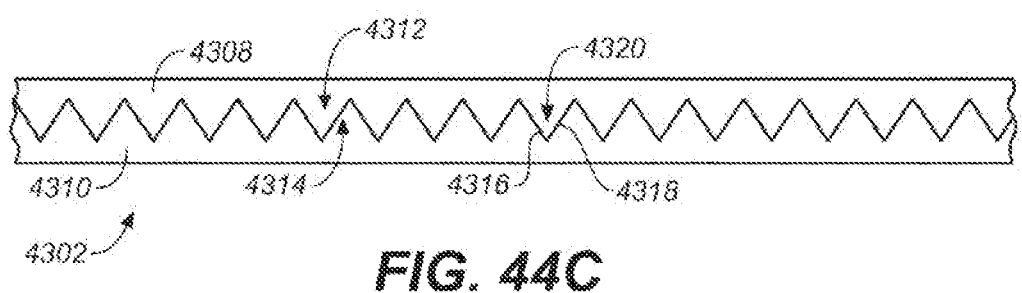

In the variation depicted in FIG. 43, the steerable catheter (4300) has a deformation region (4302) with a longitudinal interface (4304) that is oriented along a similar axis as the longitudinal axis of catheter body (4306) but with a zig-zag configuration. The zig-zag configuration of longitudinal interface (4304) comprises alternating protruding sections of first layer segment (4308) and second layer segment (4310). In FIGS. 44A-44C, these alternating protruding sections, shown in this particular variation as triangular sections (4312) and (4314), have side lengths (4316) and (4318) which meet to form an angle (4320) between two adjacent sides (4316) and (4318). In FIG. 44C, when deformation region (4302) is straightened from its configuration in FIG. 44B, triangular sections (4314) of first layer segment (4308) are stretched or relieved of compression as angle (4320) is increased by the angular separation of triangular sections (4314) of second layer segment (4310). In contrast, as depicted in FIG. 44A, when deformation region (4302) is acutely bent relative to FIG. 44B, triangular sections (4312) of first layer segment (4308) are compressed as angle (4320) is decreased by the angular reduction of triangular sections (4314) of second layer segment (4310). In some variations, the zig-zag pattern may reduce the incidence or degree of pinching or creasing of any conduits in deformation region (4302) by controlling compression of the lower durometer material in first layer segment (4308) with the protruding sections (4314) of the higher durometer material in second layer segment (4310). Further, in certain variations, the zig-zag pattern may provide a more even distribution of the forces along the full length of deformation region (4302), compared to simple linear or simple curved interfaces. In some variations, second layer segment may be contiguous with either the proximal and/or distal shaft of the steerable catheter.

Figure 45A:
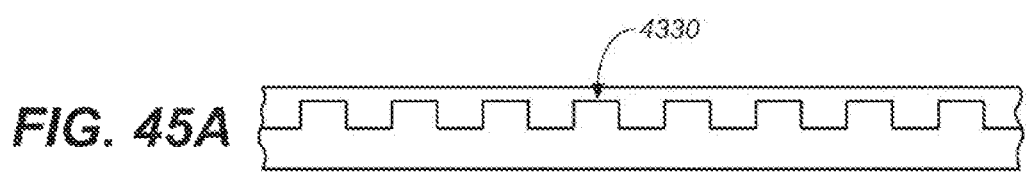
FIGS. 45A-45D are schematic elevational views of other various interfaces between two sections of catheter body material.
Figure 45B:
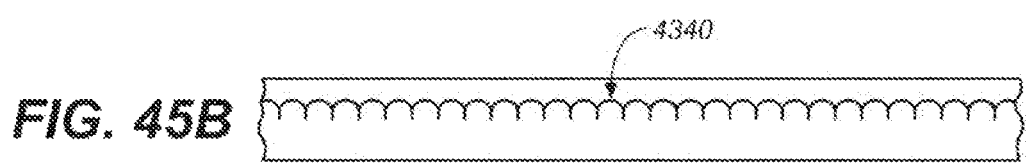
Figure 45C:
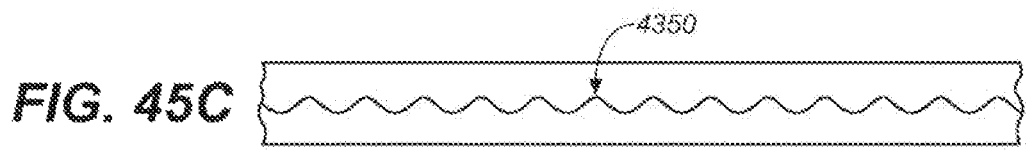
Figure 45D:
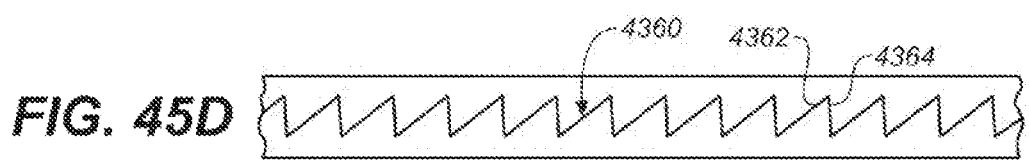

As depicted in FIGS. 45A-45C, other variations of catheter regions with multiple durometers include interfaces having a reciprocating pattern including but not limited to a square wave pattern (4330), a scalloped pattern (4340), and a sinusoidal pattern (4350), respectively. As shown in FIG. 45D, the reciprocating pattern (4360) need not have symmetric subsegments. In this variation, for example, the leading edge (4362) has a different length and angle from the trailing edge (4364).

Figure 46A:
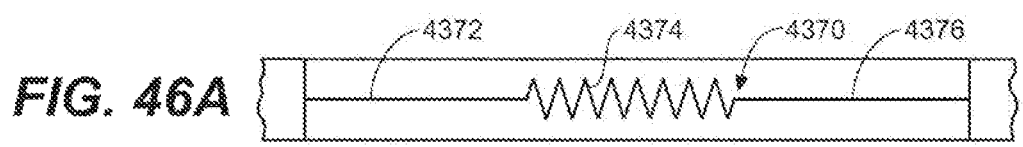
FIGS. 46A-46C are schematic elevational views of various interfaces between two sections of catheter body material.
Figure 46B:
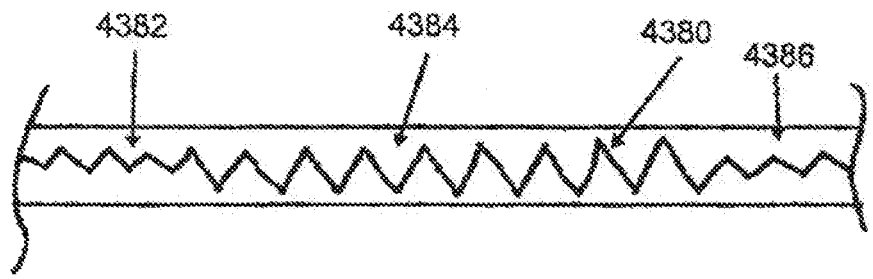
Figure 46C:
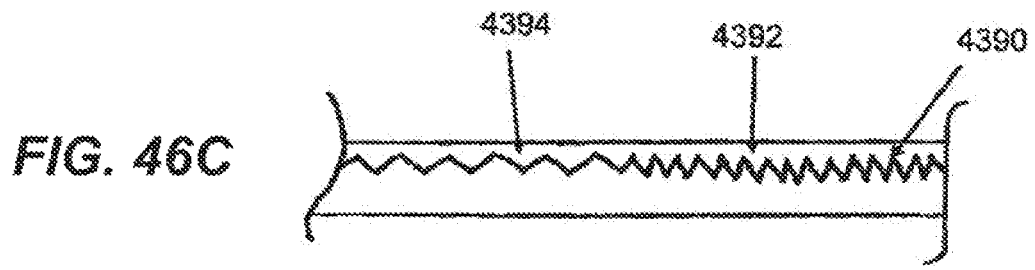

As depicted in FIGS. 46A-46C, interfaces need not comprise the same repeating pattern along their entire length. For example, in the variation depicted in FIG. 46A, an interface (4370) comprises a linear portion (4372) followed by a zig-zag portion (4374) and another linear portion (4376). In another variation depicted in FIG. 46B, an interface (4380) comprises the same pattern but with sections of low amplitude (4382) and (4386) and high amplitude (4384). In still another variation shown in FIG. 46C, interface (4390) comprises a pattern of similar amplitude but contains portions with relatively shorter and longer repeating lengths (4392) and (4394), respectively. These features may be mixed and matched to achieve the desired structural features in a deformation region of a catheter.

Figure 47A:
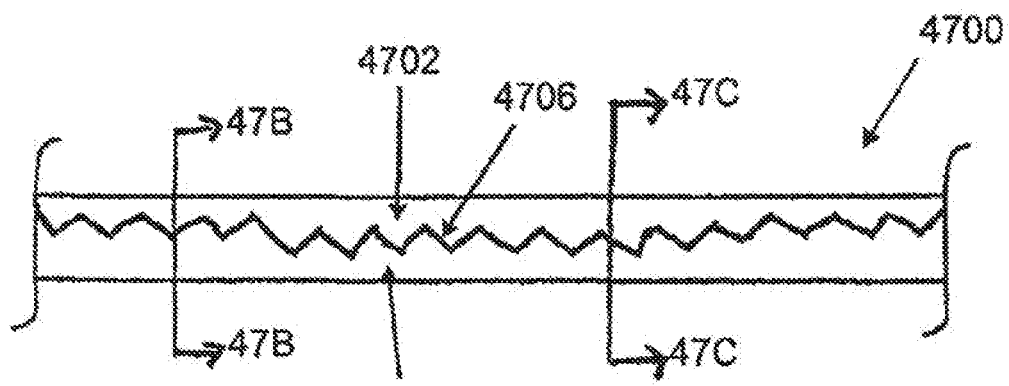
FIG. 47A is a schematic elevational view of a variation of a deformable zone of a catheter.
Figure 47B:
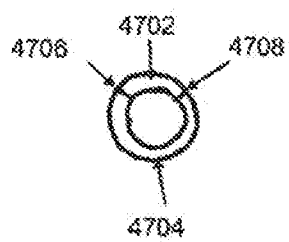
FIGS. 47B and 47C are various cross-sectional views of the deformable zone depicted in FIG. 47A.
Figure 47C:
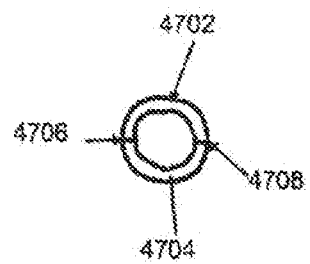
Figure 48A:
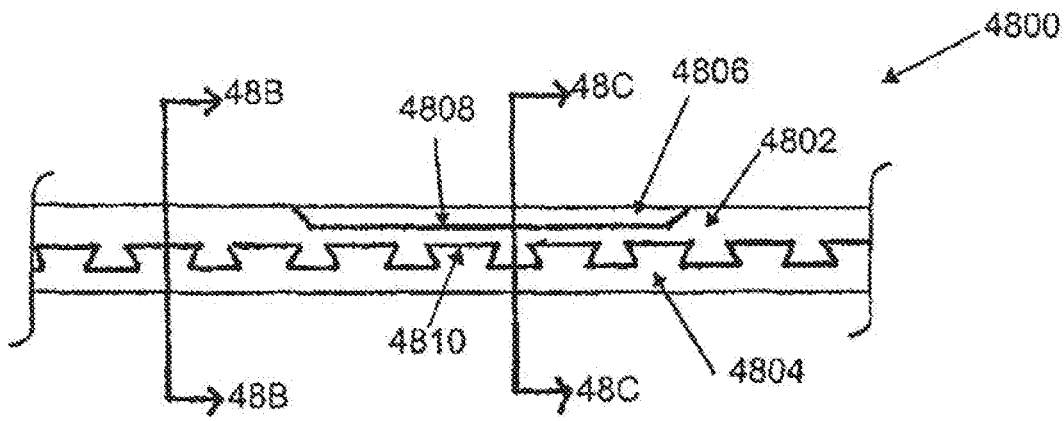
FIG. 48A is a schematic elevational view of another variation of a deformable zone of a catheter.
Figure 48B:
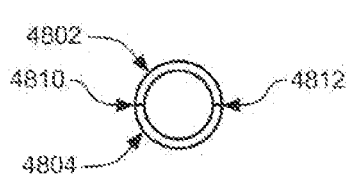
FIGS. 48B and 48C are various cross-sectional views of the deformable zone depicted in FIG. 48A.
Figure 48C:
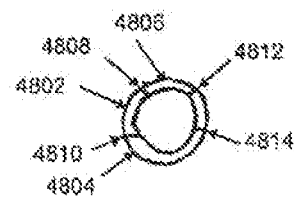

As mentioned previously, the variation depicted in FIG. 43 comprises a deformation region (4302) with two similarly sized semi-circular segments (4308) and (4310), and two interfaces (4304) about 180° apart with respect to catheter body (4306). In other variations, however, segments may have different sizes and/or shapes. In FIG. 47A, for example, the deformation region (4700) comprises a first segment (4702) with a reduced width at one or more ends and a second segment (4704) having a complementary larger size, resulting in interfaces (4706) and (4708) forming a narrower angle in one section (FIG. 47B) as compared to another section (FIG. 47C). In other variations, and as depicted in FIGS. 48A-48C, the deformation region (4800) may comprise more than two segments (4802)-(4806) and more than two interfaces (4808)-(4814).

In some variations, such as the example depicted in FIG. 43, deformation region (4302) comprises a single steering mechanism, but in other variations, multiple pull lumens with multiple pull members may be provided. In FIG. 49A, for example, the steerable catheter (4900) comprises a deformation region (4902) with three layer segments (4904)-(4908) arranged to facilitate the bending of the deformation region in opposite directions. As shown in FIG. 49B, two steering mechanisms (4910) and (4912) may be provided to facilitate bending in opposite directions. In certain variations, two or more steering mechanisms may be located at least about 15° (e.g., about 15°, about 30°, about 45°, about 60°, about 75°, about 90°, about 105°, about 120°, about 135°, about 150°, about 165°, about 180°, about 195°, about 210°, about 225°, about 240°, about 255°, about 270°, about 285°, about 300°, about 315°, about 330°, or about 345°) with respect to the plane of the curved configuration. In some variations, multiple steering mechanisms with different distal longitudinal terminations along the length of catheter body (4904) may be provided, to facilitate along different lengths of bending. The longitudinal separation may be about 1 centimeter to about 50 centimeters or more, sometimes about 5 centimeters to about 20 centimeters, and other times about 5 centimeters to about 10 centimeters apart.

Example 13

A 14 Fr guide catheter (i.e., having an outer diameter of 4.67 millimeters) including six different sections is formed.

In order of the most distal section to the most proximal section, the guide catheter includes: a first distal-most section having a length of 5 millimeters and comprising PEBAX® 35D polymer, a second section having a length of 11 millimeters or 19 millimeters (depending on the configuration of any curve regions in the catheter) and comprising PEBAX® 63D polymer, a third section having a length of 2 millimeters and comprising PEBAX® 55D polymer, a fourth section having a length of 2 millimeters and comprising PEBAX® 72D polymer, a fifth section having a length of 1.5 to 2 centimeters and including a segment comprising PEBAX® 72D polymer and a segment comprising PEBAX® 35D polymer, and a sixth section having a length of about 95 centimeters and comprising PEBAX® 72D polymer.

The catheter also includes a deflectable element comprising a stainless steel wire, one end of which is attached to a stainless steel ring. The stainless steel ring, in turn, is attached to the catheter shaft. During use, an operator may pull on the deflectable element to deflect the fifth section of the catheter.

The guide catheter is made by separately forming each of the above-described six sections, and then fusing the sections together using a hot box to apply heat to reflow the material. During the fusion process, fluorinated ethylene propylene (FEP) heat-shrink tubing (e.g., FEP HS 1.3:1 AWG Heat Shrink, from ZEUS, Orangeburg, S.C.) is provided around the six catheter sections to help maintain the overall outer diameter of the catheter as it is formed, and to help the different sections fuse together.

In this and other examples described herein, the non-linear configuration of the distal section of the guide catheter may act as an alignment structure or otherwise facilitate the registration or alignment of other catheters (or instruments) passed over or inserted into the guide catheter. These alignable or registerable catheters may comprise a complementary non-linear alignment configuration and the non-linear configurations of the guide catheter and/or the alignable catheter may comprise at least one non-linear semi-rigid region having a durometer of at least 50, 55, 63 or 72 on a Shore D scale. The two (or more) catheters may exhibit a reduced stress when in alignment (e.g., longitudinally and/or rotationally) and an increased stress when out of alignment. In some variations, the frictional resistance between the two catheters is sufficiently low such that the stress forces in the catheters may urge the catheters to slide into a reduced stress configuration, for example automatically aligning or registering the two catheters when they are close to alignment or registration. In some variations, increased tactile resistance from sliding the two catheters out of their reduced stress configuration may provide additional guidance during alignment, as well as visual markers located on one or both catheters, which may be viewed on fluoroscopy or other imaging modalities.

The complementary configuration of the alignable catheter may be the same as or similar to any of the catheter configurations described herein, but configured with a smaller or larger diameter for insertion into or passage over the guide catheter, respectively. In some examples, the complementary configuration may comprise a shorter or greater length than the non-linear configuration of the guide catheter. The complementary configuration may also comprise a material (or materials) that may be the same as, or different from, the corresponding section(s) of the guide catheter. The durometer(s) of the complementary configuration may be the same as, lower than, or higher than the corresponding areas on the guide catheter. For example, use of a flexible material in the complementary configuration of the alignable catheter that corresponds to the sections of the guide catheter having tighter bends further facilitate the desired relative positioning of the two catheters.

In some variations, the non-linear configuration of the guide catheter may be located at the distalmost portion of the guide catheter, or proximal to the distal end. The non-linear configuration may be located next to the catheter regions to be aligned, and may be located anywhere along the length of a catheter. In some specific examples, the non-linear configuration is distal to the deflectable portion of the guide catheter and proximal to the distal end. The location of the complementary non-linear configuration of the alignable catheter may vary depending upon the relative extension distance of the alignable catheter when the two catheters are aligned. In some examples, the extension distance of the alignable catheter may be in the range of about 1 cm to about 20 cm or more, sometimes about 2 cm to about 15 cm, and other times about 5 cm to about 10 cm, and still other times about 6 cm to about 8 cm. In one specific example, the aligning catheter comprises a multi-opening guide tunnel catheter where the complementary non-linear alignment configuration is located proximal to the multiple openings of the guide tunnel.

While the methods, devices, and kits have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims. As an example, in some variations, a catheter may be custom-made for a particular patient. For example, computed tomography (CT) scans of the patient's anatomy may be used to design a catheter (e.g., a diagnostic catheter, a visualization catheter, a guide catheter, and/or an anchor deployment catheter) appropriate for the patient (e.g., using one or more computer imaging methods, such as described above). As another example, in certain variations a catheter may include one or more sensors that may be used to indicate when the catheter is adjacent to a tissue wall, such as a heart wall. In this way, the sensor or sensors may be used to help position the catheter at a target site. As an additional example, in some variations, a heart chord may be manipulated (e.g., severed) by application of heat to a region of the heart chord (e.g., using a catheter comprising a heating member). As a further example, in certain variations, a heart chord may be severed using one or more rotating cutters and/or rotating grinders. As another example, in some variations, an operator may manipulate one or more heart chords during a surgical method. For example, an operator may see one or more interfering heart chords during a surgical method, and may sever the chord(s).

What is claimed is:

1. A shaped catheter configured for advancement into a subvalvular space of a heart comprising:
   an elongated member comprising a proximal end, a distal end, and a lumen therethrough, and further comprising an aortic arch curve region defining a first plane, a transition curve region distal to the aortic arch curve region and defining a second plane at a first angle with respect to the first plane, and a valve curve region distal to the transition curve region and defining a third plane at a second angle with respect to the second plane,
   wherein the aortic arch curve region comprises a first preformed curve that corresponds to a curve of an aortic arch and has a first arc defining a central angle of about 60° to about 270°, the transition curve region comprises a second preformed curve that corresponds to a curve between an aortic root and a subannular groove of a mitral valve and has a second arc defining a central angle of about 90° to about 270°, and the valve curve region comprises a third preformed curve that corresponds to a curve of the subannular groove of the mitral valve and has a third arc defining a central angle of about 60° to about 120°.

2. The catheter of claim 1, wherein the first angle is from about 30° to about 90°, and the second angle is from about 1° to about 50°.

3. The catheter of claim 1, wherein the first angle is from about 30° to about 65° and the second angle is from about 5° to about 45°.

4. The catheter of claim 3, wherein the second angle is from about 15° to about 35°.

5. The catheter of claim 3, wherein the second angle is from about 20° to about 45°.

6. The catheter of claim 1, wherein the first angle is from about 50° to about 80°.

7. The catheter of claim 6, wherein the second angle is from about 5° to about 45°.

8. The catheter of claim 7, wherein the second angle is from about 15° to about 35°.

9. The catheter of claim 7, wherein the second angle is from about 20° to about 45°.

10. The catheter of claim 1, wherein the catheter has a size of 4 Fr to 9 Fr.

11. The catheter of claim 1, wherein the catheter has a size of 5 Fr to 10 Fr.

12. The catheter of claim 1, wherein the elongated member comprises a deflectable portion.

13. The catheter of claim 12, wherein the deflectable portion comprises a first polymer and a second polymer having a different durometer from the first polymer.

14. The catheter of claim 1, wherein the first preformed curve directs the catheter away from a center of a ventricular cavity when the catheter is located within vasculature near the heart.

15. The catheter of claim 14, wherein the first preformed curve directs the catheter toward an endocardial surface when the catheter is located within vasculature near the heart.

16. The catheter of claim 1, wherein the first preformed curve comprises an arc having a diameter of about 3.5 inches to about 5 inches.

17. The catheter of claim 1, wherein the second preformed curve directs the catheter toward an anterior side of the left ventricle when the catheter is located within vasculature near the heart.

18. The catheter of claim 1, wherein the second preformed curve comprises an arc having a diameter of about 1 inch to about 3 inches.

19. The catheter of claim 1, wherein the second preformed curve presses against a septal wall of the heart when the distal end is positioned in the subannular groove.

20. The catheter of claim 1, wherein the third preformed curve comprises an arc having a diameter of about 0.75 inch to about 1.5 inches.

21. The catheter of claim 1, wherein one or more of the aortic arch curve region, transition curve region, and the valve curve region comprises a bracing point that contacts an interior portion of vasculature near the heart to stabilize the position of the catheter within the vasculature.

22. The catheter of claim 17, wherein the aortic arch curve region comprises a first bracing point that contacts a length of the aortic arch and a second bracing point that contacts a length of the aortic root.

23. The catheter of claim 1, wherein the curves of the aortic arch curve region, transition curve region, and the valve curve region automatically register the distal end of the catheter within the subannular groove.

24. The catheter of claim 1, wherein the central angle of the first preformed curve is about 90°.

25. The catheter of claim 1, wherein the central angle of the second preformed curve is about 90°.

26. The catheter of claim 1, wherein the central angle of the third preformed curve is about 90°.

* * * * *